(12) United States Patent
Daridon

(10) Patent No.: US 8,658,418 B2
(45) Date of Patent: Feb. 25, 2014

(54) MICROFLUIDIC PARTICLE-ANALYSIS SYSTEMS

(75) Inventor: Antoine Daridon, Belmont, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 12/501,982

(22) Filed: Jul. 13, 2009

(65) Prior Publication Data

US 2010/0120077 A1 May 13, 2010

Related U.S. Application Data

(63) Continuation of application No. 10/640,510, filed on Aug. 12, 2003, now abandoned, which is a continuation-in-part of application No. 10/405,092, filed on Mar. 31, 2003, now abandoned.

(60) Provisional application No. 60/378,464, filed on May 6, 2002, provisional application No. 60/369,538, filed on Apr. 1, 2002.

(51) Int. Cl.
  *C12M 1/34* (2006.01)
  *C12M 3/00* (2006.01)

(52) U.S. Cl.
  USPC .................. 435/288.5; 435/287.2; 435/288.3; 435/288.4; 435/305.1; 435/305.2

(58) Field of Classification Search
  USPC .......... 435/287.2, 288.3, 288.4, 288.5, 305.1, 435/305.2
  See application file for complete search history.

(56) References Cited

U.S. PATENT DOCUMENTS 2,656,508 A 10/1953 Coulter
(Continued)

FOREIGN PATENT DOCUMENTS

DE 299 17 313 A1 2/2001
EP 0 579 997 A1 1/1994
(Continued)

OTHER PUBLICATIONS

"Acuosto-Optic Modulators" available at www.brimrose.com/acousto_modulators.html, Sep. 27, 2000.
(Continued)

*Primary Examiner* — Nathan Bowers
(74) *Attorney, Agent, or Firm* — Kilpatrick Townsend & Stockton LLP

(57) ABSTRACT

The invention provides systems, including apparatus, methods, and kits, for the microfluidic manipulation and/or detection of particles, such as cells and/or beads. The invention provides systems, including apparatus, methods, and kits, for the microfluidic manipulation and/or analysis of particles, such as cells, viruses, organelles, beads, and/or vesicles. The invention also provides microfluidic mechanisms for carrying out these manipulations and analysis. These mechanisms may enable controlled input, movement/positioning, retention/localization, treatment, measurement, release, and/or output of particles. Furthermore, these mechanisms may be combined in any suitable order and/or employed for any suitable number of times within a system. Accordingly, these combinations may allow particles to be sorted, cultured, mixed, treated, and/or assayed, among others, as single particles, mixed groups of particles, arrays of particles, heterogeneous particle sets, and/or homogeneous particle sets, among others, in series and/or in parallel. In addition, these combinations may enable microfluidic systems to be reused. Furthermore, these combinations may allow the response of particles to treatment to be measured on a shorter time scale than was previously possible. Therefore, systems of the invention may allow a broad range of cell and particle assays, such as drug screens, cell characterizations, research studies, and/or clinical analysis, among others, to be scaled down to microfluidic size. Such scaled-down assays may use less sample and reagent, may be less labor intensive, and/or may be more informative than comparable macrofluidic assays.

9 Claims, 90 Drawing Sheets

(56) References Cited

U.S. PATENT DOCUMENTS

| | | |
|---|---|---|
| 3,560,754 A | 2/1971 | Kamentsky |
| 3,570,515 A | 3/1971 | Kinner |
| 3,747,628 A | 7/1973 | Holster et al. |
| 3,839,176 A | 10/1974 | McCoy et al. |
| 3,915,652 A | 10/1975 | Natelson |
| 3,984,307 A | 10/1976 | Kamentsky et al. |
| 4,018,565 A | 4/1977 | Fletcher, III et al. |
| 4,046,159 A | 9/1977 | Pegourie |
| 4,119,368 A | 10/1978 | Yamazaki |
| 4,153,855 A | 5/1979 | Feingold |
| 4,245,673 A | 1/1981 | Bouteille et al. |
| 4,344,064 A | 8/1982 | Bitler et al. |
| 4,373,527 A | 2/1983 | Fischell |
| 4,399,219 A | 8/1983 | Weaver |
| 4,434,704 A | 3/1984 | Surjaatmadja |
| 4,575,681 A | 3/1986 | Grosso et al. |
| 4,581,624 A | 4/1986 | O'Connor |
| 4,585,209 A | 4/1986 | Aine et al. |
| 4,662,710 A | 5/1987 | ten Berge |
| 4,675,300 A | 6/1987 | Zare et al. |
| 4,707,237 A | 11/1987 | Lepp et al. |
| 4,797,842 A | 1/1989 | Nackman et al. |
| 4,876,504 A | 10/1989 | Blake et al. |
| 4,898,582 A | 2/1990 | Faste |
| 4,908,112 A | 3/1990 | Pace |
| 4,936,465 A | 6/1990 | Zold |
| 4,963,498 A | 10/1990 | Hillman et al. |
| 4,965,743 A | 10/1990 | Malin et al. |
| 4,992,312 A | 2/1991 | Frisch |
| 5,032,381 A | 7/1991 | Bronstein et al. |
| 5,085,562 A | 2/1992 | Van Lintel |
| 5,088,515 A | 2/1992 | Kamen |
| 5,091,652 A | 2/1992 | Mathies et al. |
| 5,096,388 A | 3/1992 | Weinberg |
| 5,100,627 A | 3/1992 | Buican et al. |
| 5,126,022 A | 6/1992 | Soane et al. |
| 5,126,115 A | 6/1992 | Fujita et al. |
| 5,140,161 A | 8/1992 | Hillman et al. |
| 5,143,854 A | 9/1992 | Pirrung et al. |
| 5,164,558 A | 11/1992 | Huff et al. |
| 5,164,598 A | 11/1992 | Hillman et al. |
| 5,171,132 A | 12/1992 | Miyazaki et al. |
| 5,171,764 A | 12/1992 | Katayama et al. |
| 5,224,843 A | 7/1993 | Van Lintel |
| 5,242,797 A | 9/1993 | Hirschfeld |
| 5,259,737 A | 11/1993 | Kamisuki et al. |
| 5,265,327 A | 11/1993 | Faris et al. |
| 5,271,724 A | 12/1993 | van Lintel |
| 5,290,240 A | 3/1994 | Horres, Jr. |
| 5,304,487 A | 4/1994 | Wilding et al. |
| 5,307,186 A | 4/1994 | Izumi et al. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,417,235 A | 5/1995 | Wise et al. |
| 5,423,287 A | 6/1995 | Usami et al. |
| 5,434,049 A | 7/1995 | Okuno et al. |
| 5,445,934 A | 8/1995 | Fodor et al. |
| 5,452,878 A | 9/1995 | Gravesen et al. |
| 5,454,472 A | 10/1995 | Benecke et al. |
| 5,486,335 A | 1/1996 | Wilding et al. |
| 5,487,003 A | 1/1996 | Iwasawa et al. |
| 5,496,009 A | 3/1996 | Farrell et al. |
| 5,498,392 A | 3/1996 | Wilding et al. |
| 5,500,071 A | 3/1996 | Kaltenbach et al. |
| 5,512,131 A | 4/1996 | Kumar et al. |
| 5,525,464 A | 6/1996 | Drmanac et al. |
| 5,529,465 A | 6/1996 | Zengerle et al. |
| 5,558,998 A | 9/1996 | Hammond et al. |
| 5,571,410 A | 11/1996 | Swedberg et al. |
| 5,574,893 A | 11/1996 | Southgate et al. |
| 5,580,523 A | 12/1996 | Bard |
| 5,589,136 A | 12/1996 | Northrup et al. |
| 5,593,130 A | 1/1997 | Hansson et al. |
| 5,595,650 A | 1/1997 | Manz |
| 5,604,098 A | 2/1997 | Mead et al. |
| 5,608,519 A | 3/1997 | Gourley |
| 5,632,876 A | 5/1997 | Zanzucchi et al. |
| 5,637,469 A | 6/1997 | Wilding et al. |
| 5,639,423 A | 6/1997 | Northrup et al. |
| 5,641,400 A | 6/1997 | Kaltenbach et al. |
| 5,642,015 A | 6/1997 | Whitehead et al. |
| 5,646,039 A | 7/1997 | Northrup et al. |
| 5,656,155 A | 8/1997 | Norcross et al. |
| 5,659,171 A | 8/1997 | Young et al. |
| 5,660,370 A | 8/1997 | Webster |
| 5,661,222 A | 8/1997 | Hare |
| 5,665,070 A | 9/1997 | McPhee |
| 5,674,742 A | 10/1997 | Northrup et al. |
| 5,681,024 A | 10/1997 | Lisec et al. |
| 5,681,484 A | 10/1997 | Zanzucchi et al. |
| 5,702,618 A | 12/1997 | Saaski et al. |
| 5,705,018 A | 1/1998 | Hartley |
| 5,716,852 A | 2/1998 | Yager et al. |
| 5,726,404 A | 3/1998 | Brody |
| 5,726,751 A | 3/1998 | Altendorf et al. |
| 5,750,015 A | 5/1998 | Soane et al. |
| 5,757,482 A | 5/1998 | Fuchs et al. |
| 5,759,014 A | 6/1998 | Van Lintel |
| 5,775,371 A | 7/1998 | Pan et al. |
| 5,779,868 A | 7/1998 | Parce et al. |
| 5,788,468 A | 8/1998 | Dewa et al. |
| 5,800,690 A | 9/1998 | Chow et al. |
| 5,802,856 A | 9/1998 | Schaper et al. |
| 5,807,522 A | 9/1998 | Brown et al. |
| 5,812,394 A | 9/1998 | Lewis et al. |
| 5,815,306 A | 9/1998 | Sheridon et al. |
| 5,832,165 A | 11/1998 | Reichert et al. |
| 5,833,926 A | 11/1998 | Wurzel et al. |
| 5,836,750 A | 11/1998 | Cabuz |
| 5,837,200 A | 11/1998 | Diessel et al. |
| 5,837,832 A | 11/1998 | Chee et al. |
| 5,839,722 A | 11/1998 | Berlin et al. |
| 5,842,787 A | 12/1998 | Kopf-Sill et al. |
| 5,846,396 A | 12/1998 | Zanzucchi et al. |
| 5,846,708 A | 12/1998 | Hollis et al. |
| 5,852,495 A | 12/1998 | Parce |
| 5,854,684 A | 12/1998 | Stabile et al. |
| 5,856,174 A | 1/1999 | Lipshutz et al. |
| 5,858,187 A | 1/1999 | Ramsey et al. |
| 5,858,195 A | 1/1999 | Ramsey |
| 5,858,649 A | 1/1999 | Asgari et al. |
| 5,863,502 A | 1/1999 | Southgate et al. |
| 5,863,722 A | 1/1999 | Brenner |
| 5,863,801 A | 1/1999 | Southgate et al. |
| 5,866,345 A | 2/1999 | Wilding et al. |
| 5,867,399 A | 2/1999 | Rostoker et al. |
| 5,869,004 A | 2/1999 | Parce et al. |
| 5,871,697 A | 2/1999 | Rothberg et al. |
| 5,872,010 A | 2/1999 | Karger et al. |
| 5,875,817 A | 3/1999 | Carter |
| 5,876,187 A | 3/1999 | Afromowitz |
| 5,876,675 A | 3/1999 | Kennedy |
| 5,876,946 A | 3/1999 | Burbaum et al. |
| 5,880,071 A | 3/1999 | Parce et al. |
| 5,885,470 A | 3/1999 | Parce et al. |
| 5,888,778 A | 3/1999 | Shuber |
| 5,904,824 A | 5/1999 | Oh |
| 5,922,591 A | 7/1999 | Anderson et al. |
| 5,922,604 A | 7/1999 | Stapleton et al. |
| 5,928,880 A | 7/1999 | Wilding et al. |
| 5,932,100 A | 8/1999 | Yager et al. |
| 5,932,799 A | 8/1999 | Moles |
| 5,939,709 A | 8/1999 | Ghislain et al. |
| 5,942,443 A | 8/1999 | Parce et al. |
| 5,948,227 A | 9/1999 | Dubrow |
| 5,958,344 A | 9/1999 | Levine et al. |
| RE36,350 E | 10/1999 | Swedberg et al. |
| 5,965,001 A | 10/1999 | Chow et al. |
| 5,971,355 A | 10/1999 | Biegelsen et al. |
| 5,972,639 A | 10/1999 | Parandoosh |
| 5,976,822 A | 11/1999 | Landrum et al. |

(56) References Cited

U.S. PATENT DOCUMENTS

| | | | |
|---|---|---|---|
| 5,994,696 A | 11/1999 | Tai et al. |
| 5,997,961 A | 12/1999 | Feng et al. |
| 6,004,442 A | 12/1999 | Choulga et al. |
| 6,004,515 A | 12/1999 | Parce et al. |
| 6,007,309 A | 12/1999 | Hartley |
| 6,007,690 A | 12/1999 | Nelson et al. |
| 6,015,531 A | 1/2000 | Colin et al. |
| 6,018,616 A | 1/2000 | Schaper et al. |
| 6,040,166 A | 3/2000 | Erlich et al. |
| 6,042,709 A | 3/2000 | Parce et al. |
| 6,043,080 A | 3/2000 | Lipshutz et al. |
| 6,045,994 A | 4/2000 | Zabeau et al. |
| 6,046,056 A | 4/2000 | Parce et al. |
| 6,048,498 A | 4/2000 | Kennedy |
| 6,056,428 A | 5/2000 | Devoino et al. |
| 6,062,261 A | 5/2000 | Jacobson et al. |
| 6,074,827 A | 6/2000 | Nelson et al. |
| 6,089,534 A | 7/2000 | Biegelsen et al. |
| 6,094,274 A | 7/2000 | Yokoi |
| 6,103,199 A | 8/2000 | Bjornson et al. |
| 6,103,537 A | 8/2000 | Ullman et al. |
| 6,107,044 A | 8/2000 | Nikiforov |
| 6,117,634 A | 9/2000 | Langmore et al. |
| 6,123,769 A | 9/2000 | Sanjoh |
| 6,132,580 A | 10/2000 | Mathies et al. |
| 6,132,685 A | 10/2000 | Kercso et al. |
| 6,136,212 A | 10/2000 | Mastrangelo et al. |
| 6,140,045 A | 10/2000 | Wohlstadter et al. |
| 6,146,842 A | 11/2000 | Josiah et al. |
| 6,149,787 A | 11/2000 | Chow et al. |
| 6,149,870 A | 11/2000 | Parce et al. |
| 6,150,119 A | 11/2000 | Kopf-Sill et al. |
| 6,150,180 A | 11/2000 | Parce et al. |
| 6,155,282 A | 12/2000 | Zachary et al. |
| 6,165,694 A | 12/2000 | Liu |
| 6,167,910 B1 | 1/2001 | Chow |
| 6,171,850 B1 | 1/2001 | Nagle et al. |
| 6,174,365 B1 | 1/2001 | Sanjoh |
| 6,174,675 B1 | 1/2001 | Chow et al. |
| 6,182,020 B1 | 1/2001 | Fairbanks |
| 6,197,595 B1 | 3/2001 | Anderson et al. |
| 6,214,246 B1 | 4/2001 | Craighead |
| 6,221,654 B1 | 4/2001 | Quake et al. |
| 6,225,109 B1 | 5/2001 | Juncosa et al. |
| 6,227,809 B1 | 5/2001 | Forster et al. |
| 6,235,175 B1 | 5/2001 | Dubrow et al. |
| 6,235,471 B1 | 5/2001 | Knapp et al. |
| 6,246,330 B1 | 6/2001 | Nielsen |
| 6,274,337 B1 | 8/2001 | Parce et al. |
| 6,296,673 B1 | 10/2001 | Santarsiero et al. |
| 6,306,659 B1 | 10/2001 | Parce et al. |
| 6,315,940 B1 * | 11/2001 | Nisch et al. ............... 435/287.1 |
| 6,321,791 B1 | 11/2001 | Chow |
| 6,329,209 B1 | 12/2001 | Wagner et al. |
| 6,344,325 B1 | 2/2002 | Quake et al. |
| 6,345,502 B1 | 2/2002 | Tai et al. |
| 6,352,838 B1 | 3/2002 | Krulevitch et al. |
| 6,355,420 B1 | 3/2002 | Chan |
| 6,358,387 B1 | 3/2002 | Kopf-Sill et al. |
| 6,361,671 B1 | 3/2002 | Mathies et al. |
| 6,375,871 B1 | 4/2002 | Bentsen et al. |
| 6,376,971 B1 | 4/2002 | Pelrine et al. |
| 6,408,878 B2 | 6/2002 | Unger et al. |
| 6,409,832 B2 | 6/2002 | Weigl et al. |
| 6,431,212 B1 | 8/2002 | Hayenga et al. |
| 6,444,426 B1 | 9/2002 | Short et al. |
| 6,488,832 B2 | 12/2002 | Heller |
| 6,488,872 B1 | 12/2002 | Beebe et al. |
| 6,500,323 B1 | 12/2002 | Chow et al. |
| 6,505,125 B1 | 1/2003 | Ho |
| 6,508,988 B1 * | 1/2003 | Van Dam et al. ............ 422/102 |
| 6,520,936 B1 | 2/2003 | Mann |
| 6,528,249 B1 | 3/2003 | Short |
| 6,533,914 B1 | 3/2003 | Liu |
| 6,537,799 B2 | 3/2003 | Chow et al. |
| 6,540,895 B1 | 4/2003 | Spence et al. |
| 6,541,071 B1 | 4/2003 | Bookbinder et al. |
| 6,555,315 B1 | 4/2003 | Short |
| 6,563,111 B1 | 5/2003 | Moon et al. |
| 6,569,382 B1 | 5/2003 | Edman et al. |
| 6,581,441 B1 | 6/2003 | Paul |
| 6,596,545 B1 | 7/2003 | Wagner et al. |
| 6,605,472 B1 | 8/2003 | Skinner et al. |
| 6,627,076 B2 | 9/2003 | Griffiths |
| 6,632,619 B1 | 10/2003 | Harrison et al. |
| 6,637,463 B1 | 10/2003 | Lei et al. |
| 6,645,432 B1 | 11/2003 | Anderson et al. |
| 6,662,818 B2 | 12/2003 | Paul et al. |
| 6,664,104 B2 | 12/2003 | Pourahmadi et al. |
| 6,667,124 B2 | 12/2003 | Suenaga et al. |
| 6,677,131 B2 | 1/2004 | Yuen |
| 6,689,473 B2 | 2/2004 | Guire et al. |
| 6,695,765 B1 * | 2/2004 | Beebe et al. ............... 600/33 |
| 6,713,327 B2 | 3/2004 | Leedy |
| 6,716,378 B2 | 4/2004 | Yang et al. |
| 6,736,978 B1 | 5/2004 | Porter et al. |
| 6,749,814 B1 | 6/2004 | Bergh et al. |
| 6,752,922 B2 | 6/2004 | Huang et al. |
| 6,765,279 B2 | 7/2004 | Leedy |
| 6,767,706 B2 | 7/2004 | Quake et al. |
| 6,829,753 B2 | 12/2004 | Lee et al. |
| 6,833,242 B2 | 12/2004 | Quake et al. |
| 6,847,153 B1 | 1/2005 | Balizer |
| 6,866,785 B2 | 3/2005 | Zare et al. |
| 6,884,346 B2 | 4/2005 | Zare et al. |
| 6,885,982 B2 | 4/2005 | Harris et al. |
| 6,936,462 B1 * | 8/2005 | Owen et al. ............... 435/287.7 |
| 6,951,632 B2 | 10/2005 | Unger et al. |
| 6,960,437 B2 | 11/2005 | Enzelberger et al. |
| 6,977,145 B2 | 12/2005 | Fouillet et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Van Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 2001/0027745 A1 | 10/2001 | Weigl et al. |
| 2001/0029983 A1 | 10/2001 | Unger et al. |
| 2001/0041357 A1 | 11/2001 | Fouillet et al. |
| 2002/0005354 A1 | 1/2002 | Spence et al. |
| 2002/0012926 A1 | 1/2002 | Quake et al. |
| 2002/0014673 A1 | 2/2002 | Leedy |
| 2002/0037499 A1 | 3/2002 | Quake et al. |
| 2002/0045297 A1 | 4/2002 | Leedy |
| 2002/0058332 A1 | 5/2002 | Quake et al. |
| 2002/0064885 A1 | 5/2002 | Bedingham et al. |
| 2002/0108096 A1 | 8/2002 | Lee et al. |
| 2002/0108097 A1 | 8/2002 | Harris et al. |
| 2002/0109114 A1 | 8/2002 | Driggs et al. |
| 2002/0124896 A1 | 9/2002 | O'Connor et al. |
| 2002/0127736 A1 | 9/2002 | Fu et al. |
| 2002/0145231 A1 | 10/2002 | Hansen et al. |
| 2002/0158022 A1 | 10/2002 | Huang et al. |

(56) References Cited

U.S. PATENT DOCUMENTS

| | | |
|---|---|---|
| 2002/0164816 A1 | 11/2002 | Quake |
| 2002/0183996 A1 | 12/2002 | Lee et al. |
| 2002/0197603 A1 | 12/2002 | Chow et al. |
| 2003/0008308 A1 | 1/2003 | Enzelberger et al. |
| 2003/0019833 A1 | 1/2003 | Unger et al. |
| 2003/0080442 A1 | 5/2003 | Unger |
| 2003/0119177 A1 | 6/2003 | Gruber et al. |
| 2003/0134129 A1 | 7/2003 | Lammertink et al. |
| 2003/0138829 A1 | 7/2003 | Unger et al. |
| 2003/0143120 A1 | 7/2003 | Ruediger et al. |
| 2003/0175947 A1 | 9/2003 | Liu et al. |
| 2003/0196695 A1 | 10/2003 | O'Connor et al. |
| 2004/0072278 A1 | 4/2004 | Chou et al. |
| 2004/0096960 A1 | 5/2004 | Burd Mehta et al. |
| 2004/0115838 A1* | 6/2004 | Quake et al. .......... 436/538 |
| 2004/0141887 A1 | 7/2004 | Mainquist et al. |
| 2004/0166555 A1* | 8/2004 | Braff et al. .............. 435/29 |
| 2004/0180377 A1 | 9/2004 | Manger et al. |
| 2004/0209354 A1 | 10/2004 | Mathies et al. |
| 2004/0224380 A1 | 11/2004 | Chou et al. |
| 2004/0248167 A1 | 12/2004 | Quake et al. |
| 2005/0000900 A1 | 1/2005 | Huang et al. |
| 2005/0019792 A1 | 1/2005 | McBride et al. |
| 2005/0037471 A1 | 2/2005 | Liu et al. |
| 2005/0053952 A1 | 3/2005 | Hong et al. |
| 2005/0065735 A1 | 3/2005 | Lee et al. |
| 2005/0069913 A1* | 3/2005 | Mian et al. ............... 435/6 |
| 2005/0084421 A1 | 4/2005 | Unger et al. |
| 2005/0123947 A1 | 6/2005 | Quake et al. |
| 2005/0129581 A1 | 6/2005 | McBride et al. |
| 2005/0145496 A1 | 7/2005 | Goodsaid et al. |
| 2005/0164376 A1 | 7/2005 | Balagadde et al. |
| 2005/0180891 A1 | 8/2005 | Webster |
| 2005/0196785 A1 | 9/2005 | Quake et al. |
| 2005/0197652 A1 | 9/2005 | Nat |
| 2005/0221373 A1 | 10/2005 | Enzelberger et al. |
| 2005/0252773 A1 | 11/2005 | McBride et al. |
| 2006/0172408 A1 | 8/2006 | Quake et al. |
| 2006/0233674 A1 | 10/2006 | Nelson |
| 2006/0281183 A1 | 12/2006 | Sun et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |

FOREIGN PATENT DOCUMENTS

| | | |
|---|---|---|
| EP | 0 592 094 A2 | 4/1994 |
| EP | 0 703 364 A | 3/1996 |
| EP | 0 706 004 A2 | 4/1996 |
| EP | 0 745 682 B1 | 12/1996 |
| EP | 0 778 351 B1 | 6/1997 |
| EP | 0 779 436 A2 | 6/1997 |
| EP | 0 829 360 A2 | 3/1998 |
| EP | 0 845 603 A1 | 6/1998 |
| EP | 0 846 776 | 6/1998 |
| EP | 0 999 055 A2 | 5/2000 |
| EP | 1 065 378 A2 | 1/2001 |
| GB | 2 097 692 A | 11/1982 |
| GB | 2 155 152 A | 9/1985 |
| GB | 2 264 296 A | 8/1993 |
| GB | 2 264 496 A | 9/1993 |
| GB | 2 308 460 A | 6/1997 |
| JP | 9-043251 | 2/1997 |
| WO | WO 90/04652 A1 | 5/1990 |
| WO | WO 90/15070 A1 | 12/1990 |
| WO | WO 91/13338 A2 | 9/1991 |
| WO | WO 91/15750 A1 | 10/1991 |
| WO | WO 92/16657 A1 | 10/1992 |
| WO | WO 94/05414 A1 | 3/1994 |
| WO | WO 95/33846 A1 | 12/1995 |
| WO | WO 95/33853 A1 | 12/1995 |
| WO | WO 96/04547 A1 | 2/1996 |
| WO | WO 96/27025 A1 | 9/1996 |
| WO | WO 97/02357 A1 | 1/1997 |
| WO | WO 97/27324 A1 | 7/1997 |
| WO | WO 97/38300 A1 | 10/1997 |
| WO | WO 97/45644 A1 | 12/1997 |
| WO | WO 98/00231 A1 | 1/1998 |
| WO | WO 98/04742 A1 | 2/1998 |
| WO | WO 98/07069 A1 | 2/1998 |
| WO | WO 98/08931 A1 | 3/1998 |
| WO | WO 98/10267 A1 | 3/1998 |
| WO | WO 98/45481 A1 | 10/1998 |
| WO | WO 98/52691 A1 | 11/1998 |
| WO | WO 99/00655 A2 | 1/1999 |
| WO | WO 99/04361 A1 | 1/1999 |
| WO | WO 99/14311 A1 | 3/1999 |
| WO | WO 99/17093 A1 | 4/1999 |
| WO | WO 99/36760 A1 | 7/1999 |
| WO | WO 99/52633 A1 | 10/1999 |
| WO | WO 99/61888 A2 | 12/1999 |
| WO | WO 00/00678 A1 | 1/2000 |
| WO | WO 00/43748 A1 | 7/2000 |
| WO | WO 00/53801 A1 | 9/2000 |
| WO | WO 00/60345 A1 | 10/2000 |
| WO | WO 00/68414 A2 | 11/2000 |
| WO | WO 00/70082 A1 | 11/2000 |
| WO | WO 01/01025 A2 | 1/2001 |
| WO | WO 01/06529 A1 | 1/2001 |
| WO | WO 01/06575 A1 | 1/2001 |
| WO | WO 01/07061 A1 | 2/2001 |
| WO | WO 01/09595 A2 | 2/2001 |
| WO | WO 01/09595 A3 | 2/2001 |
| WO | WO 01/18246 A1 | 3/2001 |
| WO | WO 01/24937 A2 | 4/2001 |
| WO | WO 01/32930 A1 | 5/2001 |
| WO | WO 01/34302 | 5/2001 |
| WO | WO 01/45843 | 6/2001 |
| WO | WO 01/53794 A1 | 7/2001 |
| WO | WO 01/67369 A2 | 9/2001 |
| WO | WO 01/89695 | 11/2001 |
| WO | WO 02/00343 A2 | 1/2002 |
| WO | WO 02/29106 A2 | 4/2002 |
| WO | WO 02/30486 A2 | 4/2002 |
| WO | WO 02/40874 A2 | 5/2002 |
| WO | WO 02/43615 A2 | 6/2002 |
| WO | WO 02/060582 A2 | 8/2002 |
| WO | WO 02/065005 A1 | 8/2002 |
| WO | WO 02/072892 A1 | 9/2002 |

(56) References Cited

FOREIGN PATENT DOCUMENTS

| WO | WO 02/081729 A2 | 10/2002 |
|----|----|----|
| WO | WO 02/081935 A2 | 10/2002 |
| WO | WO 02/082047 A2 | 10/2002 |
| WO | WO 03/037781 A1 | 5/2003 |
| WO | WO 03/048295 A1 | 6/2003 |
| WO | WO 2007/033385 A2 | 3/2007 |
| WO | WO 2007/044091 A2 | 4/2007 |
| WO | WO 2008/043046 A2 | 4/2008 |
| WO | WO 2009/100449 A1 | 8/2009 |
| WO | WO 2010/011852 A1 | 1/2010 |
| WO | WO 2010/017210 A1 | 2/2010 |
| WO | WO 2010/077618 A1 | 7/2010 |

OTHER PUBLICATIONS

"Last Chance for Micromachines," The Economist Technology Quarterly, 8 pages, Dec. 7, 2000.
"The Liver Chip," Technology Review, pp. 64-67, Mar. 2003.
"Biochips," Nature Biotechnology, vol. 18, Supplement 2000, pp. IT43-1T44, 2000.
"Chapter 9: Microfluidic Devices," Micromachined Transducers Sourcebook, pp. 779-882, 1998.
Affholter, Joseph et al., "Engineering a Revolution," Chemistry in Britain, pp. 48-51, Apr. 1999.
Anderson, Janelle R. et al., "Fabrication of Topologically Complex Three-Dimensional Microfluidic Systems in PDMS by Rapid Prototyping," Analytical Chemistry, vol. 72, No. 14, pp. 3158-3164, Jul. 15, 2000.
Andersson et al., "Consecutive Microcontact Printing—Ligands for Asymmetric Catalysis in Silicon Channel," Sensors & Actuators B, vol. 3997, pp. 1-7, 2001.
Angell, James B. et al., "Silicon Micromechanical Devices," Scientific American, pp. cover, 44-55, Apr. 1983.
Applied Biosystems, "TaqMan® PCR Reagent Kit With AmpliTaq Gold® DNA Polymerase Protocol," Jan. 2003.
Armani, Deniz et al., "Re-Configurable Fluid Circuits by PDMS Elastomer Micromachining," IEEE Int. Conf. Micro Electro Mech. Syst. Tech. Digest, vol. 12, pp. 222-227, 1999.
Arnold, Frances H., "Design by Directed Evolution," Accounts of Chemical Research, vol. 31, No. 3, pp. 125-131, 1998.
Ashkin, A. et al., "Optical Trapping and Manipulation of Single Cells Using Infrared Laser Beams," Nature, vol. 330, No. 24, pp. 769-771, Dec. 31, 1987.
Ashkin, A. et al., "Optical Trapping and Manipulation of Viruses and Bacteria," Science, vol. 235, pp. 1517-1520, Mar. 20, 1987.
Axelrod, Daniel, "Cell-Substrate Contacts Illuminated by Total Internal Reflection Fluorescence," Journal of Cell Biology, vol. 89, pp. 141-145, Apr. 1981.
Bader, Joel S. et al., "DNA Transport by a Micromachined Brownian Ratchet Device," PNAS, vol. 96, No. 23, pp. 13165-13169, Nov. 9, 1999.
Ballantyne, J. P. et al., "Selective Area Metallization by Electron-Beam Controlled Direct Metallic Deposition," J. Vac. Sci. Technol., vol. 10, No. 6, pp. 1094-1097, Nov. 1973.
Barron, Annelise E. et al., "Capillary Electrophoresis of DNA in Uncross-Linked Polymer Solutions," Journal of Chromatography A, vol. 652, pp. 3-16, 1993.
Barron, Annelise E. et al., "DNA Separations by Slab Gel and Capillary Electrophoresis—Theory and Practice," Separation and Purification Methods, vol. 24, No. 1, pp. 1-118, 1995.
Barron, Annelise E. et al., "The Use of Coated and Uncoated Capillaries for the Electrophoretic Separation of DNA in Dilute Polymer-Solutions," Electrophoresis, vol. 16, pp. 64-74, 1995.
Bein, Thomas, "Efficient Assays for Combinatorial Methods for the Discovery of Catalysts," Angew. Chem. Int. Ed., vol. 38, No. 3, pp. 323-326, 1999.
Belgrader et al., "A Battery-Powered Notebook Thermal Cycler for Rapid Multiplex Real Time PCR Analysis," Anal. Chem., vol. 73, pp. 286-289, 2001.

Belgrader et al., "PCR Detection of Bacteria in Seven Minutes," Science, 284(5413), pp. 449-450, 1999.
Belgrader, Phillip et al., "Rapid Pathogen Detection Using a Microchip PCR Array Instrument," Clinical Chemistry, vol. 44, No. 10, pp. 2191-2194, 1998.
Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.
Black, Harvey, "Tiny Technology Promises Tremendous Profits," The Scientist, vol. 15, No. 21, 4 pages, Oct. 29, 2001.
Blanch, Harvey W. et al., Biochemical Engineering, pp. 2 cover pages and 305, 1996.
Blankenstein, Gert et al., "Modular Concept of a Laboratory on a Chip for Chemical and Biochemical Analysis," Biosensors & Bioelectronics, vol. 13, Nos. 3-4, pp. 427-438, 1998.
Bloomstein, T. M. et al., "Laser-Chemical Three-Dimensional Writing for Microelectromechanics and Application to Standard-Cell Microfluidics," J. Vac. Sci. Technol. B, vol. 10, No. 6, pp. 2671-2674, Nov. 1992.
Bousse, Luc et al., "Electrokinetically Controlled Microfluidic Analysis Systems," Annu. Rev. Biophys. Biomol. Struct., vol. 29, pp. 155-181, 2000.
Braslavsky et al.; "Single Molecule Measurements of DNA Polymerase Activity: A Step Towards Single Molecule Sequencing", Biophysics Journal Abstracts Issue, 2002, p. 507A, vol. 82, No. 1.
Brechtel, R. et al., "Control of the Electroosmotic Flow by Metal-Salt-Containing Buffers," Journal of Chromatography A, vol. 716, pp. 97-105, 1995.
Breslauer, Kenneth J. et al., "Predicting DNA Duplex Stability From The Base Sequence," Proc. Natl. Acad. Sci. USA, vol. 83, pp. 3746-3750, Jun. 1986.
Brody, J. P. et al., "Low Reynolds Number Micro-Fluidic Devices," in Proc. of Solid-State Sensor and Actuator Workshop, pp. 105-108, Jun. 1996.
Brody, James P. et al., "Significance and Statistical Errors in The Analysis of DNA Microarray Data," PNAS, vol. 99, No. 20, pp. 12975-12978, Oct. 1, 2002.
Brush, Michael, "Automated Laboratories," The Scientist, vol. 13, No. 4, 10 pages, Feb. 15, 1999.
Bryzek, Janusz et al., "Micromachines on the March", IEEE Spectrum, vol. 31, No. 5, pp. 20-31, May 1994.
Buchaillot, Lionel et al., "Silicon Nitride Thin Films Young's Modulus Determination by an Optical Non Destructive Method," Jpn. J. Appl. Phys., vol. 36, Part 2, No. 6B, pp. L794-L797, Jun. 15, 1997.
Budowle, Bruce et al., "Analysis of the VNTR Locus DIS80 by the PCR Followed by High-Resolution PAGE," Am. J. Hum. Genet., vol. 48, pp. 137-144, 1991.
Buican, Tudor N. et al., "Automated Single-Cell Manipulation and Sorting by Light Trapping," Applied Optics, vol. 26, No. 24, pp. 5311-5316, Dec. 15, 1987.
Bulyk, Martha L. et al., "Quantifying DNA-Protein Interactions by Double-Stranded DNA Arrays," Nature Biotechnology, vol. 17, pp. 573-577, Jun. 1999.
Burbaum, Jonathan J. et al., "New Technologies for High-Throughput Screening," Current Opinion in Chemical Biology, vol. 1, pp. 72-78, 1997.
Burns et al., "An Integrated Nanoliter DNA Analysis Device," Science, vol. 282, pp. 484-487, 1998.
Busch, J. et al., Methods for the Differentiation of Microorganisms, Journal of Chromatography B, vol. 722, pp. 263-278, 1999.
Cai, Weiwen, et al., "High-Resolution Restriction Maps of Bacterial Artificial Chromosomes Constructed by Optical Mapping," Proc. Natl. Acad. Sci. USA, vol. 95, pp. 3390-3395, Mar. 1998.
Calkins, Kathryn, "Mycometrix: Rubber Chips," BioCentury, 2 pages, Oct. 16, 2000.
Castro, Alonso et al., "Fluorescence Detection and Size Measurement of Single DNA Molecules," Analytical Chemistry, vol. 85, No. 7, pp. 849-852, Apr. 1, 1993.
Chan, Jason H. et al., "Microfabricated Polymer Devices for Automated Sample Delivery of Peptides for Analysis by Electrospray Ionization Tandem Mass Spectrometry," Analytical Chemistry, vol. 71, No. 20, pp. 4437-4444, Oct. 15, 1999.

(56) References Cited

OTHER PUBLICATIONS

Chang, Jun Keun et al., "Functional Integration of Serial Dilution and Capillary Electrophoresis on a PDMS Microchip," Biotechnology and Bioprocess Engineering, vol. 8, No. 4, pp. 233-239, 2003.
Chaudhari et al., "Transient Liquid Crystal Thermometry of Microfabricated PCR Vessel Arrays," J. Microelectromechanical Systems, 7(4), pp. 345-355, 1998.
Chee, Mark et al., "Accessing Genetic Information With High-Density DNA Arrays," Science, vol. 274, pp. 610-614, Oct. 25, 1996.
Chen, Chihchen et al., "Gray-Scale Photolithography Using Microfluidic Photomasks," PNAS, vol. 100, No. 4, pp. 1499-1504, Feb. 18, 2003.
Chiang, Yuh-Min et al., "Characterizing the Process of Cast Molding Microfluidic Systems," SPIE, vol. 3877, pp. 303-311, Sep. 1999.
Chiem, N. H. et al., "Microchip Systems for Immunoassay: An Integrated Immunoreactor With Electrophoretic Separation for Serum Theophylline Determination," Clinical Chemistry, vol. 44, No. 3, p. 591, 1998.
Chiou et al., "A Closed-Cycle Capillary Polymerase Chain," Anal. Chem., vol. 73, pp. 2018-2021, 2001.
Chiu, Chi-Sung et al., "Single Molecule Measurements Calibrate Green Fluorescent Protein Surface Densities on Transparent Beads for Use With 'Knock-In' Animals and Other Expression Systems," Journal of Neuroscience Methods, vol. 105, pp. 55-63, 2001.
Chiu, Daniel T. et al., "Patterned Deposition of Cells and Proteins Onto Surfaces by Using Three-Dimensional Microfluidic Systems," PNAS, vol. 97, No. 6, pp. 2408-2413, Mar. 14, 2000.
Chou, Hou-Pu et al., "A Microfabricated Device for Sizing and Sorting DNA Molecules," Proc. Natl. Acad. Sci., vol. 96, pp. 11-13, Jan. 1999.
Chou, Hou-Pu et al., "A Microfabricated Rotary Pump," Biomedical Microdevices, vol. 3, No. 4, pp. 323-330, 2001.
Chou, Hou-Pu et al., "Disposable Microdevices for DNA Analysis and Cell Sorting," Proc. Solid-State Sensor and Actuator Workshop, Hilton Head, South Carolina, pp. 11-14, Jun. 8-11, 1998.
Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head, South Carolina, 4 pages, 2000.
Chou, Hou-Pu et al., "Microfabricated Devices for Sizing DNA and Sorting Cells," Micro- and Nanofabricated Structures and Devices for Biomedical Environmental Applications, Proceedings of SPIE, vol. 3258, pp. 181-187, 1998.
Chou, Hou-Pu et al., "Multiple Disease Diagnostics on a Single Chip," Biophysics Lab, Caltech, pp. 1-4, Mar. 1, 2000.
Chou, Hou-Pu, "Microfabricated Devices for Rapid DNA Diagnostics," Doctoral Thesis, California Institute of Technology, pp. i-xii and 1-106, May 30, 2000.
Costerton, J. William et al., "Microbial Biofilms," Annu. Rev. Microbiol., vol. 49, pp. 711-745, 1995.
Cowen, S. et al., "An On-Chip Miniature Liquid Chromatography System: Design, Construction and Characterization," Micro Total Analysis Systems, Proceedings of the µTAS '94 Workshop, University of Twente, The Netherlands, pp. 2 cover pages and 295-298, 1995.
Crosland-Taylor, P. J., "A Device for Counting Small Particles Suspended in a Fluid Through a Tube," Nature, vol. 171, pp. 37-38, Jan. 3, 1953.
Davila, Herman Moreno, "Molecular and Functional Diversity of Voltage-Gated Calcium Channels," Annals of the New York Academy of Sciences, vol. 868, pp. cover, 102-117, 1999.
Delamarche, Emmanuel et al., "Patterned Delivery of Immunoglobulins to Surfaces Using Microfluidic Networks," Science, vol. 276, pp. 779-781, May 2, 1997.
Delisa, Matthew P. et al., "Mapping Stress-Induced Changes in Autoinducer AI-2 Production in Chemostat-Cultivated *Escherichia coli* K-12," Journal of Bacteriology, vol. 183, No. 9, pp. 2918-2928, May 2001.
Dharmatilleke, Saman et al., "Three-Dimensional Silicone Device Fabrication and Interconnection Scheme for Microfluidic Applications Using Sacrificial Wax Layers," Micro Electro-Mechanical Systems (MEMS), vol. 2, pp. 413-418, 2000.
Drmanac, R. et al., "DNA Sequence Determination by Hybridization: A Strategy for Efficient Large-Scale Sequencing," Science, vol. 260, pp. 1649-1652, Jun. 11, 1993.
Drmanac, Snezana et al., "Accurate Sequencing by Hybridization for DNA Diagnostics and Individual Genomics," Nature Biotechnology, vol. 16, pp. 54-58, Jan. 1998.
Duffy, David C. et al., "Patterning Electroluminescent Materials With Feature Sizes As Small As 5µm Using Elastomeric Membranes As Masks for Dry Lift-Off," Advanced Materials, vol. 11, No. 7, pp. 546-552, 1999.
Duffy, David C. et al., "Rapid Prototyping of Microfluidic Switches in Poly(dimethyl siloxane) and Their Actuation by Electro-Osmotic Flow," J. Micromech. Microeng., vol. 9, pp. 211-217, 1999.
Duffy, David C. et al., "Rapid Prototyping of Microfluidic Systems in Poly(dimethylsiloxane)," Analytical Chemistry, vol. 70, No. 23, pp. 4974-4984, Dec. 1, 1998.
Effenhauser, Carlo S. et al., "Integrated Capillary Electrophoresis on Flexible Silicone Microdevices: Analysis of DNA Restriction Fragments and Detection of Single DNA Molecules on Microchips," Analytical Chemistry, vol. 69, No. 17, pp. 3451-3457, Sep. 1, 1997.
Effenhauser, Carlo S. et al., "Integrated Chip-Based Capillary Electrophoresis," Electrophoresis, vol. 18, pp. 2203-2213, 1997.
Effenhauser, Carlo S. et al., "Miniaturizing a Whole Analytical Laboratory Down to Chip Size," American Laboratory, vol. 26, No. 14, pp. cover, 15, 16, 18, 1994.
Effenhauser, Carlo S., "Integrated Chip-Based Microcolumn Separation Systems," Topics in Current Chemistry, vol. 194, pp. cover, 52-82, 1998.
Ericson, Christer et al., "Electroosmosis- and Pressure-Driven Chromatography in Chips Using Continuous Beds," Analytical Chemistry, vol. 72, No. 1, pp. 81-87, Jan. 1, 2000.
Erlich, H.A., PCR Technology, Basic Methodology: Stockton Press, New York, pp. 1-5, 1989.
Eyal, Shulamit et al., "Velocity-Independent Microfluidic Flow Cytometry," Electrophoresis, vol. 23, pp. 2653-2657, 2002.
Fahrenberg, J. et al., "A Microvalve System Fabricated by Thermoplastic Molding," J. Micromech. Microeng., vol. 5, pp. 169-171, 1995.
Felix, Arthur M. et al., "Pegylated Peptides IV—Enhanced Biological Activity of Site-Directed Pegylated GRF Analogs," International Journal of Peptide & Protein Research, vol. 46, pp. 253-264, 1995.
Felix, Arthur M., "Site-Specific Poly(ethylene glycol)ylation of Peptides," Poly(Ethylene Glycol) Chemistry and Biological Applications, vol. 680, pp. 2 cover pages, 218-238, 1997.
Fettinger, J. C. et al., "Stacked Modules for Micro Flow Systems in Chemical Analysis: Concept and Studies Using an Enlarged Model," Sensors and Actuators B, vol. 17, pp. 19-25, 1993.
Fiedler, Stefan et al., "Dielectrophoretic Sorting of Particles and Cells in a Microsystem," Analytical Chemistry, vol. 70, No. 9, pp. 1909-1915, May 1, 1998.
Figeys, Daniel et al., "An Integrated Microfluidics-Tandem Mass Spectrometry System for Automated Protein Analysis," Analytical Chemistry, vol. 70, No. 18, pp. 3728-3734, Sep. 15, 1998.
Figeys, Daniel et al., "Nanoflow Solvent Gradient Delivery From a Microfabricated Device for Protein Identifications by Electrospray Ionization Mass Spectrometry," Analytical Chemistry, vol. 70, No. 18, pp. 3721-3727, Sep. 15, 1998.
Fitzgerald, Deborah A., "Making Every Nanoliter Count," The Scientist, vol. 15, No. 21, 8 pages, Oct. 29, 2001.
Fodor, Stephen P. A. et al., "Light-Directed, Spatially Addressable Parallel Chemical Synthesis," Science, vol. 251, pp. 767-773, Feb. 15, 1991.
Folch, A. et al., "Molding of Deep Polydimethylsiloxane Microstructures for Microfluidics and Biological Applications," Journal of Biomechanical Engineering, vol. 121, pp. 28-34, Feb. 1999.
Fotin, Alexander V. et al., "Parallel Thermodynamic Analysis of Duplexes on Oilgodeoxyribonucleotide Microchips," Nucleic Acids Research, vol. 26, No. 6, pp. 1515-1521, 1998.
Fu, Anne Y. et al., "A Microfabricated Fluorescence-Activated Cell-Sorter," Nature Biotechnology, vol. 17, pp. 1109-1111, Nov. 1999.

(56) References Cited

OTHER PUBLICATIONS

Fu, Anne Y. et al., "An Integrated Microfabricated Cell Sorter," Analytical Chemistry, vol. 74, No. 11, pp. 2451-2457, Jun. 1, 2002.
Fulwyler, M. J., "Electronic Separation of Biological Cells by Volume," Science, pp. 910-911, Nov. 1965.
Galambos, Paul et al., "Electrical and Fluidic Packaging of Surface Micromachined Electro-Microfluidic Devices," 8 pages, no date.
Gao, Jun et al., "Integrated Microfluidic System Enabling Protein Digestion, Peptide Separation, and Protein Identification," Analytical Chemistry, vol. 73, No. 11, pp. 2648-2655, Jun. 1, 2001.
Garno, Jayne C. et al., "Production of Periodic Arrays of Protein Nanostructures Using Particle Lithography," Langmuir, vol. 18, No. 21, pp. 8186-8192, 2002.
Gass, V. et al., "Integrated Flow-Regulated Silicon Micropump," Sensors and Actuators A, vol. 43, pp. 335-338, 1994.
Geng, Xindu et al., "Retention Model for Proteins in Reversed-Phase Liquid Chromatography," Journal of Chromatography, vol. 296, pp. 15-30, 1984.
Gerlach, Torsten, "Pumping Gases by a Silicon Micro Pump With Dynamic Passive Valves," Transducers '97, 1997 International Conference on Solid-State Sensors and Actuators, Chicago, Illinois, pp. 357-360, Jun. 16-19, 1997.
Ginsberg, Michael A., "New Laser System Measure DNA Fragments," Biophotonics International, p. 20, Nov./Dec. 1996.
Giusti, Alan et al., "Application of Deoxyribonucleic Acid (DNA) Polymorphisms to the Analysis of DNA Recovered From Sperm," Journal of Forensic Sciences, vol. 31, No. 2, pp. 409-417, Apr. 1986.
Goll, C. et al., "Microvalves With Bistable Buckled Polymer Diaphragms," J. Micromech. Microeng., vol. 6, pp. 77-79, 1996.
Gombotz, W. R. et al., "Pegylation: A Tool to Enhance Protein Delivery," Abstracts of Papers, American Chemical Society, vol. 217, Part 2, 2 pages, Mar. 21-25, 1999.
Gonzalez, Jesus E. et al., "Improved Indicators of Cell Membrane Potential That Use Fluorescence Resonance Energy Transfer," Chemistry & Biology, vol. 4, No. 4, pp. 269-277, Apr. 1997.
Goodwin, Peter M. et al., "Rapid Sizing of Individual Fluorescently Stained DNA Fragments by Flow Cytometry," Nucleic Acids Research, vol. 21, No. 4, pp. 803-806, 1993.
Granjeaud, Samuel et al., "Expression Profiling: DNA Arrays in Many Guises," BioEssays, vol. 21, pp. 781-790, 1999.
Gravesen, Peter et al., "Microfluidics—A Review," J. Micromech. Microeng., vol. 3, pp. 168-192, 1993.
Greene, Chana, "Characterizing the Properties of PDMS," pp. 1-11, Summer 2000.
Grover, William H. et al., "Monolithic Membrane Valves and Diaphragm Pumps for Practical Large-Scale Integration Into Glass Microfluidic Devices," Sensors and Actuators B, vol. 89, pp. 315-323, 2003.
Guérin, L. J. et al., "Simple and Low Cost Fabrication of Embedded Micro-Channels by Using a New Thick-Film Photoplastic," Transducers '97, 1997 International Conference on Solid-State Sensors and Actuators, Chicago, Illinois, pp. 1419-1422, Jun. 18-19, 1997.
Guerra, Patricia I. et al., "PEGylation Prevents The N-Terminal Degradation of Megakaryocyte Growth and Development Factor," Pharmaceutical Research, vol. 15, No. 12, pp. 1822-1827, 1998.
Gunderson et al., Genome Research, 1998, vol. 8, p. 1142-1153.
Gunderson, Kevin L. et al., "Mutation Detection by Ligation to Complete n-mer DNA Arrays," Genome Research, vol. 8, pp. 1142-1153, 1998.
Guo, Zhen et al., "Enhanced Discrimination of Single Nucleotide Polymorphisms by Artificial Mismatch Hybridization," Nature Biotechnology, vol. 15, pp. 331-335, Apr. 1997.
Hancock, Robert E. W., "A Brief on Bacterial Biofilms," Nature Genetics, vol. 29, p. 360, Dec. 2001.
Hanes, Jozef, et al., "In Vitro Selection and Evolution of Functional Proteins by Using Ribosome Display," Proc. Natl. Acad. Sci. USA, vol. 94, pp. 4937-4942, May 1997.
Hansen, Carl. L. et al., "A Robust and Scalable Microfluidic Metering Method That Allows Protein Crystal Growth by Free Interface Diffusion," PNAS, vol. 99, No. 26, pp. 16531-16536, Dec. 24, 2002.
Hansen, Carl. L. et al., "Systematic Investigation of Protein-Phase Behavior With a Microfluidic Formulator," PNAS Early Edition, 6 pages, 2004.
Harrison, D. Jed et al., "Integration of Analytical Systems Incorporating Chemical Reactions and Electrophoretic Separation," Micro Total Analysis Systems, Proceedings of the μTAS '94 Workshop, University of Twente, The Netherlands, pp. 2 cover pages and 105-115, 1995.
Harrison, D. Jed et al., "Micromachining a Miniaturized Capillary Electrophoresis-Based Chemical Analysis System on a Chip," Science, vol. 261, pp. 895-897, Aug. 13, 1993.
Henion, Jack et al., "Capillary Electrophoresis/Mass Spectrometry: From One Meter Capillaries to Chip-Based Devices," 2 pages, 1999.
Heo, Jinseok et al., "A Microfluidic Bioreactor Based on Hydrogel-Entrapped E. coli: Cell Viability, Lysis, and Intracellular Enzyme Reactions," Analytical Chemistry, vol. 75, No. 1, Jan. 1, 2003.
Herbert, D., "Continuous Culture of Bacteria," The Journal of General Microbiology, vol. 15, pp. 2 cover pages and iv, 1956.
Herbert, D., "Continuous Culture of Bacteria: Principles and Applications," Chemistry and Industry, pp. 381, Mar. 29, 1958.
Hermanson, Greg T. et al., "Chapter 2—Activation Methods," Immobilized Affinity Ligand Techniques, Academic Press, pp. 2 cover pages, 51-136, 1992.
Hicks, Jennifer, "Genetics and Drug Discovery Dominate Microarray Research," R&D Magazine, pp. 28-33, Feb. 1999.
Hoffmuller, Ulrich et al., "In Vitro Evolution and Selection of Proteins: Ribosome Display for Larger Libraries," Angew. Chem. Int. Ed., vol. 37, No. 23, pp. 3241-3243, 1998.
Hofmann, Oliver et al., "Modular Approach to Fabrication of Three-Dimensional Microchannel Systems in PDMS—Application to Sheath Flow Microchips," Lab on a Chip, vol. 1, pp. 108-114, 2001.
Hoheisel, Jorg D., "Sequence-Independent and Linear Variation of Oligonucleotide DNA Binding Stabilities," Nucleic Acids Research, vol. 24, No. 3, pp. 430-432, 1996.
Hong et al., "Integration of Gene Amplification and Capillary Gel Electrophoresis on a Polydimethylsiloxane-Glass Hybrid Microchip," Electrophoresis, vol. 22, pp. 328-333, 2001.
Hong, Jong Wook et al., "A Nanoliter-Scale Nucleic Acid Processor With Parallel Architecture," Nature Biotechnology, vol. 22, No. 4, pp. 1-5, Apr. 2004.
Hopfgartner, Gerard et al., "Exact Mass Measurement of Product Ions for the Structural Elucidation of Drug Metabolites With a Tandem Quadrupole Orthogonal-Acceleration Time-of-Flight Mass Spectrometer," Journal of the American Society for Mass Spectrometry, vol. 10, pp. cover, 1305-1314, Dec. 1999.
Horn, Howard, "Lab Chips Sector: Microtechnologies Are Changing Healthcare and More," Life Sciences, pp. 19-21, Mar. 20, 2001.
Hornbeck, Larry J. et al., "Bistable Deformable Mirror Device," Spatial Light Modulators and Applications 1988 Technical Digest Series, vol. 8, Postconference Edition, pp. cover, 107-110, Jun. 15-17, 1988.
Hosokawa, Kazuo et al., "A Microfluidic Device for Mixing of Capillary-Driven Liquids," IEEJ Trans. SM, vol. 123, No. 1, pp. 23-24, 2003.
Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.
Hosokawa, Kazuo et al., "Handling of Picoliter Liquid Samples in a Poly(dimethylsiloxane)-Based Microfluidic Device," Analytical Chemistry, vol. 71, No. 20, pp. 4781-4785, Oct. 15, 1999.
Ibrahim et al., "Real-Time Microchip PCR for Detecting Single-Base Differences In Viral and Human DNA," Anal. Chem., vol. 70, pp. 2013-2017, 1998.
Igloi, Gabor L., "Variability in the Stability of DNA-Peptide Nucleic Acid (PNA) Single-Base Mismatched Duplexes: Real-Time Hybridization During Affinity Electrophoresis in PNA Containing Gels," Proc. Natl. Acad. Sci. USA, vol. 95, pp. 8562-8567, Jul. 1998.
Ikuta, Koji et al., "Three Dimensional Micro Integrated Fluid Systems (MIFS) Fabricated by Stereo Lithography," IEEE, pp. 1-6, 1994.
Ingraham, John L. et al., Growth of the Bacterial Cell, pp. 3 cover pages and 230, 1983.

(56) References Cited

OTHER PUBLICATIONS

Jackman, Rebecca J. et al., "Design and Fabrication of Topologically Complex, Three Dimensional Microstructures," Science, vol. 280, pp. 2089-2091, Jun. 26, 1998.
Jacobson, Ken et al., "International Workshop on the Application of Fluorescence Photobleaching Techniques to Problems in Cell Biology," Federation Proceedings, vol. 42, No. 1, pp. 72-79, Jan. 1983.
Jacobson, Stephen C. et al., "Open Channel Electrochromatography on a Microchip," Analytical Chemistry, vol. 66, No. 14, pp. 2369-2373, Jul. 15, 1994.
Jacobson, Stephen C. et al., "High-Speed Separations on a Microchip," Analytical Chemistry, vol. 66, No. 7, pp. 1114-1118, Apr. 1, 1994.
Jacobson, Stephen C. et al., "Microfluidic Devices for Electrokinetically Driven Parallel and Serial Mixing," Analytical Chemistry, vol. 71, No. 20, pp. 4455-4459, Oct. 15, 1999.
Jannasch, H. W. et al., "Experimental Bacterial Ecology Studied in Continuous Culture," Advances in Microbial Physiology, vol. 11, pp. cover and 165-212, 1974.
Jeffreys, Alec J. et al., "Hypervariable 'Minisatellite' Regions in Human DNA," Nature, vol. 314, pp. 67-73, Mar. 7, 1985.
Jerman, Hal, "Electrically-Activated, Normally-Closed Diaphragm Valves," Transducers '91, 1991 International Conference on Solid-State Sensors and Actuators, pp. cover, 1045-1048, 1991.
Jermutus, Lutz, et al., "Recent Advances in Producing and Selecting Functional Proteins by using Cell-Free Translation," Curren Opinion in Biotechnology, vol. 9, pp. 534-548, 1998.
Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.
Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.
Ju, Li-Ya et al., "Application of Silver Staining to the Rapid Typing of the Polymorphism of HLA-DQ Alleles by Enzymatic Amplification and Allele-Specific Restriction Fragment Length Polymorphism," Electrophoresis, vol. 12, pp. 270-273, 1991.
Juárez-Martinez, G. et al., "High-Throughput Screens for Postgenomics: Studies of Protein Crystallization Using Microsystems Technology," Analytical Chemistry, vol. 74, No. 14, pp. 3505-3510, Jul. 15, 2002.
Jung, D. R. et al., "Chemical and Physical Interactions At Metal/Self-Assembled Organic Monolayer Interfaces," pp. 1-54, 1994.
Kagan, C. R., "Organic-Inorganic Hybrid Materials As Semiconducting Channels in Thin-Film Field-Effect Transistors," Science, vol. 286, pp. 945-947, Oct. 29, 1999.
Kamentsky, Louis A. et al., "Spectrophotometer: New Instrument for Ultrarapid Cell Analysis," Science, vol. 150, pp. 630-631, Oct. 29, 1965.
Kane et al., "Finite element analysis of nonsmooth contact", *Computer Methods in Applied Mechanics and Engineering*, 180(1-2):1-26 (1999).
Kane, R. S. et al., "Patterning Proteins and Cells Using Soft Lithography," Biomaterials, vol. 20, pp. 2363-2376, 1999.
Kanter, Evan et al., "Analysis of Restriction Fragment Length Polymorphisms in Deoxyribonucleic Acid (DNA) Recovered From Dried Bloodstains," Journal of Forensic Sciences, vol. 31, No. 2, pp. 403-408, Apr. 1986.
Kapur, Ravi et al., "Fabrication and Selective Surface Modification of 3-Dimensionally Textured Biomedical Polymers From Etched Silicon Substrates," Journal of Biomedical Materials Research, vol. 33, pp. 205-216, 1996.
Kawano, Yasushi et al., "Rapid Isolation and Identification of Staphylococcal Exoproteins by Reverse Phase Capillary High Performance Liquid Chromatography-Electrospray Ionization Mass Spectrometry," FEMS Microbiology Letters, vol. 189, pp. 103-108, 2000.

Keller, Richard A. et al., "Single-Molecule Fluorescence Analysis in Solution," Applied Spectroscopy, vol. 50, No. 7, pp. 12A-30A, Jul. 1996.
Kenis, Paul J. A. et al., "Microfabrication Inside Capillaries Using Multiphase Laminar Flow Patterning," Science, vol. 285, pp. 83-85, Jul. 2, 1999.
Khandurina et al., "Integrated System for Rapid PCR-Based DNA Analysis in Microfluidic Devices," Anal. Chem., vol. 72, pp. 2995-3000, 2000.
Khandurina, J. et al. "Bioanalysis in Microfluidic Devices," Journal of Chromatography A, vol. 943, Ino. 2, Jan. 18, 2002, Elsevier Science B.V., pp. 159-183.
Khoo, Melvin et al., "A Novel Micromachined Magnetic Membrane Microfluid Pump," pp. 1-4, no date.
Kim, Enoch et al., "Micromolding in Capillaries: Applications in Materials Science," J. Am. Chem. Soc., vol. 118, No. 24, pp. 5722-5731, 1996.
Kim, Enoch et al., "Polymer Microstructures Formed by Moulding in Capillaries," Nature, vol. 376, pp. 581-584, Aug. 17, 1995.
Kodera, Yoh et al., "Pegylation of Proteins and Bioactive Substances for Medical and Technical Applications," Prog. Polym. Sci., vol. 23, pp. 1233-1271, 1998.
Kopp, Martin U. et al., "Chemical Amplification: Continuous-Flow PCR on a Chip," Science, vol. 280, pp. 1046-1048, May 15, 1998.
Kuhn, Lawrence et al., "Silicon Charge Electrode Array for Ink Jet Printing," IEEE Transactions on Electron Devices, vol. ED-25, No. 10, pp. 1257-1260, Oct. 1978.
Kumar, Amit et al., "Features of Gold Having Micrometer to Centimeter Dimensions Can Be Formed Through a Combination of Stamping With an Elastomeric Stamp and an Alkanethiol 'Ink' Followed by Chemical Etching," Appl. Phys. Lett., vol. 63, No. 14, pp. 2002-2004, Oct. 4, 1993.
Kumar, Amit et al., "Patterning Self-Assembled Monolayers: Applications in Materials Science," Langmuir, vol. 10, pp. 1498-1511, 1994.
Kutyavin, Igor V. et al., "3'-Minor Groove Binder-DNA Probes Increase Sequence Specificity At PCR Extension Temperatures," Nucleic Acids Research, vol. 28, No. 2, pp. 655-661, 2000.
Lagally, E. T. et al., "Single-Molecule DNA Amplification and Analysis in an Integrated Microfluidic Device," Analytical Chemistry, vol. 73, No. 3, pp. 565-570, Feb. 1, 2001.
Lagally, Eric T. et al., "Fully Integrated PCR-Capillary Electrophoresis Microsystem for DNA Analysis," Lab on a Chip, vol. 1, pp. 102-107, 2001.
Lagally, Eric T. et al., "Monolithic Integrated Microfluidic DNA Amplification and Capillary Electrophoresis Analysis System," Sensors and Actuators B, vol. 63, pp. 138-146, 2000.
Lammerink, T. S. J. et al., "Modular Concept for Fluid Handling Systems," IEEE, pp. 389-394, 1996.
Lane, P. G., "Analysis of a Continuous-Culture Technique for the Selection of Mutants Tolerant to Extreme Environmental Stress," Biotechnology and Bioengineering, vol. 65, No. 4, pp. 397-406, Nov. 20, 1999.
Lawrence, J. R. et al., "Optical Sectioning of Microbial Biofilms," Journal of Bacteriology, vol. 173, No. 20, pp. 6558-6567, Oct. 1991.
Lazar, Iulia M. et al., "Novel Microfabricated Device for Electrokinetically Induced Pressure Flow and Electrospray Ionization Mass Spectrometry," Journal of Chromatography A, vol. 892, pp. 195-201, 2000.
Lee, L. Stanford et al., "Prolonged Circulating Lives of Single-Chain Fv Proteins Conjugated With Polyethylene Glycol: A Comparison of Conjugation Chemistries and Compounds," Bioconjugate Chem., vol. 10, pp. 973-981, 1999.
Lessard, Guillaume A. et al., "A Scanning Apertureless Fluorescence Microscope," 8 pages, no date.
Levine, Leanna M. et al., "Measurement of Specific Protease Activity Utilizing Fluorescence Polarization," Analytical Biochemistry, vol. 247, pp. 83-88, 1997.
Li, Jianjun et al., "Integration of Microfabricated Devices to Capillary Electrophoresis-Electrospray Mass Spectrometry Using a Low Dead Volume Connection: Application to Rapid Analyses of Proteolytic Digests," Analytical Chemistry, vol. 71, No. 15, pp. 3036-3045, Aug. 1, 1999.

(56) References Cited

OTHER PUBLICATIONS

Li, Paul C. H. et al., "Transport, Manipulation, and Reaction of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source for Mass Spectrometry," Analytical Chemistry, vol. 72, No. 2, pp. 367-375, Jan. 15, 2000.

Lin, L. Y. et al., "Free-Space Micromachined Optical Switches for Optical Networking," IEEE Journal of Selected Topics in Quantum Electronics, vol. 5, No. 1, pp. 4-9, Jan. 1999.

Lin, Yuehe et al., "Laser Micromachined Isoelectric Focusing Device on Polymer Substrate for Electrospray Mass Spectrometry," SPIE, vol. 3877, pp. 28-35, Sep. 1999.

Liu, Hanghui et al., "Development of Multichannel Devices With an Array of Electrospray Tips for High-Throughput Mass Spectrometry," Analytical Chemistry, vol. 72, No. 14, pp. 3303-3310, Jul. 15, 2000.

Liu, Jian et al., "A Nanoliter Rotary Device for Polymerase Chain Reaction," Electrophoresis, vol. 23, pp. 1531-1536, 2002.

Liu, Jian et al., "Solving the 'World-To-Chip' Interface Problem With a Microfluidic Matrix," Analytical Chemistry, vol. 75, No. 18, pp. 4718-4723, Sep. 15, 2003.

Llopis, Juan et al., "Ligand-Dependent Interactions of Coactivators Steroid Receptor Coactivator-1 and Peroxisome Proliferator-Activated Receptor Binding Protein With Nuclear Hormone Receptors Can Be Imaged in Live Cells and Are Required for Transcription," PNAS, vol. 97, No. 8, pp. 4363-4368, Apr. 11, 2000.

Lorenz, Patrick et al., "Screening for Novel Enzymes for Biocatalytic Processes: Accessing the Metagenome as a Resource of Novel Functional Sequence Space," Current Opinion in Biotechnology, vol. 13, pp. 572-577, 2002.

Lötters, J C et al., "The Mechanical Properties of the Rubber Elastic Polymer Polydimethylsiloxane for Sensor Applications," J. Micromech. Microeng., vol. 7, pp. 145-147, 1997.

Lucy, Charles A. et al., "Characterization of the Cationic Surfactant Induced Reversal of Electroosmotic Flow in Capillary Electrophoresis," Anal. Chem., vol. 68, pp. 300-305, 1996.

Mahajan, Nupam P. et al., "Novel Mutant Green Fluorescent Protein Protease Substrates Reveal the Activation of Specific Caspases During Apoptosis," Chemistry & Biology, vol. 6, No. 6, pp. 401-409, Jun. 1999.

Maier, Elmar et al., "Automated Array Technologies for Gene Expression Profiling," DDT, vol. 2, No. 8, pp. 315-324, Aug. 1997.

Maldonado-Rodriguez, Rogelio et al., "Mutation Detection by Stacking Hybridization on Genosensor Arrays," Molecular Biotechnology, vol. 11, pp. 13-25, 2000.

Maluf, N., "An Introduction to Microelectromechanical Systems Engineering," Artech House Publishers, Boston London, pp. 42-45, Dec. 1999.

Manz, A. et al., "Micromachining of Monocrystalline Silicon and Glass for Chemical Analysis Systems," Trends in Analytical Chemistry, vol. 10, No. 5, pp. 144-149, 1991.

Marešová, H. et al., "A Chemostat Culture As a Tool for the Improvement of a Recombinant E. coli Strain Over-Producing Penicillin G Acylase," Biotechnology and Bioengineering, vol. 75, No. 1, pp. 46-52, Oct. 5, 2001.

Marshall, SID, "Fundamental Changes Ahead for Lab Instrumentation," R&D Magazine, 5 pages, Feb. 1999.

Marsili, Ray, "Lab-on-a-Chip Poised to Revolutionize Sample Prep," R&D Magazine, 5 pages, Feb. 1999.

Marton, Matthew J. et al., "Drug Target Validation and Identification of Secondary Drug Target Effects Using DNA Microarrays," Nature Medicine, vol. 4, No. 11, pp. 1293-1301, Nov. 1998.

Mastrangelo, C. H. et al., "Vacuum-Sealed Silicon Micromachined Incandescent Light Source," IEDM, pp. 503-506, 1989.

Maule, John, "Pulsed-Field Gel Electrophoresis," Molecular Biotechnology, vol. 9, pp. 107-126, 1998.

McDonald, J. Cooper et al., "Fabrication of Microfluidic Systems in Poly(dimethylsiloxane)," Electrophoresis, vol. 21, pp. 27-40, 2000.

McDonald, J. Cooper et al., "Poly(dimethylsiloxane) As a Material for Fabricating Microfluidic Devices," Accounts of Chemical Research, vol. 35, No. 7, pp. 491-499, 2002.

Meiners, Jens-Christian et al., "Direct Measurement of Hydrodynamic Cross Correlations Between Two Particles in an External Potential," Physical Review Letters, vol. 82, No. 10, pp. 2211-2214, Mar. 8, 1999.

Menchen, Steve et al., "Flowable Networks As DNA Sequencing Media in Capillary Columns," Electrophoresis, vol. 17, pp. 1451-1459, 1996.

Moldavan, Andrew, "Photo-Electric Technique for the Counting of Microscopical Cells," Science, vol. 80, No. 2069, pp. 188-189, Aug. 24, 1934.

Monod, Jacques, "The Growth of Bacterial Cultures," Annual Review of Microbiology, vol. III, pp. cover and 371-394, 1949.

Muller, Richard S. et al., "Surface-Micromachined Microoptical Elements and Systems," Proceedings of the IEEE, vol. 86, No. 8, pp. 1705-1720, Aug. 1998.

Murray, Vincent et al., "Detection of Polymorphisms Using Thermal Cycling With a Single Oligonucleotide on a DNA Sequencing Gel," Human Mutation, vol. 2, pp. 118-122, 1993.

Nagai, Yasuo et al., "A Fluorescent Indicator for Visualizing cAMP-Induced Phosphorylation In Vivo," Nature Biotechnology, vol. 18, pp. 313-316, Mar. 2000.

Nakamura, Yusuke et al., "Variable Number of Tanden Repeat (VNTR) Markers for Human Gene Mapping," Science, vol. 235, pp. 1616-1622, Mar. 27, 1987.

Nakano et al., "High Speed Polymerase Chain Reaction in Constant Flow," Biosci. Biotech. Biochem., 58(2), pp. 349-352, 1994.

New Objective, Inc., "What Is Electrospray," www.newobjective.com/electrospray/electrospray.html, 4 pages, 1999.

NG, Jessamine M. K. et al., "Components for Integrated Poly(Dimethylsiloxane) Microfluidic Systems," Electrophoresis, vol. 23, pp. 3461-3473, 2002.

Nielsen, Jens et al., Bioreaction Engineering Principles, Second Edition, pp. 2 cover pages and 42-45, 2003.

Nolan, John P. et al., "The Emergence of Flow Cytometry for Sensitive, Real-Time Measurements of Molecular Interactions," Nature Biotechnology, vol. 16, pp. 633-638, Jul. 1998.

Novick, Aaron et al., "Description of the Chemostat," Science, vol. 112, pp. 715-716, Dec. 15, 1950.

Novick, Aaron et al., "Experiments With the Chemostat on Spontaneous Mutations of Bacteria," Proc. N. A. S., vol. 36, pp. 708-719, 1950.

Oakley and Knight, "Adaptive dynamic relaxation algorithm for non-linear hyperelastic structures", *Computer Methods in Applied Mechanics and Engineering*, 126:67-89 (1995).

Ogden, "Elastic Deformations of Rubberlike Solids", in *Mechanics of Solids*, pp. 499-537 (1982).

Oleschuk, Richard D. et al., "Analytical Microdevices for Mass Spectrometry," Trends in Analytical Chemistry, vol. 19, No. 6., pp. 379-388, 2000.

Olsson, Anders et al., "Simulation Studies of Diffuser and Nozzle Elements for Valve-Less Micropumps," Transducers '97, 1997 International Conference on Solid-State Sensors and Actuators, Chicago, Illinois, pp. 1039-1042, Jun. 16-19, 1997.

O'Reilly, Marie-Anne J. et al., "The Technique of Pulsed Field Gel Electrophoresis and Its Impact on Molecular Immunology," Journal of Immunological Methods, vol. 131, pp. 1-13, 1990.

Parker, Gregory J. et al., "Development of High Throughput Screening Assays Using Fluorescence Polarization: Nuclear Receptor-Ligand-Binding and Kinase/Phophatase Assays," Journal of Biomolecular Screening, vol. 5, No. 2, pp. 77-88, 2000.

Persson, Bjorn et al., "Analysis of Oligonucleotide Probe Affinities Using Surface Plasmon Resonance: A Means for Mutational Scanning," Analytical Biochemistry, vol. 246, pp. 34-44, 1997.

Pethig, Ronald et al., "Applications of Dielectrophoresis in Biotechnology," Tibtech, vol. 15, pp. 426-432, Oct. 1997.

Petty, Jeffrey T. et al., "Characterization of DNA Size Determination of Small Fragments by Flow Cytometry," Anal. Chem., vol. 67, pp. 1755-1761, 1995.

(56) References Cited

OTHER PUBLICATIONS

Phillips, W.C. and Rayment, I. "A systematic method for aligning double focusing mirrors." Methods in Enzymology, 1985, vol. 114 (Wyckoff, Hirs and Timasheff, eds.), 316-329, Academic Press.

Poplawski, M. E. et al., "A Simple Packaging Process for Chemical Sensors," Solid-State Sensor and Actuator Workshop, Hilton Head, South Carolina, pp. 25-28, Jun. 13-16, 1994.

PROTANA website, "NanoES Products," www.protana.com/products/default.asp, 3 pages, Sep. 19, 2000.

Qin, Dong et al., "Photolithography With Transparent Reflective Photomasks," J. Vac. Sci. Technol. B, vol. 16, No. 1, pp. 98-103, Jan. 1998.

Qin, Dong et al., "Elastomeric Light Valves," Adv. Mater., vol. 9, No. 5, pp. 407-410, 1997.

Qu, Mingbo et al., "Toxicity and Biodegradation of Formaldehyde in Anaerobic Methanogenic Culture," Biotechnology and Bioengineering, vol. 55, No. 5, pp. 727-736, Sep. 5, 1997.

Quake, Stephen R. et al., "From Micro- to Nanofabrication With Soft Materials," Science, vol. 290, pp. 1536-1540, Nov. 24, 2000.

Rapp, R. et al., "LIGA Micropump for Gases and Liquids," Sensors and Actuators A, vol. 40, pp. 57-61, Jan. 1994.

Roberts, Richard W. et al., "RNA-Peptide Fusions for the In Vitro Selection of Peptides and Proteins," Proc. Natl. Acad. Sci. USA, vol. 94, pp. 12297-12302, Nov. 1997.

Rondon, Michelle R. et al., "Cloning the Soil Metagenome: A Strategy for Accessing the Genetic and Functional Diversity of Uncultured Microorganism," Applied and Environmental Microbiology, pp. 2541-2547, Jun. 2000.

Rotman, Boris, "A Simplified Device for Continuous Growth of Microorganisms," Journal of Bacteriology, vol. 70, pp. 485-486, 1955.

Rouhi, Maureen, "Sizing, Sorting DNA One Piece at a Time," C&EN, pp. 5-6, Jan. 11, 1999.

Roylance, Lynn Michelle et al., "A Batch-Fabricated Silicon Accelerometer," IEEE Transactions on Electron Devices, vol. ED-26, No. 12, pp. 1911-1917, Dec. 1979.

Samad, Akhtar et al., "Optical Mapping: A Novel, Single-Molecule Approach to Genomic Analysis," Genome Research, pp. 1-4, 1995.

Sandia National Laboratories, "Electro Microfluidic Dual In-Line Package (EMDIP)," 2 pages, no date.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping and Development of Microfluidic and BioMEMS Devices," IVD Technology, 12 pages, Jun. 2002.

Schasfoort, Richard B. M. et al., "Field-Effect Flow Control for Microfabricated Fluidic Networks," Science, vol. 286, pp. 942-945, Oct. 29, 1999.

Schena, Mark et al., "Quantitative Monitoring of Gene Expression Patterns With a Complementary DNA Microarray," Science, vol. 270, pp. 467-470, Oct. 20, 1995.

Schloss, Patrick D. et al., "Biotechnological Prospects From Metagenomics," Current Opinion in Biotechnology, vol. 14, pp. 303-310, 2003.

Schomburg, W. K. et al., "Fabrication of Polymer Microcomponents With the AMANDA-Process," New Materials and Directions, Eurosensors XII, pp. 711-714, Sep. 13-16, 1998.

Schueller, Olivier J. A. et al., "Fabrication of Glassy Carbon Microstructures by Soft Lithography," Sensors and Actuators A, vol. 72, pp. 126-139, 1999.

Schullek, John R., "A High-Density Screening Format for Encoded Combinatorial Libraries: Assay Miniaturization and Its Application to Enzymatic Reactions," Analytical Biochemistry, vol. 246, pp. 20-29, 1997.

Schwartz, David C. et al., "Optical Mapping Approaches to Molecular Genomics," Current Opinion in Biotechnology, vol. 8, pp. 70-74, 1997.

Seethala, Ramakrishna et al., "A Fluorescence Polarization Competition Immunoassay for Tyrosine Kinases," Analytical Biochemistry, vol. 255, pp. 257-262, 1998.

Shevchenko, Andrej et al., "Rapid 'de Novo' Peptide Sequencing by a Combination of Nanoelectospray, Isotopic Labeling and a Quadrupole/Time-of-Flight Mass Spectometer," Rapid Communications in Mass Spectrometry, vol. 11, pp. 1015-1024, 1997.

Shinohara, Jun et al., "A High Pressure-Resistance Micropump Using Active and Normally-Closed Valves," IEEE, pp. 86-91, 2000.

Shoji, Shuichi et al., "Smallest Dead Volume Microvalves for Integrated Chemical Analyzing Systems," Transducers '91, 1991 International Conference on Solid-State Sensors and Actuators, San Francisco, California, pp. cover, 1052-1055, 1991.

Shoji, Shuichi, "Fluids for Sensor Systems," Topics in Current Chemistry, vol. 194, pp. 163-188, 1998.

Shuler, Michael L. et al., "Chapter 6—How Cells Grow," Bioprocess Engineering Basic Concepts, Second Edition, pp. 2 cover pages and 155-200, 2002.

Sklar, Larry A. et al., Sample Handling for Kinetics and Molecular Assembly in Flow Cytometry, SPIE, vol. 3256, pp. 144-153, 1998.

Smits, J.G., "Piezoelectric Micropump With Three Valves Working Peristaltically," Sensors and Actuators, vol. A21-A23, pp. 203-206, 1990.

Sohn, L. L. et al., "Capacitance Cytometry: Measuring Biological Cells One by One," PNAS, vol. 97, No. 20, pp. 10687-10690, Sep. 26, 2000.

Sosnowski, Ronald G. et al., "Rapid Determination of Single Base Mismatch Mutations in DNA Hybrids by Direct Electric Field Control," Proc. Natl. Acad. Sci. USA, vol. 94, pp. 1119-1123, Feb. 1997.

Southern, E. M. et al., "Analyzing and Comparing Nucleic Acid Sequences by Hybridization to Arrays of Oligonucleotides: Evaluation Using Experimental Models," Genomics, vol. 13, pp. 1008-1017, 1992.

Spellman, Paul T. et al., "Comprehensive Identification of Cell Cycle-Regulated Genes of The Yeast *Saccharomyces cerevisiae* by Microarray Hybridization," Molecular Biology of the Cell, vol. 9, pp. 3273-3297, Dec. 1998.

Spicer, C. C., "The Theory of Bacterial Constant Growth Apparatus," Biometrics, pp. 225-230, Jun. 1955.

Stemmer, Willem P. C. et al., "Rapid Evolution of a Protein in vitro by DNA Shuffling," Nature, vol. 370, pp. 389-390, Aug. 4, 1994.

Stomakhin, Andrey A. et al., "DNA Sequence Analysis by Hybridization With Oligonucleotide Microchips: MALDI Mass Spectrometry Identification of 5mers Contiguously Stacked to Microchip Oligonucleotides," Nucleic Acids Research, vol. 28, No. 5, pp. 1193-1198, 2000.

Studer et al., "Nanoembossing of thermoplastic polymers for microfluidic applications", *Applied Physics Letters* 80:3614-16 (2002).

Sussman, Norman L. et al., "The Predictive Nature of High-Throughput Toxicity Screening Using a Human Hepatocyte Cell Line," Cell Notes, Issue 3, pp. 7-10, 2002.

Swart, Remco et al., "Recent Progress in Open Tubular Liquid Chromatography," Trends in Analytical Chemistry, vol. 16, No. 6, pp. 332-342, 1997.

Sweet, Richard G., "Chapter 9—Flow Sorters for Biologic Cells," Flow Cytometry and Sorting, John Wiley & Sons, pp. 5 cover pages and 177-189, 1979.

Takahashi, Akiyuki et al., "Measurement of Intracellular Calcium," Physiological Reviews, vol. 79, No. 4, pp. 1089-1125, Oct. 1999.

Tatari, Zohreh et al., "HLA-Cw Allele Analysis by PCR-Restriction Fragment Length Polymorphism: Study of Known and Additional Alleies," Proc. Natl. Acad. Sci. USA, vol. 92, pp. 8803-8807, Sep. 1995.

Tawfik, Dan S. et al., "Man-Made Cell-Like Compartments for Molecular Evolution," Nature Biotechnology, vol. 16, pp. 652-656, Jul. 1998.

Taylor, Anne M. et al., "Microfluidic Multicompartment Device for Neuroscience Research," Langmuir, vol. 19, pp. 1551-1556, 2003.

Terry, Stephen C. et al., "A Gas Chromatographic Air Analyzer Fabricated on a Silicon Wafer," IEEE Transactions on Electron Devices, vol. ED-26, pp. 1880-1886, Dec. 1979.

(56) References Cited

OTHER PUBLICATIONS

Thompson, H. Garrett R. et al., "Identification and Confirmation of a Module of Coexpressed Genes," Genome Research, vol. 12, pp. 1517-1522, 2002.

Thompson, L. F. et al., "Introduction to Microlithography," 185th Meeting of the American Chemical Society, Seattle, WA, pp. 2 cover pages, 1-13, Mar. 20-25, 1983.

Thorsen, Todd et al., "Dynamic Pattern Formation in a Vesicle-Generating Microfluidic Device," Physical Review Letters, vol. 86, No. 18, pp. 4163-4166, Apr. 30, 2001.

Thorsen, Todd et al., "Microfluidic Large-Scale Integration," Science, vol. 298, No. 5593, pp. 580-584, Oct. 18, 2002.

Todd, Paul et al., "Chapter 12—Cell Electrophoresis," Flow Cytometry and Sorting, John Wiley & Sons, pp. 5 cover pages and 217-229, 1979.

Toussaint, Ariane et al., "A New Evaluation of Our Life-Support System," EMBO Reports, vol. 4, No. 9, pp. 820-824, 2003.

Tufte, O. N. et al., "Silicon Diffused-Element Piezoresistive Diaphragms," Journal of Applied Physics, vol. 33, No. 11, pp. 3322-3327, Nov. 1962.

Tyagi et al., "Molecular Beacons: Probes that Fluoresce upon Hybridization," Nature Biotechnology, 14:303-308 (1996).

Ullmann's Encyclopedia of Industrial Chemistry, Sections 6 to 6.3, Topic: Carbon Black, Sixth Edition, 7 pages, 1999.

Umdanhowar, P. B. et al., "Monodisperse Emulsion Generation Via Drop Break Off in a Coflowing Stream," Langmuir, vol. 16, pp. 347-351, 2000.

Underwood et al., "Dynamic relaxation", in *Computational Methods for Transient Dynamic Analysis*, Belytschko and Hughes, eds., pp. 245-265, Elsevier Science Publishers, Amsterdam (1983).

Unger, Marc A. et al., "Monolithic Microfabricated Valves and Pumps by Multilayer Soft Lithography," Science, vol. 288, pp. 113-116, Apr. 7, 2000.

Unger, Marc A. et al., "Single-Molecule Fluorescence Observed With Mercury Lamp Illumination," Biotechniques, vol. 27, No. 5, pp. 1008-1014, Nov. 1999.

Vahey, Paul G. et al., "Development of a Positive Pressure Driven Micro-Fabricated Liquid Chromatographic Analyzer Through Rapid-Prototyping With Poly(dimethylsiloxane) Optimizing Chromatographic Efficiency With Sub-Nanoliter Injections," Talanta, vol. 51, pp. 1205-1212, 2000.

Van Dam, R. Michael et al., "Gene Expression Analysis With Universal n-mer Arrays," Genome Research, vol. 12, pp. 145-152, 2002.

Van De Pol, F.C.M. et al., "A Thermo-Pneumatic Actuation Principle for a Microminiature Pump and Other Micromechanical Devices," Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the µTAS '94 Workshop, University of Twente, The Netherlands, 17 pages, Nov. 21-22, 1994.

Van Der Woerd, Mark et al., "Lab-on-a-Chip Based Protein Crystallization," National Aeronautics and Space Administration and Caliper, pp. 1-27, Oct. 25, 2001.

Van Der Woerd, Mark et al., "The Promise of Macromolecular Crystallization in Microfluidic Chips," Journal of Structural Biology, vol. 142, pp. 180-187, 2003.

Van Dilla, M. A. et al., "Cell Microfluorometry: A Method for Rapid Fluorescence Measurement," Science, vol. 163, pp. 1213-1214, Mar. 14, 1969.

Van Dilla, Marvin A. et al., "Chapter 2—Introduction and Resume of Flow Cytometry and Sorting," Flow Cytometry and Sorting, John Wiley & Sons, pp. 5 cover pages and 11-37, 1979.

Van Orden, Alan et al., "High-Throughput Flow Cytometric DNA Fragment Sizing," Anal. Chem., vol. 72, No. 1, pp. 37-41, Jan. 1, 2000.

Velev, Orlin D., "On-Chip Manipulation of Free Droplets," Nature, vol. 426, pp. 515-516, Dec. 4, 2003.

Veronese, F. M. et al., "Influence of PEGylation on the Release of Low and High Molecular-Weight Proteins From PVA Matrices," Journal of Bioactive and Compatible Polymers, vol. 14, pp. 315-330, Jul. 1999.

Veronese, Francesco M., "Peptide and Protein PEGylation: A Review of Problems and Solutions," Biomaterials, vol. 22, pp. 405-417, 2001.

Verpoorte, Elisabeth M. J. et al., "Three-Dimensional Micro Flow Manifolds for Miniaturized Chemical Analysis Systems," J. Micromech. Microeng., vol. 7, pp. 246-256, 1994.

Vieider, Christian et al., "A Pneumatically Actuated Micro Valve With a Silicon Rubber Membrane for Integration With Fluid Handling Systems," Transducers '95, 8th International Conference on Solid-State Sensors and Actuators and Eurosensors IX, Stockholm, Sweden, pp. 284-286, Jun. 25-29, 1995.

Vogelstein, Bert et al., "Digital PCR," Proc. Natl. Acad. Sci. USA, vol. 96, pp. 9236-9241, Aug. 1999.

Volkmuth, W. D. et al., "DNA Electrodiffusion in a 2D Array of Posts," Physical Review Letters, vol. 72, No. 13, pp. 2117-2120, Mar. 28, 1994.

Volkmuth, W. D. et al., "DNA Electrophoresis in Microlithographic Arrays," Nature, vol. 358, pp. 600-602, Aug. 13, 1992.

Ward, Keith B. et al., "Automatic Preparation of Protein Crystals Using Laboratory Robotics and Automated Visual Inspection," Journal of Crystal Growth, vol. 90, pp. 325-339, 1988.

Washizu, Masao et al., "Molecular Dielectrophoresis of Biopolymers," IEEE Transactions on Industry Applications, vol. 30, No. 4, pp. 835-843, Jul. 1994.

Waters, L. C. et al., "Microchip Devices for Cell Lysis, Multiplex PCR Amplification, and Electrophoretic Sizing," Analytical Chemistry, vol. 70, No. 1, pp. 158-162, Jan. 1, 1998.

Webster, J. R. et al., "Monolithic Capillary Gel Electrophoresis Stage With On-Chip Detector," IEEE, pp. 491-496, 1996.

Weigl, Bernhard H., "Microfluidics-Based Lab-on-a-Chip Systems," IVD Technology Magazine, 8 pages, Nov./Dec. 2000.

Whelen, A. Christian et al., "The Role of Nucleic Acid Amplification and Detection in the Clinical Microbiology Laboratory," Annu. Rev. Microbiol., vol. 50, pp. 349-373, 1996.

Whitesides, George M. et al., "Flexible Methods for Microfluidics," Physics Today, pp. 42-48, Jun. 2001.

Whitesides, George M. et al., "Soft Lithography in Biology and Biochemistry," Annu. Rev. Biomed. Eng., vol. 3, pp. 335-373, 2001.

Wiebe, Marilyn G. et al., "Evolution of a Recombinant (Gucoamylase-Producing) Strain of *Fusarium venenatum* A3/5 in Chemostat Culture," Biotechnology and Bioengineering, vol. 73, No. 2, pp. 146-156, Apr. 20, 2001.

Wilbur, James L. et al., "Lithographic Molding: A Convenient Route to Structures With Sub-Micrometer Dimensions," Adv. Mater., vol. 7, No. 7, pp. 649-652, 1995.

Wilm, Matthias et al., "Femtomole Sequencing of Proteins From Polyacrylamide Gels by Nano-Electrospray Mass Spectrometry," Nature, vol. 379, pp. 466-469, Feb. 1, 1996.

Wooley et al., "Functional Integration of PCR Amplification and Capillary Electrophoresis in a Microfabricated DNA Analysis Device," Anal. Chem., vol. 68, pp. 4081-4086, 1996.

Wooley, A. T. et al., "Capillary Electrophoresis Chips With Integrated Electrochemical Detection," Analytical Chemistry, vol. 70, No. 4, pp. 684-688, Feb. 15, 1998.

Wu, Chunhung et al., "Viscosity-Adjustable Block Copolymer for DNA Separation by Capillary Electrophoresis," Electrophoresis, vol. 19, pp. 231-241, 1998.

Wu, Hongkai et al., "Fabrication of Complex Three-Dimensional Microchannel Systems in Pdms," J. Am. Chem. Soc., vol. 125, No. 2, pp. 554-559, 2003.

Wu, Shuyun et al., "MEMS Flow Sensors for Nano-Fluidic Applications," Sensors and Actuators A, vol. 89, pp. 152-158, 2001.

Xia, Younan et al., "Micromolding of Polymers in Capillaries: Applications in Microfabrication," Chem. Mater., vol. 8, No. 7, pp. 1559-1566, 1996.

Xia, Younan et al., "Complex Optical Surfaces Formed by Replica Molding Against Elastomeric Masters," Science, vol. 273, pp. 347-349, Jul. 19, 1996.

(56) References Cited

OTHER PUBLICATIONS

Xia, Younan et al., "Reduction in the Size of Features of Patterned SAMs Generated by Microcontact Printing With Mechanical Compression of the Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures by Soft Lithography," Adv. Mater., vol. 11, No. 14, pp. 1186-1189, 1999.

Xu, Jingdong et al., "Room-Temperature Imprinting Method for Plastic Microchannel Fabrication," Analytical Chemistry, vol. 72, No. 8, pp. 1930-1933, Apr. 15, 2000.

Xu, Xiang et al., "Detection of Programmed Cell Death Using Fluorescence Energy Transfer," Nucleic Acids Research, vol. 26, No. 8, pp. 2034-2035, 1998.

Xue, Qifeng et al., "Integrated Multichannel Microchip Electrospray Ionization Mass Spectrometry: Analysis of Peptides From On-Chip Tryptic Digestion of Melittin," Rapid Communications in Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, T. J. et al., "An Apertureless Near-Field Microscope for Fluorescence Imaging," Applied Physics Letters, vol. 76, No. 3, pp. 378-380, Jan. 17, 2000.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Yershov, Gennady et al., "DNA Analysis and Diagnostics on Oligonucleotide Microchips," Proc. Natl. Acad. Sci. USA, vol. 93, pp. 4913-4918, May 1996.

Yokobayashi, Yohei et al., "Evolutionary Design of Genetic Circuits and Cell-Cell Communications," Advances in Complex Systems, vol. 6, No. 1, pp. 37-45, 2003.

Young, A. M. et al., "Contoured Elastic-Membrane Microvalves for Microfluidic Network Integration," Journal of Biomechanical Engineering, vol. 121, pp. 2-6, Feb. 1999.

Zaccolo, Manuela et al., "A Genetically Encoded, Fluorescent Indicator for Cyclic AMP in Living Cells," Nature Cell Biology, vol. 2, pp. 25-29, Jan. 2000.

Zalipsky, Samuel, "Chemistry of Polyethyelene Glycol Conjugates With Biologically Active Molecules," Advanced Drug Delivery Reviews, vol. 16, pp. 157-182, 1995.

Zdeblick, Mark J. et al., "A Microminiature Electric-To-Fluidic Valve," Transducers '87, Proceedings of the 4th International Conference on Solid-State Sensors and Actuators, reprinted in Micromechanics and MEMS Classic and Seminal Papers to 1990, pp. 2 cover pages, 437-439, Jun. 1987.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation of Microminiaturized Membrane Pumps," 7th International Conference on Solid-State Sensors and Actuators, Yokohama, Japan, pp. 2 cover pages, 106-109, Jun. 7-10, 1993.

Zhang, B. et al., "Microfabricated Devices for Capillary Electrophoresis-Electrospray Mass Spectrometry," Analytical Chemistry, vol. 71, No. 15, pp. 3258-3264, Aug. 1, 1999.

Zhao, Zhan, et al., "An Integrated Biochip Design and Fabrication," Proceedings of SPIE, vol. 4936, pp. 321-326, 2002.

Zheng, Bo et al., "A Droplet-Based, Composite PDMS/Glass Capillary Microfluidic System For Evaluating Protein Crystallization Conditions by Microbatch and Vapor-Diffusion Methods With On-Chip X-Ray Diffraction," Angew. Chem., pp. 1-4, 2004.

Ziauddin, Junaid et al., "Microarrays of Cells Expressing Defined cDNAs," Nature, vol. 411, pp. 107-110, May 3, 2001.

\* cited by examiner

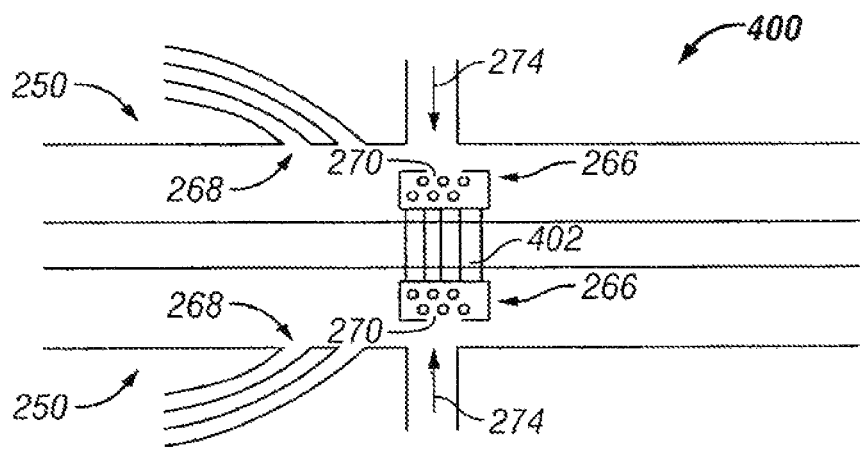
FIG. 11A
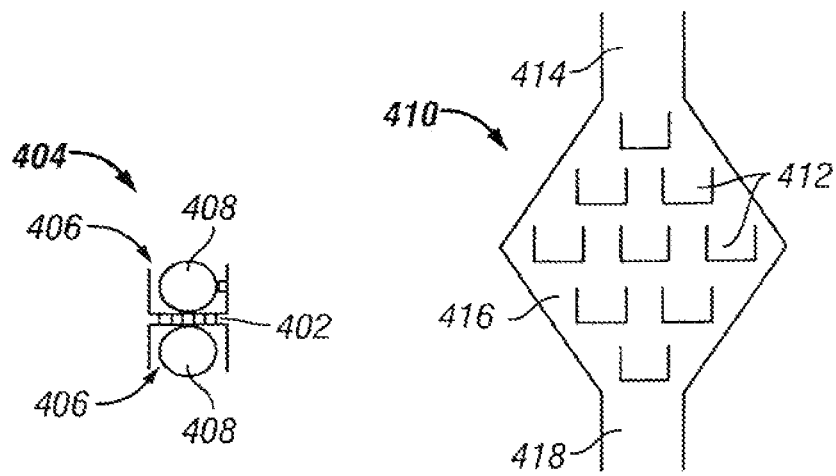
FIG. 11B
FIG. 11C

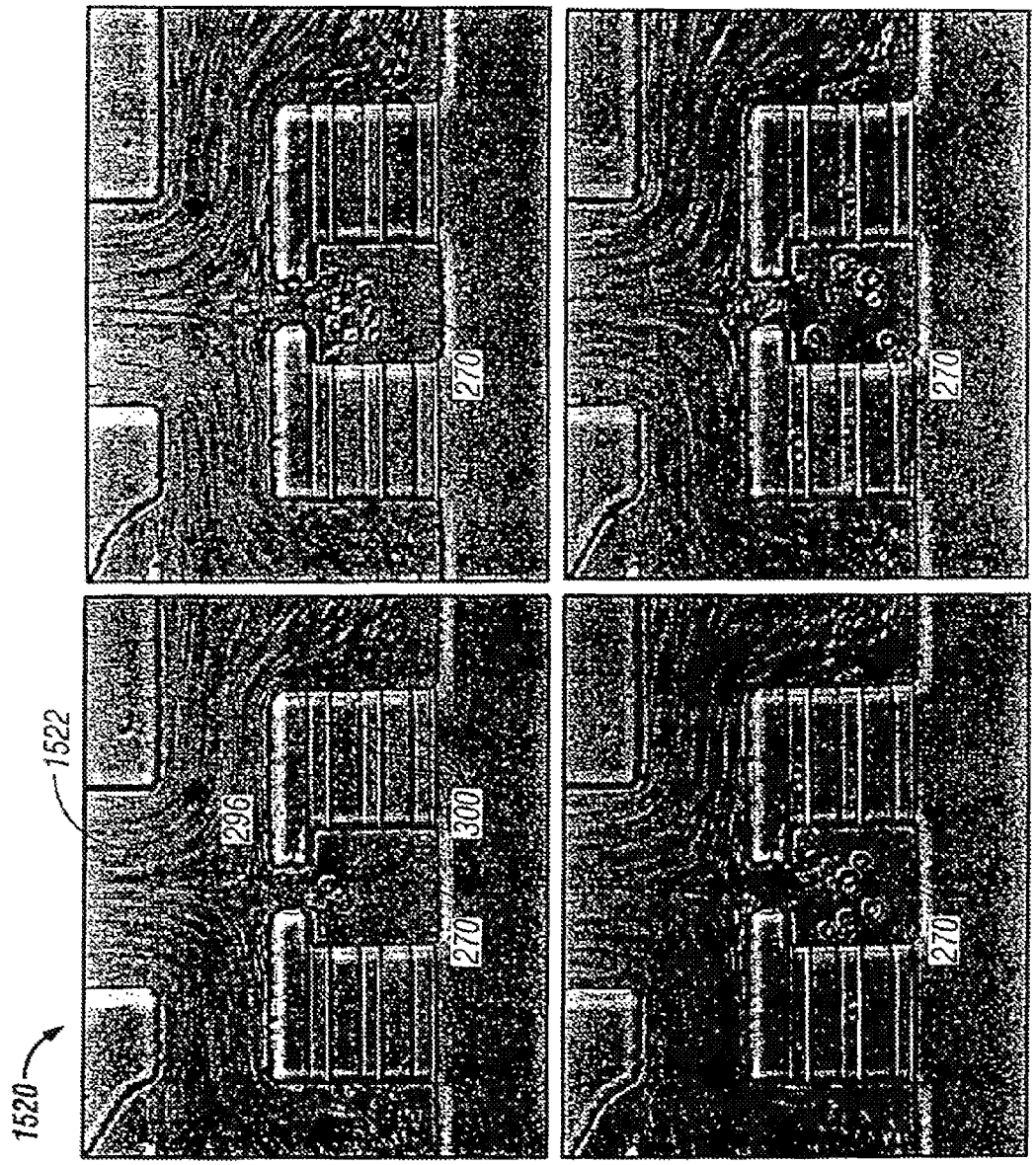

Schematic of the wild-type streptavidin binding pocket. Protein residues S45 and D128 are shown in relation to bound biotin. The resonance form of biotin is shown with partial charges on the ureido oxygen and nitrogens.

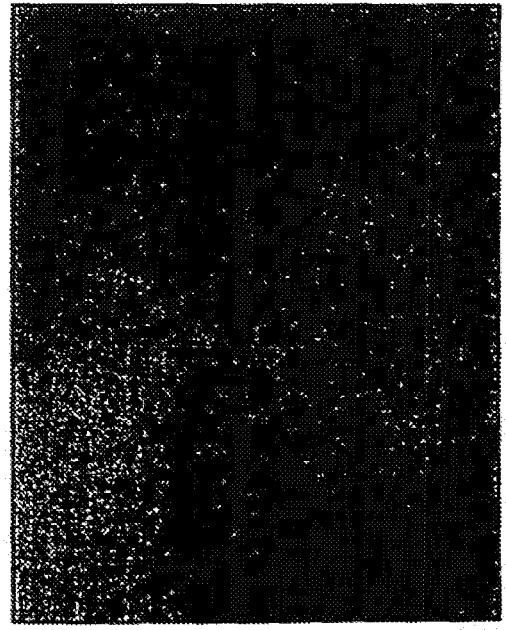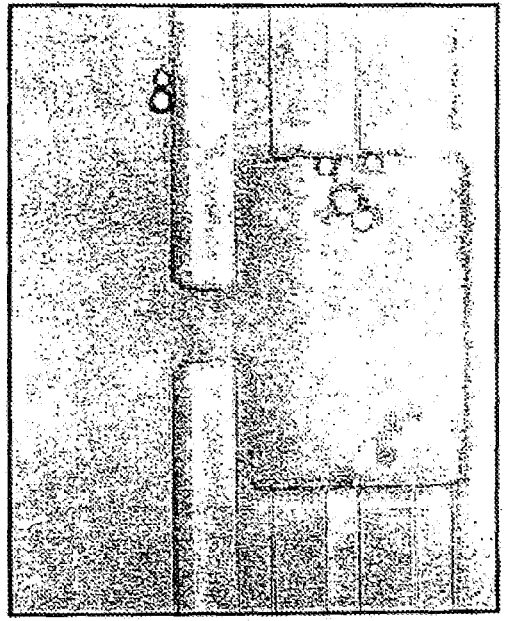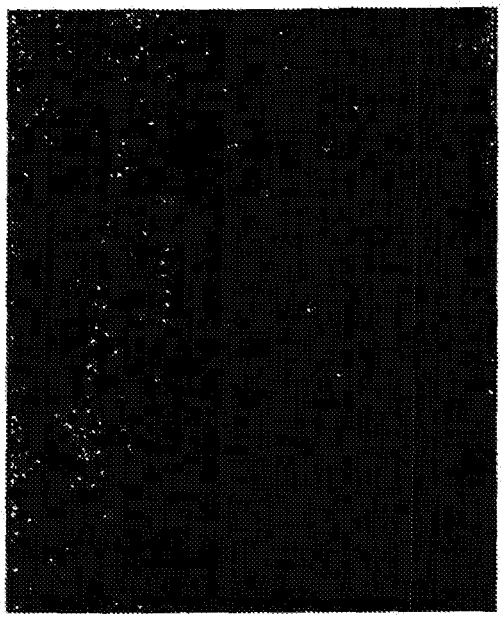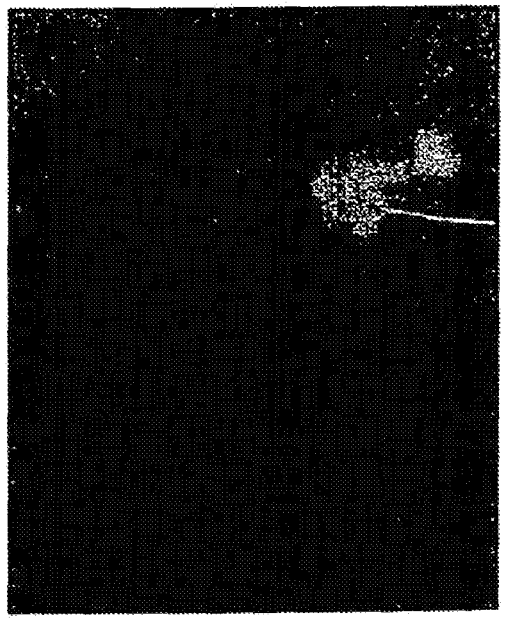
FIG. 74

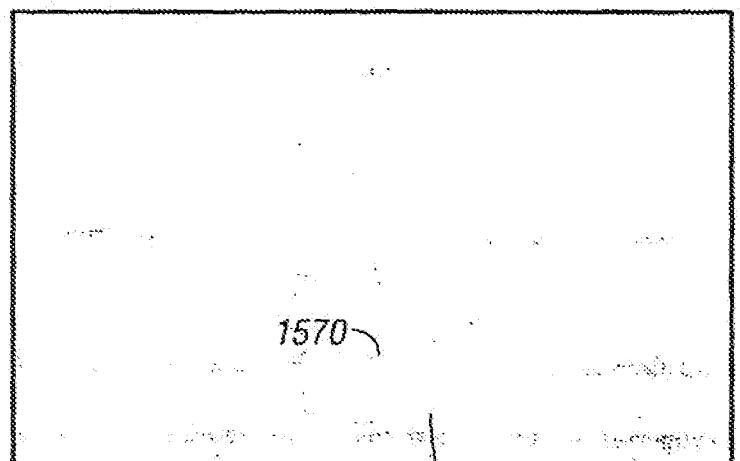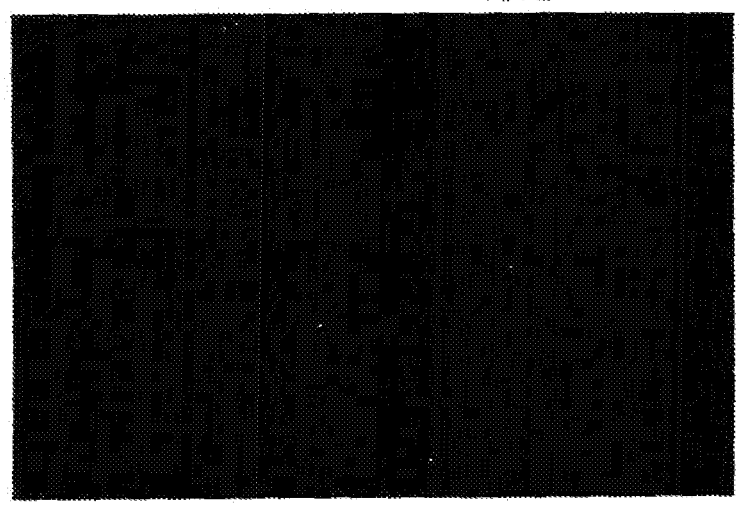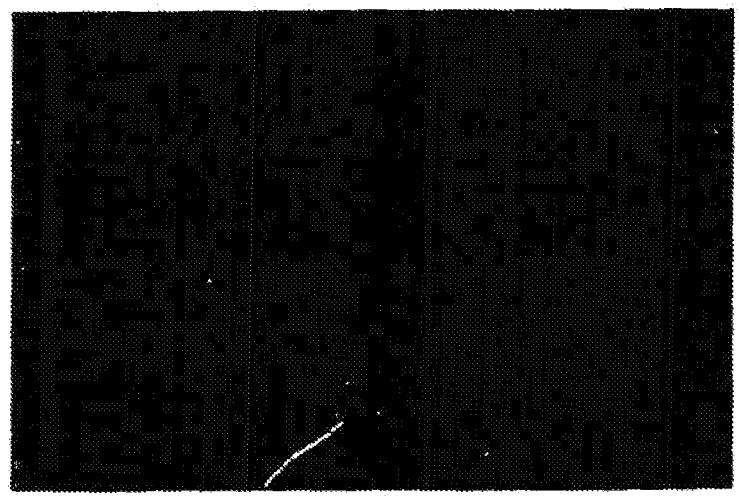
FIG. 75

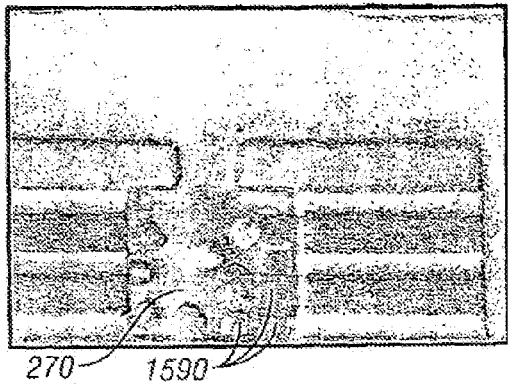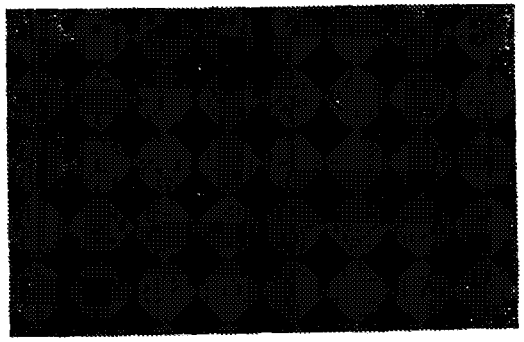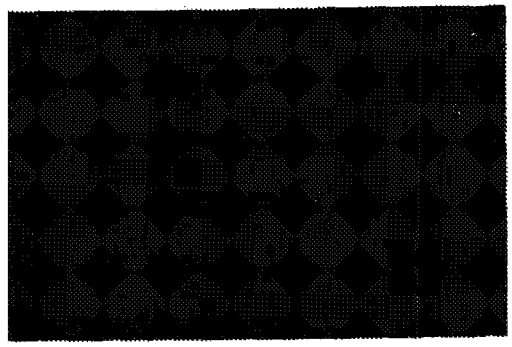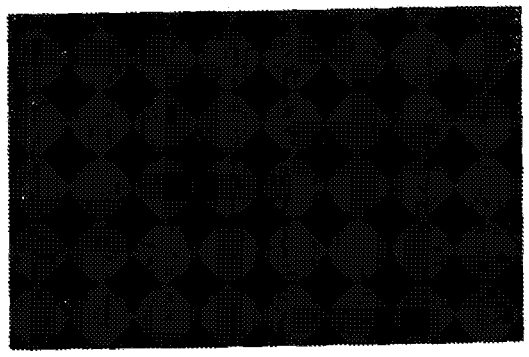
*FIG. 76*

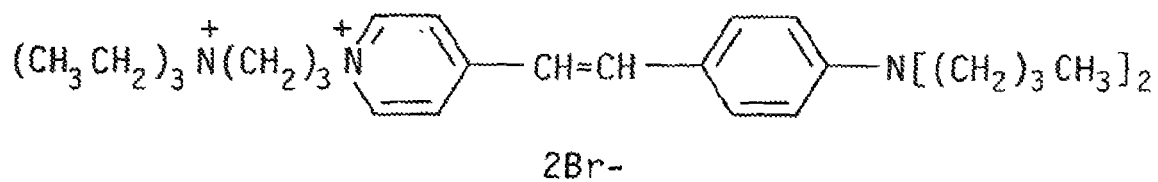
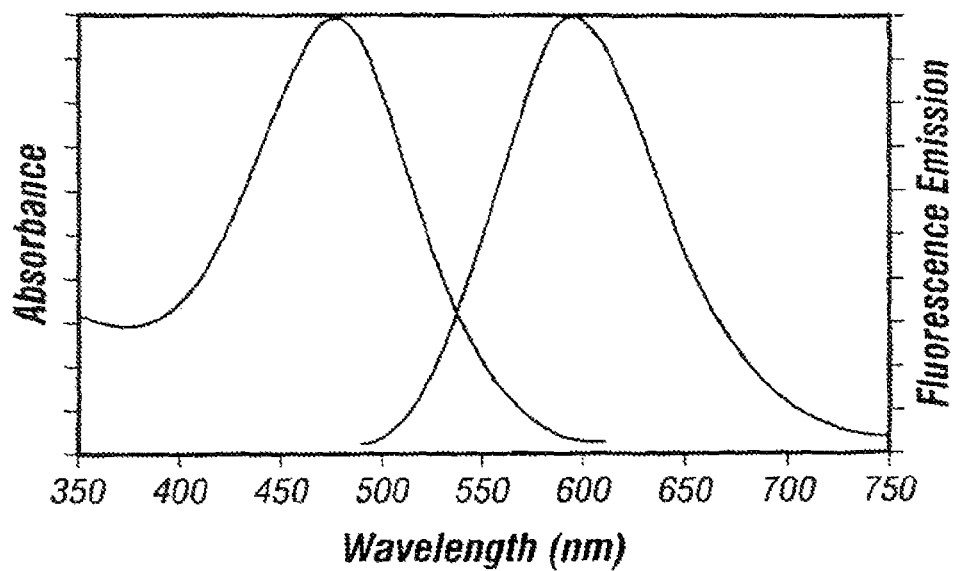
FIG. 77

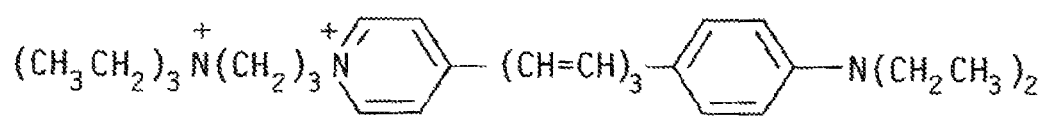
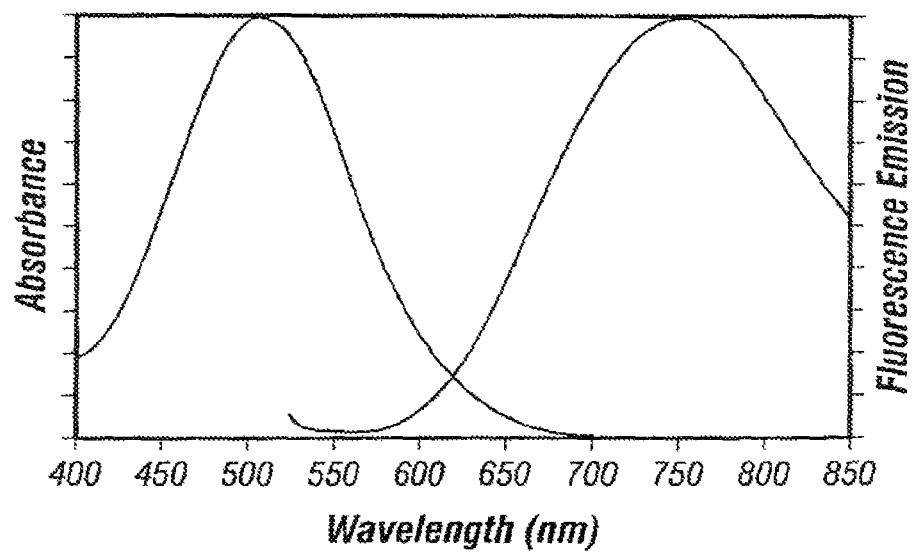
*FIG. 78*

Load Cells into chambers

Isolate chambers and expose cells to compounds

Reverse flow through chambers
and expose cells to detection reagents

MICROFLUIDIC PARTICLE-ANALYSIS SYSTEMS

CLAIM OF PRIORITY

This application claims the benefit of priority under 35 U.S.C. §119(e) to provisional applications Ser. No. 60/369,538, filed Apr. 1, 2002 and 60/378,464, filed May 6, 2002, both of which are hereby incorporated by reference in their entirety for all purposes and those purposes stated herein and therein. This application further claims priority under 35 U.S.C. §120 as a continuation-in-part of the non-provisional patent application titled "Microfluidic Particle-Analysis Systems", by Chou et al., filed on Mar. 31, 2003, which is hereby incorporated by reference for all purposes.

CROSS-REFERENCE TO PATENT APPLICATIONS

This application incorporates by reference in their entirety for all purposes the following U.S. patent applications: Ser. No. 09/605,520, filed Jun. 27, 2000; Ser. No. 09/724,784, filed Nov. 28, 2000; Ser. No. 09/724,967, filed Nov. 28, 2000; Ser. No. 09/796,378, filed Feb. 28, 2001; Ser. No. 09/796,666, filed Feb. 28, 2001; Ser. No. 09/796,871, filed Feb. 28, 2001; Ser. No. 09/826,583, filed Apr. 6, 2001; and Ser. No. 09/724,784, filed Nov. 28, 2001, titled MICROFABRICATED ELASTOMERIC VALVE AND PUMP SYSTEMS, and naming Marc A. Unger, Hou-Pu Chou, Todd A. Thorsen, Axel Scherer, Stephen R. Quake, Jian Liu, Mark L. Adams, and Carl L. Hansen as inventors.

CROSS-REFERENCES TO OTHER MATERIALS

This application incorporates by reference in their entirety for all purposes the following publications: Joe Sambrook and David Russell, Molecular Cloning: A Laboratory Manual ($3^{rd}$ ed. 2000); and R. Ian Freshney, Culture of Animal Cells: A Manual of Basic Technique ($4^{th}$ ed. 2000).

FIELD OF THE INVENTION

The invention relates to systems for the manipulation and/or detection of particles. More particularly, the invention relates to microfluidic systems for the manipulation and/or detection of particles, such as cells and/or beads.

BACKGROUND OF THE INVENTION

The ability to perform molecular and cellular analyses of biological systems has grown explosively over the past three decades. In particular, the advent and refinement of molecular and cellular techniques, such as DNA sequencing, gene cloning, monoclonal antibody production, cell transfection, amplification techniques (such as PCR), and transgenic animal formation, have fueled this explosive growth. These techniques have spawned an overwhelming number of identified genes, encoded proteins, engineered cell types, and assays for studying these genes, proteins, and cell types. As the number of possible combinations of samples, reagents, and assays becomes nearly incalculable, it has become increasingly apparent that novel approaches are necessary even to begin to make sense of this complexity, especially within reasonable temporal and monetary limitations.

One approach to these difficulties has been to reduce the scale of assays. Accordingly, substantial effort has been directed to developing assay methods and instrumentation for high-density microtiter plates. However, very small assay volumes in high-density microtiter plates, particularly assays with cells, may suffer from a number of shortcomings. For example, cells may be lost easily from wells, may be harmed by rapid fluid evaporation, may contaminate nearby wells, and may be difficult to remove efficiently from wells for additional analysis or culture. Thus, there is a need for systems that can effectively manipulate and analyze cells and other small particles, such as beads, in small volumes.

SUMMARY OF THE INVENTION

The invention provides systems, including apparatus, methods, and kits, for the microfluidic manipulation and/or detection of particles, such as cells and/or beads.

BRIEF DESCRIPTION OF THE DRAWINGS

FIG. 11A is a fragmentary, top plan view of a microfluidic system for measuring cell-cell communication, based on a duplicated version of the system of FIG. 8, in accordance with aspects of the invention.

FIG. 11B is a top plan view of selected portions of an alternative embodiment of the system of FIG. 11A, in accordance with aspects of the invention.

FIG. 11C is a top plan view of a two-dimensional array of particle capture chambers that may be used in a microfluidic system, in accordance with aspects of the invention.

FIG. 72 is a time-lapse set of photographic images recording size-selective flow of blood cells through a microfluidic system, in accordance with aspects of the invention.

FIG. 74 is a time-lapse set of photographic images recording interaction of specific binding pairs on beads in a microfluidic system, in accordance with aspects of the invention.

FIG. 75 is a time-lapse set of photographic images recording stimulation of ion flux in a microfluidic system, in accordance with aspects of the invention.

FIG. 76 is a time-lapse set of photographic images recording apoptosis and necrosis in a microfluidic system, in accordance with aspects of the invention.

FIGS. 77 and 78 are diagrams showing the structures and excitation/emission spectra for membrane dyes used in the analysis of Example 22.

DETAILED DESCRIPTION

Figure 1:
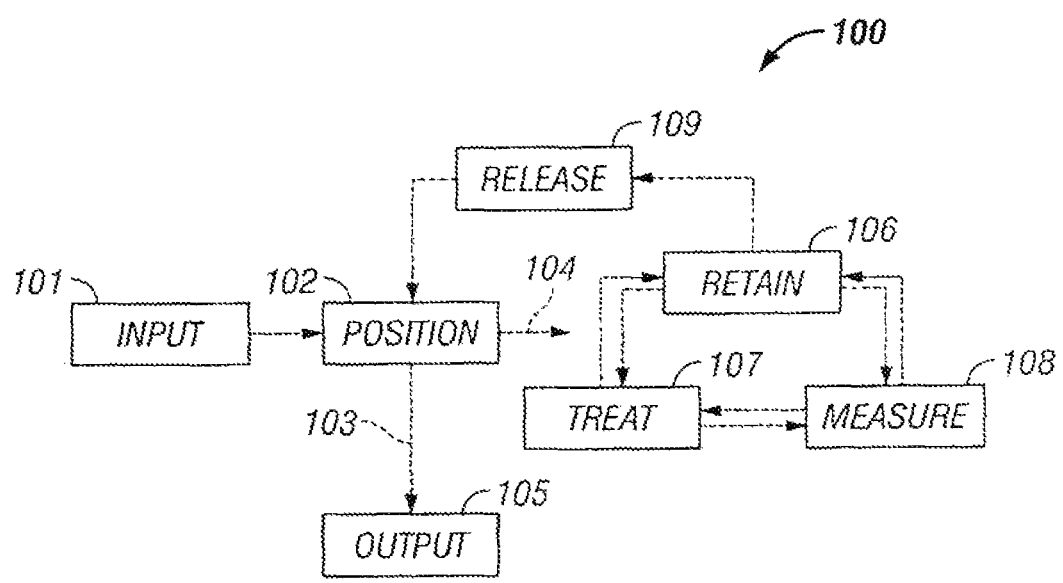
FIG. 1 is a flow chart showing potential temporal relationships between method steps for manipulation and/or detection of particles in a microfluidic system, in accordance with aspects of the invention.

The invention provides systems, including apparatus, methods, and kits, for the microfluidic manipulation and/or analysis of particles, such as cells, viruses, organelles, beads, and/or vesicles. The invention also provides microfluidic mechanisms for carrying out these manipulations and analyses. These mechanisms may enable controlled input, movement/positioning, retention/localization, treatment, measurement, release, and/or output of particles. Furthermore, these mechanisms may be combined in any suitable order and/or employed for any suitable number of times within a system. Accordingly, these combinations may allow particles to be sorted, cultured, mixed, treated, and/or assayed, among others, as single particles, mixed groups of particles, arrays of particles, heterogeneous particle sets, and/or homogeneous particle sets, among others, in series and/or in parallel. In addition, these combinations may enable microfluidic systems to be reused. Furthermore, these combinations may allow the response of particles to treatment to be measured on a shorter time scale than was previously possible. Therefore, systems of the invention may allow a broad range of cell and particle assays, such as drug screens, cell characterizations, research studies, and/or clinical analyses, among others, to be scaled down to microfluidic size. Such scaled-down assays may use less sample and reagent, may be less labor intensive, and/or may be more informative than comparable macrofluidic assays.

Further aspects of the invention are described in the following sections: (I) microfluidic systems, (II) physical structures of fluid networks, (III) particles, (IV) input mechanisms, (V) positioning mechanisms, (VI) retention mechanisms, (VII) treatment mechanisms, (VIII) measurement mechanisms, (IX) release mechanisms, (X) output mechanisms, (XI) cell culture mechanisms, (XII) particle-based manipulations, and (XIII) examples.

Microfluidic Systems

Definitions and Overview

Particle manipulations and analyses are performed in microfluidic systems. A microfluidic system generally comprises any system in which very small volumes of fluid are stored and manipulated, generally less than about 500 μL, typically less than about 100 μL, and more typically less than about 10 μL. Microfluidic systems carry fluid in predefined paths through one or more microfluidic passages. A microfluidic passage may have a minimum dimension, generally height or width, of less than about 200, 100, or 50 μm. Passages are described in more detail below in Section II.

Microfluidic systems may include one or more sets of passages that interconnect to form a generally closed microfluidic network. Such a microfluidic network may include one, two, or more openings at network termini, or intermediate to the network, that interface with the external world. Such openings may receive, store, and/or dispense fluid. Dispensing fluid may be directly into the microfluidic network or to sites external the microfluidic system. Such openings generally function in input and/or output mechanisms, described in more detail in Sections IV and X below, and may include reservoirs, described in more detail in Section II below.

Microfluidic systems also may include any other suitable features or mechanisms that contribute to fluid, reagent, and/or particle manipulation or analysis. For example, microfluidic systems may include regulatory or control mechanisms that determine aspects of fluid flow rate and/or path. Valves and/or pumps that may participate in such regulatory mechanisms are described in more detail below in Section II. Alternatively, or in addition, microfluidic systems may include mechanisms that determine, regulate, and/or sense fluid temperature, fluid pressure, fluid flow rate, exposure to light, exposure to electric fields, magnetic field strength, and/or the like. Accordingly, microfluidic systems may include heaters, coolers, electrodes, lenses, gratings, light sources, pressure sensors, pressure transducers, microprocessors, microelectronics, and/or so on. Furthermore, each microfluidic system may include one or more features that act as a code to identify a given system. The features may include any detectable shape or symbol, or set of shapes or symbols, such as black-and-white or colored barcode, a word, a number, and/or the like, that has a distinctive position, identity, and/or other property (such as optical property).

Materials

Microfluidic systems may be formed of any suitable material or combination of suitable materials. Suitable materials may include elastomers, such as polydimethylsiloxane (PDMS); plastics, such as polystyrene, polypropylene, polycarbonate, etc.; glass; ceramics; sol-gels; silicon and/or other metalloids; metals or metal oxides; biological polymers, mixtures, and/or particles, such as proteins (gelatin, polylysine, serum albumin, collagen, etc.), nucleic acids, microorganisms, etc.; and/or the like.

Exemplary materials for microfluidic systems are described in more detail in the patent applications listed above under Cross-References, which are incorporated herein by reference.

Methods of Fabrication

Microfluidic systems, also referred to as chips, may have any suitable structure. Such systems may be fabricated as a unitary structure from a single component, or as a multi-component structure of two or more components. The two or more components may have any suitable relative spatial relationship and may be attached to one another by any suitable bonding mechanism.

In some embodiments, two or more of the components may be fabricated as relatively thin layers, which may be disposed face-to-face. The relatively thin layers may have distinct thickness, based on function. For example, the thickness of some layers may be about 10 to 250 µm, 20 to 200 µm, or about 50 to 150 µm, among others. Other layers may be substantially thicker, in some cases providing mechanical strength to the system. The thicknesses of such other layers may be about 0.25 to 2 cm, 0.4 to 1.5 cm, or 0.5 to 1 cm, among others. One or more additional layers may be a substantially planar layer that functions as a substrate layer, in some cases contributing a floor portion to some or all microfluidic passages.

Components of a microfluidic system may be fabricated by any suitable mechanism, based on the desired application for the system and on materials used in fabrication. For example, one or more components may be molded, stamped, and/or embossed using a suitable mold. Such a mold may be formed of any suitable material by micromachining, etching, soft lithography, material deposition, cutting, and/or punching, among others. Alternatively, or in addition, components of a microfluidic system may be fabricated without a mold by etching, micromachining, cutting, punching, and/or material deposition.

Microfluidic components may be fabricated separately, joined, and further modified as appropriate. For example, when fabricated as distinct layers, microfluidic components may be bonded, generally face-to-face. These separate components may be surface-treated, for example, with reactive chemicals to modify surface chemistry, with particle binding agents, with reagents to facilitate analysis, and/or so on. Such surface-treatment may be localized to discrete portions of the surface or may be relatively nonlocalized. In some embodiments, separate layers may be fabricated and then punched and/or cut to produce additional structure. Such punching and/or cutting may be performed before and/or after distinct components have been joined.

Exemplary methods for fabricating microfluidic systems are described in more detail in the patent applications identified above under Cross-References, which are incorporated herein by reference.

Physical Structures of Fluid Networks

Overview

Microfluidic systems may include any suitable structure(s) for the integrated manipulation of small volumes of fluid, including moving and/or storing fluid, and particles associated therewith, for use in particle assays. The structures may include passages, reservoirs, and/or regulators, among others.

Passages

Passages generally comprise any suitable path, channel, or duct through, over, or along which materials (e.g., fluid, particles, and/or reagents) may pass in a microfluidic system. Collectively, a set of fluidically communicating passages, generally in the form of channels, may be referred to as a microfluidic network. In some cases, passages may be described as having surfaces that form a floor, a roof, and walls. Passages may have any suitable dimensions and geometry, including width, height, length, and/or cross-sectional profile, among others, and may follow any suitable path, including linear, circular, and/or curvilinear, among others. Passages also may have any suitable surface contours, including recesses, protrusions, and/or apertures, and may have any suitable surface chemistry or permeability at any appropriate position within a channel. Suitable surface chemistry may include surface modification, by addition and/or treatment with a chemical and/or reagent, before, during, and/or after passage formation.

In some cases, passages, and particularly channels, may be described according to function. For example, passages may be described according to direction of material flow in a particular application, relationship to a particular reference structure, and/or type of material carried. Accordingly, passages may be inlet passages (or channels), which generally carry materials to a site, and outlet passages (or channels), which generally carry materials from a site. In addition, passages may be referred to as particle passages (or channels), reagent passages (or channels), focusing passages (or channels), perfusion passages (or channels), waste passages (or channels), and/or the like.

Passages may branch, join, and/or dead-end to form any suitable microfluidic network. Accordingly, passages may function in particle positioning, sorting, retention, treatment, detection, propagation, storage, mixing, and/or release, among others.

Further aspects of passages are included throughout this Detailed Description, and in the patent applications identified above under Cross-References, which are incorporated herein by reference.

Reservoirs

Reservoirs generally comprise any suitable receptacle or chamber for storing materials (e.g., fluid, particles and/or reagents), before, during, between, and/or after processing operations (e.g., measurement and/or treatment). Reservoirs, also referred to as wells, may include input, intermediate, and/or output reservoirs. Input reservoirs may store materials (e.g., fluid, particles, and/or reagents) prior to inputting the materials to a microfluidic network(s) portion of a chip. By contrast, intermediate reservoirs may store materials during and/or between processing operations. Finally, output reservoirs may store materials prior to outputting from the chip, for example, to an external processor or waste, or prior to disposal of the chip.

Further aspects of reservoirs are included in the patent applications identified above under Cross-References, which are incorporated herein by reference.

Regulators

Regulators generally comprise any suitable mechanism for generating and/or regulating movement of materials (e.g., fluid, particles, and/or reagents). Suitable regulators may include valves, pumps, and/or electrodes, among others. Regulators may operate by actively promoting flow and/or by restricting active or passive flow. Suitable functions mediated by regulators may include mixing, sorting, connection (or isolation) of fluidic networks, and/or the like.

Further aspects of regulators, particularly the structure, fabrication, and operation of valves and pumps, are included in the patent applications identified above under Cross-References, which are incorporated herein by reference, and in Section XIII, particularly Example 8.

Particles

Overview

Microfluidic systems may be used to manipulate and/or analyze particles. A particle generally comprises any object that is small enough to be inputted and manipulated within a microfluidic network in association with fluid, but that is large enough to be distinguishable from the fluid. Particles, as used here, typically are microscopic or near-microscopic, and may have diameters of about 0.005 to 100 µm, 0.1 to 50 µm, or about 0.5 to 30 µm. Alternatively, or in addition, particles may have masses of about $10^{-20}$ to $10^{-5}$ grams, $10^{-16}$ to $10^{-7}$ grams, or $10^{-14}$ to $10^{-8}$ grams. Exemplary particles may include cells, viruses, organelles, beads, and/or vesicles, and aggregates thereof, such as dimers, trimers, etc.

Cells

Overview

Cells, as used here, generally comprise any self-replicating, membrane-bounded biological entity, or any nonreplicating, membrane-bounded descendant thereof. Nonreplicating descendants may be senescent cells, terminally differentiated cells, cell chimeras, serum-starved cells, infected cells, nonreplicating mutants, anucleate cells, etc.

Cells used as particles in microfluidic systems may have any suitable origin, genetic background, state of health, state of fixation, membrane permeability, pretreatment, and/or population purity, among others. Origin of cells may be eukaryotic, prokaryotic, archae, etc., and may be from animals, plants, fungi, protists, bacteria, and/or the like. Cells may be wild-type; natural, chemical, or viral mutants; engineered mutants (such as transgenics); and/or the like. In addition, cells may be growing, quiescent, senescent, transformed, and/or immortalized, among others, and cells may be fixed and/or unfixed. Living or dead, fixed or unfixed cells may have intact membranes, and/or permeabilized/disrupted membranes to allow uptake of ions, labels, dyes, ligands, etc., or to allow release of cell contents. Cells may have been pretreated before introduction into a microfluidic system by any suitable processing steps. Such processing steps may include modulator treatment, transfection (including infection, injection, particle bombardment, lipofection, coprecipitate transfection, etc.), processing with assay reagents, such as dyes or labels, and/or so on. Furthermore, cells may be a monoculture, generally derived as a clonal population from a single cell or a small set of very similar cells; may be presorted by any suitable mechanism such as affinity binding, FACS, drug selection, etc.; and/or may be a mixed or heterogeneous population of distinct cell types.

Eukaryotic Cells

Eukaryotic cells, that is, cells having one or more nuclei, or anucleate derivatives thereof, may be obtained from any suitable source, including primary cells, established cells, and/or patient samples. Such cells may be from any cell type or mixture of cell types, from any developmental stage, and/or from any genetic background. Furthermore, eukaryotic cells may be adherent and/or nonadherent. Such cells may be from any suitable eukaryotic organism including animals, plants, fungi, and/or protists.

Eukaryotics cells may be from animals, that is, vertebrates or invertebrates. Vertebrates may include mammals, that is, primates (such as humans, apes, monkeys, etc.) or nonprimates (such as cows, horses, sheep, pigs, dogs, cats, marsupials, rodents, and/or the like). Nonmammalian vertebrates may include birds, reptiles, fish, (such as trout, salmon, goldfish, zebrafish, etc.), and/or amphibians (such as frogs of the species *Xenopus, Rana*, etc.). Invertebrates may include arthropods (such as arachnids, insects (e.g., *Drosophila*), etc.), mollusks (such as clams, snails, etc.), annelids (such as earthworms, etc.), echinoderms (such as various starfish, among others), coelenterates (such as jellyfish, coral, etc.), porifera (sponges), platyhelminths (tapeworms), nemathelminths (flatworms), etc.

Eukaryotic cells may be from any suitable plant, such as monocotyledons, dicotyledons, gymnosperms, angiosperms, ferns, mosses, lichens, and/or algae, among others. Exemplary plants may include plant crops (such as rice, corn, wheat, rye, barley, potatoes, etc.), plants used in research (e.g., *Arabadopsis*, loblolly pine, etc.), plants of horticultural values (ornamental palms, roses, etc.), and/or the like.

Eukaryotic cells may be from any suitable fungi, including members of the phyla Chytridiomycota, Zygomycota, Ascomycota, Basidiomycota, Deuteromycetes, and/or yeasts. Exemplary fungi may include *Saccharomyces cerevisiae, Schizosaccharomyces pombe, Pichia pastoralis, Neurospora crassa*, mushrooms, puffballs, imperfect fungi, molds, and/or the like.

Eukaryotic cells may be from any suitable protists (protozoans), including amoebae, ciliates, flagellates, coccidia, microsporidia, and/or the like. Exemplary protists may include *Giardia lamblia, Entamoeba*. histolytica, *Cryptosporidium*, and/or *N. fowleri*, among others.

Particles may include eukaryotic cells that are primary, that is, taken directly from an organism or nature, without subsequent extended culture in vitro. For example, the cells may be obtained from a patient sample, such as whole blood, packed cells, white blood cells, urine, sputum, feces, mucus, spinal fluid, tumors, diseased tissue, bone marrow, lymph, semen, pleural fluid, a prenatal sample, an aspirate, a biopsy, disaggregated tissue, epidermal cells, keratinocytes, endothelial cells, smooth muscle cells, skeletal muscle cells, neural cells, renal cells, prostate cells, liver cells, stem cells, osteoblasts, and/or the like. Similar samples may be manipulated and analyzed from human volunteers, selected members of the human population, forensic samples, animals, plants, and/or natural sources (water, soil, air, etc.), among others.

Alternatively, or in addition, particles may include established eukaryotic cells. Such cells may be immortalized and/or transformed by any suitable treatment, including viral infection, nucleic acid transfection, chemical treatment, extended passage and selection, radiation exposure, and/or the like. Such established cells may include various lineages such as neuroblasts, neurons, fibroblasts, myoblasts, myotubes, chondroblasts, chondrocytes, osteoblasts, osteocytes, cardiocytes, smooth muscle cells, epithelial cells, keratinocytes, kidney cells, liver cells, lymphocytes, granulocytes, and/or macrophages, among others. Exemplary established cell lines may include Rat-1, NIH 3T3, HEK 293, COS1, COS7, CV-1, C2C12, MDCK, PC12, SAOS, HeLa, Schneider cells, Junkat cells, SL2, and/or the like.

Prokaryotic Cells

Particles may be prokaryotic cells, that is, self-replicating, membrane-bounded microorganisms that lack membrane-bound organelles, or nonreplicating descendants thereof. Prokaryotic cells may be from any phyla, including Aquificae, Bacteroids, Chlorobia, Chrysogenetes, Cyanobacteria, Fibrobacter, Firmicutes, Flavobacteria, Fusobacteria, Proteobacteria, Sphingobacteria, Spirochaetes, Thermomicrobia, and/or Xenobacteria, among others. Such bacteria may be gram-negative, gram-positive, harmful, beneficial, and/or pathogenic. Exemplary prokaryotic cells may include *E. coli, S. typhimurium, B subtilis, S. aureus, C. perfringens, V. parahaemolyticus,* and/or *B. anthracis,* among others.

Viruses

Viruses may be manipulated and/or analyzed as particles in microfluidic systems. Viruses generally comprise any microscopic/submicroscopic parasites of cells (animals, plants, fungi, protists, and/or bacteria) that include a protein and/or membrane coat and that are unable to replicate without a host cell. Viruses may include DNA viruses, RNA viruses, retroviruses, virions, viroids, prions, etc. Exemplary viruses may include HIV, RSV, rabies, hepatitis virus, Epstein-Barr virus, rhinoviruses, bacteriophages, prions that cause various diseases (CJD (Creutzfeld-Jacob disease, kuru, GSS (Gerstmann-Straussler-Scheinker syndrome), FFI (Fatal Familial Insomnia), Alpers syndrome, etc.), and/or the like.

Organelles

Organelles may be manipulated and/or analyzed in microfluidic systems. Organelles generally comprise any particulate component of a cell. For example, organelles may include nuclei, Golgi apparatus, lysosomes, endosomes, mitochondria, peroxisomes, endoplasmic reticulum, phagosomes, vacuoles, chloroplasts, etc.

Beads

Particle assays may be performed with beads. Beads generally comprise any suitable manufactured particles. Beads may be manufactured from inorganic materials, or materials that are synthesized chemically, enzymatically and/or biologically. Furthermore, beads may have any suitable porosity and may be formed as a solid or as a gel. Suitable bead compositions may include plastics (e.g., polystyrene), dextrans, glass, ceramics, sol-gels, elastomers, silicon, metals, and/or biopolymers (proteins, nucleic acids, etc.). Beads may have any suitable particle diameter or range of diameters. Accordingly, beads may be a substantially uniform population with a narrow range of diameters, or beads may be a heterogeneous population with a broad range of diameters, or two or more distinct diameters.

Beads may be associated with any suitable materials. The materials may include compounds, polymers, complexes, mixtures, phages, viruses, and/or cells, among others. For example, the beads may be associated with a member of a specific binding pair (see Section VI), such as a receptor, a ligand, a nucleic acid, a member of a compound library, and/or so on. Beads may be a mixture of distinct beads, in some cases carrying distinct materials. The distinct beads may differ in any suitable aspect(s), such as size, shape, an associated code, and/or material carried by the beads. In some embodiments, the aspect may identify the associated material. Codes are described further in Section XII below.

Vesicles

Particles may be vesicles. Vesicles generally comprise any noncellularly derived particle that is defined by a lipid envelope. Vesicles may include any suitable components in their envelope or interior portions. Suitable components may include compounds, polymers, complexes, mixtures, aggregates, and/or particles, among others. Exemplary components may include proteins, peptides, small compounds, drug candidates, receptors, nucleic acids, ligands, and/or the like.

Input Mechanisms

Overview

Microfluidic systems may include one or more input mechanisms that interface with the microfluidic network(s). An input mechanism generally comprises any suitable mechanism for inputting material(s) (e.g., particles, fluid, and/or reagents) to a microfluidic network of a microfluidic chip, including selective (that is, component-by-component) and/or bulk mechanisms.

Internal/External Sources

The input mechanism may receive material from internal sources, that is, reservoirs that are included in a microfluidic chip, and/or external sources, that is, reservoirs that are separate from, or external to, the chip.

Input mechanisms that input materials from internal sources may use any suitable receptacle to store and dispense the materials. Suitable receptacles may include a void formed in the chip. Such voids may be directly accessible from outside the chip, for example, through a hole extending from fluidic communication with a fluid network to an external surface of the chip, such as the top surface. The receptacles may have a fluid capacity that is relatively large compared to the fluid capacity of the fluid network, so that they are not quickly exhausted. For example, the fluid capacity may be at least about 1, 5, 10, 25, 50, or 100 µL. Accordingly, materials may be dispensed into the receptacles using standard laboratory equipment, if desired, such as micropipettes, syringes, and the like.

Input mechanisms that input materials from external sources also may use any suitable receptacle and mechanism to store and dispense the materials. However, if the external sources input materials directly into the fluid network, the external sources may need to interface effectively with the fluid network, for example, using contact and/or noncontact dispensing mechanisms. Accordingly, input mechanisms from external sources may use capillaries or needles to direct fluid precisely into the fluid network. Alternatively, or in addition, input mechanisms from external sources may use a noncontact dispensing mechanism, such as "spitting," which may be comparable to the action of an inkjet printer. Furthermore, input mechanisms from external sources may use ballistic propulsion of particles, for example, as mediated by a gene gun.

Facilitating Mechanisms

The inputting of materials into the microfluidics system may be facilitated and/or regulated using any suitable facilitating mechanism. Such facilitating mechanisms may include gravity flow, for example, when an input reservoir has greater height of fluid than an output reservoir. Facilitating mechanisms also may include positive pressure to push materials into the fluidic network, such as mechanical or gas pressure, or centrifugal force; negative pressure at an output mechanism to draw fluid toward the output mechanism; and/or a positioning mechanism acting within the fluid network. The positioning mechanism may include a pump and/or an electrokinetic mechanism. Positioning mechanisms are further described below, in Section V. In some embodiments, the facilitating mechanism may include a suspension mechanism to maintain particles such as cells in suspension prior to inputting, for example, as described in Example 7.

Positioning Mechanisms

Overview

Microfluidic systems may include one or more positioning mechanisms. A positioning mechanism generally comprises any mechanism for placing particles at preselected positions on the chip after inputting, for example, for retention, growth, treatment, and/or measurement, among others. Positioning mechanisms may be categorized without limitation in various ways, for example, to reflect their origins and/or operational principles, including direct and/or indirect, fluid-mediated and/or non-fluid-mediated, external and/or internal, and so on. These categories are not mutually exclusive. Thus, a given positioning mechanism may position a particle in two or more ways; for example, electric fields may position a particle directly (e.g., via electrophoresis) and indirectly (e.g., via electroosmosis).

The positioning mechanisms may act to define particle position longitudinally and/or transversely. The term "longitudinal position" denotes position parallel to or along the long axis of a microfluidic channel and/or a fluid flow stream within the channel. In contrast, the term "transverse position" denotes position orthogonal to the long axis of a channel and/or an associated main fluid flow stream. Both longitudinal and transverse positions may be defined locally, by equating "long axis" with "tangent" in curved channels.

The positioning mechanisms may be used alone and/or in combination. If used in combination, the mechanisms may be used serially (i.e., sequentially) and/or in parallel (i.e., simultaneously). For example, an indirect mechanism such as fluid flow may be used for rough positioning, and a direct mechanism such as optical tweezers may be used for final positioning (and/or subsequent retention, as described elsewhere).

The remainder of this section describes without limitation a variety of exemplary positioning mechanisms, sorted roughly as direct and indirect mechanisms.

Direct Positioning Mechanisms

Direct positioning mechanisms generally comprise any mechanisms in which a force acts directly on a particle(s) to position the particle(s) within a microfluidic network. Direct positioning mechanisms may be based on any suitable mechanism, including optical, electrical, magnetic, and/or gravity-based forces, among others. Optical positioning mechanisms use light to mediate or at least facilitate positioning of particles. Suitable optical positioning mechanisms include "optical tweezers," which use an appropriately focused and movable light source to impart a positioning force on particles. Electrical positioning mechanisms use electricity to position particles. Suitable electrical mechanisms include "electrokinesis," that is, the application of voltage and/or current across some or all of a microfluidic network, which may, as mentioned above, move charged particles directly (e.g., via electrophoresis) and/or indirectly, through movement of ions in fluid (e.g., via electroosmosis). Magnetic positioning mechanisms use magnetism to position particles based on magnetic interactions. Suitable magnetic mechanisms involve applying a magnetic field in or around a fluid network, to position particles via their association with ferromagnetic and/or paramagnetic materials in, on, or about the particles. Gravity-based positioning mechanisms use the force of gravity to position particles, for example, to contact adherent cells with a substrate at positions of cell culture.

Indirect Positioning Mechanisms

Indirect positioning mechanisms generally comprise any mechanisms in which a force acts indirectly on a particle(s), for example, via fluid, to move the particle(s) within a microfluidic network, longitudinally and/or transversely.

Longitudinal Indirect Positioning Mechanisms

Longitudinal indirect positioning mechanisms generally may be created and/or regulated by fluid flow along channels and/or other passages. Accordingly, longitudinal positioning mechanisms may be facilitated and/or regulated by valves and/or pumps that regulate flow rate and/or path. In some cases, longitudinal positioning mechanisms may be facilitated and/or regulated by electroosmotic positioning mechanisms. Alternatively, or in addition, longitudinal positioning mechanisms may be input-based, that is, facilitated and/or regulated by input mechanisms, such as pressure or gravity-based mechanisms, including a pressure head created by unequal heights of fluid columns.

Transverse Indirect Positioning Mechanisms

Transverse indirect positioning mechanisms generally may be created and/or regulated by fluid flow streams at channel junctions, laterally disposed regions of reduced fluid flow, and/or channel bends. Channel junctions may be unifying sites or dividing sites, based on the number of channels that carry fluid to the sites relative to the number that carry fluid away from the sites. Transverse indirect positioning mechanisms may be based on laminar flow, stochastic partitioning, and/or centrifugal force, among others.

Laminar Flow-Based Transverse Positioning Mechanisms

Transverse positioning of particles and/or reagents in a microfluidic system may be mediated at least in part by a laminar flow-based mechanism. Laminar flow-based mechanisms generally comprise any positioning mechanism in which the position of an input flow stream within a channel is determined by the presence, absence, and/or relative position(s) of additional flow streams within the channel. Such laminar flow-based mechanisms may be defined by a channel junction(s) that is a unifying site, at which inlet flow streams from two, three, or more channels, flowing toward the junction, unify to form a smaller number of outlet flow streams, preferably one, flowing away from the junction. Due to the laminar flow properties of flowstreams on a microfluidic scale, the unifying site may maintain the relative distribution of inlet flow streams after they unify as laminar outlet flow streams. Accordingly, particles and/or reagents may remain localized to any selected one or more of the laminar flow streams, based on which inlet channels carry particles and/or reagents, thus positioning the particles and/or reagents transversely.

The relative size (or flow rate) and position of each inlet flow stream may determine both transverse position and relative width of flow streams that carry particles and/or reagents. For example, an inlet flow stream for particles/reagents that is relatively small (narrow), flanked by two larger (wider) flow streams, may occupy a narrow central position in a single outlet channel. By contrast, an inlet flow stream for particles/reagents that is relatively large (wide), flanked by a comparably sized flow stream and a smaller (narrower) flow stream, may occupy a wider position that is biased transversely toward the smaller flow stream. In either case, the laminar flow-based mechanism may be called a focusing mechanism, because the particles/reagents are "focused" to a subset of the cross-sectional area of outlet channels. Laminar flow-based mechanisms may be used to individually address particles and/or reagents to plural distinct retention sites. Exemplary laminar flow-based positioning mechanisms are further described below, in Examples 2-4, 7, 9, 11, and 26, among others.

A laminar flow-based mechanism may be a variable mechanism to vary the transverse position of particles/reagents. As described above, the relative contribution of each inlet flow stream may determine the transverse position of particles/reagents flow streams. Altered flow of any inlet flow stream may vary its contribution to the outlet flow stream(s), shifting particles/reagents flow streams accordingly. In an extreme case, referred to as a perfusion mechanism, a reagent (or particle) flow stream may be moved transversely, either in contact with, or spaced from, retained particles (reagents), based on presence or absence of flow from an adjacent inlet flow stream. Such a mechanism also may be used to effect variable or regulated transverse positioning of particles, for example, to direct particles to retention sites having different transverse positions. Exemplary variable or regulated transverse positioning mechanisms, referred to as perfusion mechanisms, are further described below, in Examples 2-4, 6, 7, 11, and 26, among others.

Stochastic Transverse Positioning Mechanisms

Transverse positioning of particles and/or reagents in a microfluidic system may be mediated at least in part by a stochastic (or portioned flow) positioning mechanism. Stochastic transverse positioning mechanisms generally comprise any positioning mechanism in which an at least partially randomly selected subset of inputted particles or reagent is distributed laterally away from a main flow stream to a region of reduced fluid flow within a channel (or, potentially, to a distinct channel). The region of reduced flow may promote particle retention, treatment, detection, minimize particle damage, and/or promote particle contact with a substrate. Stochastic positioning mechanisms may be determined by dividing flow sites and/or locally widened channels, among others.

Dividing flow sites may effect stochastic positioning by forming regions of reduced fluid flow rate. Dividing flow sites generally include any channel junction at which inlet flow streams from one (preferably) or more inlet channels are divided into a greater number of outlet channels, including two, three, or more, channels. Such dividing sites may deliver a subset of particles, which may be selected stochastically and/or based on a property of the particles (such as mass), to a region of reduced flow rate or quasi-stagnant flow formed at or near the junction. The fraction of particles represented by the subset may be dependent upon the relative flow directions of the outlet channels relative to the inlet channels. These flow directions may be generally orthogonal to an inlet flow stream, being directed in opposite directions, to form a "T-junction." Alternatively, outlet flow directions may form angles of less than and/or greater than 90°. Exemplary reduced-velocity, dividing-flow positioning mechanisms are further described below, in Examples 1, 2, 3, 4, 6, 7, and 26, among others.

The dividing-flow positioning mechanism, with two or more outlet channels, may be used as a portioned-flow mechanism. Specifically, fluid, particles, and/or reagents carried to the channel junction may be portioned according to fluid flow through the two or more outlet channels. Accordingly, the fractional number or volume of particles or reagent that enters the two or more channels may be regulated by the relative sizes of the channels and/or the flow rate of fluid through the channels, which in turn may be regulated by valves, or other suitable flow regulatory-mechanisms. In a first set of embodiments, outlet channels may be of very unequal sizes, so that only a small fraction of particle and/or reagents are directed to the smaller channel. In a second set of embodiments, valves may be used to forms desired dilutions of reagents. In a third set of embodiments, valves may be used to selectively direct particles to one of two or more fluid paths. Examples of these three sets of embodiments are further described below, in Examples 11, 8, and 7, respectively.

Locally widened channels may promote stochastic positioning by producing regions of decreased flow rate lateral to a main flow stream. The decreased flow rate may deposit a subset of inputted particles at a region of decreased flow rate. Such widened channels may include nonlinear channels that curve or bend at an angle. Alternatively, or in addition, widened regions may be formed by recesses formed in a channel wall(s), chambers that intersect channels, and/or the like, particularly at the outer edge of a curved or bent channel. Exemplary locally widened channels that promote stochastic transverse positioning are described further in Example 10.

Centrifugal-Force-Based Transverse Positioning Mechanisms

Transverse positioning of particles and/or reagents also may be mediated at least in part by a centrifugal positioning mechanism. In centrifugal positioning mechanisms, particles may experience a centrifugal force determined by a change in velocity, for example, by moving through a bend in a fluid path. Size and/or density of particles may determine the rate of velocity change, distributing distinct sizes and/or densities of particle to distinct transverse positions. Exemplary centrifugal positioning mechanisms are further described below, in Example 9.

Retention Mechanisms

Overview

Microfluidic systems may include one or more retention mechanisms. A retention mechanism generally comprises any suitable mechanism for retaining (or holding, capturing, or trapping) particles at preselected positions or regions of microfluidic networks, including single or plural mechanisms, operating in series and/or in parallel. Retention mechanisms may act to overcome the positioning force exerted by fluid flow. Furthermore, retention mechanisms, also referred to as capture or trapping mechanisms, may retain any suitable number of particles, including single particles or groups/populations of particles. Suitable retention mechanisms may be based on physical barriers coupled with flow, chemical interactions, vacuum forces, fluid flow in a loop, gravity, centrifugal forces, magnetic forces, electrical forces, and/or optically generated forces, among others.

Retention mechanisms may be selective or nonselective. Selective mechanisms may be fractionally selective, that is, retaining less than all (a subset of) inputted particles. Fractionally selective mechanisms may rely at least in part on stochastic positioning mechanisms, such as that exemplified in Example 2. Alternatively, or in addition, selective mechanisms may be particle-dependent, that is, retaining particles based on one or more properties of the inputted particle, such as size, surface chemistry, density, magnetic character, electrical charge, optical property (such as refractive index), and/or the like.

Physical Barrier-Based Retention Mechanisms

Retention mechanisms may be based at least partially on particle contact with any suitable physical barrier(s) disposed in a microfluidic network. Such particle-barrier contact generally restricts longitudinal particle movement along the direction of fluid flow, producing flow-assisted retention. Flow-assisted particle-barrier contact also may restrict sideto-side/orthogonal (transverse) movement. Suitable physical barriers may be formed by protrusions that extend inward from any portion of a channel or other passage (that is, walls, roof, and/or floor). For example, the protrusions may be fixed and/or movable, including columns, posts, blocks, bumps, walls, and/or partially/completely closed valves, among others. Some physical barriers, such as valves, may be movable or regulatable. Alternatively, or in addition, a physical barrier may be defined by a recess(es) formed in a channel or other passage, or by a fluid-permeable membrane. Other physical barriers may be formed based on the cross-sectional dimensions of passages. For example, size-selective channels may retain particles that are too large to enter the channels. (Size-selective channels also may be referred to as filter channels, microchannels, or particle-restrictive or particle-selective channels.)

Further aspects of physical barriers and size-selective channels are described below in Section XIII, and in the patent applications listed in the Cross-References, which are incorporated herein by reference.

Chemical Retention Mechanisms

Chemical retention mechanisms may retain particles based on chemical interactions. The chemical interactions may be covalent and/or noncovalent interactions, including ionic, electrostatic, hydrophobic, van der Waals, and/or metal coordination interactions, among others. Chemical interactions may retain particles selectively and/or nonselectively. Selective and nonselective retention may be based on specific and/or nonspecific chemical interactions between particles and passage surfaces.

Chemical interactions may be specific. Specific mechanisms may use specific binding pairs (SBPs), for example, with first and second SBP members disposed on particles and passage surfaces, respectively. Exemplary SBPs may include biotin/avidin, antibody/antigen, lectin/carbohydrate, etc. These and additional exemplary SBPs are listed below in Table 1, with the designations of first and second being arbitrary. SBP members may be disposed locally within microfluidic networks before, during and/or after formation of the networks. For example, surfaces of a substrate and/or a fluid layer component may be locally modified by adhesion/attachment of a SBP member before the substrate and fluid layer component are joined. Alternatively, or in addition, an SBP member may be locally associated with a portion of a microfluidic network after the network has been formed, for example, by local chemical reaction of the SBP member with the network (such as catalyzed by local illumination with light).

TABLE 1

Representative Specific Binding Pairs

| First SBP Member | Second SBP Member |
| --- | --- |
| Antigen | antibody |
| Biotin | avidin or streptavidin |
| Carbohydrate | lectin or carbohydrate receptor |
| DNA | antisense DNA or DNA-binding protein |
| enzyme substrate or inhibitor | enzyme |
| Histidine | NTA (nitrilotriacetic acid) |
| IgG | protein A or protein G |
| RNA | antisense RNA |

Chemical interactions also may be relatively nonspecific. Nonspecific interaction mechanisms may rely on local differences in the surface chemistry of microfluidic networks. Such local differences may be created before, during and/or after passage/microfluidic network formation, as described above. The local differences may result from localized chemical reactions, for example, to create hydrophobic or hydrophilic regions, and/or localized binding of materials. The bound materials may include poly-L-lysine, poly-D-lysine, polyethylenimine, albumin, gelatin, collagen, laminin, fibronectin, entactin, vitronectin, fibrillin, elastin, heparin, keratan sulfate, heparan sulfate, chondroitin sulfate, hyaluronic acid, and/or extracellular matrix extracts/mixtures, among others.

Other Retention Mechanisms

Other retention mechanisms may be used alternatively, or in addition to, physical barrier-based and/or chemical interaction-based retention. Some or all of these mechanisms, and/or the mechanisms described above, may rely at least partially on friction between particles and passages to assist retention.

Retention mechanisms may be based on vacuum forces, fluid flow, and/or gravity. Vacuum-based retention mechanisms may exert forces that pull particles into tighter contact with passage surfaces, for example, using a force directed outwardly from a channel. Application of a vacuum, and/or particle retention, may be assisted by an aperture/orifice in the wall of a channel or other passage. By contrast, fluid flow-based retention mechanisms may produce fluid flow paths, such as loops, that retain particles. These fluid flow paths may be formed by a closed channel-circuit having no outlet (e.g., by valve closure and active pumping), and/or by an eddy, such as that produced by generally circular fluid-flow within a recess. Gravity-based retention mechanisms may hold particles against the bottom surfaces of passages, thus combining with friction to restrict particle movement. Gravity-based retention may be facilitated by recesses and/or reduced fluid flow rates. Further aspects of vacuum-based and fluid flow-based retention mechanisms are described below in Examples 11 and 12, and Example 10, respectively.

Retention mechanisms may be based on centrifugal forces, magnetic forces, and/or optically generated forces. Retention mechanisms based on centrifugal force may retain particles by pushing the particle against passage surfaces, typically by exerting a force on the particles that is generally orthogonal to fluid flow. Such forces may be exerted by centrifugation of a microfluidic chip and/or by particle movement within a fluid flow path (see Example 9). Magnetic force-based retention mechanisms may retain particles using magnetic fields, generated external and/or internal to a microfluidic system. The magnetic field may interact with ferromagnetic and/or paramagnetic portions of particles. For example, beads may be formed at least partially of ferromagnetic materials, or cells may include surface-bound or internalized ferromagnetic particles. Electrical force-based retention mechanisms may retain charged particles and/or populations using electrical fields. By contrast, retention mechanisms that operate based on optically generated forces may use light to retain particles. Such mechanisms may operate based on the principal of optical tweezers, among others.

Another form of retention mechanism is a blind-fill channel, where a channel has a inlet, but no outlet, either fixedly or transiently. For example, when the microfluidic device is made from a gas permeable material, such as PDMS, gas present in a dead-end channel can escape, or be forced out of the channel through the gas permeable material when urged out by the inflow of liquid through the inlet. This is a preferred example of blind-filling. Blind-filling can be used with a channel or chamber that has an inlet, and an outlet that is gated or valved by a valve. In this example, blind filling of a gas filled channel or chamber occurs when the outlet valve is closed while filling the channel or chamber through the inlet. If the inlet also has a valve, that valve can then be closed after the blind fill is complete, and the outlet can then be opened to expose the channel or chamber contents to another channel or chamber. If a third inlet is in communication with the channel or chamber, that third inlet can introduce another fluid, gas or liquid, into the channel or chamber to expel the blind-filled liquid to be expelled from the channel or chamber in a measured amount. The result is similar to a sample loop system of an HPLC.

Further Aspects of Retention Mechanisms are Described in Sections V and XIII.

Treatment Mechanisms

Overview

Treatment mechanisms generally comprise any suitable mechanisms for exposing a particle(s) to a reagent(s) and/or a physical condition(s), including fluid-mediated and non-fluid-mediated mechanisms.

Reagents

Particles may be exposed to reagents. A reagent generally comprises any chemical substance(s), compound(s), ion(s), polymer(s), material(s), complex(es), mixture(s), aggregate(s), and/or biological particle(s), among others, that contacts a particle or particle population in a microfluidic system. Reagents may play a role in particle analysis, including operating as chemical/biological modulators (interaction reagents), detection/assay reagents, solvents, buffers, media, washing solutions, and/or so on.

Chemical modulators or biological modulators may include any reagent that is being tested for interaction with particles. Interaction generally includes specific binding to particles and/or any detectable genotypic and/or phenotypic effect on particles (or modulators). Further aspects of interactions and genotypic/phenotypic effects that may be suitable are described below in Section XII.

Chemical modulators may include ligands that interact with receptors (e.g., antagonists, agonists, hormones, etc.). Ligands may be small compounds, peptides, proteins, carbohydrates, lipids, etc. Further aspects of ligands and receptors, and their use in measuring interaction, or effects on signal transduction pathways, are described below in Section XII.

Alternatively, or in addition, chemical modulators may be nucleic acids. The nucleic acids may be DNA, RNA, peptide nucleic acids, modified nucleic acids, and/or mixtures thereof, and may be single, double, and/or triple-stranded. The nucleic acids may be produced by chemical synthesis, enzymatic synthesis, and/or biosynthesis, and may be plasmids, fragments, sense/antisense expression vectors, reporter genes, vectors for genomic integration/modification (such as targeting nucleic acids/vectors (for knockout/-down/-in)), viral vectors, antisense oligonucleotides, dsRNA, siRNA, nucleozymes, and/or the like. Nucleic acid reagents may also include transfection reagents to promote uptake of the nucleic acids by cells, such as lipid reagents (e.g., lipofectamine), precipitate-forming agents (such as calcium phosphate), DMSO, polyethylene glycol, viral coats that package the nucleic acids, and/or so on.

Modulators may be miscellaneous chemical materials and/or biological entities. Miscellaneous chemical modulators may be ions (such as calcium, sodium, potassium, lithium, hydrogen (pH), chloride, fluoride, iodide, etc.), dissolved gases (NO, $CO_2$, $O_2$, etc.), carbohydrates, lipids, organics, polymers, etc. In some embodiments, biological modulators may be exposed to cells, for example, to infect cells, to measure cell-cell interactions, etc. Biological modulators may include any cells, viruses, or organelles, as described above in Section III.

Reagents may be detection/assay reagents. Detection/assay reagents generally comprise any reagents that are contacted with particles to facilitate processing particles (or particle components) for detection of a preexisting or newly created aspect of the particles (or components). Detection/assay reagents may include dyes, enzymes, substrates, cofactors, and/or SBP members (see Table 1 of Section VI above), among others. Dyes, also referred to as labels, generally include any optically detectable reagent. Suitable dyes may be luminophores, fluorophores, chromogens, chromophores, and/or the like. Such dyes may be conjugated to, or may be, SBP members; may act as enzyme substrates; may inherently label cells or cell structures (e.g., DNA dyes, membrane dyes, trafficking dyes, etc.); may act as indicator dyes (such as calcium indicators, pH indicators, etc.); and/or the like. Enzymes may operate in particle assays by incorporating dyes into products and/or by producing a product that may be detected subsequently with dyes, among others. Suitable enzymes may include polymerases (RNA and/or DNA), heat-stable polymerases (such as Taq, VENT, etc.), peroxidases (such as HRP), phosphatases (such as alkaline phosphatase), kinases, methylases, ligases, proteases, galactosidases (such as beta-galactosidase, glucuronidase, etc.), transferases (such as chloramphenicol acetyltransferase), oxidoreductases (such as luciferase), and/or nucleases (such as DNAses, RNAses, etc.), among others. SBP members, such as antibodies, digoxigenin, nucleic acids, etc., may be directly conjugated to dyes, enzymes, and/or other SBP members; may be noncovalently bound to dyes and/or enzymes (either pre-bound or bound in an additional exposure step); and/or so on. Further aspects of detection/assay reagents, including the types of assays in which these reagents may be used, are described below in Section XII.

Fluid-Mediated Mechanisms

Treatment mechanisms may use fluid-mediated mechanisms to expose particles to reagents. The reagents may be brought to the particles, for example, when the particles are retained, or the particles may be brought to the reagents, for example, when the reagents are present (and optionally retained) in specific portions of fluid networks.

Fluid-mediated mechanisms may be flow-based, field-based, and/or passive, among others. Flow-based treatment mechanisms may operate by fluid flow, mediated, for example, by gravity flow or active flow (pumping), to carry reagents to particles, or vice versa. In some embodiments, the flow-based treatment mechanisms may operate by regulated transverse (side-to-side) positioning, as described above/below in Sections V and XIII, to precisely regulate exposure of reagents (or particles) to particles (or reagents). By contrast, field-based mechanisms may combine particles and reagents by moving reagents (or particles) with electric fields. The electric fields may produce any suitable electrokinetic effects, such as electrophoresis, dielectrophoresis, electroosmosis, etc. Alternatively, or in addition, reagents may be combined with particles by diffusion of the reagents.

Non-Flow-Mediated Mechanisms

Particles in microfluidic systems may be exposed to physical modulators/conditions using non-fluid-mediated mechanisms. However, these "non-fluid-mediated" mechanisms may use properties of fluid to assist in their operation, such as transfer of thermal energy or pressure to particles via fluid. The physical modulators/conditions may be applied to particles from sources that are external and/or internal to the microfluidic systems. Exemplary physical modulators/conditions may include thermal energy (heat), radiation (light), radiation (particle), an electric field, a magnetic field, pressure (including sound), a gravitational field, etc.

Treatment Targets

Treatment mechanisms may act on any suitable particles, including any of the particles described above in Section III. The particles may be intact, permeabilized, and/or lysed. Accordingly, treatment mechanisms may act on released cell components. Particles may be treated in arrays, either serially, for example, using a shared treatment mechanism, and/or in parallel, for example, using distinct and/or shared treatment mechanisms.

Further aspects of treatment mechanisms are described above in Section V (positioning reagents/fluid/particles) and below in Section XIII.

Measurement Mechanisms

Overview

Particles manipulated by a microfluidic system may be analyzed by one or more measurement mechanisms at one or more measurement sites. The measurement mechanisms generally comprise any suitable apparatus or method for detecting a preselected particle or particle characteristic (provided, for example, by the particle, a particle component, and/or an assay product, among others). The measurement sites generally comprise any suitable particle position or positions at which a measurement is performed, internal and/or external to the system.

Detection Methods

The measurement mechanism may employ any suitable detection method to analyze a sample, qualitatively and/or quantitatively. Suitable detection methods may include spectroscopic methods, electrical methods, hydrodynamic methods, imaging methods, and/or biological methods, among others, especially those adapted or adaptable to the analysis of particles. These methods may involve detection of single or multiple values, time-dependent or time-independent (e.g., steady-state or endpoint) values, and/or averaged or (temporally and/or spatially) distributed values, among others. These methods may measure and/or output analog and/or digital values.

Spectroscopic methods generally may include detection of any property of light (or a wavelike particle), particularly properties that are changed via interaction with a sample. Suitable spectroscopic methods may include absorption, luminescence (including photoluminescence, chemiluminescence, and electrochemiluminescence), magnetic resonance (including nuclear and electron spin resonance), scattering (including light scattering, electron scattering, and neutron scattering), diffraction, circular dichroism, and optical rotation, among others. Suitable photoluminescence methods may include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), fluorescence activated cell sorting (FACS), and their phosphorescence and other analogs, among others.

Electrical methods generally may include detection of any electrical parameter. Suitable electrical parameters may include current, voltage, resistance, capacitance, and/or power, among others.

Hydrodynamic methods generally may include detection of interactions between a particle (or a component or derivative thereof) and its neighbors (e.g., other particles), the solvent (including any matrix), and/or the microfluidic system, among others, and may be used to characterize molecular size and/or shape, or to separate a sample into its components. Suitable hydrodynamic methods may include chromatography, sedimentation, viscometry, and electrophoresis, among others.

Imaging methods generally may include detection of spatially distributed signals, typically for visualizing a sample or its components, including optical microscopy and electron microscopy, among others.

Biological methods generally may include detection of some biological activity that is conducted, mediated, and/or influenced by the particle, typically using another method, as described above. Suitable biological methods are described below in detail in Section XII.

Detection Sites

The measurement mechanism may be used to detect particles and/or particle characteristics at any suitable detection site, internal and/or external to the microfluidic system.

Suitable internal detection sites may include any site(s) in or on a microfluidic system (a chip). These sites may include channels, chambers, and/or traps, and portions thereof. Particles or particle characteristics may be detected while the particles (or released components/assay products) are stationary or moving. Stationary particles may be encountered following particle retention, for example, cells growing in a cell chamber. Moving particles may be encountered before and/or after particle retention, or upon confinement to a region. In particular, particles may be moved past a detection site by any suitable positioning mechanism, for example, by fluid flow (flow-based detection).

Suitable external detection sites may include any site(s) away from or independent of a microfluidic system. External detection sites may be used to detect a particle or particle characteristic after removal of particles (or particle components) from a microfluidic system. These external sites may be used instead of and/or in addition to internal sites, allowing particles (or particle components) to be further manipulated and/or detected. These further manipulations and/or detection methods may overlap with, but preferably complement, the manipulations and/or methods performed in the microfluidic system, including mass spectrometry, electrophoresis, centrifugation, PCR, introduction into an organism, use in clinical treatment, and/or cell culture, among others.

Detected Characteristics

The measurement method may detect and/or monitor any suitable characteristic of a particle, directly and/or indirectly (e.g., via a reporter molecule). Suitable characteristics may include particle identity, number, concentration, position (absolute or relative), composition, structure, sequence, and/or activity among others. The detected characteristics may include molecular or supramolecular characteristics, such as the presence/absence, concentration, localization, structure/modification, conformation, morphology, activity, number, and/or movement of DNA, RNA, protein, enzyme, lipid, carbohydrate, ions, metabolites, organelles, added reagent (binding), and/or complexes thereof, among others. The detected characteristics also may include cellular characteristics, such as any suitable cellular genotype or phenotype, including morphology, growth, apoptosis, necrosis, lysis, alive/dead, position in the cell cycle, activity of a signaling pathway, differentiation, transcriptional activity, substrate attachment, cell-cell interaction, translational activity, replication activity, transformation, heat shock response, motility, spreading, membrane integrity, and/or neurite outgrowth, among others.

Further aspects of detected characteristics and their use in particle assays are described below in Sections XII and XIII.

Release Mechanisms

Overview

A microfluidic system may include any suitable number of particle release mechanisms. A release mechanism generally comprises any mechanism(s) for allowing a retained particle to move away from a preselected site/area at which it is retained, including removing, overcoming, and/or rendering ineffective the retention mechanism(s) that retains the particle. Release mechanisms that are suitable may be selected based, at least partially, on the retaining force. After release, particles (or particle components) may have any suitable destination.

Removing the Retaining Force

A release mechanism may operate by removing the retaining force. Accordingly, particles that are retained by a specific mechanism may be released by terminating that mechanism. For example, particles retained by a chemical interaction/bond may be released by cleaving the bond, such as with a protease(s) (e.g., trypsin), or otherwise disrupting the interaction, such as with altered ionic conditions (e.g., with EDTA) or pH, or with an excess of a SBP member. Similarly, particles retained by a physical barrier, such as a closed valve, may be released by moving/removing the barrier. Furthermore, particles retained by fluid flow, a vacuum, light, an electrical field, a magnetic field, and/or a centrifugal force may be released by removing/redirecting the corresponding flow, force, field, etc.

Overcoming the Retaining Force

A release mechanism may operate by overcoming a retaining force with a greater force. Accordingly, particles may be released by any positioning mechanism(s) that applies a force greater than the retaining force. For example, retained particles may be released by a releasing flow. The releasing flow may be an increased flow rate in the direction of bulk fluid flow, for example, when a particle is weakly retained (such as by gravity/friction, or weak chemical interactions). Alternatively, the releasing flow may act counter to a retaining flow, for example orthogonal or opposite to the retaining flow. For example, the releasing flow may reposition particles to be out of contact with a retaining physical barrier (see Example 7). Alternatively, or in addition, retained particles may be released by any other suitable positioning mechanism(s), as described above in Section V, that is capable of generating sufficient force.

Rendering Ineffective the Retaining Force

A release mechanism may operate by rendering ineffective the retaining force on a particle. Such a release mechanism may operate by releasing components of the particle. For example, retained cells may be lysed to release intracellular components, producing a lysate, or beads may be treated to release associated materials and/or to fragment/disintegrate the beads. Lysis generally includes any partial or complete disruption of the integrity of a cell-surface membrane, and may be produced via temperature, a detergent, a ligand, chemical treatment, a change in ionic strength, an electric field, etc.

Destination of Released Particles/Components

Released particles and/or particle components may have any suitable destination(s). Suitable immediate destinations may include a positioning mechanism and/or fluid surrounding the particles. After release, particles may be repositioned with a positioning mechanism, either nonselectively or selectively. Selective positioning may position the particle based on a measured characteristic. Positioning may be to a second retention mechanism (and/or a culture chamber), to a detection mechanism (such as a flow-based mechanism), and/or to an output mechanism. Fluid surrounding the particles may be a suitable destination for particle components (such as cells lysates and/or bead components) to be contacted with detection/assay reagents. Alternatively, cell lysates and/or bead components may be repositioned as with intact particles.

Further aspects of release mechanisms and destinations of released particles/components are described below in Section XIII.

Output Mechanisms

Microfluidic systems may include one or more output mechanisms that interface with the microfluidic network(s). An output mechanism generally comprises any suitable mechanism for outputting material(s) (e.g., fluid, particles, and/or reagents) from a microfluidic system, or portions thereof, including selective and/or bulk mechanisms. The output mechanism may direct outputted material to any suitable location, such as an internal and/or external sink. A sink generally comprises any receptacle or other site for receiving outputted materials, for disposal (e.g., a waste site) or for further study or manipulation (e.g., a collection site). The outputting of materials from the microfluidics system may be facilitated and/or regulated using any suitable facilitating mechanism, such as sources of internal pressure and/or external vacuum. The output mechanism may include a selection mechanism, such as a filter, that selects outputted materials based on some criterion, such as whether the material is a particle or a fluid.

Cell Culture Mechanisms

Overview

Cells may be cultured using a cell culture mechanism in microfluidic systems. The cell culture mechanism generally comprises any suitable mechanism for growing cells, including maintenance and/or propagation. Suitable cells are described above in Section III.

Structural Matters

A cell culture mechanism of a microfluidic system may include one or more culture chambers in which to culture cells. Culture chambers may have any suitable size, shape, composition, and/or relationship to other aspects of microfluidic systems, based on the number of cells to be cultured, size of cells, assays to performed on the cells, and/or growth characteristics of the cells, among others. The size of a culture chamber may be only large enough to hold one cell, several cells or more (2 to 50), or many cells (50 to 1000 or more) of a given cell size. Accordingly, culture chambers may be defined by a selected portion of a passage, an entire passage, or a set of passages. In some embodiments, culture chambers may be formed by substantially enlarged channels. Culture chambers may have any suitable height that allows cells of interest to enter the chamber. This height may be greater than, less than, and/or equal to other portions of the microfluidic network. Some or all of the surfaces of a culture chamber, such as the walls, roof, and/or substrate, may be treated or modified to facilitate aspects of cell culture, particularly specific or nonspecific cell attachment, cell survival, cell growth, and/or cell differentiation (or lack thereof), among others. Suitable methods of passage treatment and treatment agents are described above in Section VI, relative to chemical retention mechanisms.

Culture Conditions

The cell culture mechanism may culture cells under any suitable environmental conditions using any appropriate environmental control mechanisms. Suitable environmental conditions may include a desired gas composition, temperature, rate and frequency of media exchange, and/or the like. Environmental control mechanisms may operate internal and/or external to a microfluidic system. Internal mechanisms may include on-board heaters, gas conduits, and/or media reservoirs. External mechanisms may include an atmosphere- and/or temperature-controlled incubator/heat source, and/or a media source external to the system. An atmosphere-controlled incubator may be more suitable when the system is at least partially formed of a gas-permeable material, such as PDMS. Media, including gas-conditioned media, may be introduced from an external source by any suitable input mechanism, including manual pipetting, automated pipetting, noncontact spitting, etc. In some embodiments, the chip may be preincubated with media, which may then be discarded, prior to the introduction of cells and/or other biological materials.

Further aspects of cell culture mechanisms, culture chambers, and culture conditions are described below in Example 10, and the materials listed in Cross-References, particularly R. Ian Freshney, Culture of Animal Cells: A Manual of Basic Technique ($4^{th}$ ed. 2000), which is incorporated herein by reference.

Particle-Based Manipulations

Overview

Microfluidic systems are used for particle manipulations. Particle manipulations generally comprise any suitable sequence of unitary operations, for performing a desired function or assay. Unitary operations may be performed by each of the mechanisms described above in Sections IV to X, among others.

Exemplary Sequences of Operations

FIG. 1 shows an exemplary method 100 for microfluidic manipulation and analysis of particles with systems of the invention. Each step of method 100 may be repeated any suitable number of times and in any appropriate order, as described below, based on the application. Exemplary sequences of steps are indicated by arrows.

Particles typically are initially inputted in an input step, shown at 101. Particle input introduces particles to a microfluidic system and may be mediated by any of the input mechanisms described above in Section IV.

Particles next are typically positioned, shown at 102. Positioning moves particles to selected positions along passages (longitudinal positioning), and/or to selected positions along one or more axes generally orthogonal to the long axis (transverse positioning). Suitable positioning mechanisms that mediate one or both of these particle movements are described above in Section V.

Particle positioning may lead to one of two paths, shown at 103 and 104. Path 103 leads to particle output, shown at 105. Particle output may be mediated by one of the output mechanisms described above in Section X, and may be used to discard, collect, and/or transfer particles for further analysis, among others. Path 104 leads to one or more of three operations, particle retention 106, particle treatment 107, and/or particle measurement/detection 108. These operations may be conducted in any suitable order, for any desired number of times. Particle retention mechanisms, treatment mechanisms, and measurement mechanisms are described above in Sections VI, VII, and VIII, respectively.

The steps of treating and/or measuring particles may be carried out with or without particle retention. Accordingly, the steps of treating and/or measuring particles may be followed directly by additional positioning 102, or first may use a release step, shown at 109, if particles have been retained. Suitable release mechanisms are described above in Section IX. Alternatively, microfluidic systems may be discarded before particle release, additional positioning, and/or output.

Particles that have returned to the positioning step after entering path 104 may be manipulated further. Some or all of these particles may be repositioned to path 103 to be outputted 105. Alternatively, or in addition, some or all of these particles may be directed back to path 104 to be further treated, retained, and/or measured. Therefore, method 100 enables any suitable sequence of particle manipulations and analyses at one or plural positions within a microfluidic system.

Exemplary sequences of operations may be illustrated further as follows. For the following discussion, the operations performed by the steps of method 100 are abbreviated with the following single underlined letters: Input, Position, Retain, Treat, Measure, rElease, and Output.

A basic manipulation of microfluidic analyses is IP. This sequence of steps may lead to output (IPO) or to (path 104), resulting in the basic retention sequence IPR, flow-based measurement, IPM, or flow-based treatment, IPT.

Retained particles may be subjected to any suitable additional steps. The particles may be treated (IPRT), measured (IPRM), repeatedly measured over time (IPRMMM . . . ), treated and then measured (IPRTM), or repeatedly treated and measured (IPRTMTMTM . . . ). Retained particles may be released (IPR . . . E) after optional treatment and/or measurement. Released particles may be repositioned and then outputted (IPR . . . EPO); measured during flow (IPR . . . EPM); treated (IPR . . . EPT); treated and measured (IPR . . . EPTM); retained and treated (IPR . . . EPRT); retained, treated, and measured, (IPR . . . EOPRTM); and/or so on.

Cell-Based Assays/Methods

The microfluidic systems of the invention may be used for any suitable cell assays or methods, including any combinations of cells, cell selection(s) (by selective retention), treatment(s), and/or measurement(s), as described above in Sections III, VI, VII, and VIII, respectively.

The cell assays may characterize cells, either with or without addition of a modulator. Cell assays may measure cell genotypes, phenotypes, and/or interactions with modulators. These assays may characterize individual cells and/or cell populations/groups of any suitable size. Cells may be characterized in the absence of an added modulator to define one or more characteristics of the cells themselves. Alternatively, or in addition, cell may be characterized in the presence of an added modulator to measure interaction(s) between the cells and the modulator. Moreover, cells may be exposed to a selected concentration of a reagent, or a plurality of concentrations of a reagent. In other embodiments, cells are exposed to a gradient of concentrations of reagent to determine whether such cells will be attracted or repelled by increasing amounts of such reagent.

In other embodiments, a quantity of cells may be measured out by first filling a measuring chamber having at least one inlet, the inlet having at least one valve, where the valve is opened, cells are introduced into the chamber, preferably by blind filling a dead-end chamber, or by opening up an outlet valve to an outlet in communication with the chamber, the outlet having a retention mechanism for preventing the cells from exiting the chamber. The measure amount of cells is then displaced to a culturing region for culturing.

In other embodiments, a first type of cell is grown in fluid communication with a second type of cell, wherein the first type of cell is affected by the presence of the second type of cell, preferably as a co-culture or feeder type relationship. The cells of the first type and the cells of the second type are kept separate from each other by a retention mechanism, although fluid, preferably liquid, is permitted to be in joint contact with each type of cell so that sub-cellular or biochemical materials may be exchanged between cell types.

Genotypic Assays

Genotypic assays may be conducted on cells in microfluidic systems to measure the genetic constitution of cells. The genotypic assays may be conducted on any suitable cell or cell populations, for example, patient samples, prenatal samples (such as embryonic, fetal, chorionic villi, etc.), experimentally manipulated cells (such as transgenic cells), and/or so on. Such genotypic aspects may include copy number (such as duplication, deletion, amplification, and/or the like) and/or structure (such as rearrangement, fusion, number of repeats (such as dinucleotide, triplet repeats, telomeric repeats, etc.), mutation, gene/pseudogene, specific allele, presence/absence/identity/frequency of single nucleotide polymorphisms, integration site, chromosomal/episomal, and/or the like) of a nuclear and/or mitochondrial gene(s), genomic region(s), and/or chromosomal region (s) (such as telomeres, centromeres, repetitive sequences, etc.). Methods for genotypic assays may include nucleic acid hybridization in situ (on intact cells/nuclei) or with DNA released from cells, for example, by lysing the cells. Nucleic acid hybridization with nucleic acids may be carried out with a dye-labeled probe, a probe labeled with a specific binding pair (see Section VI), a stem-loop probe carrying an energy transfer pair (such as a "molecular beacon"), and/or with a probe that is labeled enzymatically after hybridization (such as by primer extension with a polymerase, modification with terminal transferase, etc). Alternatively, or in addition, methods for genotypic assays may include polymerase-mediated amplification of nucleic acids, for example, by thermal cycling (PCR) or by isothermal strand-displacement methods. In some embodiments, genotypic assays may use electrophoresis to assist in analysis of nucleic acids. Related gene-based assays may measure other aspects of gene regions, genes, chromosomal regions, whole chromosomes, or genomes, using similar assay methods, and suitable probes or DNA dyes (such as propidium iodide, Hoechst, etc.). These other aspects may include total DNA content (for example 2N, 4N, 8N, etc., to measure diploid, tetraploid, or polyploid genotypes and/or cell cycle distribution), number or position of specific chromosomes, and/or position of specific genes (such as adjacent the nuclear membrane, another nuclear structure, and so on).

Phenotypic Assays

Phenotypic assays may be conducted to characterize cells in microfluidic systems, based on genetic makeup and/or environmental influences, such as presence of modulators. These assays may measure any molecular or cellular aspect of whole cells, cellular organelles, and/or endogenous (native) or exogenous (foreign) cell constituents/components.

Aspects of a whole cell or whole cell population may include number, size, density, shape, differentiation state, spreading, motility, translational activity, transcriptional activity, mitotic activity, replicational activity, transformation, status of one or more signaling pathways, presence/absence of processes, intact/lysed, live/dead, frequency/extent of apoptosis or necrosis, presence/absence/efficiency of attachment to a substrate (or to a passage), growth rate, cell cycle distribution, ability to repair DNA, response to heat shock, nature and/or frequency of cell-cell contacts, etc.

Aspects of cell organelles may include number, size, shape, distribution, activity, etc. of a cell's (or cell population's) nuclei, cell-surface membrane, lysosomes, mitochondria, Golgi apparatus, endoplasmic reticulum, peroxisomes, nuclear membrane, endosomes, secretory granules, cytoskeleton, axons, and/or neurites, among others.

Aspects of cell constituents/components may include presence/absence or level, localization, movement, activity, modification, structure, etc. of any nucleic acid(s), polypeptide(s), carbohydrate(s), lipid(s), ion(s), small molecule, hormone, metabolite, and/or a complex(es) thereof, among others. Presence/absence or level may be measured relative to other cells or cell populations, for example, with and without modulator. Localization may be relative to the whole cell or individual cell organelles or components. For example, localization may be cytoplasmic, nuclear, membrane-associated, cell-surface-associated, extracellular, mitochondrial, endosomal, lysosomal, peroxisomal, and/or so on. Exemplary cytoplasmic/nuclear localization may include transcription factors that translocate between these two locations, such as NF-κB, NFAT, steroid receptors, nuclear hormone receptors, and/or STATs, among others. Movement may include intracellular trafficking, such as protein targeting to specific organelles, endocytosis, exocytosis, recycling, etc. Exemplary movements may include endocytosis of cell-surface receptors or associated proteins (such as GPCRs, receptor tyrosine kinases, arrestin, and/or the like), either constitutively or in response to ligand binding. Activity may include functional or optical activity, such as enzyme activity, fluorescence, and/or the like, for example, mediated by kinases, phosphatases, methylases, demethylases, proteases, nucleases, lipases, reporter proteins (for example beta-galactosidase, chloramphenicol acetyltransferase, luciferase, glucuronidase, green fluorescent protein (and related derivatives), etc.), and/or so on. Modification may include the presence/absence, position, and/or level of any suitable covalently attached moiety. Such modifications may include phosphorylation, methylation, ubiquitination, carboxylation, and/or farnesylation, among others. Structure may include primary structure, for example after processing (such as cleavage or ligation), secondary structure or tertiary structure (e.g., conformation), and/or quaternary structure (such as association with partners in, on, or about cells). Methods for measuring modifications and/or structure may include specific binding agents (such as antibodies, etc.), in vivo or in vitro incorporation of labeled reagents, energy transfer measurements (such as FRET), surface plasmon resonance, and/or enzyme fragment complementation or two-hydrid assays, among others.

Nucleic acids may include genomic DNA, mitochondrial DNA, viral DNA, bacterial DNA, phage DNA, synthetic DNA, transfected DNA, reporter gene DNA, etc. Alternatively, or in addition, nucleic acids may include total RNAs, hnRNAs, mRNAs, tRNAs, siRNAs, dsRNAs, snRNAs, ribozymes, structural RNAs, viral RNAs, bacterial RNAs, gene-specific RNAs, reporter RNAs (expressed from reporter genes), and/or the like. Methods for assaying nucleic acids may include any of the techniques listed above under genotypic assays. In addition, methods for assaying nucleic acids may include ribonuclease protection assays.

Polypeptides may include any proteins, peptides, glycoproteins, proteolipids, etc. Exemplary polypeptides include receptors, ligands, enzymes, transcription factors, transcription cofactors, ribosomal components, regulatory proteins, cytoskeletal proteins, structural proteins, channels, transporters, reporter proteins (such as those listed above which are expressed from reporter genes), and/or the like. Methods for measuring polypeptides may include enzymatic assays and/or use of specific binding members (such as antibodies, lectins, etc.), among others. Specific binding members are described in Section VI.

Carbohydrates, lipids, ions, small molecules, and/or hormones may include any compounds, polymers, or complexes. For example, carbohydrates may include simple sugars, di- and polysaccharides, glycolipids, glycoproteins, proteoglycans, etc. Lipids may include cholesterol and/or inositol lipids (e.g., phosphoinositides), among others; ions may include calcium, sodium, chloride, potassium, iron, zinc, hydrogen, magnesium, heavy metals, and/or manganese, among other; small molecules and/or hormones may include metabolites, and/or second messengers (such as cAMP or cGMP, among others), and/or the like. Concentration gradients and/or movement of ions may provide electrical measurements, for example, by patch-clamp analysis, as described in Examples 11 and 12.

Interaction Assays

Interaction generally comprises any specific binding of a modulator to a cell or population of cells, or any detectable change in a cell characteristic in response to the modulator. Specific binding is any binding that is predominantly to a given partner(s) that is in, on, or about the cell(s). Specific binding may have a binding coefficient with the given partner of about $10^{-3}$ M and lower, with preferred specific binding coefficients of about $10^{-4}$ M, $10^{-6}$ M, or $10^{-8}$ M and lower. Alternatively, interaction may be any change in a phenotypic or genotypic characteristic, as described above, in response to the modulator.

Interaction assays may be performed using any suitable measurement method. For example, the modulator may be labeled, such as with an optically detectable dye, and may be labeled secondarily after interaction with cells. Binding of the dye to the cell or cells thus may be quantified. Alternatively, or in addition, the cell may be treated or otherwise processed to enable measurement of a phenotypic characteristic produced by modulator contact, as detailed above and in Section VIII.

Cells and/or cell populations may be screened with libraries of modulators to identify interacting modulators and/or modulators with desired interaction capabilities, such as a desired phenotypic effect (such as reporter gene response, change in expression level of a native gene/protein, electrophysiological effect, etc.) and/or coefficient of binding. A library generally comprises a set of two or more members (modulators) that share a common characteristic, such as structure or function. Accordingly, a library may include two or more small molecules, two or more nucleic acids, two or more viruses, two or more phages, two or more different types of cells, two or more peptides, and/or two or more proteins, among others.

Signal Transduction Assays

Microfluidic assays of cells and/or populations may measure activity of signal transduction pathways. The activity may be measured relative to an arbitrary level of activity, relative to other cells and/or populations (see below), and/or as a measure of modulator interaction with cells (see above).

Signal transduction pathways generally comprise any flow of information in a cell. In many cases, signal transduction pathways transfer extracellular information, in the form of a ligand(s) or other modulator(s), through the membrane, to produce an intracellular signal. The extracellular information may act, at least partially, by triggering events at or near the membrane by binding to a cell-surface receptor, such as a G Protein-Coupled Receptor (GPCR), a channel-coupled receptor, a receptor tyrosine kinase, a receptor serine/threonine kinase, and/or a receptor phosphatase, among others. These events may include changes in channel activity, receptor clustering, receptor endocytosis, receptor enzyme activity (e.g., kinase activity), and/or second messenger production (e.g., cAMP, cGMP, diacylglcyerol, phosphatidylinositol, etc.). Such events may lead to a cascade of regulatory events, such as phosphorylation/dephosphorylation, complex formation, degradation, and/or so on, which may result, ultimately, in altered gene expression. In other cases, modulators pass through the membrane and directly bind to intracellular receptors, for example with nuclear receptors (such as steroid receptors (GR, ER, PR, MR, etc.), retinoid receptors, retinoid X receptor (RXRs), thyroid hormone receptors, peroxisome proliferation-activating receptors (PPARs), and/or xenobiotic receptors, among others). Therefore, any suitable aspect of this flow of information may be measured to monitor a particular signal transduction pathway.

The activity measured may be based at least partially, on the type of signal transduction pathway being assayed. Accordingly, signal transduction assays may measure ligand binding; receptor internalization; changes in membrane currents; association of receptor with another factor, such as arrestin, a small G-like protein such as rac, or rho, and/or the like; calcium levels; activity of a kinase, such as protein kinase A, protein kinase C, CaM kinase, myosin light chain kinase, cyclin dependent kinases, PI3-kinase, etc.; cAMP levels; phosholipase C activity; subcellular distribution of proteins, for example, NF-κB, nuclear receptors, and/or STATs, among others. Alternatively, or in addition, signal transduction assays may measure expression of native target genes and/or foreign reporter genes that report activity of a signal transduction pathway(s). Expression may be measured as absence/presence or level of RNA, protein, metabolite, or enzyme activity, among others, as described above.

Comparison of Cells and/or Cell Populations

Cell-based assays may be used to compare genotypic, phenotypic, and/or modulator interaction of cells and/or populations of cells. The cells and/or populations may be compared in distinct microfluidic systems or within the same microfluidic system. Comparison in the same microfluidic system may be conducted in parallel using a side-by-side configuration, as exemplified by Example 3, in parallel at isolated sites, as exemplified by Example 4, and/or in series, as exemplified by Example 5.

Single-Cell Assays

Microfluidic systems may be used to perform single-cell assays, which generally comprise any assays that are preferably or necessarily performed on one cell at a time. Examples of single cell assays include patch-clamp analysis, single-cell PCR, single-cell fluorescence in situ hybridization (FISH), subcellular distribution of a protein, and/or differentiation assays (conversion to distinct cell types). In some cases, single-cell assays may be performed on a retained group of two or more cells, by measuring an individual characteristic of one member of the group. In other cases, single-cell assays may require retention of a single cell, for example, when the cell is lysed before the assay.

Sorting/Selection

Microfluidic systems may be used to sort or select single cells and/or cell populations. The sorted/selected cells or populations may be selected by stochastic mechanisms (see Example 2), size, density, magnetic properties, cell-surface properties (that is, ability to adhere to a substrate), growth and/or survival capabilities, and/or based on a measured characteristic of the cells or populations (such as response to a ligand, specific phenotype, and/or the like). Cells and/or populations may be sorted more than once during manipulation and/or analysis in a microfluidic system. In particular, heterogeneous populations of cells, such as blood samples or clinical biopsies, partially transfected or differentiated cell populations, disaggregated tissues, natural samples, forensic samples, etc. may be sorted/selected. Additional aspects of cell sorting and suitable cells and cell populations are described above in Section III and below in Examples 9, 15, 23, and 26.

Storage/Maintenance

Microfluidic systems may perform storage and/or maintenance functions for cells. Accordingly, cells may be introduced into micro fluidic systems and cultured for prolonged periods of time, such as longer than one week, one month, three months, and/or one year. Using microfluidic systems for storage and/or maintenance of cells may consume smaller amounts of media and space, and may maintain cells in a more viable state than other storage/maintenance methods. Additional aspects of storing and maintaining cells in microfluidic systems are included in Section XI above and Example 10 below.

Assays/Methods with Other Particles

Microfluidic systems may be used for any suitable virally based, organelle-based, bead-based, and/or vesicle-based assays and/or methods. These assays may measure binding (or effects) of modulators (compounds, mixtures, polymers, biomolecules, cells, etc.) to one or more materials (compounds, polymers, mixtures, cells, etc.) present in/on, or associated with, any of these other particles. Alternatively, or in addition, these assays may measure changes in activity (e.g., enzyme activity), an optical property (e.g., chemiluminescence, fluorescence, or absorbance, among others), and/or a conformational change induced by interaction.

In some embodiments, beads may include detectable codes. Such codes may be imparted by one or more materials having detectable properties, such as optical properties (e.g., spectrum, intensity, and or degree of fluorescence excitation/emission, absorbance, reflectance, refractive index, etc.). The one or more materials may provide nonspatial information or may have discrete spatial positions that contribute to coding aspects of each code. The codes may allow distinct samples, such as cells, compounds, proteins, and/or the like, to be associated with beads having distinct codes. The distinct samples may then be combined, assayed together, and identified by reading the code on each bead. Suitable assays for cell-associated beads may include any of the cell assays described above.

Suitable protocols for performing some of the assays described in this section are included in Joe Sambrook and David Russell, Molecular Cloning: A Laboratory Manual ($3^{rd}$ ed. 2000), which is incorporated herein by reference.

EXAMPLES

The following examples describe selected aspects and embodiments of the invention, including methods of fabricating, integrating, and using microfluidic systems, and devices, and mechanisms for manipulation and analysis of particles. These examples are included for illustration and are not intended to limit or define the entire scope of the invention.

Many of the examples presented below include figures showing molds, fluid layers, and/or control layers that are color-coded. Since molds and fluid or control layers have complementary patterns, the color-coded schemes generally represent both molds and fluid or control layers, although one or the other is often designated in the corresponding description. Throughout these examples, the colors of molds and/or fluidic layers have the following meanings: regions in red have a height of approximately 20 μm, and a rectangular cross-sectional geometry; regions in blue have a height of about 20 μm, and a semi-circular/arcuate cross-sectional geometry; regions in turquoise have a height of about 5 μm and a rectangular cross-sectional geometry; and regions in white are not raised from the general surface of the mold and/or form a portion of the substrate-contacting surface of a fluid layer. The widths of these regions are generally cited in the text.

Dimensions and cross-sectional geometries presented in these examples are exemplary only, being designed for particles of about 8 to 12 μm in diameter. Accordingly, any absolute or relative dimensions or cross-sectional geometries may be selected based the application and the size of input particles being analyzed. Thus, the regions in red and blue may have a height of about 0.5 to 100, 1 to 75, or 2 to 50 μm. Regions in turquoise may have a height of about 0.1 to 50, 0.2 to 25, or about 0.5 to 20 μm. In addition, these regions may have any suitable cross-sectional geometries based on the application. Furthermore, regions in red and blue may have any suitable width based on their function. For example, regions in red used for particle positioning may have widths of at least about 2, 10, 20, or 50 μm. By contrast, regions in red used for reagent dispensing may have smaller widths of at least about 0.2, 1, 2, or 5 μm. Regions in blue may have widths of at least about 5, 10, 20, or 50 μm.

Example 1

Cell Positioning and Retention Mechanisms

Figure 2A:
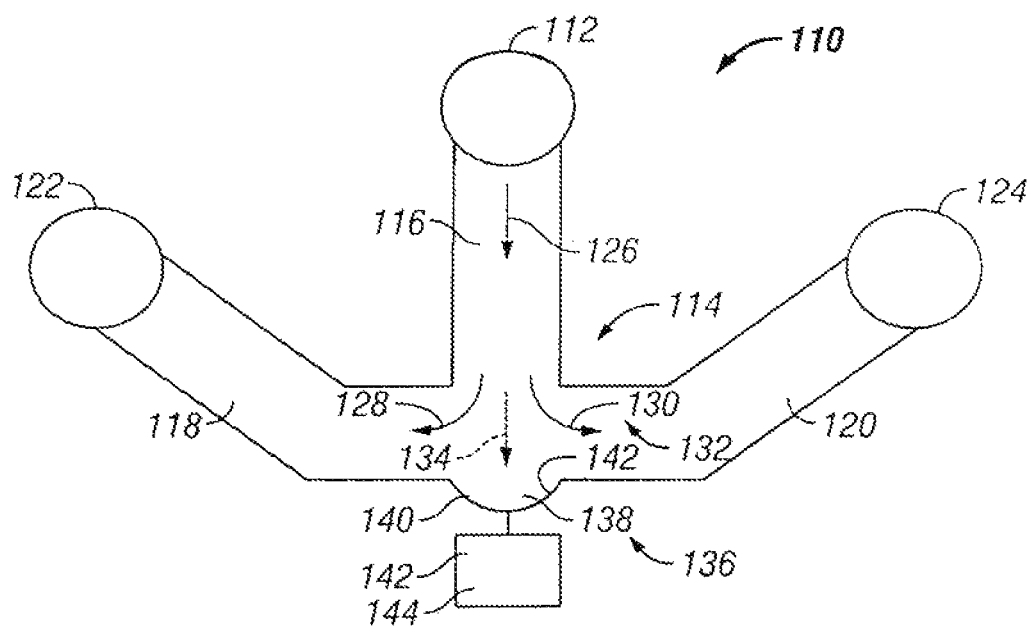
FIG. 2A is a top plan view of a microfluidic system for retaining and analyzing a subset of input particles, in accordance with aspects of the invention.
Figure 2B:
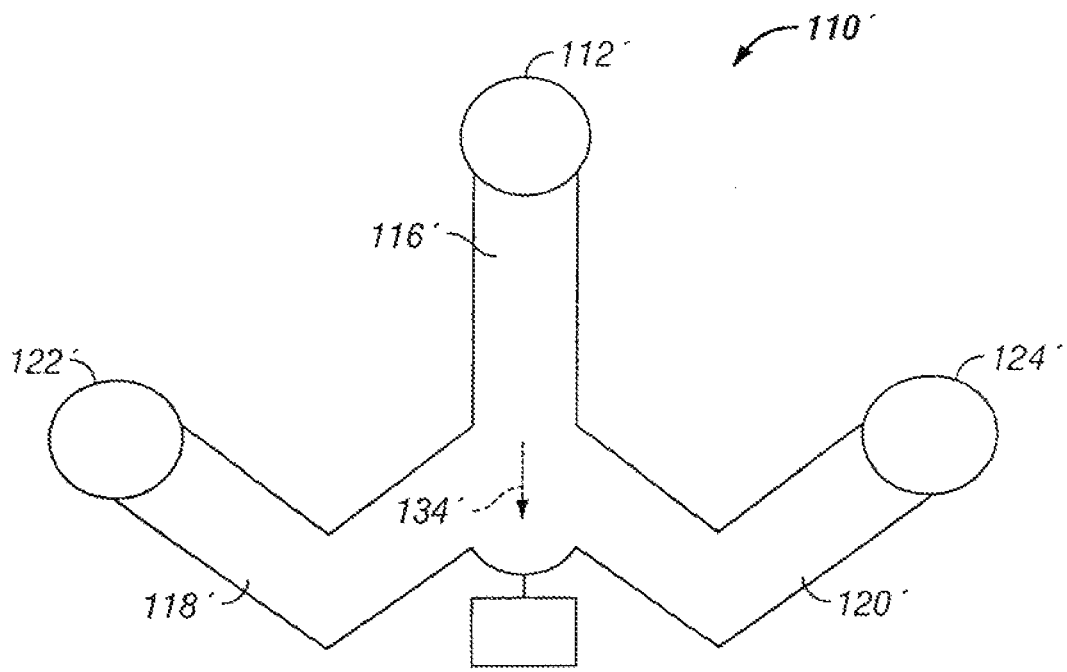
FIG. 2B is a top plan view of another microfluidic system for retaining and analyzing a subset of input particles, in accordance with aspects of the invention.
Figure 3:
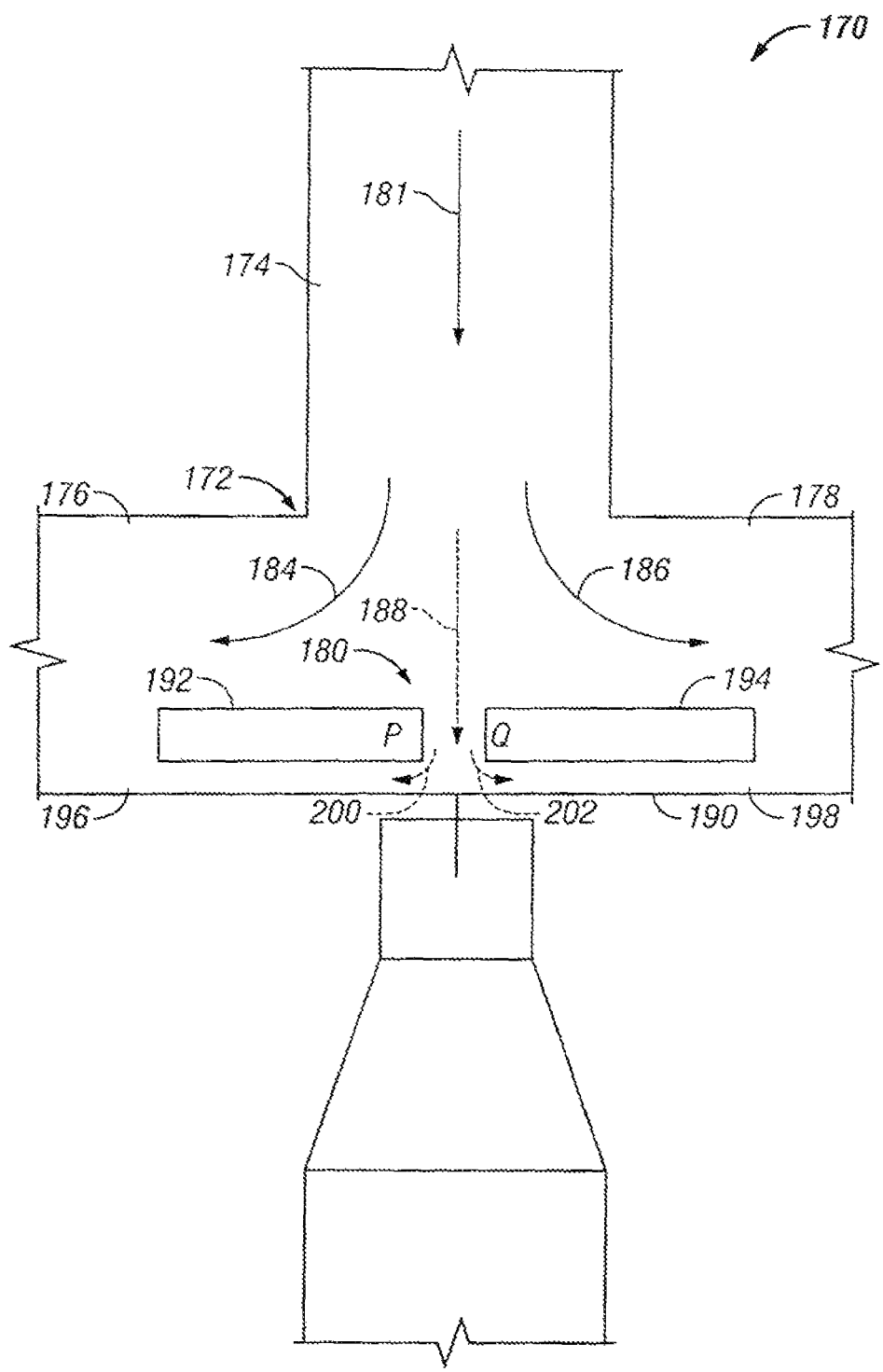
FIG. 3 is a fragmentary, top plan view of yet another microfluidic system for retaining and analyzing a subset of input particles, in accordance with aspects of the invention.
Figure 4:
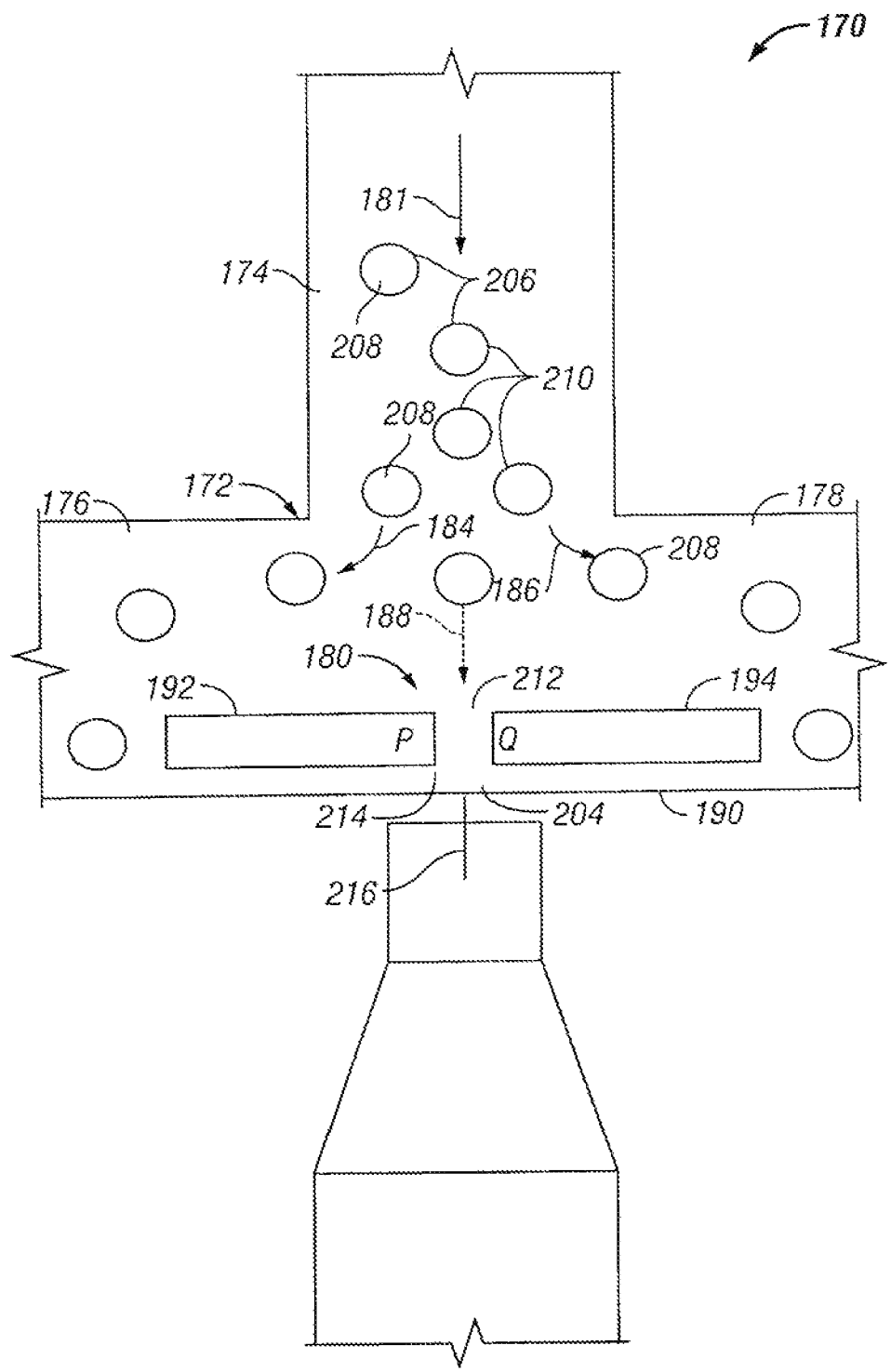
FIG. 4 is a view of the system of FIG. 3 during particle positioning and retention, illustrating the various flow paths followed by particles, in accordance with aspects of the invention.

This example describes microfluidic systems for positioning and/or retaining single particles or groups of particles, based, at least in part, on divergent flow paths; see FIGS. 2-4.

Background

There are many cell analyses that benefit from or require the precise positioning and retention of a single cell or a small group of cells. In particular, positioned and retained cells may be treated and observed in real time. However, currently available mechanisms for positioning and retaining cells are either expensive and labor intensive, or imprecise and deleterious to cells. For example, micromanipulators enable a user to select and precisely position a single cell. However, micromanipulators are expensive, and require that users observe the cell throughout the micromanipulation. Hence, the user can only position one cell at a time. At the other extreme, filters offer a crude, but much cheaper and faster mechanism for positioning and retaining cells. However, filters have a number of disadvantages. For example, they are easy to clog, difficult to control (particularly with regard to the number of retained cells), and potentially harmful to particles such as cells due to the pressure drop across the filter. Therefore, there is a need for cell positioning and retention systems that are economical, guided automatically without optical monitoring, and/or able to gently manipulate cells without substantially damaging them.

Description

This example describes mechanisms for positioning and/or retaining particles such as cells and/or beads without requiring optical monitoring. Once retained, the particles may be analyzed by any suitable method, including optical and electrical methods, among others. The described mechanisms use a microfluidic flow path that diverges to form a quasi-stagnant fluidic region at the position of divergence. Particles entering this quasi-stagnant fluidic region from a microfluidic stream experience a reduction in velocity, which may be exploited to effect their "soft landing" in a suitable retention structure or trap. Accordingly, the retained particles are more likely to be undamaged and suitable for subsequent analyses.

Embodiment 1

FIG. 2A shows a system 110 for microfluidic manipulation and/or analysis of particles, in accordance with aspects of the invention. System 110 includes (1) an input reservoir 112, (2) a microfluidic network 114 having three fluidic channels 116, 118, 120, and (3) two output or waste reservoirs 122, 124. Particles are loaded, generally in suspension, into input reservoir 112. The loaded particles may enter network 114 in response to net fluid flow, shown as flow streams 126, 128, 130, between the input and waste reservoirs. The net fluid flow may be determined by active and/or passive flow, mediated, for example, by pumping and/or gravity, respectively.

The bifurcation of fluid flow stream 126 into flow streams 128, 130 creates a positioning mechanism 132. This positioning mechanism uses a reduced-velocity flow stream 134, shown as a dotted arrow, to gently position a fraction of particles through an extension of flow stream 126.

Particles may be carried by flow stream 134 into a suitable retention mechanism 136. In system 110, this retention mechanism includes a recess 138 formed in opposing wall 140, near a terminal end of reduced-velocity flow stream 134. Recess 138 may have a width and depth that accommodates one particle or a group of two or more particles. Recess 138 includes retention structures 142 that block movement of retained particles, generally in the direction of flow streams 128, 130. The depth of recess 138, coupled with any extension of retention structures 142, generally away from wall 140, may determine the number of particles retained and their associated retention efficiency. Thus, retention mechanism 136 may effect stable or transient retention of particles. Transient retention may provide an average time of occupancy that is suitable for treatment and/or analysis, followed by stochastic loss and replacement of a particle or particles by other particles entering along reduced-velocity flow stream 134.

Particles retained by retention mechanism 136 may be treated and/or analyzed. In some embodiments, retained particles are analyzed electrically, for example, using an electrode 143. Alternatively, or in addition, retained particles may be treated and/or analyzed and then removed by a suitable release mechanism 144. For example, in system 110, the release mechanism applies a dislodging pressure on retained cells that opposes flow stream 134. Release mechanisms are described further in Section IX above and in Examples 7 and 26 below.

Embodiment 2

FIG. 2B shows another system 110' for microfluidic manipulation and/or analysis of particles, in accordance with aspects of the invention. The operational principles for system 110' of FIG. 2B are similar to those for system 110 of FIG. 2A. However, channels 118' and 120' diverge less than 90° from channel 116' in system 110', in contrast to their orthogonally directed counterparts in system 110. Consequently, a greater fraction of particles may be positioned in flow stream 134' in system 110' than in flow stream 134 in system 110, but a greater dislodging force also may be present. In other embodiments, the output channels may have any suitable angles of divergence, including greater than 90°, and/or they may have unequal angles of divergence. The angles of divergence and any asymmetry in the two fluid paths may be alterable to select the number of particles trapped and/or retained and their positions within the trap.

Embodiment 3

FIG. 3 shows yet another system 170 for microfluidic manipulation and/or analysis of particles, in accordance with aspects of the invention. System 170 includes (1) a fluidic network 172 of channels 174, 176, 178 and (2) a retention mechanism or trap 180. A flow stream 181 brings input sample and fluid to a T-junction 182, at which stream 181 is divided into orthogonally directed, primary flow-streams 184, 186. As in systems 110, 110' of FIGS. 2A and 2B, a reduced velocity, positioning flow-stream 188 extends from stream 181, between primary streams 184, 186, toward opposing wall 188. However, unlike systems 110 and 110', system 170 also includes partitions 192, 194 ("P" and "Q", respectively) in the form of rectangular blocks. Partitions 192, 194 divide the main channels to create secondary channels 196, 198, which extend generally parallel to main channels 176, 178. These secondary channels divide positioning flow-stream 188 and direct it orthogonally in opposite directions, as shown by secondary flow streams 200, 202. Secondary flow streams transport fluid at a lower velocity than primary streams 184, 186 because of their position within network 172.

FIG. 4 shows system 170 during particle input, after positioning and retention of a single particle 204 between partitions 192, 194 by trap 180. Particles 206 entering network 172 may travel along flow stream 181, generally in both central and lateral positions within channel 174. Laterally positioned cells, such as cells 208, follow primary flow streams 184, 186 along channels 176, 178. In contrast, centrally positioned cells, such as cells 210, follow positioning stream 188 toward a slot or gap 212 between partitions 192, 194. In this embodiment, gap 212 is slightly wider than the diameter of cells 206, so that it will accept only one cell. In other embodiments, and/or for other cells, gap 212 may be wide enough to accept two or more cells. Whatever the width of gap 212, wall 190 and partitions 192, 194, form a retention site 214 at which cell 204 or cells may be stably retained. Once cell 204 is positioned at the retention site by trap 180, its presence may tend to block or diminish fluid flow along secondary streams 200, 202, through secondary channels 196, 198 (see FIG. 3). Accordingly, secondary streams 200, 202 have diminished capacity to draw additional cells between partitions 192, 194. As a result, in some embodiments, trap 180 may preferentially retain only one cell automatically, without any need for optical monitoring during positioning and/or retention. Thus, retention site 214 may be dimensioned based on the size of cells to be retained. For example, eukaryotic cells typically are about 2 to 10 μm in diameter, so gap 212 may be slightly wider than this diameter, whereas secondary channels 196, 198 may be slightly narrower than this diameter, to prevent entry of cells into these channels.

Retained cell 204 may be treated and/or analyzed using any suitable method, such as optical and/or electrical detection of cell characteristics, as described above in Section VIII. This treatment and/or analysis may be facilitated by a microchannel 216 that extends outward from wall 190 into chamber 218. Microchannel 216 is smaller than the diameter of retained cell 204 and may be used to exert positive and/or negative pressure on the retained cell, or apply and/or measure an electrical potential and/or current across the retained cell, among others, as described below in Examples 11 and 12.

Example 2

Microfluidic Systems for Trapping and Perfusing Particles

This example describes microfluidic systems that position and retain single particles or sets of particles, and allow rapid, precise perfusion of the retained particles or sets of particles with reagents; see FIGS. 5-11C.

Background

Many cell studies benefit from analysis of a population of cells. The population may provide discrete information from individual cells of the population and averaged information from the entire population. Accordingly, a population of cells may allow concurrent analysis of distinct types of cells when the population is heterogeneous, or a range of cell phenotypes or responses when the population is homogeneous or clonal.

Therefore, studies of cells in a microfluidic environment would benefit from microfluidic systems that automatically position and/or retain a set of cells at a preselected site on a microfluidic chip. Furthermore, these studies would benefit from mechanisms that allow the retained set of cells to be perfused with selected reagents, such as drugs, test compounds, or labels, in a controllable and definable manner.

Description

This example describes microfluidic systems that enable a user to trap multiple cells within a cell retention chamber, and perfuse the trapped cells with reagents for controlled intervals. These systems may be formed by any suitable method, including multilayer soft lithography involving multiple layers of photoresist, for example, using molds fabricated as described below in Example 13 and elsewhere in this Detailed Description, and in the patent applications listed above under Cross-References and incorporated herein by reference. Accordingly, in some embodiments, the cross-sectional geometry of fluidic channels may vary between rectangular in flow channels and arcuate at the position of valves.

Embodiment 1

FIGS. 5-11 show a system 250 for microfluidic analysis of cell populations. This system is described in detail below, including (a) system description, (b) system production, (c) system operation, and (d) system protocols.

System Description

Figure 5:
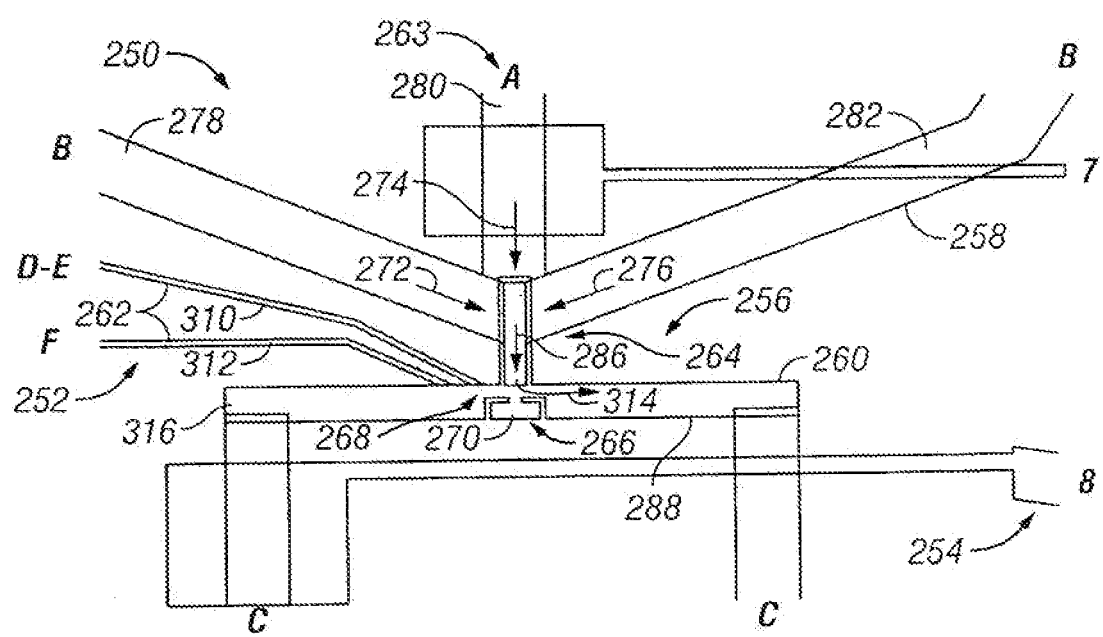
FIG. 5 is a fragmentary, top plan view of a microfluidic system for positioning and retaining a group of particles, and for perfusing the retained group with selected reagents, in accordance with aspects of the invention.

FIG. 5 shows a portion of a system 250 for microfluidic analysis of cell populations. System 250 includes a microfluidic layer 252 and a control layer 254. Microfluidic layer 252 forms a microfluidic network 256 of interconnected channels, depicted in blue and orange. Control layer 254 is positioned over, and abutting, the microfluidic layer, and includes valves and pumps (see also FIG. 8), depicted in purple. Exemplary dimensions presented below for system 250 are based on cell diameters of about 8 to 12 µm.

The microfluidic layer includes microfluidic channels with distinct geometries and functions. Blue, flow channels 258 have a semi-circular or arcuate cross-sectional profile and are positioned generally upstream and downstream of mechanisms for cell positioning, retention, and/or treatment, which are described below. These flow channels have cross-sectional profiles that allow the channels to be acted upon effectively by valves and pumps present in control layer 254. In this example, flow channels are about 200 µm wide and 20 µm high. In contrast, orange, cell channels 260 have a rectangular profile. In this example, cell channels are about 100 µm wide and 20 µm high. Because channel height does not restrict lateral movement, at least to first order, the cells or particles can travel freely within the cell channel, following the walls or more central positions based on the particular laminar flow stream that carries a particular cell or particle. Thus, these cell channels are used to position cells to preselected laminar flow streams and preselected regions of the microfluidic network. Perfusion channels 262, described more fully below, also are shown in orange and function to controllably perfuse retained cells. In this particular example, perfusion channels are about 10 µm wide.

System 250 includes an input mechanism 263, a positioning mechanism 264, a retention mechanism 266, and a perfusion mechanism 268. The positioning and retention mechanisms function together to position and trap cells in a retention or capture chamber 270. The perfusion mechanism functions to effect delivery of reagents to the cells in retention chamber 270, typically after cell retention.

Input mechanism 263 introduces particles into the system, using an input reservoir or well, as described below (see FIG. 8).

Positioning mechanism 264 operates to increase the probability that input cells will enter the retention chamber. Mechanism 264 operates through convergent flow streams that join but remain segregated in a laminar distribution. Input flow streams 272, 274, 276 carry fluid along flow channels 278, 280, 282, respectively. However, channel 280 also may carry cells, whereas flanking channels 278, 282 generally do not. As a result, at confluence 284, flow stream 274 occupies a central portion, flanked by flow streams 272, 276. Accordingly, the accompanying cells are focused to a central portion of combined stream 286. In some embodiments, additional flow streams may be included, and/or cells may be included in other flow streams, as exemplified below in Example 3.

Figure 6:
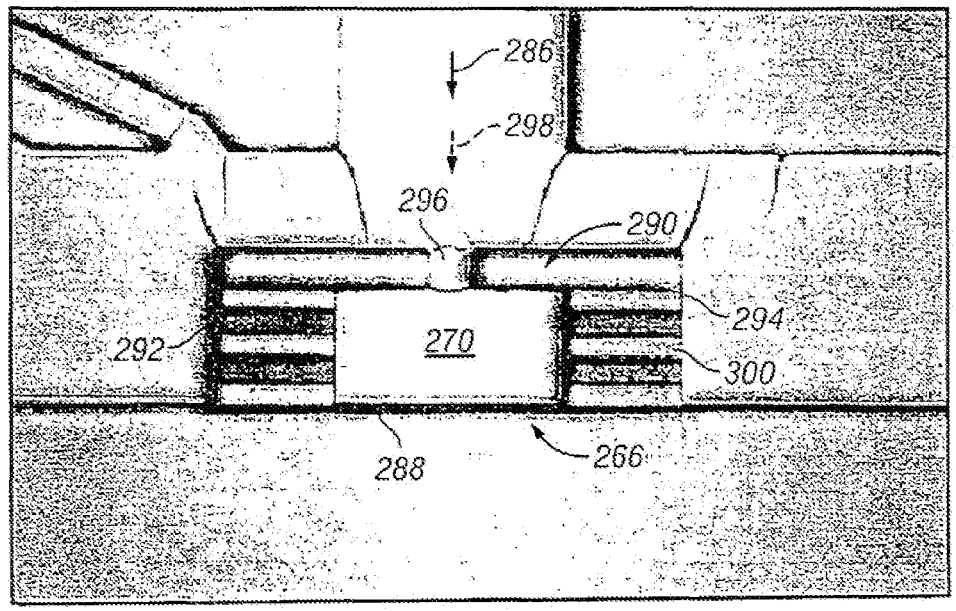
FIG. 6 is a photographic image of a portion of a chip fabricated according to the system of FIG. 5, in accordance with aspects of the invention.
Figure 7:
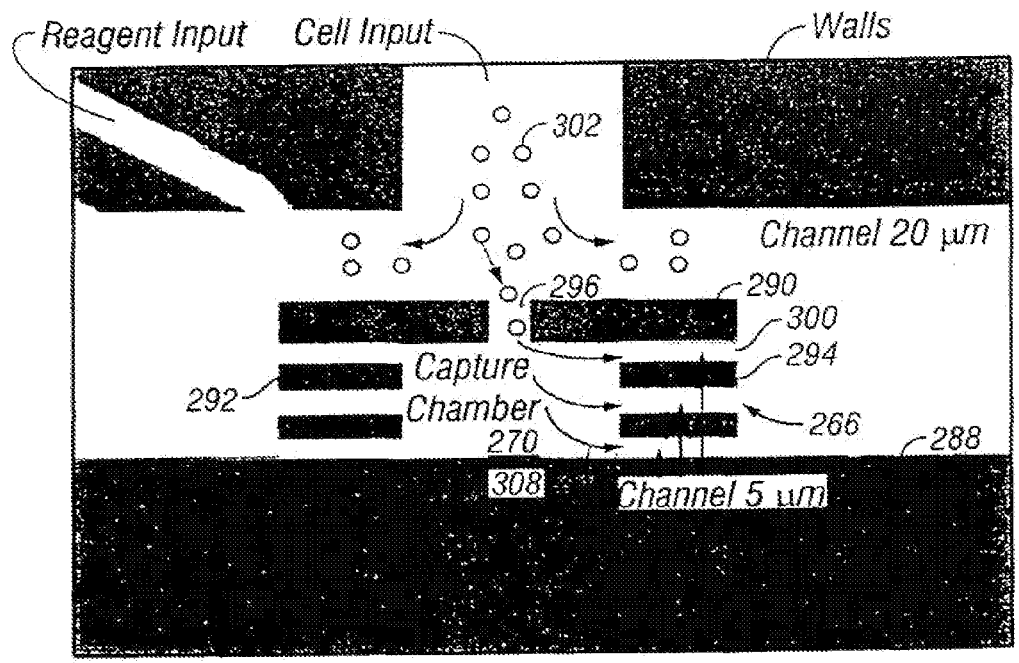
FIG. 7 is a schematic rendition of the image of FIG. 6, illustrating paths of fluid flow and particle movement relative to a particle-retention or -capture chamber, in accordance with aspects of the invention.

FIGS. 6 and 7 show, respectively, corresponding actual and schematic views of the retention mechanism or trap 266 of FIG. 5. The retention mechanism includes a partially closed retention or capture chamber 270. Chamber 270 may have a size of about 60-100 µm long, 50-100 µm wide, and 20 µm high. Chamber 270 is formed by opposing channel wall 288, front wall 290, side walls 292, 294, and top and bottom walls (not shown). Front wall includes an aperture 296 through which cells enter the chamber from a reduced-velocity stream 298, extending from combined stream 286. The reduced-velocity stream may be less damaging to cells that enter the chamber, increasing viability and the probability of a fruitful analysis. Aperture 296 is about 5-20 µm wide and may have a height corresponding to some or all of the channel height. Fluid entering aperture 296 as part of stream 298 may pass through side-wall channels 300. In this example, each side wall includes three side-wall channels 300, which have a rectangular profile about 10 µm wide and 5 µm high. In general, the side-wall channels are dimensioned to selectively retain cells or particles of interest, while allowing fluid or smaller cells or particles to pass through. Thus, chamber 270 functions as a filter. However, in contrast to standard filters, only a fraction of input cells enter chamber 270. The fraction may be less than about 1 in 10, 1 in 100 or 1 in 1,000, among others, depending on the design of the retention chamber, the speed of the input fluid stream, and the size and density of particles, among others.

FIG. 7 shows a focused stream of cells 302 flowing toward chamber 270. Cells 302 either enter aperture 296 or are carried orthogonally by channels 304, 306. Within chamber 270 microstreams 308 connect chamber 270 with side-wall channels 300.

Perfusion mechanism 268 provides precisely controlled exposure to reagents for trapped cells in chamber 270. FIG. 5 shows the general design of the perfusion mechanism. Trapped cells are selectively exposed to buffer or reagent streams carried by one of two or more perfusion channels 310, 312. Fluid, such as media, buffer, and/or reagent, flows through perfusion channels 310 and/or 312 and joins focusing buffer stream 314. During perfusion, focusing buffer stream 314 is produced by input fluid from one or more input reservoirs "B," described more fully below, flowing past chamber 270 in a single stream. Thus, the stream no is longer split as occurs during cell positioning and retention, as shown in FIG. 7. Due to laminar flow and the position of perfusion channels 310, 312, fluid from either one of these channels enters to join main flow stream 314 on the side of the main flow stream nearest chamber 270. Therefore, the trapped cells are exposed to fluid from perfusion channel 310 or 312. However, if fluid is flowing from both perfusion channels, fluid from perfusion channel 312 shields trapped cells from fluid flowing from perfusion channel 310, such as a reagent. Accordingly, the contents of perfusion channel 312 may be referred to as a shield liquid or shield buffer. With concurrent flow from both perfusion channels, cells may be rapidly exposed to a reagent from perfusion channel 310 by stopping flow from channel 312. Stopping the flow of the perfusion buffer may expose cells to reagent within a very short time, in some cases about 150 msec after stopping flow. Therefore, cell analyses that require precise control of reagent exposure to measure rapid cell responses may be conducted reproducibly with the rapid response times afforded by this microfluidic system.

Perfusion mechanism 268 may be modified to achieve similar perfusion or to change the exposure response time. For example, similar perfusion may be obtained by disposing perfusion channels on opposing sides of transverse channel 316, or disposing both perfusion channels on opposing wall 288. Alternatively, or in addition, the exposure time may be increased or reduced by moving perfusion channel 310 closer to, or farther from, main flow stream 314. Example 3 shows a perfusion channel that empties directly into the focusing buffer stream.

Figure 8:
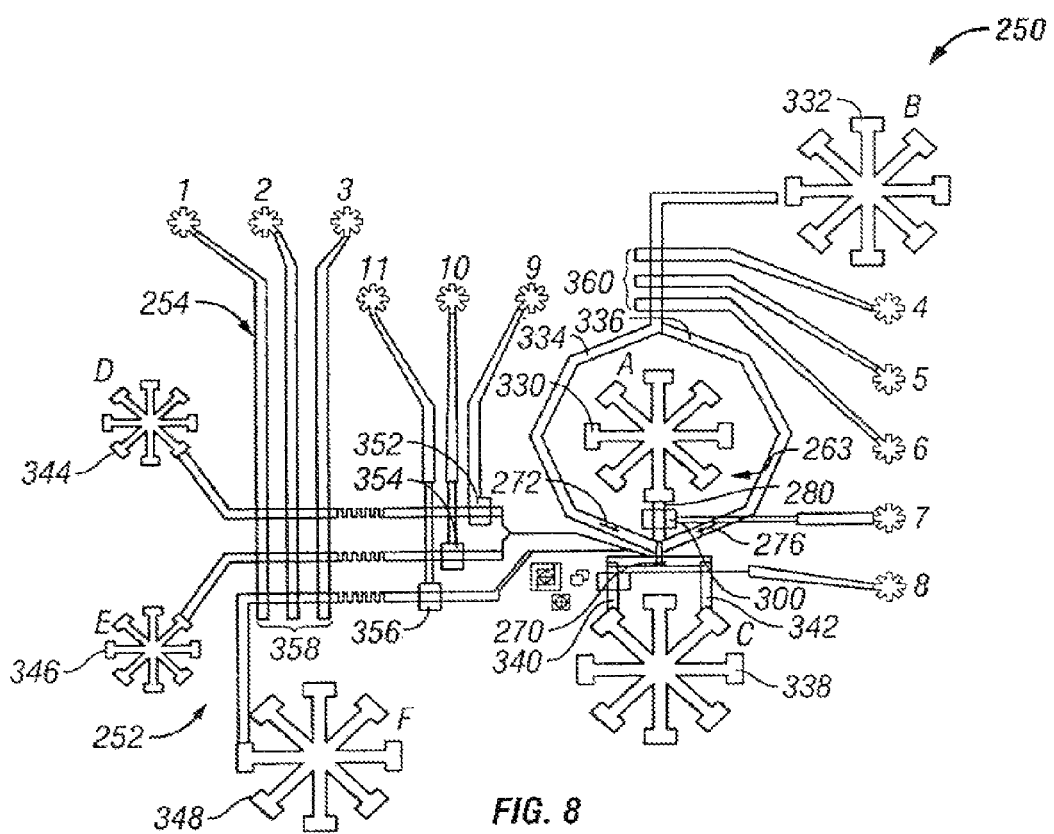
FIG. 8 is a full top plan view of the system of FIG. 5.

FIG. 8 shows additional aspects of microfluidic system 250. These additional aspects include macrofluidic reservoirs, and valves and/or pumps of the control layer that control fluid flow within the microfluidic network.

Macrofluidic reservoirs allow system 250 to interface with the macroscopic world. Each reservoir or well functions as a fluidic inlet or outlet connected directly to at least one microfluidic channel. Fluidic inlet-well A, shown at 330, provides for particle input, generally as a cell suspension. Fluidic inlet-well B, shown at 332, holds a focusing buffer, which is split into two focusing channels, 334, 336, that ultimately form converging flow streams 272, 276. Fluidic outlet-well C, shown at 338, holds output liquid, generally waste liquid, that flows through the system. Well C accepts fluid from one or both of fluid channels 340, 342. Fluidic inlet-wells D and E, shown at 344 and 346, may hold first and second reagents for exposure to trapped cells. Fluidic inlet-well F, shown at 348, holds the shield buffer that blocks exposure of the reagents until desired.

Control layer interfaces are numbered one through eleven. Each interface acts as a gas inlet to regulate opening and closing of one or more valves. Interface seven controls cell input valve 350. Similarly, interface eight controls fluid channel 340, determining whether main flow stream 314 bifurcates or is a single stream. Interfaces nine, ten, and eleven control valves 352, 354, 356, which regulate inflow of reagent or shield buffer from fluidic inlets D, E, and F, respectively. Interfaces 1 through 3 and 4 through 6 control sets of values, shown at 358 and 360, respectively. Valves within each set are actuated in a defined sequence to pump liquid by peristalsis from inlets B (valve set 360) or D-F combined (valve set 358).

System Production

System 250 may be formed using any suitable method. In an exemplary approach, the system is formed by layering and fusing microfluidic layer 252, control layer 254, and a substrate layer, formed, for example, by a cover slip (not shown). Specifically, in this approach, the microfluidic and control layers are molded by soft lithography and then fused. Next, the resulting fused multilayer structure is bonded to the cover slip substrate layer. Finally, microfluidic channels are wetted with deionized water.

System Operation

System 250 may be used to load, position, and/or retain particles, such as cells, using any suitable method. In an exemplary approach, valves 7, 9, 10, 11 are closed, and the remaining valves, including the pump valves, are opened. Wells B and F are loaded with focusing and shield buffers, respectively, wells D and E are loaded with reagents, and well A is loaded with a cell suspension. Valve 7 is then opened, after ensuring that waste well C is at least partly empty, enabling cells to flow towards well C. At this point, no liquid flows from wells D, E, and F. Buffer flows from well B to well C, and cells flow from well A to well C. The cells flowing out of well A are focused in the center of combined flow stream 286 (see FIG. 7) by focusing fluid streams coming from well B, thereby flanking cells flowing from well A. The focusing fluid streams 272, 276 increase the likelihood that input cells will enter retention chamber 270, which is placed near where focusing occurs. The focused stream of cells is split into two streams adjacent the retention chamber. Each stream flows in a direction orthogonal to the focused stream and opposite to each other, as described above. The trap is placed at a point of the flow stream below where the stream splits, so that the velocity of flow is lower than in the rest of the channel, therefore increasing the likelihood that retained cells are viable. Once a sufficient number of cells are captured, valve 7 is closed to stop the flow of cells from well A.

System Protocols

System 250 may be used for any suitable protocols or procedures involving positioned and/or retained particles. In a exemplary protocol, cells are exposed to reagents in wells D and/or E, as described below. This protocol is exemplified by successive exposure of retained cells to first and second reagents, such as a cell stain specific for dead/fixed cells and a cell fixative, respectively; see FIGS. 9-11.

The system is readied for perfusion as follows. First, valve 8 is closed, so that the flow of focusing buffer from well B no longer is split adjacent retention chamber 270. As a result, the focusing buffer moves predominantly or exclusively along main flow stream 314, which is unbranched (see FIG. 5). Next, pumps that control valve sets 354, 356 are activated and run through the entire protocol. A suitable frequency for valve closure is about 60 Hz.

Shield buffer flow is initiated as follows. Initially, valves 7-11 are in a closed position, so that only focusing buffer from well B flows towards waste well C. Then, valve 11 is opened, so that shield buffer flows from F to C and focusing buffer flows from B to C.

Flow of the first reagent, in this case Trypan blue, is initiated as follows. Valve 9 is opened, so that fluid flows through both valves 9 and 11. Valves 7, 8, and 10 are maintained in their closed positions. Since the shield buffer is flowing, the first reagent is spaced from the cell retention chamber by the shield buffer. Therefore, this configuration readies the system for perfusion and may be used to wash the fluidic network without exposing the cells to either of the first and second reagents.

Perfusion of the first reagent is initiated as follows. Once the fluid lines are washed with the first reagent, the shielding buffer is turned off, and the cells are exposed rapidly to the already flowing first reagent. Specifically, valve 11 is closed, joining already-closed valves 7, 8, and 10. In contrast, valve 9 remains open. In this way, the shield buffer no longer separates the flow stream of the first reagent and the cell retention chamber, allowing the first reagent to perfuse the cells.

Figure 9:
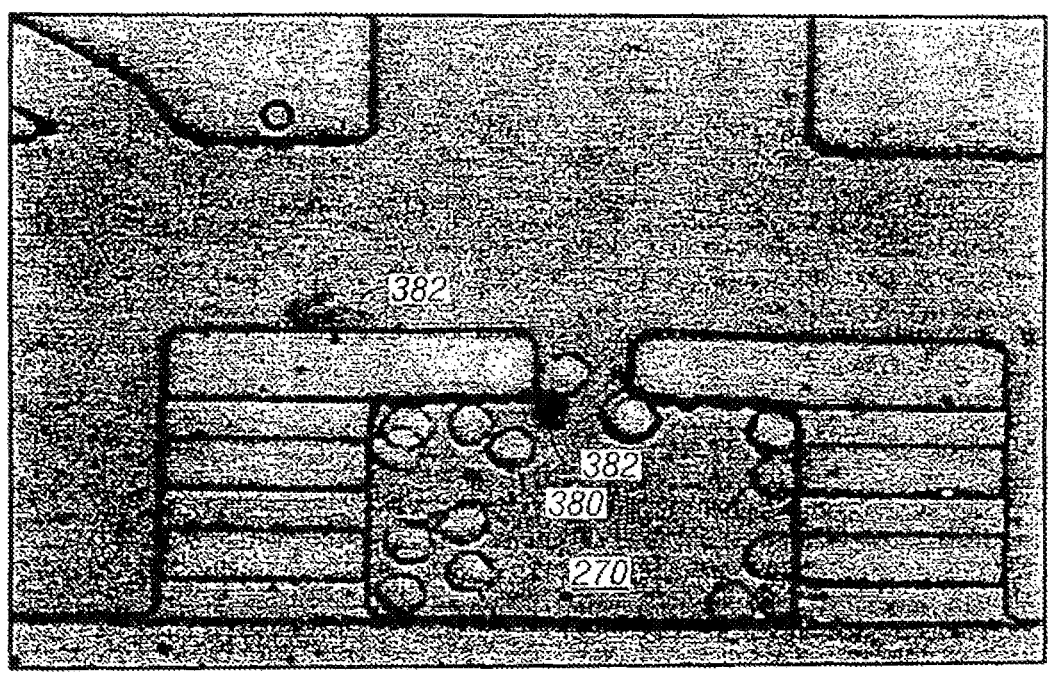
FIG. 9 is a photographic image of cells in a retention chamber, after exposure to Trypan blue to stain lysed cells, but before cell fixation, in accordance with aspects of the invention.

After a suitable exposure time, the first reagent is washed out of the cell retention chamber as follows. Valve 11 is opened to restart flow of the shield buffer. In addition, valve 9 is closed to stop flow of the first reagent, joining already-closed valves 7, 8, and 10. In some cases, valve 9 may be left open to facilitate repeated exposure of the cells to the first reagent over a short time interval. FIG. 9 shows about twenty Jurkat cells 380 in retention chamber 270 after exposure to a dye, Trypan blue, that stains fixed cells and a shield buffer to wash away the dye. Debris 382 is stained, but cells 380 are unstained.

Flow of the second reagent, in this case methanol, is initiated as follows. Valve 10 is opened, joining already-open valve 11. Valves 7, 8, and 9 remain closed. This configuration is used to wash the fluidic network with the second reagent without exposing the trapped cells to this reagent.

Figure 10:
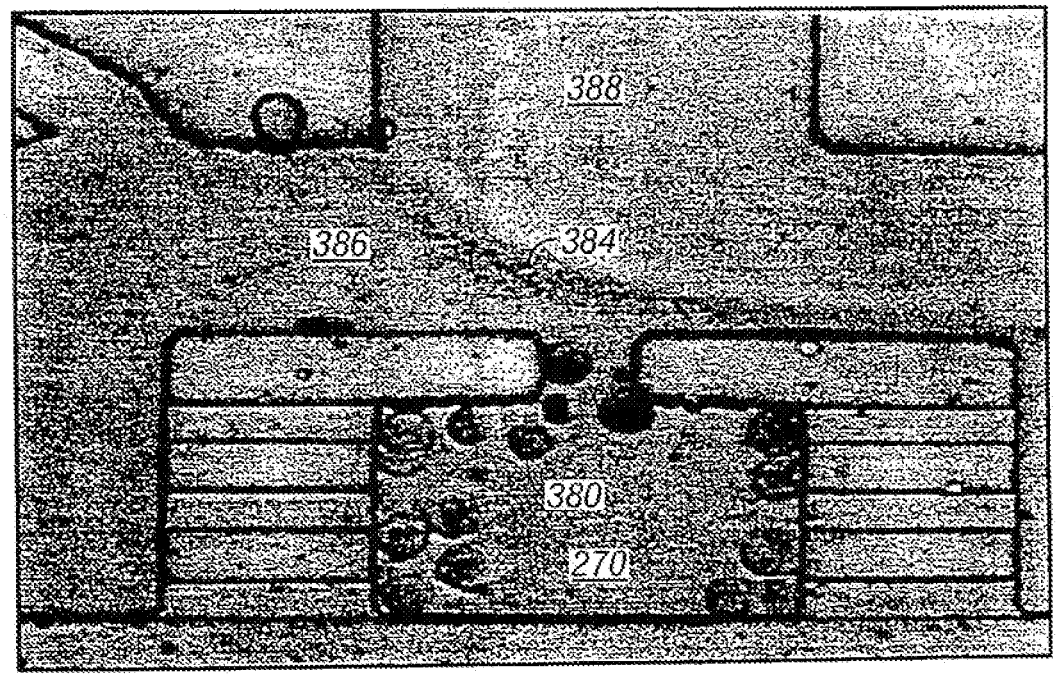
FIG. 10 is another photographic image of the cells and chamber of FIG. 9, after exposure to methanol to lyse and fix the cells, in accordance with aspects of the invention.

Perfusion of the second reagent is initiated as follows. Valve 11 is closed to turn off flow of the shielding buffer, joining already closed valves 7, 8, and 9. Valve 10 remains open, to expose cells 380 to the second reagent, in this case methanol, thus fixing the cells. FIG. 10 shows cells 380 being perfused with methanol. There is an optically detectable boundary 384 between the methanol 386 and the focusing buffer 388, caused by their distinct indexes of refraction.

After a suitable exposure time, the second reagent is washed out of the cell retention chamber as follows. Valve 11 is opened to initiate flow of the shield buffer. In contrast, valve 10 is closed, to join already-closed valves 7, 8, and 9.

Figure 11:
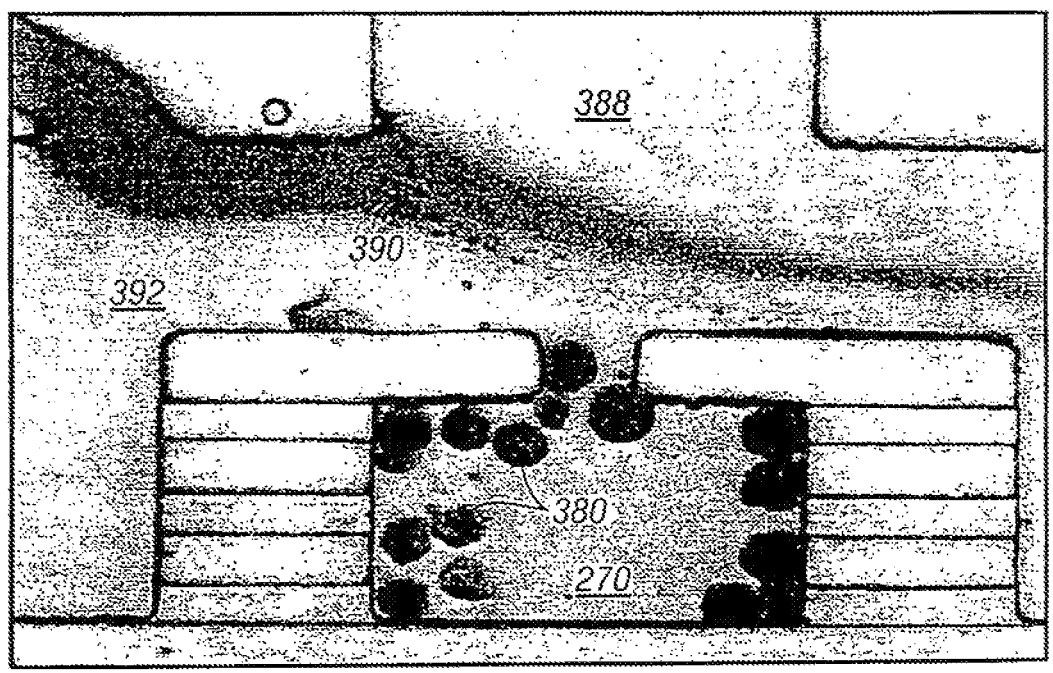
FIG. 11 is yet another photographic image of the cells and chamber of FIG. 9, after exposure to 1) methanol to lyse and fix the cells, 2) Trypan blue to stain lysed cells, and 3) a wash buffer to remove excess Trypan blue, in accordance with aspects of the invention.

Cells 380 are then exposed for a second time to the first reagent, followed by washing with the shield buffer, as follows. The sequence of valve manipulations are as described above, except that valve 9 is left open during washing with shield buffer to show a shielded flow path of the first reagent. Now, since the cells have been fixed and permeabilized by methanol, they stain with the dye carried in the first reagent. FIG. 11 shows cells 380 stained blue after their second exposure to Trypan blue and subsequent washing with shield buffer. The shielded flow path 390 of the first reagent, Trypan blue, is visible focused between shield buffer 392 and focusing buffer 388.

The microfluidic system demonstrated here can be used for any suitable assay, such as screening compounds against a small population of cells, with the size of the small population be selected to be statistically representative of cell behavior. The particles may include cells and/or beads, among others. The cells may be nonadherent and/or adherent cells, either in suspension or attached to a substrate provided by the microfluidic system. The beads similarly may be nonadherent or adherent, and may be used to carry samples, reagents, and/or cells, among others.

Embodiment 2

FIGS. 11A and 11B show a system 400 for measuring interaction between separated, but proximate particles. Such interaction may be provided by diffusible materials released by a first particle (or particle population) and received by a second, separated particle (or particle population). These diffusible materials may include cell-secreted hormones, viral particles, cell components released by cell lysis, and/or so on. The diffusible materials may produce changes in the second particle or particle population that are related to any measurable particle or population characteristic, such as cell identity, gene expression, apoptosis, hormone secretion, growth, and/or the like. Alternatively, or in addition, such communication may include long, thin processes extending from cells, such as axons and/or dendrites. Exemplary particle characteristics are described further in Sections VIII and XII above.

System 400 may be formed by disposing two versions of system 250 in a tail-to-tail configuration. Accordingly, each individual subsystem 250 may include a retention mechanism 266, an individually controlled perfusion mechanism 268 for introducing reagents to each group of captured particles, and an input flow stream 274 for carrying particles and/or buffer to the retention mechanism. However, system 400 also includes communication passages 402 that provide fluidic communication between each retention mechanism 266 and retention chamber 270.

Communication passages 402 may be size-selective channels configured to prevent movement of retained particles, generally cells, between each subsystem 250. However, passages 402 are configured to allow movement or passage of any smaller material released from the retained particles (such as molecules, polymers, molecular complexes, and/or smaller particles, such as viruses), or of processes, such as axons and/or dendrites, extending to, from, and/or between retained cells. Furthermore, perfusion mechanisms 268 may be used to determine the effect of reagents on cell-cell communication mediated by passages 402.

FIG. 11B shows an alternative embodiment of paired retention mechanisms 266, mechanism 404, that may be included in system 400. Mechanism 404 includes paired retention mechanisms 406, dimensioned to trap single particles 408. Retention mechanisms 406 are fluidically coupled through communication passages 402. Accordingly, communication between single-cells may be analyzed using mechanism 404.

Embodiment 3

FIG. 11C shows a retention mechanism 410 that may be used in system 250 or any other suitable microfluidic system to form a positioned, two-dimensional array of retained particles. Mechanism 410 includes an array of individual traps 412 oriented to receive particles from inlet channel 414. Traps 412 form a two-dimensional array of particle retention sites. Traps 412 may have any suitable configuration, including staggered rows, as shown here, orthogonally arranged rows and columns, or irregular configurations. (In some embodiments, some of traps 412 may be positioned in alternative planes (e.g., in front of and/or behind the plane of the drawing) to form three-dimensional arrays of retained particles.) Each trap 412 may be dimensioned to hold one or plural particles and may include size-selective channels or similar features to allow fluid to flow through portions of the traps. Traps 412 may be disposed within a common chamber 416 having an single or plural outlet channels 418 (such as chamber 270, described above, or chamber 1970 of Example 10 below), within a chamber having no outlet besides an inlet channel, or within a channel, such as transverse channel 316, described above, among others.

Example 3

Microfluidic Systems for Parallel Retention and/or Treatment of Particles

Figure 12:
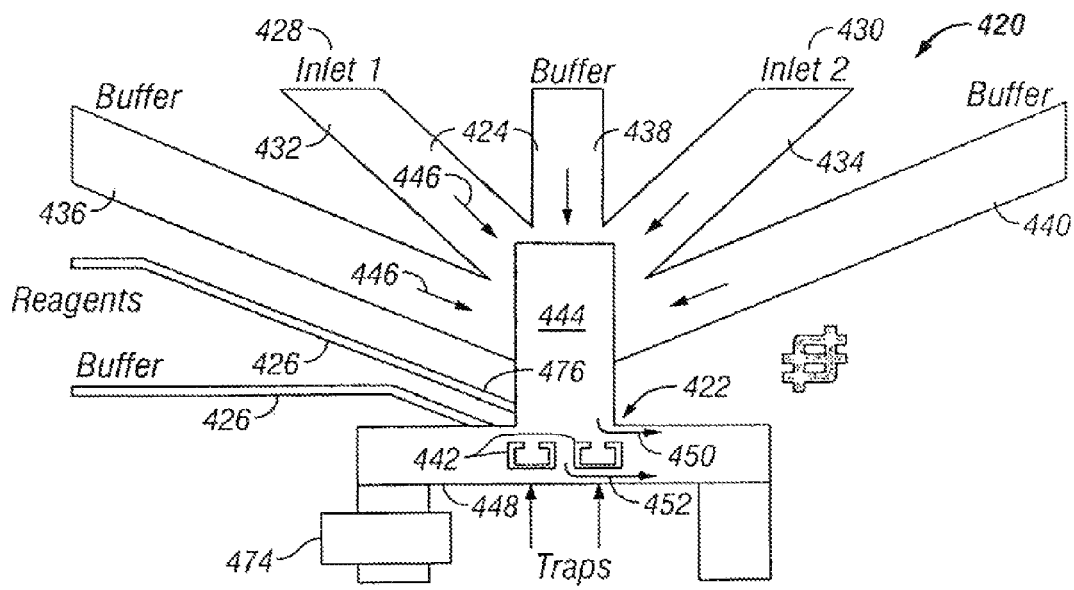
FIG. 12 is a fragmentary, top plan view of a microfluidic system for retaining and perfusing two sets of particles in parallel, in accordance with aspects of the invention.
Figure 13:
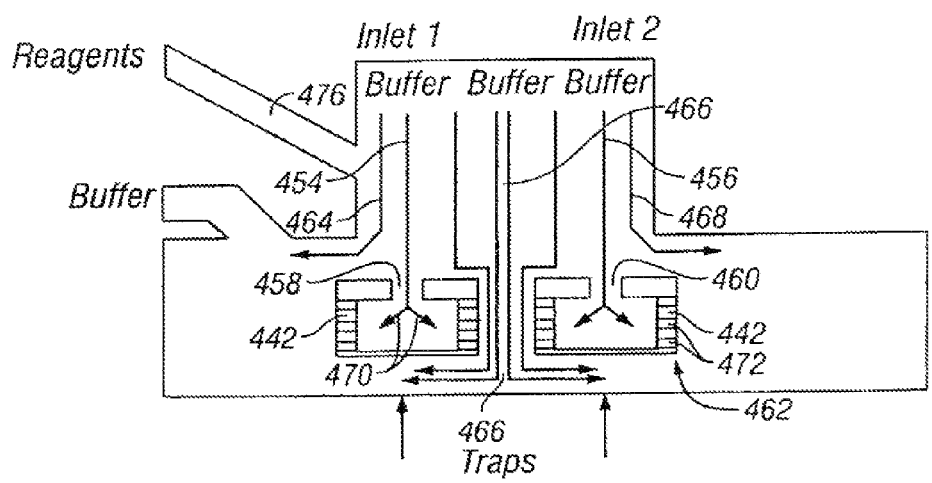
FIG. 13 is a view of selected portions of the system of FIG. 12, illustrating paths for fluid flow and particle movement relative to two adjacent retention chambers, in accordance with aspects of the invention.
Figure 13A:
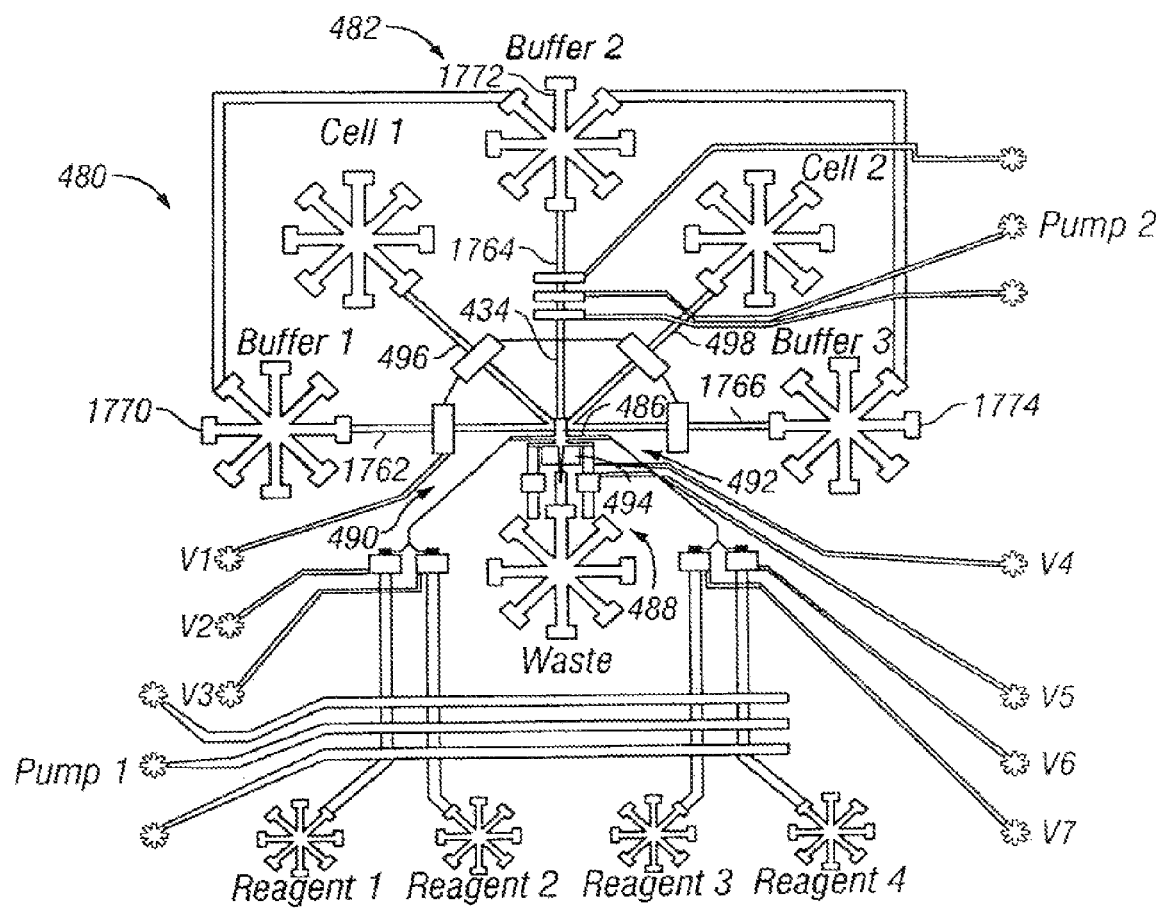
FIG. 13A is a top plan view of a microfluidic system for retaining two particles at spaced sites in a channel and perfusing the retained particles with distinct reagents, in accordance with aspects of the invention.
Figure 13B:
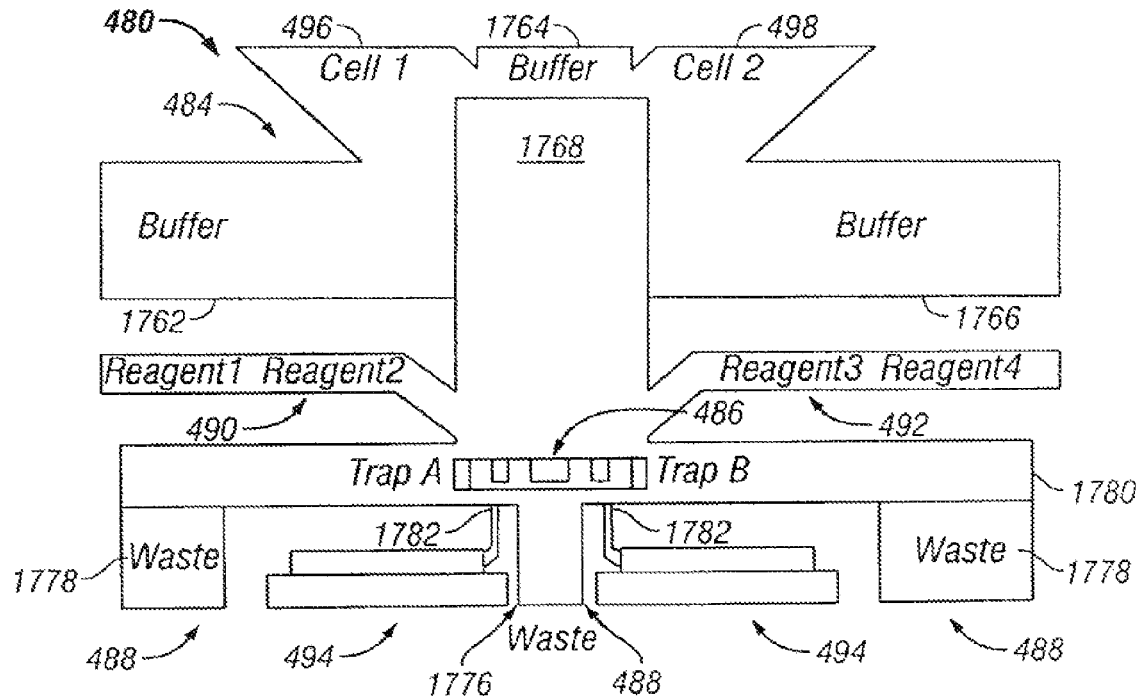
FIG. 13B is a top plan view of selected portions of the system of FIG. 13A, in accordance with aspects of the invention.
Figure 13C:
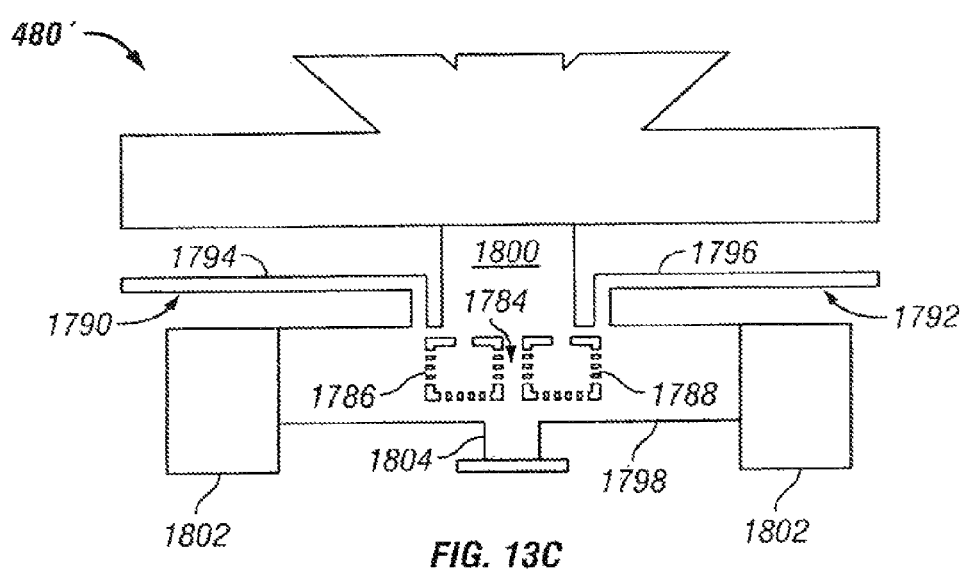
FIG. 13C is a top plan view of selected portions of an alternative embodiment of the system of FIG. 13A, in accordance with aspects of the invention.
Figure 13D:
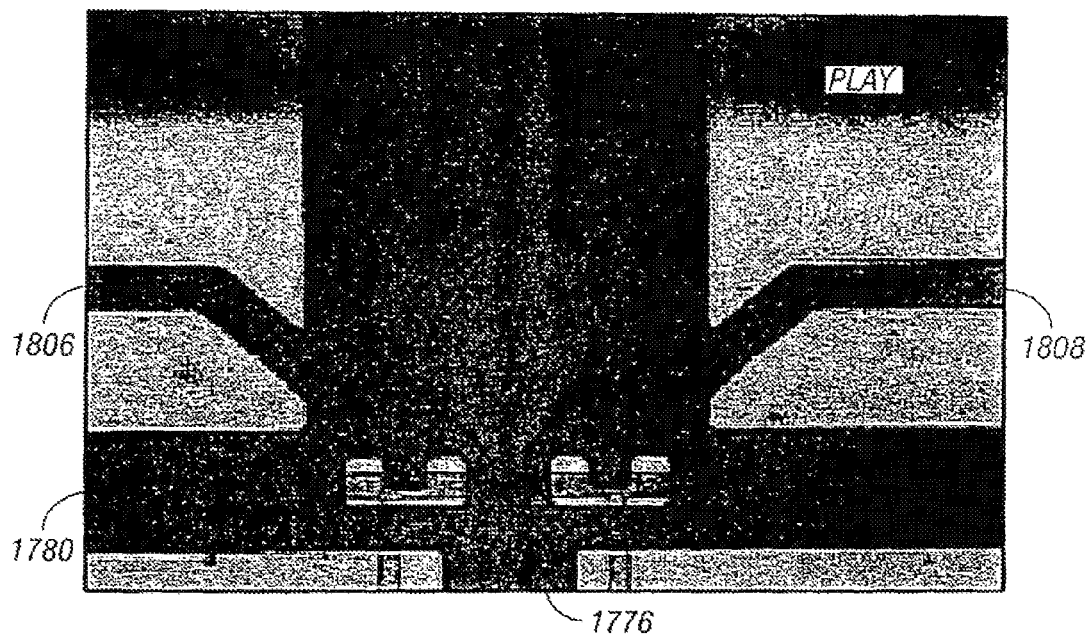
FIG. 13D is a photograph of two beads being exposed to green dye delivered by spaced treatment mechanisms, using a chip constructed according to the system of FIG. 13A, in accordance with aspects of the invention.
Figure 13E:
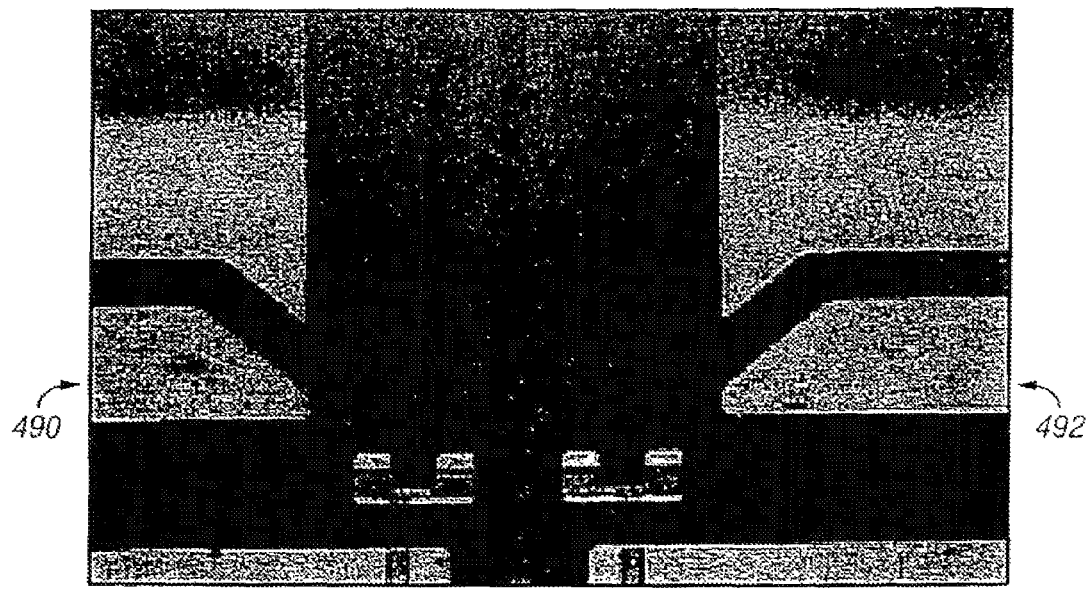
FIG. 13E is another photograph of the two beads of FIG. 13D during exposure to a red dye and a green dye delivered by spaced treatment mechanisms, in accordance with aspects of the invention.
Figure 13F:
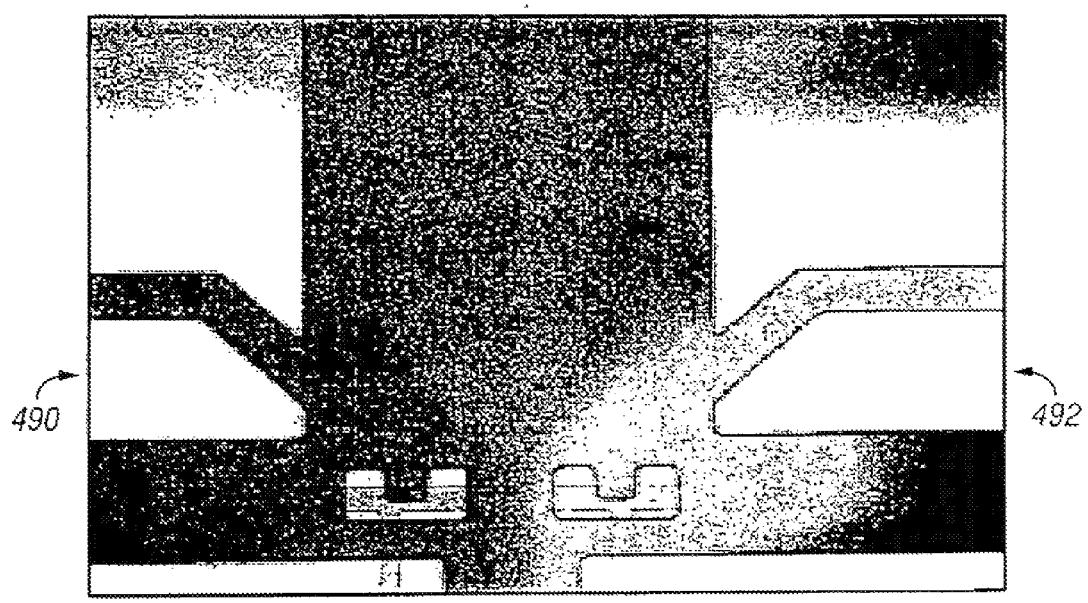
FIG. 13F is yet another photograph of the two beads of FIG. 13D during exposure to a red dye and a yellow dye delivered by spaced treatment mechanisms, in accordance with aspects of the invention.
Figure 13G:
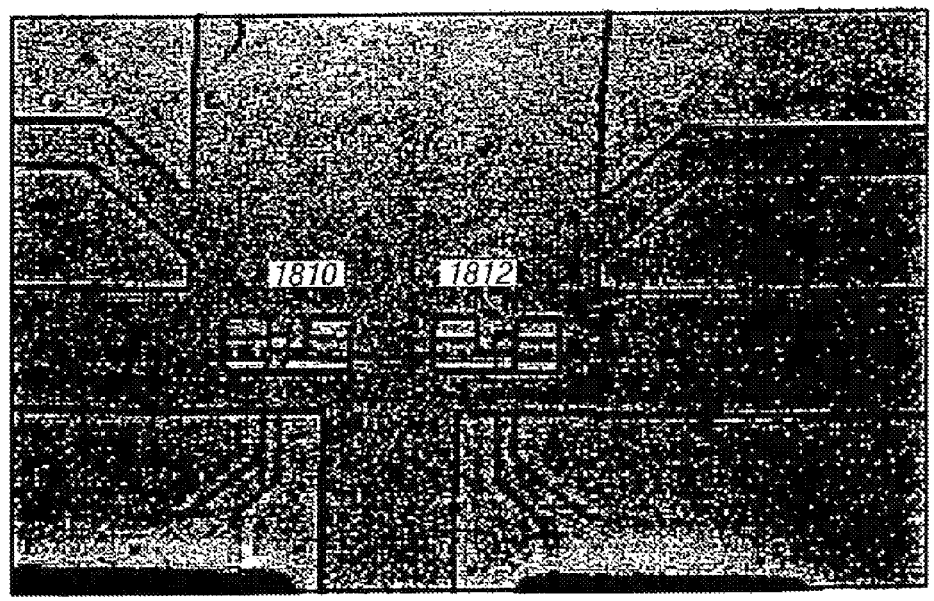
FIG. 13G is a photograph of two cells held at separate retention sites in a chip constructed according to the system of FIG. 13A, in accordance with aspects of the invention.
Figure 13H:
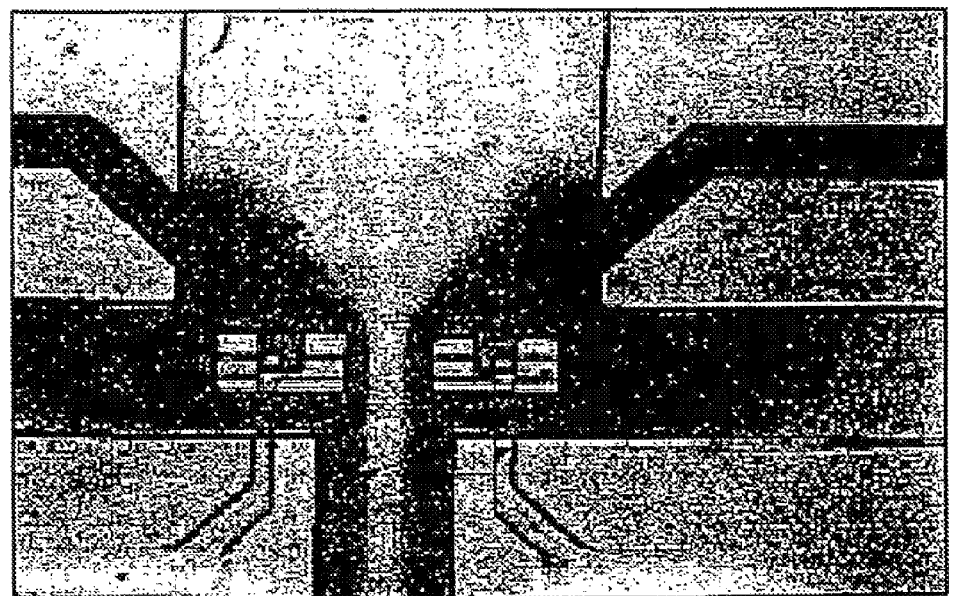
FIG. 13H is a photograph of the two cells of FIG. 13G during exposure to a blue dye delivered by spaced treatment mechanisms, in accordance with aspects of the invention.
Figure 13I:
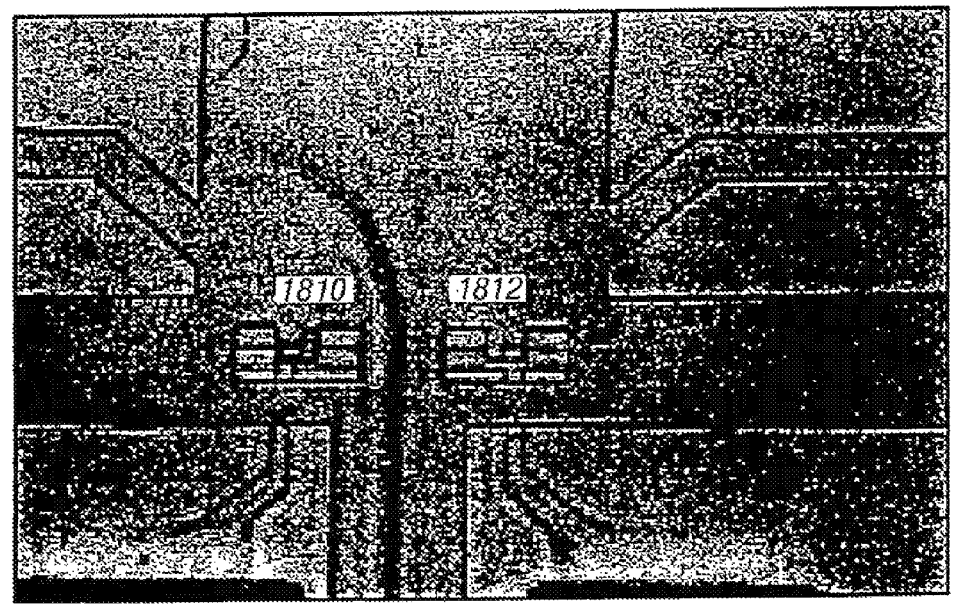
FIG. 13I is a photograph of the two cells of FIG. 13G during treatment of only one of the cells with an organic fixative, in accordance with aspects of the invention.
Figure 13J:
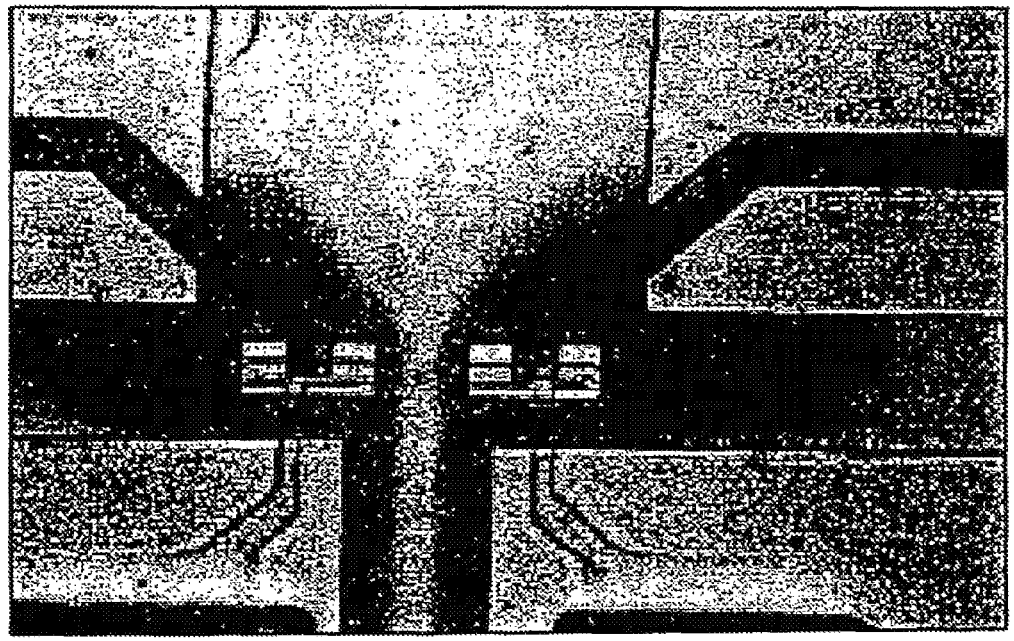
FIG. 13J is a photograph of the two cells of FIG. 13I, after fixation of the one cell and during exposure to a blue dye, delivered by spaced treatment mechanisms, in accordance with aspects of the invention.
Figure 13K:
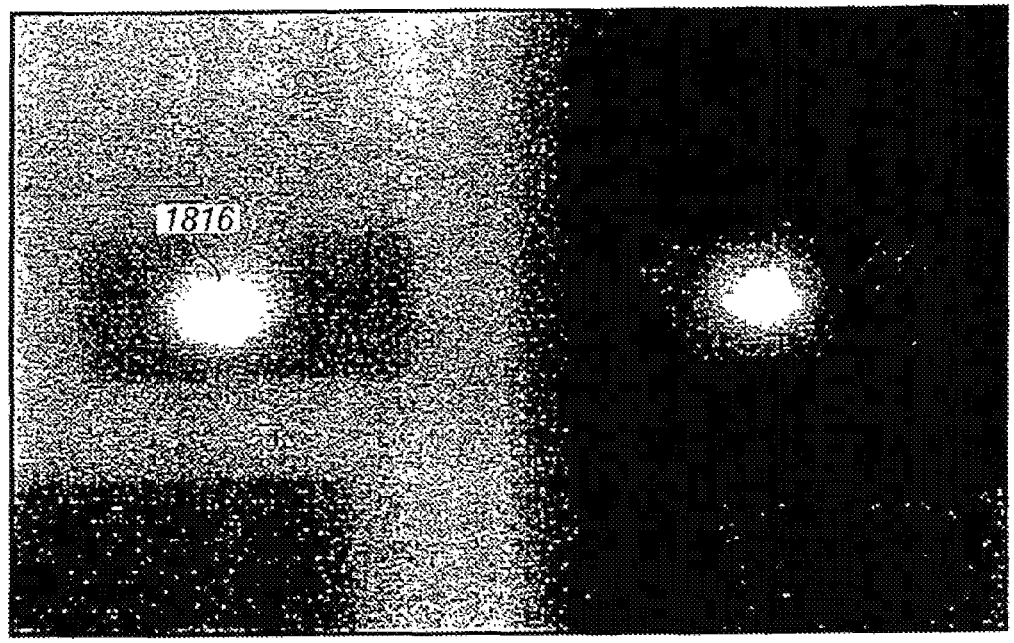
FIG. 13K is a photograph of two fluorescent beads held at two retention sites and individually exposed to a fluorescent and a chromophoric dye delivered by spaced treatment mechanisms, but without the use of a spacer buffer, using a chip constructed according to the system of FIG. 13A, in accordance with aspects of the invention.

This example describes microfluidic mechanisms and systems that position a plurality of particles and/or reagents at discrete transverse regions and flow paths within a channel or flow stream; see FIGS. 12-13K. This positioning may allow parallel retention of distinct particles at adjacent, but distinct, sites and/or parallel exposure of particles at these sites to distinct reagents.

Background

Biological analyses benefit from a capability to directly compare the phenotypes of two or more cells or groups of cells, under similar or distinct treatment regimens. However, in the macroscopic world, such cells or group of cells often are treated at distinct, relatively widely spaced sites, such as different tissue culture dishes or wells of a microtiter plate, potentially exposing the cells to undesired differences in treatment conditions. Accordingly, such analyses may need to be averaged over many experiments to achieve meaningful results. Therefore, it would be desirable to have a microfluidic system that positions, treats, and analyzes particles or groups of particles adjacent one another at a microscopic level, to allow more consistent and efficient side-by-side comparisons.

Description

The microfluidic systems described in this example position a plurality of particles or (particle populations) and/or reagents along distinct, transversely disposed flow paths or regions within a channel or flow stream. The transversely disposed flow paths may be defined by introducing the particles and/or reagents into the channel along distinct laminar flow paths, by joining separate inlet channels (or inlet flow streams) carrying the particles and/or reagents. These flow paths may abut one another or may be spaced apart by one or plural spacer fluids, such as buffers. These spacer fluids may follow one or plural interposed flow paths formed by one or plural inlet channels interposed between the inlet channels that carry the particles and/or reagents.

The transversely disposed flow paths may be used to carry distinct (or similar) particles to distinct retention sites or chambers within the channel. The distinct retention sites may retain distinct (or similar) particles for exposure to the same reagent. For example, the distinct particles may be exposed to reagents, such as modulators and/or labels, to compare characteristics of the particles, such as response to the modulators, labeling characteristics, and/or so on. Thus, the position of each retention site may be used to identify the corresponding particle(s) retained at that position. For example, one retention site may be used to hold a control particle(s), as a reference, and another retention site may be used to hold a particle(s) of interest, allowing the control particle(s) and the particle(s) of interest to be compared directly. Alternatively, one retention site may hold a bead(s) carrying a reagent, and another site may hold a cell(s) to be analyzed. In this approach, cell components released by cell lysis or secretion then may be analyzed for interaction with the reagent held by the bead.

Alternatively, or in addition, transversely disposed flow paths may be used to expose similar (or distinct) particles to distinct reagents and to identify each reagent or exposed particle based on position. Particles may be retained at positionally distinct retention sites, either inputted from distinct reservoirs or a single reservoir. Next, the retained particles may be contacted with distinct reagents carried to the distinct sites by transversely disposed flow paths. The transversely disposed flow paths may be formed by a set of inlet channels distinct from, and/or overlapping with, inlet channels that introduced the particles. Position of the retained particles identifies each of the distinct reagents exposed to the particles. In some embodiments, the distinct reagents may include a compound with a known activity that acts as a reference, and one or more test compounds for comparison.

The microfluidic systems of this example may allow more efficient and meaningful use of microfluidic space for comparative analysis of particles and/or reagents.

In certain embodiments, a junction between two inlets and an outlet may be used to transiently expose or perfuse particles, preferably cells, with selected reagents. By alternating the inlet flow between plus and minus reagent flows, the downstream conditions of the outlet will change in proportion to the rate of flow between both inlets.

Embodiment 1

FIGS. 12 and 13 show a microfluidic system 420 (Embodiment 1) for retaining separate populations of particles, and exposing the populations to one or more selected reagents.

Description of Embodiment 1

System 420 is formed by multilayer soft lithography, generally as described above (for system 250) in Example 2 and below in Example 13. Here, particle positioning region 422 is shown as red rectangles, input/focusing channels 424 as blue regions, and perfusion channels 426 as red lines. The dimensions of each region or channel and/or the number of channels may be selected based on particle size, reagent delivery volume, and/or the number of separate populations to be retained, among others.

System 420 differs from system 250 of Example 2 in several aspects. First, system 420 includes more than one reservoir for holding and introducing particles. Thus, inlets 1 and 2, shown at 428, 430, respectively, connect to particle input channels 432, 434. Second, system 420 includes three focusing channels 436, 438, 440, and corresponding reservoirs or inlets for holding buffer (not shown). The focusing channels, also referred to as spacer channels, may be used to flank and separate the particle input channels. Third, system 420 has more than one retention chamber 442, with the chambers generally positioned adjacent each other below confluence 444, where input flow streams 446 join. Fourth, system 420 spaces retention chambers 442 from wall 448, thus forming proximal and distal diverging flow streams 450 and 452, respectively.

Applications of Embodiment 1

System 420 may be used as follows. Inlets 1 and 2 are loaded with distinct suspensions of particles, such as different cell types, and inlets corresponding to focusing channels 436, 438, 440 are loaded with focusing buffer. A pump(s) is started that drives flow of the focusing buffer through the focusing channels. Valves that control the flow of particles from inlets 1 and 2 are opened. Particles enter confluence 444, but are focused to spaced, intermediate, laminar flow streams 454, 456, shown in FIG. 13, by flow from the focusing or spacer channels. Apertures 458, 460 of the retention chambers are aligned with particle flow streams 454, 456, respectively, to receive one or more particles from the corresponding flow stream. By taking advantage of the laminar flow properties of fluids in system 420, the five streams flow together but remain substantially distinct. Mixing of the fluids is limited to diffusion, which in the case of large particles, such as beads or cells, is very slow.

FIG. 13 shows the laminar flow pattern extending from confluence 444 through divergence junction 462. Focusing flow streams 464, 466, 468 flank and separate particle streams 454, 456, thus guiding particles carried by these streams toward retention chambers 442. Flow streams in junction 462 may diverge above (464, 468), below (466), and/or within (470) retention chambers 442. Microchannels 472 within each retention chamber pass fluid but retain particles.

After a sufficient number of particles have entered each retention chamber 442, analysis of the particles may begin. Flow from inlets 1 and 2 may be terminated, and flow may be converted from a divergent pattern to a unitary flow path, by closing valve 474, as described above for operation of system 250 in Example 2. Next, the trapped particles may be perfused with buffer/reagents from perfusion channels 426. In system 420, perfusion channel 476 discharges fluid directly upstream of the retention chambers. This configuration may provide more rapid perfusion of trapped particles with reagents than system 250 of Example 2 above, because the outlet end of channel 476 is very close to the retention chambers, feeding more directly into the unitary flow path produced by the focusing buffers.

System 420 may be modified by changing various parameters. For example, the number of particle input-streams and/or focusing streams may be varied, along with the number of retention chambers, to trap additional particle populations or individual particles. Thus, three or more particle input-streams may be used to trap three or more types of particles in three or more retention chambers. These three or more retention chambers may be disposed in any suitable arrangement, including linear and staggered (e.g., triangular configurations). In some embodiments, the size of the retention chambers may be varied, for example, so that only one or a very small number of particles are trapped in each chamber (see embodiment 2 of this example, and Examples 4-7, 11, and 12 below). Furthermore, as described below, focusing streams and spacer channels may be eliminated in some cases without substantial cross-contamination of particles between particle streams and retention sites.

Embodiments 2 and 3

FIGS. 13A-C shows two alternative embodiments of system 420, systems 480 (Embodiment 2) and 480' (Embodiment 3), for retaining and treating particles at separate, but adjacent sites. Similar to system 420 described above, system 480 or 480' may be used to selectively input and retain one or plural particles at each of plural retention sites positioned at discrete positions transverse to a flow direction within a channel. However, system 480 or 480' also may be used to separately contact retained particles with distinct reagents at distinct retention sites.

Description of Embodiments 2 and 3

System 480 includes an input mechanism 482, a focusing or transverse positioning mechanism 484, a retention mechanism 486, an output mechanism 488, a plurality of individually controllable and distinct treatment mechanisms 490, 492, and a release mechanism 494; see FIGS. 13A and 13B.

Input mechanism 482 includes particle input channels 496, 498 and focusing or spacer channels 1762, 1764, 1766, similar to those described above for system 420. Particles, such as cells, may be inputted from input reservoirs "Cell 1" and "Cell 2" along particle inlet channels 496, 498, to positioning channel 1768. Input mechanism 482 also may introduce focusing or spacer fluid, preferably buffer, from buffer reservoirs 1770, 1772, 1774 ("Buffer 1," "Buffer 2," and "Buffer 3," respectively) along spacer channels 1762, 1764, 1766, respectively, to positioning channel 1768.

Transverse positioning mechanism 484 may be determined by inlet channels. More specifically, the relative spatial configuration in which the inlet channels 496, 498, 1762-1766 join positioning channel 1768, along with relative sizes of, and/or flow rates from, these inlet channels, provides transverse positioning mechanism 482. Positioning mechanism 484 places each individual flow stream from each inlet channel in a laminar flow path based on this spatial configuration. Accordingly, particles from reservoirs Cell 1 and Cell 2 are spaced from each other centrally in positioning channel 1768 by buffer from inlet channel 1764 and laterally from each channel wall by buffer from inlet channels 1762, 1766, as described above for system 420.

Retention mechanism 486 includes a plurality of single-particle retention sites, here referred to as "Trap A" and "Trap B" (see FIG. 13B). Trap A and Trap B each are positioned to retain a particle introduced by one of the two particle reservoirs, Cell 1 and Cell 2, and carried at correspondingly distinct, transverse positions along positioning channel 1768; see FIG. 13B. Accordingly, Trap A is positioned to retain a particle introduced from Cell 1, and Trap B from Cell 2. Particles not retained may be carried past retention mechanism 486 to output mechanism 488, along central outlet (waste) channel 1776 or flanking outlet (waste) channels 1778.

Treatment mechanisms 490, 492 provide exposure of retained particles to distinct reagents, indicated as Reagents 1-4; see FIG. 13B. A particle retained in Trap A may be exposed to Reagent 1 and/or 2 (controlled by valves V2 and V3), and a particle retained in Trap B may be exposed to Reagent 3 and/or 4 (controlled by valves V6 and V7). These reagents may be stored and delivered (sequentially and/or simultaneously, in any desired proportion and for any desired time) using any suitable mechanism, such as those described above in Example 2 and below in Example 8. Reagents from each treatment mechanism may be separately addressed to a corresponding retention site, by transverse positioning of reagent flow streams entering positioning channel 1768. Reagents flow toward central outlet channel 1776, but occupy a discrete portion of the entire flow stream within positioning channel 1768 and transverse channel 1780 due to laminar flow. Accordingly, reagents from treatment mechanism 490 may be restricted to the left side of positioning channel 1768 in FIG. 13B (and thus Trap A), whereas reagents from treatment mechanism 492 may be restricted to the right half of the channel (and thus Trap B). Optionally, spacer buffer from central reservoir 1772, Buffer 2, may flow between reagents delivered by the treatment mechanisms, reducing the probability of any reagent crossing over, and thus contaminating, the noncorresponding retention site.

Release mechanism 494 enables release of retained particles. After release, the released particles may be analyzed further and/or collected, and/or the retention sites may accept a new set of particles for another round of treatment and analysis. Release mechanism 494, may be operated by valve V4, to produce a localized reverse or dislodging flow that propels the retained particles out of the retention sites. Release mechanism 494 is similar to the release mechanism described below in Example 7. However, in contrast to the release mechanism described below, retention sites in the present example are spaced from reverse flow channels 1782.

FIG. 13C shows selected portions of a modified version of system 480, system 480'. System 480' is distinct from system 480 in at least two aspects. First, retention mechanism 1784 includes retention chambers 1786, 1788 that are larger than the retention sites of system 480, and thus are capable of holding plural particles. Second, treatment mechanisms 1790, 1792 include reagent inlet channels 1794, 1796 that introduce reagents into transverse channel 1798, rather than positioning channel 1800. This altered position of the reagent inlet channels moves the reagents farther from retained particles, but may facilitate washing out reagents toward outlet channels 1802 after exposure. However, during treatment, reagents from inlet channels 1794, 1796 are still positioned transversely relative to the general direction of fluid flow toward central outlet channel 1804. Accordingly, reagent inlet channels may deliver reagents at any suitable sites that allow laminar flow-based localization of reagents.

Systems 480 and 480' may be modified in any suitable aspect. For example, a single population of particles, such as from a single input reservoir, may be retained at plural distinct retention sites, such as Trap A and Trap B, and then the sites separately exposed to distinct reagents introduced by distinct treatment mechanisms. Alternatively, or in addition, inlet channels provided by treatment mechanisms and particle input mechanisms may overlap or converge upstream of a common positioning channel, such as positioning channel 1768 or 1800.

Applications of Embodiment 2

Exemplary operation of system 480 is described below using cells. System 480 may be readied for operation by loading the input reservoirs with cells and buffers and equilibrating channels with the buffers, as described in other examples.

Trap A and Trap B may be loaded as follows. Valves V1, V4, and V5 are opened, and valves V2, V3, V6, and V7 are closed. Five flow streams coming from each of the five reservoirs meet before Trap A and Trap B in positioning channel 1768. The cells from reservoirs Cell 1 and Cell 2 are directed to their respective Traps A and B. Fluid and unretained cells flow past retention sites along divergent flow paths toward a plurality of outlet channels 1776, 1778.

Once a cell (or cells) is retained in each retention site, valve V4 is left open, and valves V1 and V5 are closed. Closing valve V1 blocks input of additional cells, and stops flow from lateral buffer reservoirs 1770, 1774. Closing valve V5 stops divergent flow, so that buffer (from central buffer reservoir 1772 (Buffer 2)) flows to central outlet channel 1776 along a unitary path.

Distinct reagents may be delivered to the retained cells as follows. Valve V4 is left open, and all other valves remain closed. Both pumps are running. Valve V2 and/or valve V3 may be opened to address Reagent 1 and/or 2 to Trap A. Valve V6 and/or valve V7 may opened to address Reagent 3 and/or 4 to Trap B. Valves may be partially opened as described in Example 8 to provide a desired mixture of reagents. Buffer from reservoir 1772 flows past Traps A and B to outlet channel 1776 and may be used as a barrier between the streams of reagents addressed to Traps A and B. At any suitable time, valve V5 may be closed to release the retained cells.

Exemplary Results with Chips Produced According to Embodiment 2

System 480 was tested as described below. Microfluidic chips were fabricated according to system 480 of FIG. 13A and used for analysis of flow patterns and particle treatment efficacy with colored and/or fluorescent dyes.

FIGS. 13D-F show dye patterns formed by colored dyes introduced using each treatment mechanism and a Bowing spacer buffer to separate reagents. In each figure, Trap A holds a 10 μm bead, and Trap B two 6 μm beads. FIG. 13D shows a dye pattern formed by green dye delivered from each treatment mechanism and an orange dye-labeled spacer buffer delivered by reservoir 1772. The orange spacer buffer separate the two green dyes, and each green dye flows from its corresponding inlet channel 1806, 1808 to outlet channel 1776. Some green dye also travels slowly along transverse channel 1780. FIG. 13E shows a dye pattern formed by red dye delivered from treatment mechanism 490, green dye from mechanism 492, and orange dye from buffer reservoir 1772. FIG. 13F shows a dye pattern formed by red dye delivered from treatment mechanism 490, yellow dye from mechanism 492, and orange dye from buffer reservoir 1772.

FIGS. 13G-13J show an analysis of treatment efficacy of single Jurkat cells captured in each of Traps A and B. FIG. 13G shows the two retained cells 1810, 1812 prior to treatment. FIG. 13H shows exposure of each cell to Trypan blue dye delivered by distinct treatment mechanisms. The spacer buffer forms an uncolored column of fluid 1814 between the two blue regions surrounding Traps A and B. Membranes of both cells are intact so neither stains efficiently with the dye. FIG. 13I shows exposure of cell 1810 in Trap A to methanol, to fix the cell, while cell 1812 in Trap B is addressed with buffer. FIG. 13J shows the two cells being exposed to the blue dye after fixation of cell 1810. Cell 1810 can no longer exclude the blue dye and is stained blue. Cell 1812 has not been in contact with methanol and is not stained.

FIG. 13K demonstrates that spacer buffers may not be required to prevent cross contamination of particles and/or reagents during particle loading and/or exposure to reagents. Each trap has been loaded with a fluorescent bead 1816, 1818. Bead 1816 is addressed with a fluorescent dye, fluorescein, and bead 1818 with Trypan blue, using treatment mechanisms 490, 492, respectively. No spacer buffer stream separates the two reagent streams, but the reagents do not substantially cross over and contaminate the other trap. It should be noted that the time for diffusion of reagents (or particles) transverse to their laminar flow streams is limited by the relatively short time that the laminar flow streams are in contact before passing Traps A and B. Accordingly, analyses may be conducted with or without spacer streams, with spacer streams being used to lower the probability of cross-contamination.

Embodiment 4

Figure 13L:
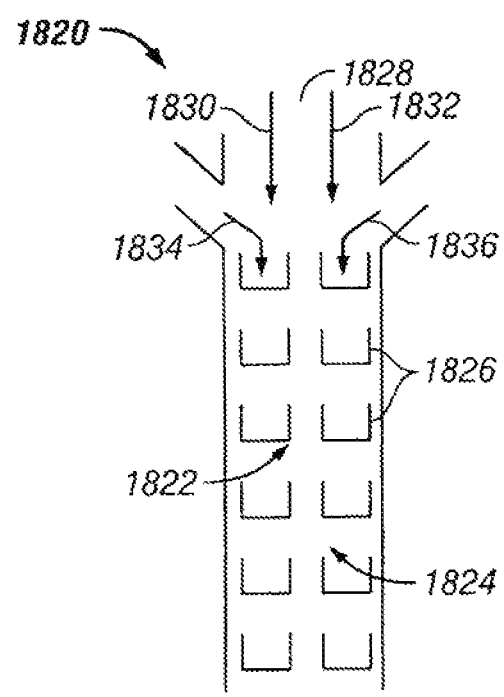
FIG. 13L is a fragmentary, top plan view of a microfluidic system having separately addressable sets of linear trap arrays, in accordance with aspects of the invention.

FIG. 13L shows a portion of microfluidic system 1820 that may be used to separately address particles and/or reagents to sets of particle traps. System 1820 includes a plurality of serially arrayed sets 1822, 1824 of particle traps 1826. Each set 1822, 1824 is disposed to a discrete transverse position with a fluid flow stream, in this case defined by a channel 1828. Accordingly, laminar flow streams carrying particles (1830, 1832) or reagents (1834, 1836) may be segregated to discrete transverse regions of channel 1828, so that each set 1822, 1824 is individually addressed. In alternative embodiments, traps 1826 are disposed in a transverse channel, such as channel 1798 or a chamber, such as a cell chamber with size-selective channel around its perimeter.

Example 4

Microfluidic System for Multiplexed Analysis of Particles in an Array

Figure 14:
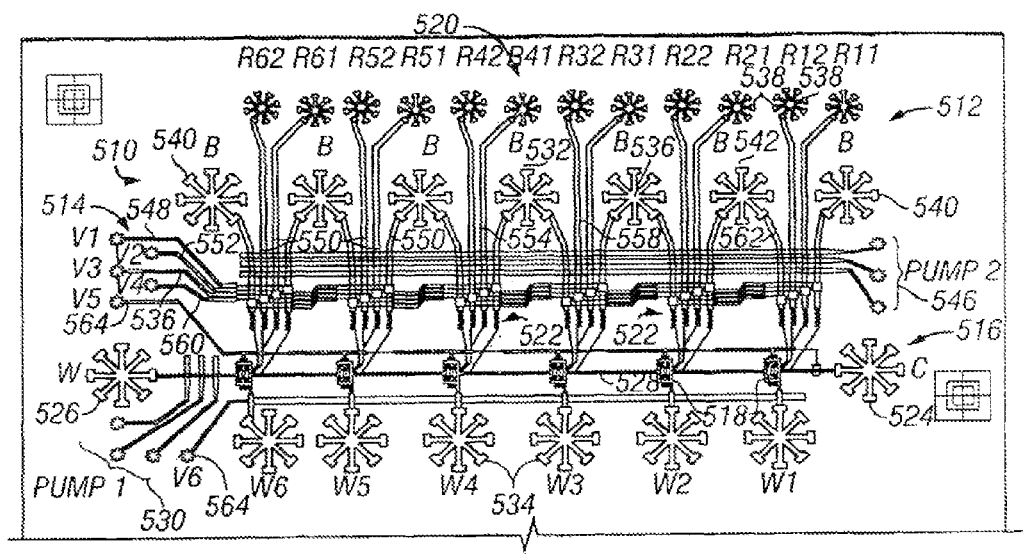
FIG. 14 is a top plan view of a microfluidic system for retaining an array of particles in series and for perfusing members of this array separately and in parallel, in accordance with aspects of the invention.
Figure 15:
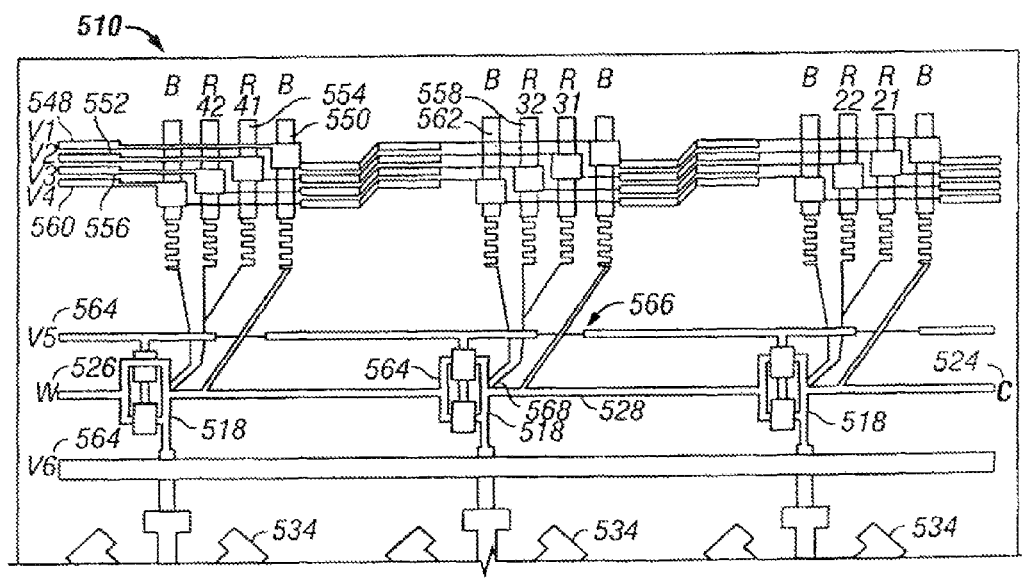
FIG. 15 is a top plan view of selected portions of the system of FIG. 14, illustrating fluid-layer and control-layer networks for treating retained particles separately and in parallel, in accordance with aspects of the invention.
Figure 16:
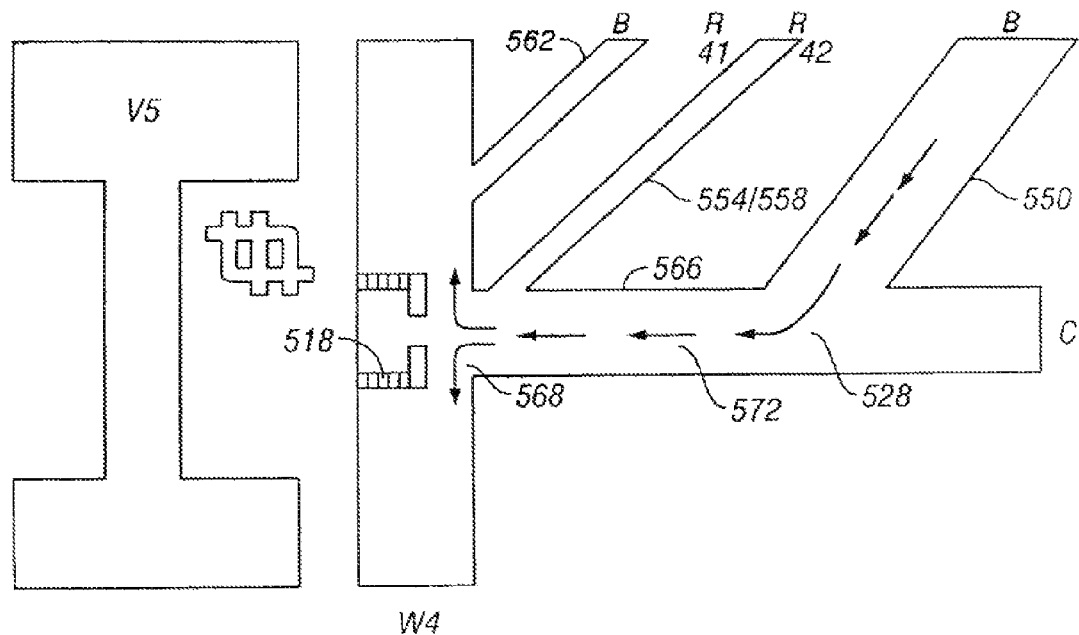
FIG. 16 is a top plan view of portions of a single retention network from the system of FIG. 14, illustrating selected paths of fluid flow, in accordance with aspects of the invention.

This example describes a microfluidic system that loads particles in a serially distributed set of particle retention sites, and separately addresses reagents to each of these sites in parallel; see FIGS. 14-16.

Background

Cell analyses often involve the use of arrays of cells or cell populations. These arrays may be formed in microtiter plates, so that individual wells within the array can be treated distinctly, for example, with distinct test compounds. During or after treatment, the microplate arrays are analyzed in multiplex to measure properties of cells within each individual well. However, such arrays are difficult to form reproducibly with microtiter plates when single cells or a small group of cells are placed in each well. Even if formed in microtiter plates, rapidly treating the cells in such microtiter plates, and measuring short-term consequences of such treatments, poses substantial technical hurdles. Therefore, a microfluidic system is needed that forms more reproducible arrays of individual cells or small groups of cells at distinct positions, and that allows separate, rapid treatment and analysis of the cells at the distinct positions.

Description

This example describes a microfluidic system that serially traps small sets of particles at preselected positions within the system, allowing treatment of the trapped particles in parallel with desired reagents. Due to serial trapping of input particles, a single loading of particles into one inlet may be used to supply particles to an entire array of traps. Thus, this design may be used to integrate a large number of traps into a single system. This microfluidic system also reduces the number of control lines required, as single control lines regulate sets of fluidic channels, such as perfusion channels, that individually interface with each of the traps. Accordingly, single control lines provide parallel control for fluidic delivery to, or output from, each of the traps. Such parallel control allows similar particles that are retained by each trap to be individually treated with distinct reagents. Furthermore, such parallel control allows all traps to be fluidically connected during particle loading, but then fluidically isolated during particle treatment and measurement. This arrangement of the traps enables the fabrication of larger microfluidic systems that may be suitable for use in high-throughput drug discovery. For example, system 510 has a footprint of 2 by 4 cm. By increasing this density somewhat and increasing the number of traps over twenty-fold, at least 128 traps may be disposed on a single substrate of 8 by 12 cm, allowing each of the 128 traps to be addressed by two distinct reagents, with a total of 256 reagents per substrate.

FIG. 14 shows a microfluidic system 510 for forming and analyzing an array of particles. System 510 may be formed by any suitable technique, such as multilayer soft lithography, to include at least two distinct layers: (1) a microfluidic network layer 512, shown in blue and orange, and (2) a control layer 514, shown in pink. Channels having distinct widths and/or cross-sectional shapes may be formed within each layer using molds fabricated, for example, as described in Example 17.

Microfluidic layer 512 includes two orthogonally directed networks. Particle loading network 516 is used to input and position particles, so that the particles are retained at a linear array of particle traps 518. Particle treatment system 520 is an array of parallel, individual perfusion networks 522 that intersect loading network 516 at individual particle traps 518.

Particle loading network 516 includes an inlet 524, an outlet 526, and a loading channel 528 extending there between. Inlet well 524, labeled C, is a reservoir that receives and holds a particle suspension to be introduced into network 516. Outlet well 526, labeled W, is a waste reservoir that receives and holds fluid and unretained particles that have traveled through network 516. Loading channel 528 carries particles between inlet well 524 and outlet well 526 to each of a plurality of particle traps 518 disposed along channel 528. Fluid is actively transported along network 516 by a three-valve pump 530, labeled "pump 1," which is positioned near the terminus of network 516 to pull fluid through the network. Positioning the pump after the traps delays potential damage to fragile particles, for example, due to compression under closing valves, until particles have passed all particle traps 518.

Each perfusion network 522 directs fluid between perfusion inlets 532, traps 518, and treatment outlets 534. Perfusion inlets 532 are of two main types: buffer inlet-wells 536, labeled "B," and reagent inlet-wells 538, labeled "$R_{xy}$." The buffer inlet-wells hold a buffer or other washing or maintenance liquid, such as water or a solvent. Based on their positions within particle treatment system 520, the buffer inlet-wells are either a terminal inlet-well 540 or an intermediate inlet-well 542. Terminal inlet-wells 540 feed fluid to only one trap, whereas intermediate inlet-wells 542 are shared between two adjacent traps. Based on whether they are intermediate or terminal inlet-wells, buffer inlet-wells feed a main stream and/or a shielding stream. The control and function of these two streams are described further below. The reagent inlet-wells hold one of two (or more) reagents (or reagent mixtures) that may be precisely exposed to an individual trap. Reagent inlet-wells are labeled "$R_{xy}$," with "x" referring to trap assignment relative to the array of traps 518, and "y" referring to one of the two reagents that can be directed to a given trap. For example, reagent inlet-well $R_{12}$ feeds the first of the plurality of traps (closest inlet C) with the second of two reagent choices for that trap. Fluid that passes each trap 518 may be directed to a corresponding treatment outlet-well 534 or waste well, labeled here as W1-W6. For example, reagents from reagent inlets $R_{41}$ and $R_{42}$ flow past and/or through trap number 4 and are collected in waste well $W_x$, where x=4.

Control layer 514 regulates fluid flow from perfusion inlet-wells 532 with a limited number of control lines that act on many fluid channels 544 in parallel; see FIGS. 14 and 15. A three-valve pump 546, "pump 2," acts simultaneously on all inlet channels 544 that extend from perfusion inlet-wells 532, to actively drive fluid from these inlet-wells to and past traps 518, and on to waste outlet-wells 534. Opening or closing each of four perfusion valves, V1-V4, determines whether fluid actually flows through each of the specific types of inlet channels 544 within the perfusion system. Valve V1 regulates control line 548, which includes a plurality of individual valves positioned over each of a corresponding plurality of focusing channels 550 included among inlet channels 544. Similarly, valve V2 regulates control line 552, which includes valves that control each of a plurality of first-reagent channels 554, valve V3 regulates line 556, which controls each of a corresponding plurality of second-reagent channels 558, and valve V4 regulates line 560, which controls each of a corresponding plurality of shield channels 562. Thus, opening or closing each of valves V1-V4 provides unified, parallel control over flow of individual inlets to each of the plurality of traps.

FIG. 15 shows a portion of system 510, including traps 2, 3, and 4, to illustrate in more detail the design and rationale for the switching valves. Insulation valves 564 function in the control layer to mediate switching between particle loading network 516 and particle treatment system 520. Insulation valve V5 controls a set of valves that block flow along loading channel 528 at a position downstream of particle inlet 524 (inlet C) and of the traps. Thus, activation of valve V5 fluidically isolates each trap and converts system 510 from a particle-loading configuration to a perfusion configuration. In contrast, insulation valve V6 controls a set of valves blocking flow to each individual treatment outlet 534, preventing diversion of particles to treatment outlets during particle loading, when valve V6 is closed. Therefore, valves V5 and V6 are primary determinants of parallel versus serial use of system 510.

FIGS. 15 and 16 show details of the loading mechanism. Loading channel 528 forms a divided flow path 564 at each trap 518. Thus, particle stream 566 diverges directly upstream of each trap 518, at a T-junction 568, following divided flow path 564, and then converging to form reunited particle stream 566. At each T-junction 568, a subset of particles do not follow divided flow path 564, but flow instead directly into trap 518. Accordingly, each trap is loaded using a divergent-flow mechanism, as described above in Example 2, but, in system 510, without the use of focusing-buffer streams during particle loading to focus particle flow within channel 528. In this example, trap 518 includes a retention chamber similar to retention chamber 270 of FIG. 5-8 in Example 2. However, any suitable traps may be used, such as single-particle traps described below in Examples 4-7, 11, and 12.

The subsequent perfusion of trapped particles uses shielding and perfusion mechanisms analogous to those of Example 2. Buffer flow from each buffer inlet 536 flows along focusing channels 550, into loading channel 528, and past trap 518 in a unitary flow path 572, shown in FIG. 16 as a dashed path, analogous to focusing buffer stream 314 of FIG. 5. Unitary flow path 572 may perform a variety of functions, such as bathing trapped particles during treatment, providing a retaining force on trapped particles during perfusion, and focusing inflowing reagents and shield buffer, in their laminar flow streams, toward the trapped particles. Similarly, combined first and second reagent channel 554/558 and shield channel 562 determine precise exposure to first and second reagents, as described above in Example 2.

Applications

An exemplary use of system 510 to load particles and expose the particles to different reagents is described below. System 510 is formed and readied for use as described elsewhere in this Detailed Description.

Loading particles into each of traps 518 may be conducted as follows. Valves 1-4 and 6 are closed, and valve 5 is open. Pump 1 is running, and pump 2 is not. The buffer inlet-wells B, shown at 536, are loaded with buffer, each of inlet-wells $R_{xy}$ is loaded with a reagent, and inlet-well C is loaded with a cell suspension. After making sure that the waste inlet-wells 526 are empty, pump 1 is allowed to pull the particles to the traps.

Conversion from a loading to a perfusion configuration may be carried out as follows. Once each of the traps has its desired occupancy and/or is full, pump 1 is stopped and valve V5 is closed. Each trap is now isolated. Next, Valve V6 is opened to allow fluidic access to waste outlet-wells 534. Then, valve V1 is opened to permit flow of buffer from each inlet-well 536.

Trapped particles are perfused with each of the first and second reagents as follows. Pump 2 is started, running at a frequency of about 60 Hz. This pump is running throughout the following treatments. Pumping action of pump 2 drives buffer through focusing channels 550, along unitary flow path 572 past each trap 518, toward waste outlet-wells 534. Prior to perfusion, valves V2, V3 and V4 are closed, so that only no fluid flows from along shield channel 562 or reagent channels 554, 558. Flow of the first reagent and the shield buffer is initiated by opening valves V2 and V4, while valve V3 remains closed. This valve configuration is used to wash the fluidic network without exposing the trapped particles to the first reagents, because the shield buffer directs the first reagent stream to a spaced flow path separated from the trapped particles. Once the fluid lines are washed with each of the first reagents, valve V4 is closed to stop from of the shield buffer, allowing each of the first reagents to contact trapped particles. After a desired duration of exposure to each first reagent, valve V2 is closed, allowing the shield buffer to wash away reagent one, and rapidly terminating exposure. Trapped particles may be exposed to each second reagent in parallel by following a comparable series of steps, but opening and then closing valve V3 instead of V2. In alternative perfusion strategies, particles may be exposed to both the first and second reagents simultaneously, by opening both valves V2 and V3 together. Furthermore, particles may be exposed to any desired ratio of first and second reagents by partially closing valves V2 and/or V3, as described below in Example 7.

Example 5

Microfluidic Device for Forming and Analyzing a Particle Array Using a "Cell Comb"

This example describes a microfluidic device for forming and analyzing arrays of small number of particles, such as cells; see FIGS. 17-20.

Background

In many applications, it is necessary to form an array of cell-analysis chambers, with each chamber containing the same number of cells. These chambers allow multiple experiments, such as drug screens, to be conducted in parallel, in a consistent and comparable fashion. Currently, standard analyses use wells of microtiter plates as cell chambers, distributing an equal volume of a cell suspension to each of the wells. The size of these chambers and thus the number of cells analyzed has been decreasing in response to efforts to reduce the use of space, reagents, and cells in these analyses. Unfortunately, results from these analyses become increasingly variable as the average number of cells per well decreases. For example, with 96-well microtiter plates, there generally are about 3000 to 5000 cells at the bottom of a well; with 384-well plates, this number drops to about 1000 cells; and, as researchers push for smaller and smaller assay volumes, such as with 1536-well plates, this number drops further to only about 250 cells. These small average numbers of cells may lead to variations in the actual number of cells among wells of as high as 20%. Such variations lead to huge errors in the detected reaction signals. Accordingly, with even fewer cells per well, for example, with single cell assays or when cells of interest are in limited supply, microtiter plates do not provide an adequate cell-analysis chamber unless cells are counted to place an equal number per well. Even then, microtiter plates are deficient for performing rapid experimental manipulations. For example, early responses to treatment with a drug are difficult to measure with microliter plates, because adding and mixing steps cannot be performed very rapidly. Therefore, many cell-analyses would benefit from systems for efficiently loading, rapidly treating, and analyzing small numbers of cells.

Description

Figure 17:
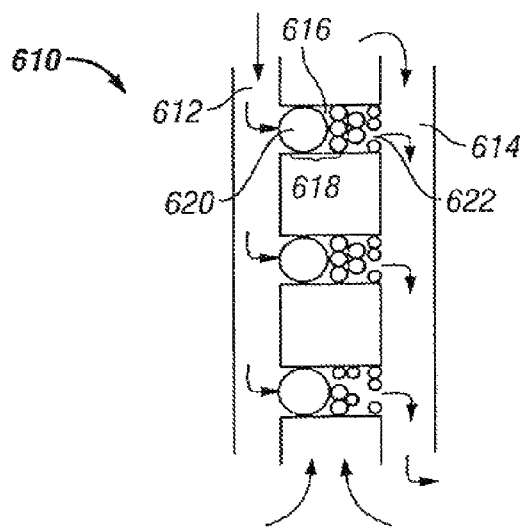
FIG. 17 is a fragmentary, top plan view of a microfluidic device for forming an array of single particles or groups of particles, in accordance with aspects of the invention.

FIG. 17 shows a microfluidic device 610 for forming an array of single particles or small groups of particles. Device 610 includes an input channel 612, a waste channel 614, and an array of filter channels 616 extending between the input and waste channels. Device 610 also includes a fixed-volume particle chamber 618 formed in each filter channel 616, and a set of valves for sample handling (see below). Device 610 may be referred to as a "cell comb" because the path for cell (particle) flow takes the shape of a comb, with chambers 614 representing the teeth of the comb.

The components of a cell comb each have a distinct function. Input channel 612 carries input particles, such as a particle 620, to each filter channel 616. A filter 622 is disposed within, or adjoining, each filter channel. Filter 622 allows fluid to pass into waste channel 614, but retains particles 620 in a portion of filter channel 616 that corresponds to chamber 618.

Filter 622 may take various forms, provided as a component(s) separate from the walls of filter channel 616 and/or integral to these walls. For example, filter 622 may be formed by a porous membrane that is specific for each chamber 618 or that is shared by two or more or all chambers 618. Alternatively, filter 622 may be formed by smaller, "leak" channels within filter channel 616, or by posts, obstacles, or protrusions that extend into a portion of filter channel 616, or that are disposed adjoining or adjacent an end of the filter channel. The diameter of the smaller channels, or the spacing of the posts/obstacles, determines the size of particle retained in chamber 618. Thus, as long as the diameters of these smaller channels, or the maximum spacing between these posts/obstacles, are sufficiently less than the diameter of a particle to be retained, the particle will be confined to chamber 618 while fluid will pass readily into waste channel 614. In addition, the passage of fluid through the filter provides a retaining force to reduce or prevent backflow of particles into input channel 612.

The capacity and retention ability of each chamber 618 is defined at least in part by filter channel 616 and filter 622. The diameter and length of filter channel 616, coupled with the position of filter 622 relative to filter channel 616, define the capacity of chamber 618. Accordingly, chamber 618 may be dimensioned to receive a fixed number of input particles 620, such as a single particle. Such input particles may have a common size, such as cells from a homogeneous cell population, or they may have a range of sizes, such as cells from blood. In some embodiments, the diameter of filter channel 616 allows size-selective retention of a single particle. For example, the diameter may be large enough to receive certain particles in a heterogeneous particle population, such as red blood cells, but small enough to exclude others, such as white blood cells. Filter 622 also acts size selectively, as described above, so in combination with chamber 618, individual filter channels 616 may be designed to retain a single cell within a defined size range. Alternatively, individual filter channels may be designed to retain a group of two or more cells, with each cell having a minimum size that is retained by filter 622.

Pressure differences within device 610 create positioning and retaining forces for particles 620. Flow between input channel 612 and waste channel 614 creates a positive pressure difference between the input channel and the waste channel across filter channel 616. As a result, particles are carried into chambers 618 by fluid and fill each of the chambers very rapidly. After the particles have filled some or all of chamber 618, a set of valves may be used to isolate each chamber 618 (see below). In particular, the closure of such valves may transform each cell chamber into an isolated reaction chamber, with a fixed number of particles for analysis.

Figure 18:
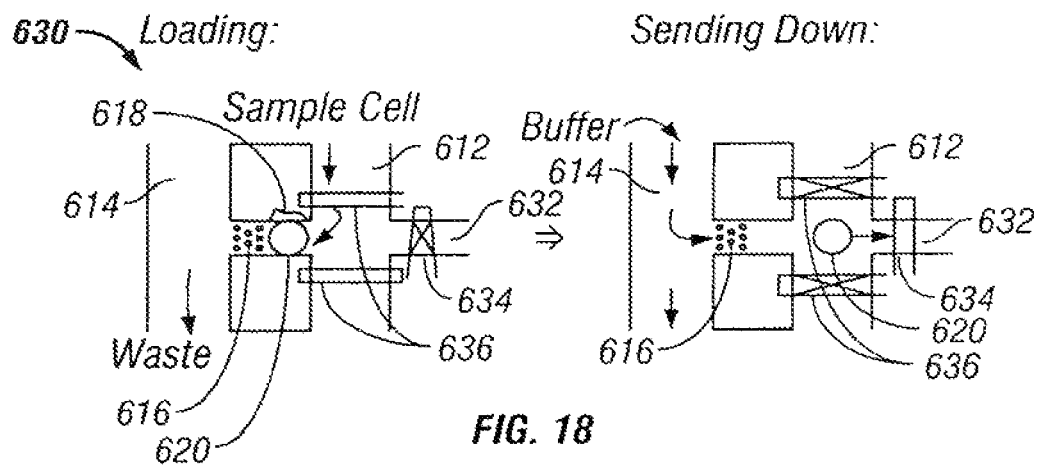
FIG. 18 is a pair of fragmentary, top plan schematic views of a microfluidic device for forming an array of retained particles that may be transferred to an array of separate sites, illustrating particle retention and transfer configurations, on the left and right respectively, in accordance with aspects of the invention.
Figure 19:
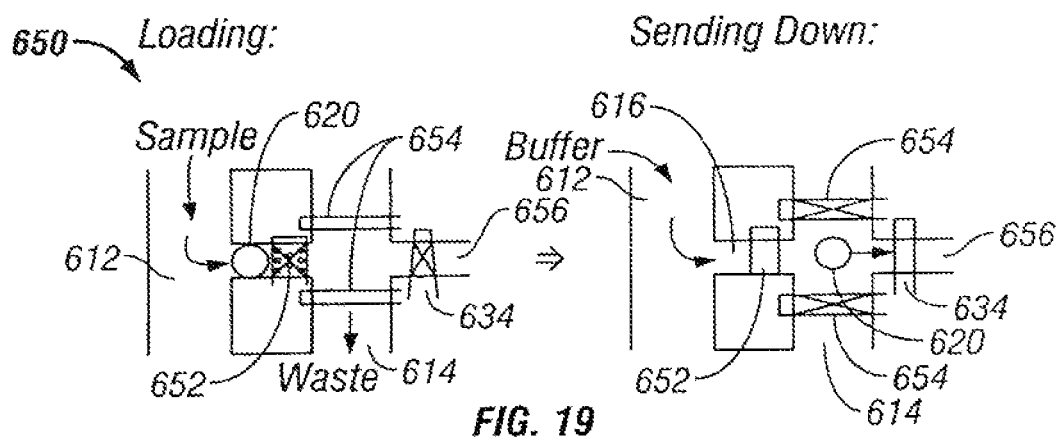
FIG. 19 is a pair of fragmentary, top plan schematic views of another microfluidic device for forming an array of retained particles that may be transferred to an array of separate sites, illustrating particle retention and transfer configurations, on the left and right respectively, in accordance with aspects of the invention.
Figure 20:
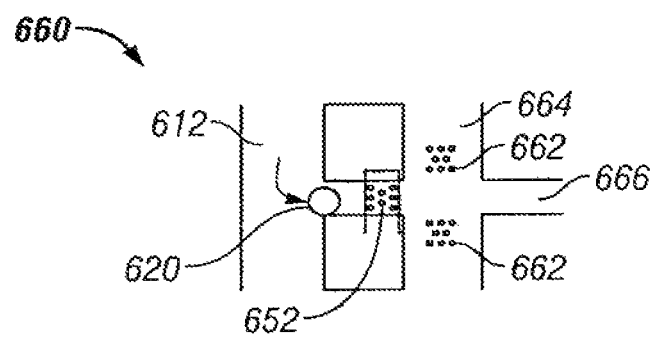
FIG. 20 is fragmentary, top plan schematic view of yet another microfluidic device for forming an array of retained particles that may be transferred to an array of separate sites, in accordance with aspects of the invention.

FIGS. 18-20 show valves, additional filters, and analysis sites that may be used with, or added to, device 610 for manipulating the contents of individual chambers 618.

FIG. 18 shows a device 630 that is similar to device 610, but that includes a separate analysis site 632 opposing each chamber 618. A site valve 634 controls access to analysis site 632, and a pair of input valves 636 isolates each chamber 618 along input channel 612. The left panel of FIG. 18 shows a loading configuration for each of valves 634, 636. Here, site valve 634 is closed (indicated by an "X") to prevent input particles 620 from entering analysis site prematurely, and input valves 636 are open to allow particles to access each chamber 618. The right panel of FIG. 18 shows repositioning of retained particle 620 to analysis site 632. Here, site valve 634 is open, but input valves 636 are closed. Particle 620 is displaced from chamber 618, by fluid flowing in reverse across filter channel 616 from waste channel 614, rather than input channel 612. Since input valves 636 are closed, fluid and particle 620 flow orthogonally to input channel 612, into analysis site 632. After particle 620 is delivered to analysis site 632, site valve 634 is closed to isolate the particle fluidically from other particles. In other embodiments, additional fluidic lines may be used to deliver reagents to analysis site 632, or analysis site 632 may be a blind channel that is preloaded with such reagents.

FIG. 19 shows a device 650 that is similar to device 630 of FIG. 18, but that includes switchable filters 652. Switchable filters 652 may be switched between a closed, filtering position, shown on the left, and an open, nonfiltering position, shown on the right. After particle loading, switchable filters 652 are opened to direct particle 620 to an analysis site. Such a switchable-filter design allows unidirectional flow across filter channel 616 to both retain and release particle 620. Accordingly, fluid flow from input channel carries out each both retention and release, using particle-laden fluid during retention, and particle-free fluid during release. Waste valves 654 are closed before switchable filter 652 is opened to direct particle 620 to analysis site 656. Switchable/regulatable filters may be formed by size-selective channels that are formed on valve membranes. With this arrangement, deflection of the valve membranes may move the size-selective channels in or out of filtering position by pressure exerted through a control layer. Alternatively, or in addition, size-selective channels may be adjacent to, or flanking, valve membranes, as described below in Example 26.

FIG. 20 shows another device 660 with a switchable filter 652. In device 660, waste channel 614 includes a series of waste filters 662 that function in place of waste valves 654 in device 650. Waste filters 662 play a dual role in allowing waste to flow down waste channel 664, while directing particle 620 toward analysis site 666. The passages of analysis sites 666 may serve as waste channels.

Applications

Cell combs, described in this example, may be useful in a variety of applications. For example, cell combs may be useful in drug discovery, serving as replacements for microtiter plates in cell assays to provide tighter control of the cell numbers. With current technology, the fabrication of each cell chamber in a cell comb device can be carried out with precision. Therefore, cell assays may be performed with an array of cells formed using this device, with reduced signal variation from chamber to chamber, even with single-cell assays. Cell combs may, more generally, be used with a variety of micron-sized particles, in addition to cells, such as fluorescently or enzymatically coated beads. This device also can operate in gas phase, as long as the size of the particles of interest is larger than the pore size of the filter units. Cell combs also can be cascaded so that objects of different sizes are filtered out at different stages.

Example 6

Particle-Retention Mechanisms

Figure 21:
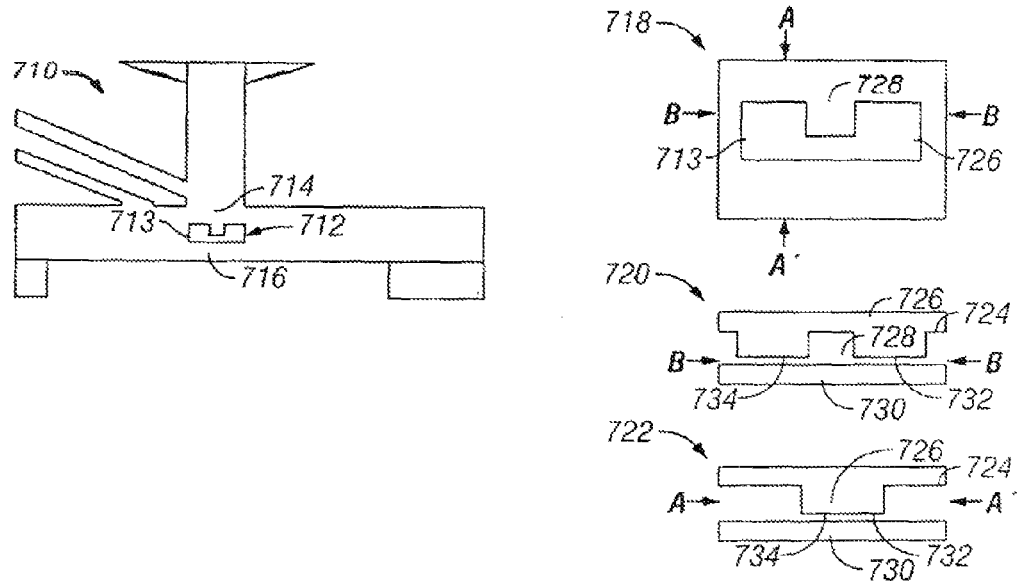
FIG. 21 is a composite of top plan and sectional views showing selected portions of a microfluidic system for retaining particles using a particle-retention chamber that is fully spaced from the floor of the system, in accordance with aspects of the invention.
Figure 22:
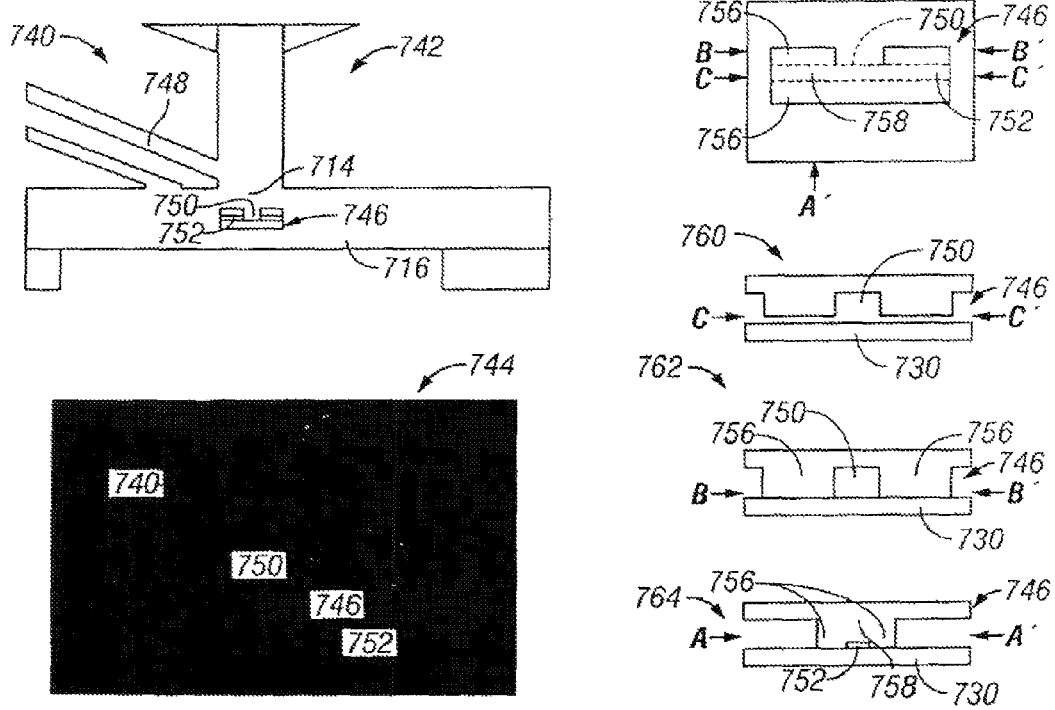
FIG. 22 is a composite of top plan and sectional views, and a photographic image, showing selected portions of a microfluidic system for retaining particles using a particle-retention chamber that is partially spaced from the floor of the system, in accordance with aspects of the invention.
Figure 23:
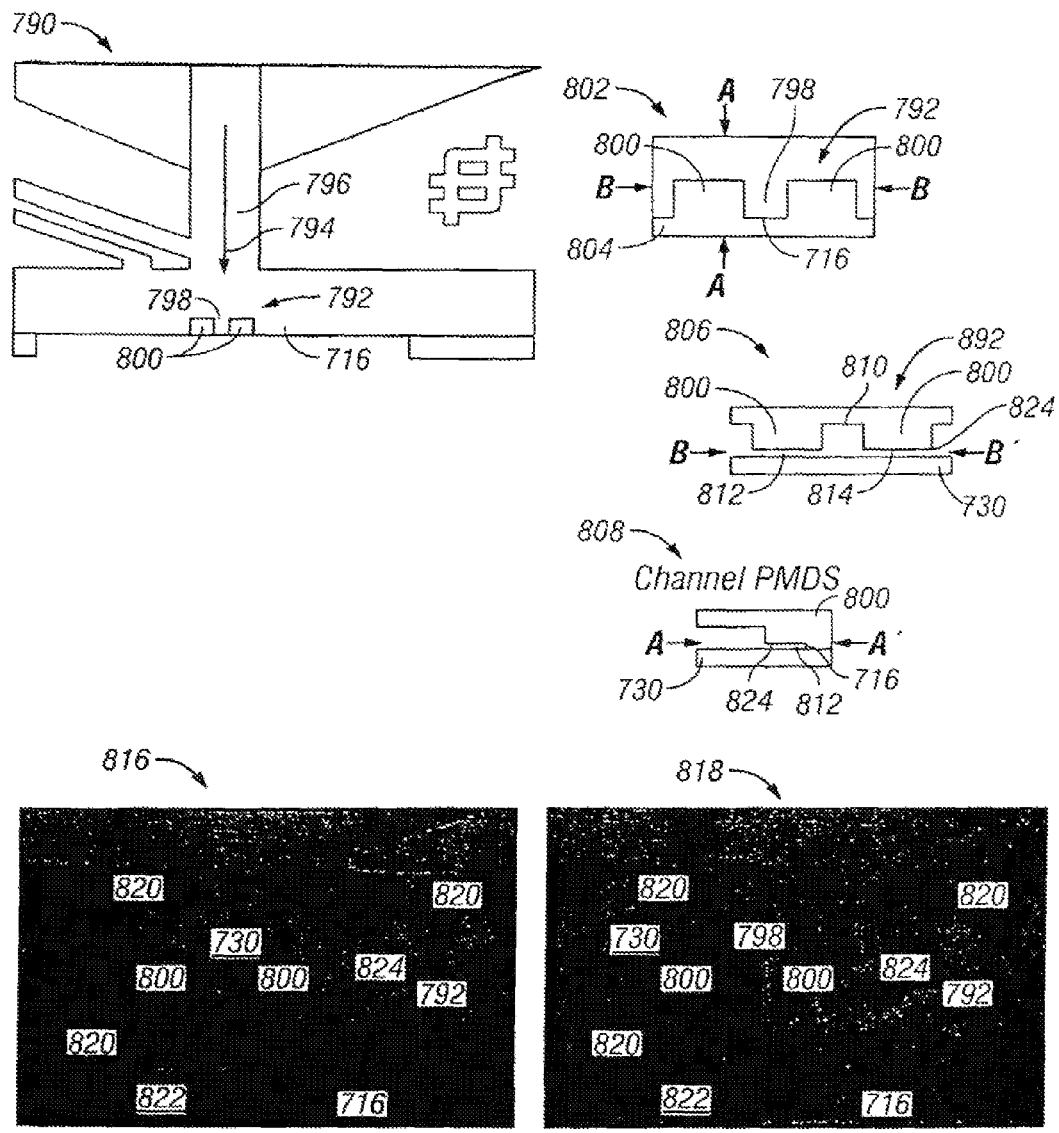
FIG. 23 is a composite of top plan and sectional views, and two photographic images, showing selected portions of another microfluidic system for retaining particles using a particle-retention chamber that is fully spaced from the floor of the system, in accordance with aspects of the invention.

This example describes mechanisms for retaining particles, using particle traps that are spaced from their corresponding substrates; see FIGS. 21-23.

Background

One goal of microfluidic systems is the capability of retaining particles at preselected positions for subsequent treatment and analysis. Traps that perform such retention functions may perform optimally if they have minimal effects on fluid flow; otherwise, flow patterns around the traps may be disrupted, slowing or reducing particle and reagent entry into the traps. Examples 1 and 2 above describe traps that may be used to retain single particles or groups of particles. However, these traps have limited flow through the traps themselves. For example, trap 180 of Example 1 includes blocks P and Q that reduce or prevent cross-flow on either side of a single retained particle. Similarly, retention chamber 270 of Example 2 includes relatively narrow microchannels 300 that may restrict fluid flow substantially. Thus, there is a need for an alternative trap that may be positioned closer to particle input flow streams without disrupting flow patterns, while allowing quicker and more efficient access by reagent and washing flow streams.

Description

This example describes retention mechanisms having improved fluid flow properties. These mechanisms are positioned downstream of a particle flow stream, near the point at which the particle flow-stream diverges at a T-junction. These mechanisms have been dimensioned to trap a single particle; however, they alternatively may be dimensioned to trap two or more particles. The microfluidic system with respect to which each retention mechanism is illustrated, particularly positioning mechanism 264 and perfusion mechanism 268, is described above in Example 2. This earlier example describes suitable fluid flow paths, and the operation of the positioning and perfusion mechanisms. However, the retention mechanisms presented in this example may be combined with any other suitable microfluidic mechanisms for particle analysis.

Embodiment 1

FIG. 21 shows a microfluidic system 710 for positioning, retaining, and/or perfusing a single particle, in accordance with aspects of the invention. Portions of system 710 that are molded from distinct photoresist layers are shown as distinct colors, as described above (see introductory section of Examples). Retention mechanism 712 includes a trap 713, shown in turquoise, positioned centrally in T-junction 714, in a spaced relation from distal wall 716. Here, view 718, on the top right, is a schematic representation of trap 713, with points of sectional view indicated; view 720, on the middle right, is a horizontal sectional view near the top of retention mechanism 712; and view 722, on the bottom right, is a vertical sectional view nearer the side of retention mechanism 712. Trap 713 extends downward from roof 724 as a U-shaped block 726. This block includes a recess 728 that acts as a retention site for a single particle. The block extends toward substrate 730, in this case formed of glass, but remains in a spaced relation, in this case about 5 μm apart from the substrate, to form a flow channel 732 that extends under all of block 726. Thus block 726 forms a stalactite-based trap with a potential flow stream below its entire bottom surface 734.

Embodiment 2

FIG. 22 shows another microfluidic system 740 for positioning, retaining, and/or perfusing a single particle, in accordance with aspects of the invention. View 742 shows a color-coded schematic of a system 740, whereas view 744 shows a photograph of an actual microfluidic system formed according to view 742, but flipped horizontally. System 740 includes a trap 746 positioned centrally at T-junction 714. Trap 746 is spaced from distal wall 716, disposing any retained particle quite close to perfusion channel 748 for very rapid exposure to reagents (see Example 2 for a more complete description of the perfusion mechanism). Trap 746 includes a retention site 750 for holding a particle, flanked by trap channels 752, shown in turquoise, that extend to the edges of trap 746. Thus, fluid can enter retention site 750 and flow laterally out trap channels. View 754 shows the structure of trap 746 schematically. Trap 746 includes three rectangular columns 756 that extend down to substrate 730, bridged by channel forming portion 758, shown in dotted outline in view 754, which extends down to 5 μm from substrate 730. Cross-sectional views 762, 764, 766 show the structure of trap 746 in more detail.

Embodiment 3

FIG. 23 shows yet another microfluidic system 790 for positioning, retaining, and/or perfusing a single particle, in accordance with aspects of the invention. System 790 includes a particle retention mechanism, trap 792, that abuts distal wall 716, in alignment with particle stream 794 focused down input channel 796. Trap 792 includes a retention site 798, which is twenty μm in height, and flanked by retention blocks 800 that are spaced from substrate 730 by about 5 μm. View 802 shows a line representation of trap 792, but includes a portion 804 of microfluidic system outside of distal wall 716. Sectional views 806, 808 show how retention blocks 800 extend outward and downward from distal wall 716 and channel roof 810, but form a trap channel 812 that extends under entire bottom surface 814 of the trap. Thus, trap 792 is structured as a stalactite.

Views 816, 818 are two photographs taken of trap 792 at different depths of focus. In view 816, the focal plane is near the substrate surface, showing sharp lines at corners 820, where the microfluidic layer 822 contacts substrate 730. The bottom perimeter 824 of blocks 800 is blurry because bottom surface 814 is raised above substrate 730 (see also views 806, 808). In view 818, the focal plane is slightly higher, raised about 5 μm, placing bottom perimeter 824 in focus. Now, corners 818 are out of focus.

Example 7

Mechanisms for Reusable Microfluidic Systems

This example describes mechanisms that promote reuse of microfluidic systems, including mechanisms for release, collection, and/or resuspension of particles; see FIGS. 24-28.

Background

Microfluidic systems often are designed for single use. Such single-use systems may be used to retain and analyze a single cell or multiple cells, but they then are not or cannot be used again because the cell or cells interfere with analysis of newly introduced cells. Thus, these single-use systems then are discarded, and additional single-use systems must be initialized for additional analysis. This approach is not an efficient use of the single-use systems. Moreover, this approach wastes macroscopic volumes of cells and reagents, and is time consuming for initialization. Thus, there is a need for a reusable microfluidic system that releases retained particles after their analysis, freeing the system (or cells) for additional analysis.

Description

This example describes microfluidic mechanisms that enable formation of reusable microfluidic systems. These microfluidic mechanisms include (1) a particle release mechanism, (2) a particle collection mechanism, and (3) a particle suspension mechanism. The particle release mechanism removes a particle(s) from a trap, generally after treatment and/or analysis in the trap. The release mechanism may provide a force that propels particles out of the trap at any selected time. The particle collection mechanism may be used to collect particles discharged by the release mechanism. Collected particles may be cultured, measured, treated, and/or or discarded. The particle suspension mechanism reduces particle settling in an inlet well, so that a single loading of particles into the inlet well produces a relatively constant particle flow from the inlet well over time. These three mechanisms alone, or in any suitable combination, may enable more efficient and economical use of microfluidic systems for particle analysis.

Embodiment 1

Figure 24:
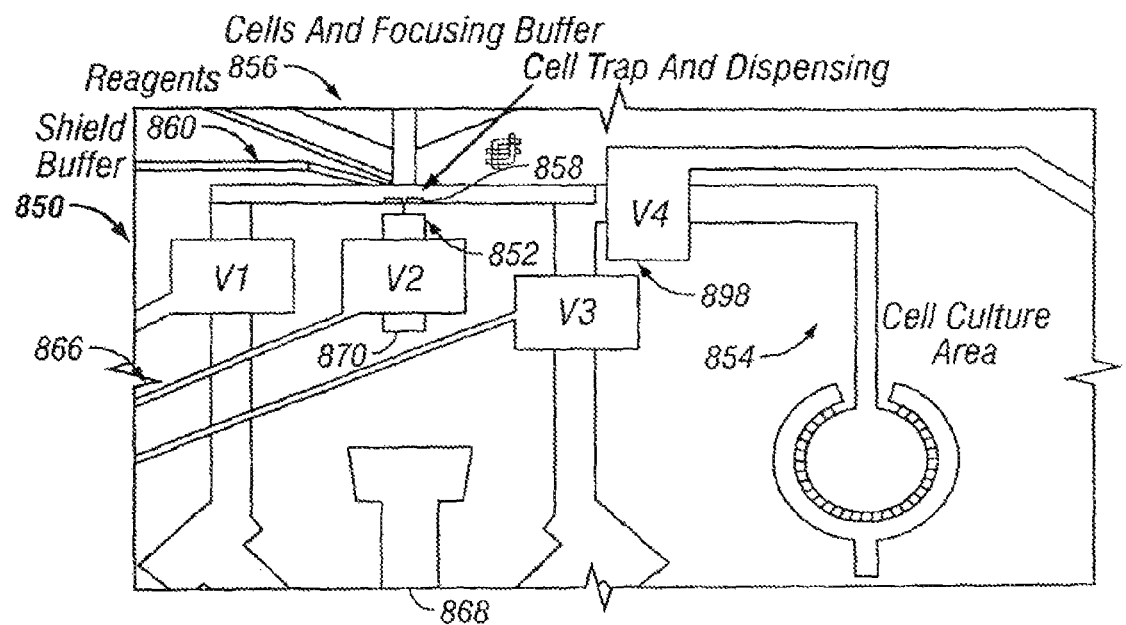
FIG. 24 is a fragmentary, top plan view of a reusable microfluidic system for repeated retention, treatment, and release of single particles, in accordance with aspects of the invention.

FIG. 24 shows a microfluidic system 850 having a particle release mechanism 852 and a particle collection mechanism 854, in accordance with aspects of the invention. The general design of system 850 is as described in Example 2, and elsewhere in this Detailed Description, including a particle focusing mechanism 856, a particle retention mechanism or trap 858, and a perfusion mechanism 860. These particle focusing and perfusion mechanisms are at least substantially equivalent to positioning and perfusion mechanisms 264, 268, respectively, shown in FIG. 5 of Example 2. System 850 may be formed as described elsewhere in this Detailed Description. The meaning of each colored region of system 850 also has been described above, and therefore will not be repeated here.

Figure 25:
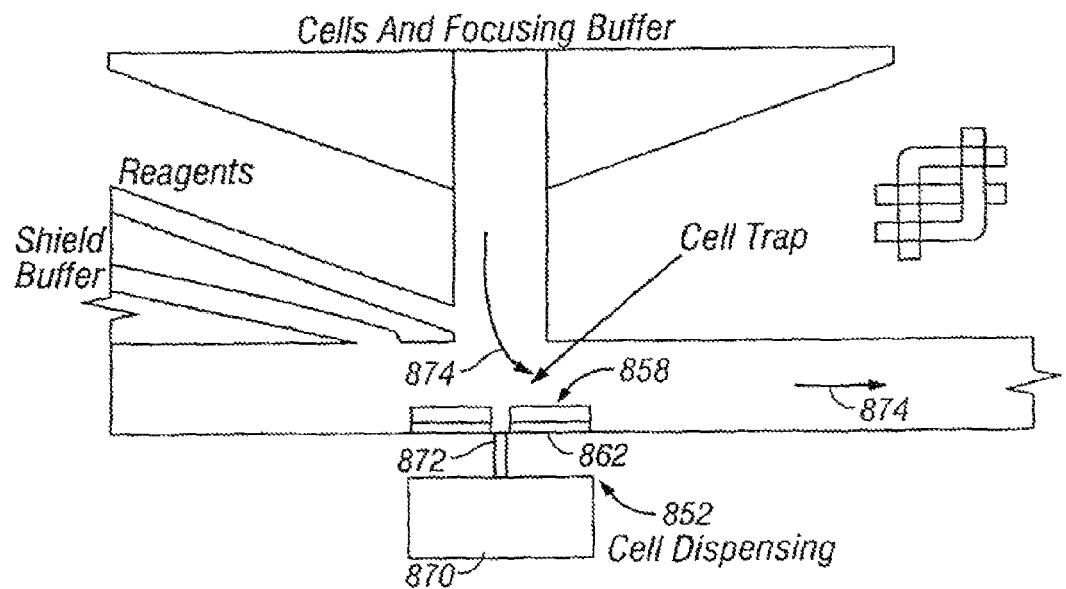
FIG. 25 is a view of selected portions of the system of FIG. 24, particularly a particle release mechanism, in accordance with aspects of the invention.

FIG. 25 shows trap 858 in more detail. Trap 858 may be dimensioned for capturing a single particle and is similar to trap 746 of FIG. 22, described above, except that trap 858 disposes channel 862 against distal wall 864, in contrast to trap 746, which spaces channel 752 away from distal wall 716.

Particle retention and treatment are essentially as described for Example 2 above, but the operation of a slightly different control layer 866 is described here for clarity. Control layer 866 includes valves V1-V4. Valve V1 corresponds to valve 8 of FIG. 8, described above, and is used to convert between divided and unified flow paths. Valve V2 controls particle release mechanism 852; its function is described below. Valves V3 and V4 control fluidic flow to waste reservoir 868 and particle collection mechanism 854, respectively. During particle loading into trap 858, valves V1, V2, and V3 are open, and valve V4 is closed. During reagent delivery by perfusion mechanism 860, valves V1 and V4 are closed, and valves V2 and V3 are open.

Particle release mechanism 852 may be used at any time to release particles, particularly after use of perfusion mechanism 860 and/or measurement of trapped particles. Release mechanism 852 operates by a dislodging flow to propel retained particles out their confinement in trap 858; see FIGS. 24 and 25. The dislodging flow originates in a reservoir channel 870 that is fluidically connected to trap 858 using a size-selective channel 872. Size-selective channel 872 has a diameter that prevents entry of particles but that does not restrict passage of fluid to, or from, reservoir channel 870.

Fluid flow through size-selective channel 872, and thus particle release, is controlled by valve V2 (see FIG. 24). Valve V2 is a control-layer valve disposed over reservoir channel 870. When valve V2 is closed, reservoir channel is compressed, forcing fluid outward through size-selective channel 872 into trap 858. This releases trapped particles, propelling them out of trap 858 into a flow stream, such as main flow stream 874, shown in FIG. 25, which carries the particles away from trap 858. Typically, in use, the focusing buffer pump is running, the reagent valves are closed, and the shield buffer is running. Thus, the main flow stream goes from the buffer wells to the cell culture area, described below. When valve V2 is opened, reservoir channel 870 expands, bringing fluid in through size-selective channel 868 and refilling the reservoir channel.

Embodiment 2

Figure 26:
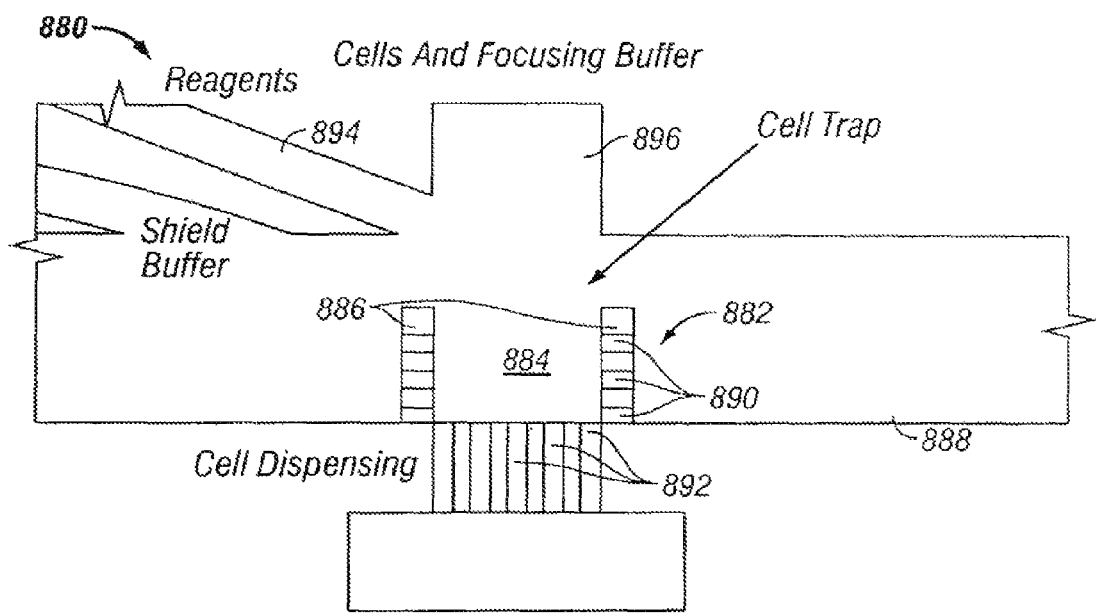
FIG. 26 is a fragmentary, top plan view of a reusable microfluidic system for repeated retention, treatment, and release of groups of particles, in accordance with aspects of the invention.

FIG. 26 shows a system 880 for retaining and releasing groups of particles, in accordance with aspects of the invention. System 880 generally is similar to system 850 (compare with FIG. 25), but with several exceptions. First, trap 882 includes a much larger retention site 884 than trap 858, capable of holding a group of particles. Thus, walls 886 extend substantially into cross channel 888, and each wall includes three size-selective channels 890, rather than the one present in trap 858. Moreover, trap 882 is wider than trap 858, so multiple expulsion channels 892 are used to release particles from confinement in trap 882, rather than one. Second, perfusion channel 894 has been moved slightly away from focusing channel 896 to ensure effective delivery of reagents to, all particles in trap 882.

Released particles generally may be discarded or saved for further treatment and/or analysis, for any trap size or configuration. Particles to be discarded may be carried toward waste reservoir 868 by opening valve V3 and closing valves V1 and V4 (see FIG. 24). Alternatively, particles to be saved may be carried toward particle collection mechanism 854 by opening valve V4 and closing valves V3 and V1 during particle release. Thus, valves V3 and V4 provide a sorting mechanism 898 to selectively discard or collect each individual particle or group of particles.

Once a retained particle has been released, system 850 may be readied to trap another particle. Toward this end, valve V4 is closed, if it was opened during particle release, and valves V1, V2, and V3 are opened. System 850 then is ready to receive another particle.

Embodiment 3

Figure 27:
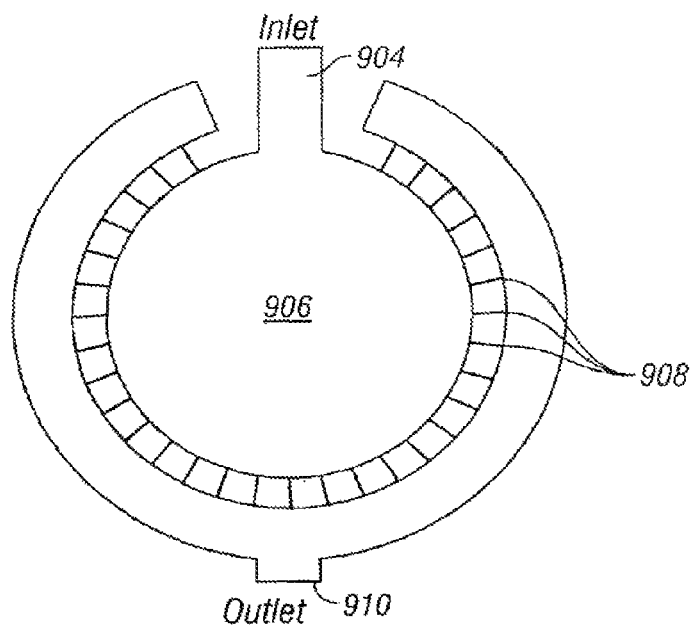
FIG. 27 is a view of selected portions of the systems of FIGS. 24 and 26, particularly a particle collection mechanism, in accordance with aspects of the invention.

FIGS. 24 and 27 show a particle collection mechanism 854, in accordance with aspects of the invention. Collection mechanism 854 includes an inlet channel 904, a retention area 906, filter channels 908, and an outlet 910. Inlet channel 904 carries released particles toward retention area 906 when valve V4 is open during release. Fluid flows though retention area 906 to outlet 910 by passing through filter channels 908, which act as size-selective channels that prevent released particles from flowing to the outlet. Thus, released particle are collected in retention area 906. When the collected particles are cells, the retention area may be used to culture cells to promote cell growth, differentiation, and/or response to a treatment, such as by perfusion mechanism 860. Alternatively, the retention area may be operatively connected to a measurement system for particle analysis, and/or may be a site of particle lysis or further treatment. In some embodiments, inlet channel 904 may be connected to other channels (not shown) that allow reagents to be introduced to retention area 906 separate from particle retention, treatment, and analysis at trap 858. Alternatively, or in addition, reagents may be introduced by perfusion mechanism 860 and/or focusing channel 896. Particles collected in retention area 906 may be released by reversed flow to send them up inlet channel 904 or by forming collection mechanism 854 so that a valve (or valves) replaces some of the filter channels.

Embodiment 4

Standard particle input mechanisms, such as inlet-well 330 of FIG. 8, are sufficient for single-use microfluidic systems.

However, these mechanisms may be inadequate for reusable systems. In reusable systems, it may be desirable to load a suspension of particles into an inlet-reservoir(s) at the beginning of an analysis, and then to use that same suspension as a source for multiple particle loadings and analyses. Unfortunately, during such extended analyses, particles typically settle out of the suspension, so that the particle input concentration decreases with time, increasing the amount of time required to load particles. Thus, there is a need for a mechanism for maintaining particles in suspension in an inlet reservoir during extended analyses, to allow repeated loading and analysis of particles from this suspension.

Figure 28:
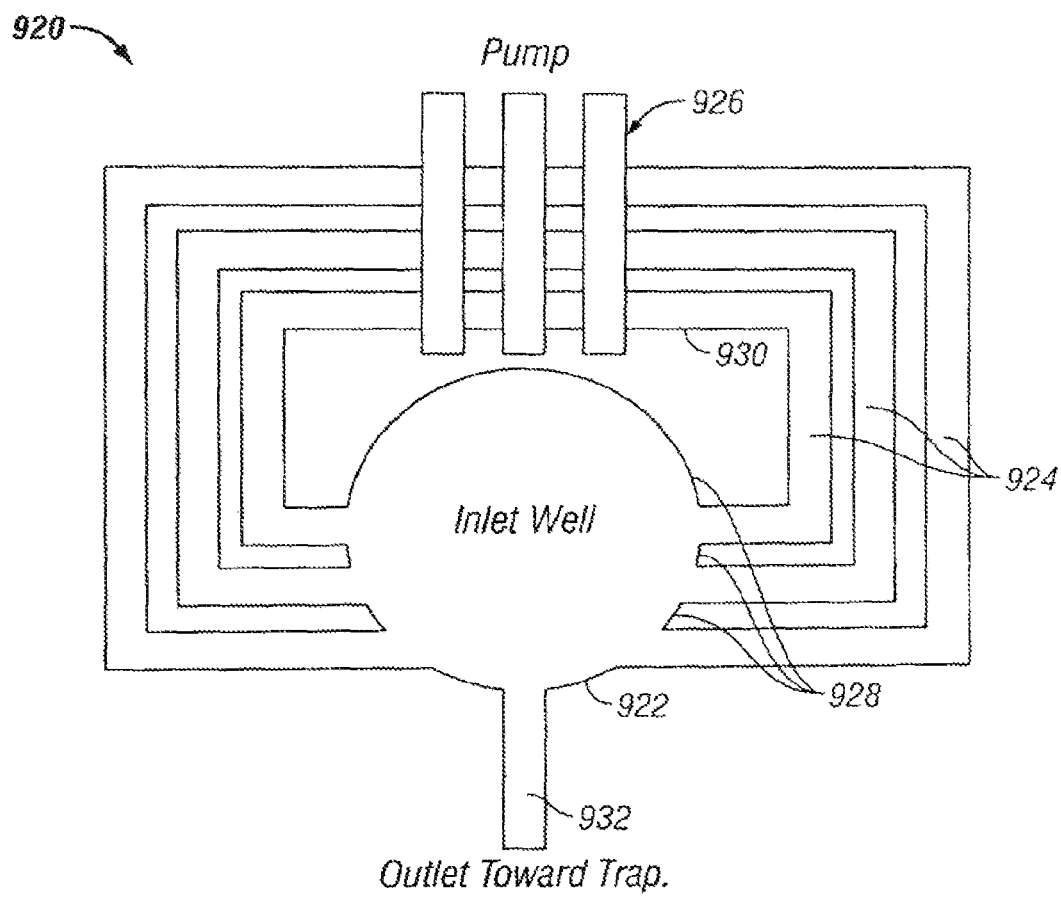
FIG. 28 is a fragmentary, top plan view of an input mechanism that includes a particle suspension mechanism, in accordance with aspects of the invention.

FIG. 28 shows a particle suspension mechanism 920 that may be integrated into reusable microfluidic systems, such as systems 850 and 880 described above. This suspension mechanism helps to maintain particles in suspension and/or helps to resuspend settled particles during the course of analyses with a reusable microfluidic system. Mechanism 920 includes an inlet reservoir 922, recirculation channels 924, and pumping valves 926. Inlet reservoir 922 receives and stores particle suspensions during analyses. Thus, reservoir 922 may be an interface with the macroscopic world. Recirculation channels 924 are joined at each end 928 to the base of reservoir, but are spaced from the reservoir at an intermediate portion 930. Pumping valves 926 are regulated by the control layer, and are coordinated to peristaltically pump fluid through recirculation channels 924, as described elsewhere in this Detailed Description. Accordingly, fluid in reservoir 922 flows away from, and then back to, reservoir 922, continuously acting to mix the contents of reservoir 922 and thus to maintain the particles in suspension. Therefore, a more stable concentration of particle flows from outlet 932 over time.

Example 8

Microfluidic Mechanisms for Adjustable Reagent Delivery

Figure 29:
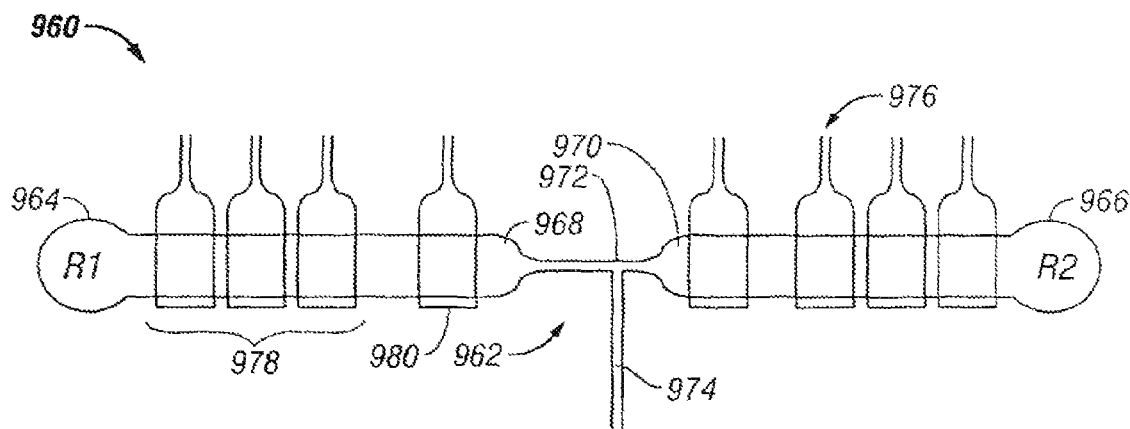
FIG. 29 is a fragmentary, top plan view of an adjustable dilution mechanism, in accordance with aspects of the invention.
Figure 30:
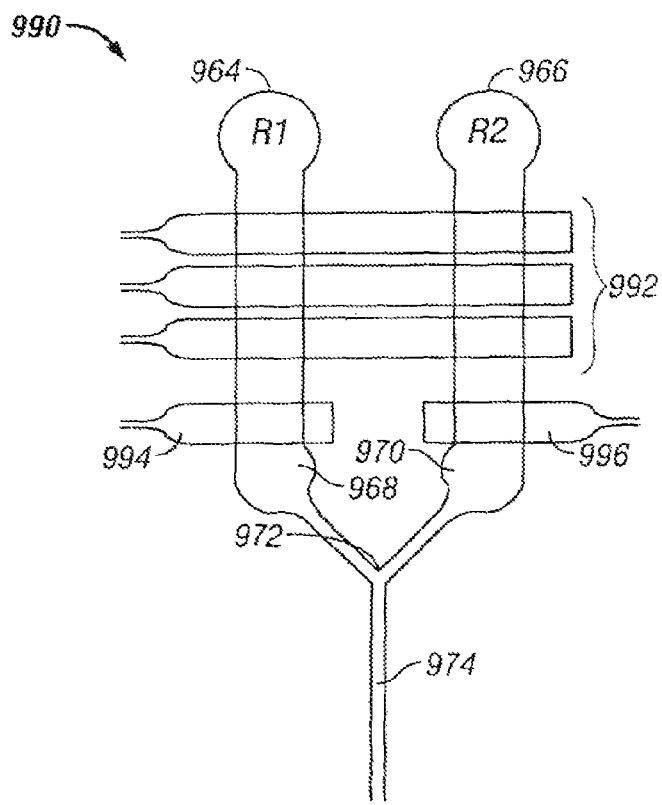
FIG. 30 is a fragmentary, top plan view of another adjustable dilution mechanism, in accordance with aspects of the invention.

This example describes mechanisms for adjustably diluting reagents so that reagents may be delivered to particles at a range of reagent concentrations, for example, as a gradient; see FIGS. 29-30.

Background

Studies of cells frequently involve dose-response analyses to determine how the cells respond to a range of concentrations of a reagent, such as a drug. These dose-response analyses may be used to determine a variety of qualitative and/or quantitative information, including an effective dose, a half-maximal response dose, a lethal dose, a dose to produce a more specific response, and so on. In many analyses, a reagent of interest is prepared as a high concentration stock solution, and then various volumes of the reagent are dispensed to provide a range of doses. However, this approach may not be suitable with microfluidic systems, because it may not be practical to dispense metered volumes in a microfluidic system and because it may require a mixer to mix and thus dilute such a dispensed volume. Thus, there is a need for a microfluidic mechanism that dispenses a premixed reagent at a range of selected concentrations, using a small number of reagent stocks.

Description

This section describes two exemplary dilution mechanisms, having independent (Embodiment 1) and coordinated (Embodiment 2) control.

Embodiment 1

FIG. 29 shows an adjustable dilution mechanism 960 for combining first and second reagents at a range of concentrations, in accordance with aspects of the invention. Dilution mechanism 960 includes a microfluidic layer 962 having first and second reagent reservoirs 964, 966, and first and second controllable flow channels 968, 970 acting as outlets for the reservoirs. The controllable flow channels narrow and meet at a junction 972 to form a common mixing channel 974. Reagents are mixed in mixing or diffusion channel 974, generally by diffusion of reagents into the adjacent flow stream(s). Thus, mixing channel 974 may be substantially narrower than flow channels 968, 970, generally about 1 to 20 µm. In contrast, flow channels 968, 970 are wide enough to be controlled by valves, with an arcuate cross-section. Here, fluid flow from each reservoir is independently controlled by control layer 976, via three-valve pumps 978, and shutoff valves 980; however, fluid flow in other embodiments may be controlled by other control mechanisms.

Dilution mechanism 960 is used to combine first and second reagents, R1 and R2, in a desired ratio based on the rate at which each pump moves fluid through flow channels 968, 970. Thus, reagent R1 may be introduced, for example, at 100%, 50%, 20%, 10% and 0% of reservoir 964 concentration, by running pumps 976 and 978 at relative pumping flow rates of 1:0, 1:1, 1:4, 1:9, and 0:1, respectively. Valves 980 may be used to override the pump and/or to modulate the effect of a specific pump rate, as described below. To improve control, the adjustable dilution mechanism may use relatively precise control of pump speed and a large number of control lines in the control layer.

Embodiment 2

FIG. 30 shows another adjustable dilution mechanism 990 for combining first and second reagents at a range of concentrations, in accordance with aspects of the invention. Dilution mechanism 990 is structured similarly to dilution mechanism 960, as indicated by components with identical numbering. However, dilution mechanism 990 uses a single pump 978, generally at a constant pumping rate, to coordinately drive flow of both reagents. Furthermore, mechanism 990 uses adjustable valves 994, 996, rather than shutoff valves. Closure of adjustable valves is controllable by regulating the pressure used to deflect the adjustable valves. Thus, each adjustable valve may be independently adjusted with a suitable pressure to provide a desired partial obstruction to flow channels 968, 970, and thus a desired flow rate and reagent mixture in diffusion channel 974. A simple dilution of a first reagent may be carried out by using an appropriate solvent or buffer as the second reagent.

Applications

The dilution mechanisms described above may be used as part(s) of any suitable microfluidic device, for any suitable applications. For example, dilution mechanism 990 may be used in microfluidic system 250 in FIG. 8 of Example 2 to prepare and deliver a desired mixture of reagents for particle perfusion, by providing empirically determined pressures to valves 9 and 10.

Example 9

Microfluidic Sorting Mechanisms Based on Centrifugal Forces

This example describes mechanisms for sorting particles based on their mass, density, and/or other properties; see FIGS. 31-38.

Background

Microfluidic analyses of particles may benefit from or even require sorting crude or heterogeneous input populations of particles into their components. For example, the input population may be a mixture of single cells, cell clusters, and/or cell debris. Alternatively, or in addition, the input population may be a mixed population of distinct cell types. In these cases, sorting may separate single cells from clusters and debris, and cells of one type from cells of another, type. Optical systems may be used to actively sort individual particles according to their different optical properties, such as fluorescence intensity. However, these optical systems require that the input particles be constantly monitored and actively directed to distinct sorting bins based on optical properties. Thus, there is a need for a microfluidic sorting mechanism that separates distinct particles, potentially passively, based on different physical properties of the distinct particles.

Description

This example describes mechanisms for passively sorting particles based on physical differences between the particles, such as mass, density, shape, and/or surface characteristics, among others. These mechanisms are passive, exploiting the centrifugal forces exerted on flowing particles during a sharp change of direction, rather than active monitoring and switching. These mechanisms are described and demonstrated as part of simplified fluidic systems lacking valves and other functional mechanisms. Instead, fluids are moved through these systems by pressure differences produced by liquid columns having different heights in input and output reservoirs. However, these sorting mechanisms may be integrated into any suitable microfluidic system.

Embodiment 1

Figure 31:
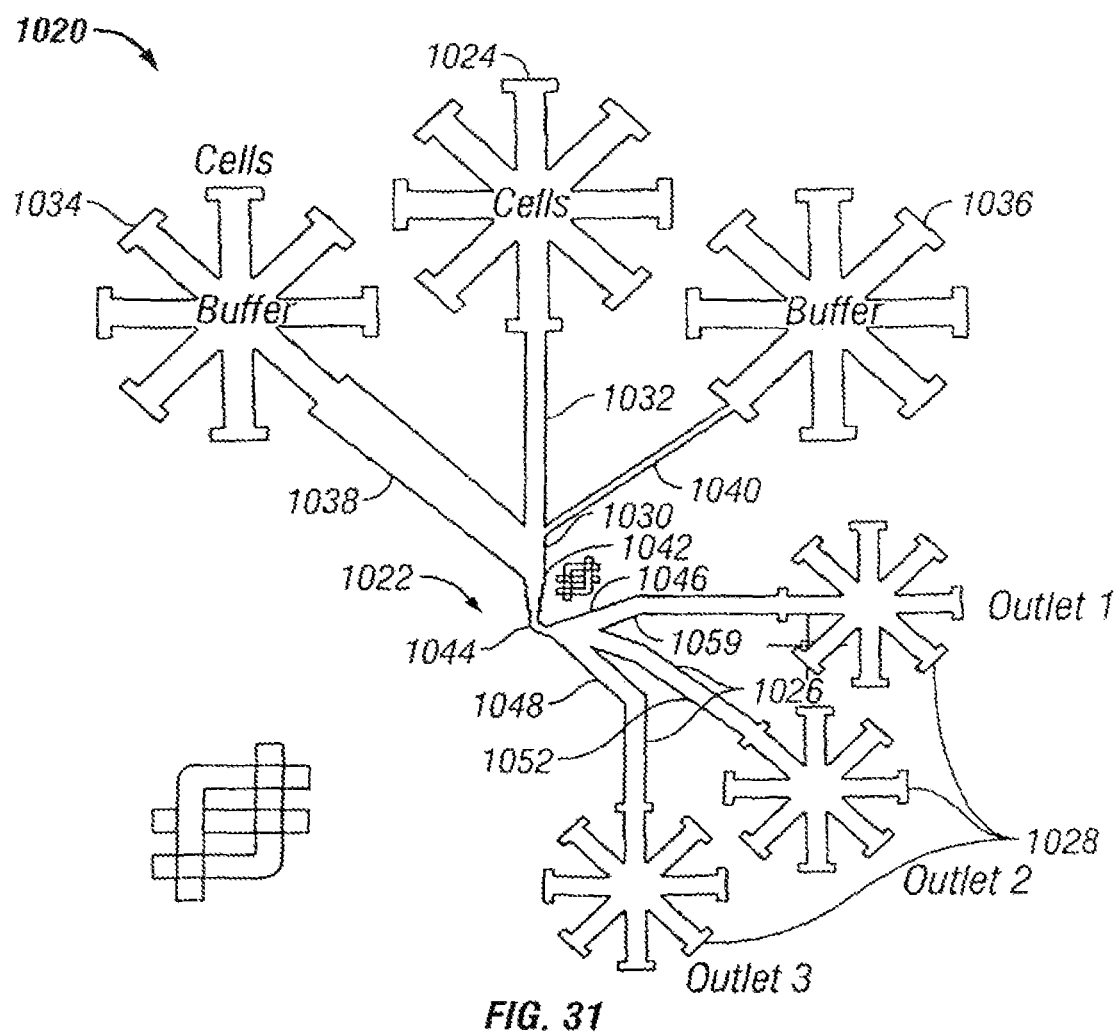
FIG. 31 is a top plan view of a microfluidic system having a sorting mechanism based on centrifugal force, in accordance with aspects of the invention.
Figure 32:
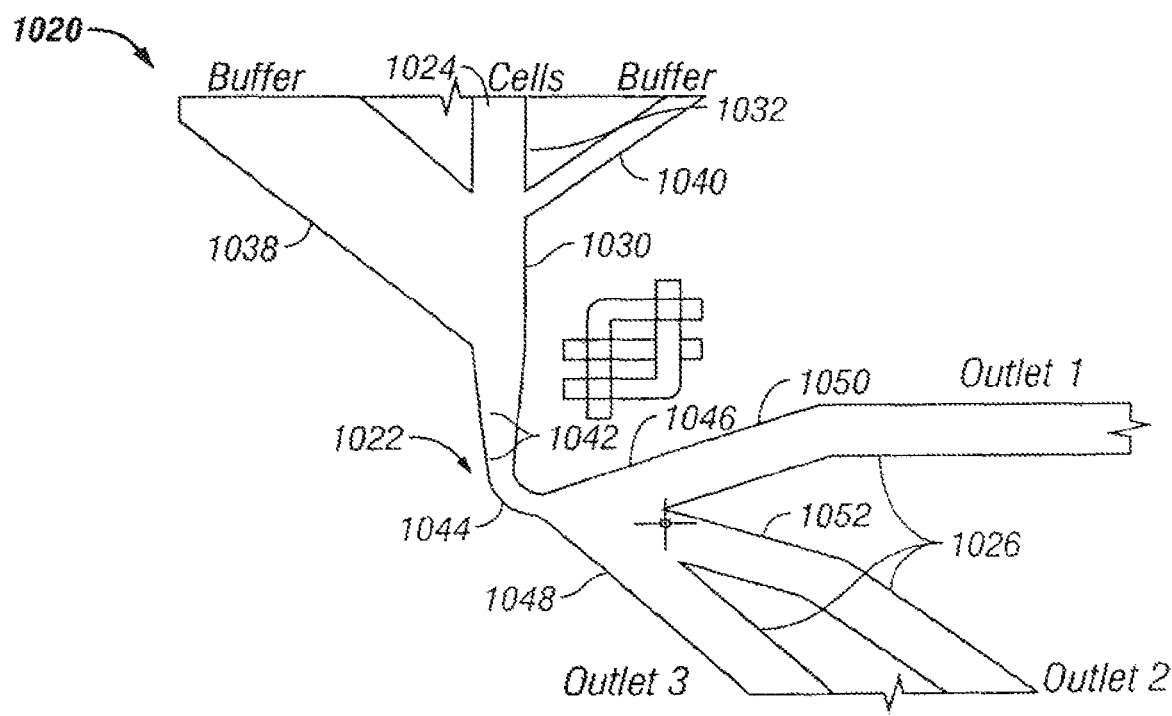
FIG. 32 is a fragmentary view of the system of FIG. 31, showing the sorting mechanism in greater detail, in accordance with aspects of the invention.

FIGS. 31 and 32 show a microfluidic system 1020 having a sorting mechanism 1022 that separates particles according to physical differences between the particles, in accordance with aspects of the invention. Here, mechanism 1022 sorts particles from inlet reservoir 1024 into one of three outlet or sorting channels 1026. These sorting channels lead to distinct outlet reservoirs 1028, labeled here as outlets 1-3. The sorting channels in this embodiment have a minimum width of about 50 µm and a height of about 17-18 µm. However, more generally, mechanism 1022 may be formed with any suitable dimensions. Furthermore, mechanism 1022 may sort particles from any suitable source, such as a microfluidic treatment or analysis, into any desired number of outlet channels and/or other microfluidic mechanisms or structures, such as culture chambers, retention mechanisms, perfusion mechanisms, and/or the like.

Mechanism 1022 includes structures that act sequentially along a flow stream. First, hydrodynamic focusing region 1030 acts to focus particles from particle inlet channel 1032 into a narrow stream. Two side reservoirs 1034, 1036, each filled with a focusing fluid, such as a buffer, are connected to inlet channel 1032 using focusing channels 1038, 1040. Focusing channels 1038, 1040 may have different widths, and thus different flow rates, to asymmetrically position the narrow stream in the inlet channel. Second, acceleration region 1042 narrows the width of the channel to increase the flow velocity and further focus particles into a single stream. Third, curved region 1044 bends sharply to give the input particles an angular velocity and a radial acceleration. Fourth, a separation region 1046 is positioned after curved region 1044. Separation region 1046 widens into a larger chamber with a number of receiving or sorting channels 1026 that act as sorting bins to segregate sorted particles. In separation region 1046, particles are distributed based on their mass (weight). The tendency of particles to continue moving in a straight line increases with mass, so that heavier particles move to the outside of the flow stream, and lighter particles remain closer to the center of the flow stream. Accordingly, in this embodiment, the heaviest particles tend to distribute more to receiving channel 1048, the lightest particles to receiving channel 1050, and the intermediate-mass particles to receiving channel 1052. In some cases, other physical properties of the particles, such as density, shape, and/or surface properties, among others, also may contribute to the relative distributions of particles between these receiving channels.

The sorting capabilities of sorting mechanism 1022 may be modified by altering one or more of several potential sorting parameters. These sorting parameters may include the extent of narrowing of the acceleration region, the radius of curvature of the curved region, the angle of broadening of the separation region, and/or the number of receiving channels/bins, among others. These parameters may impart such capabilities as improved resolution, separation into a different number of sorting channels (bins) and/or resolution of a different range of particle weights, densities, etc.; among others.

Embodiment 2

Figure 33:
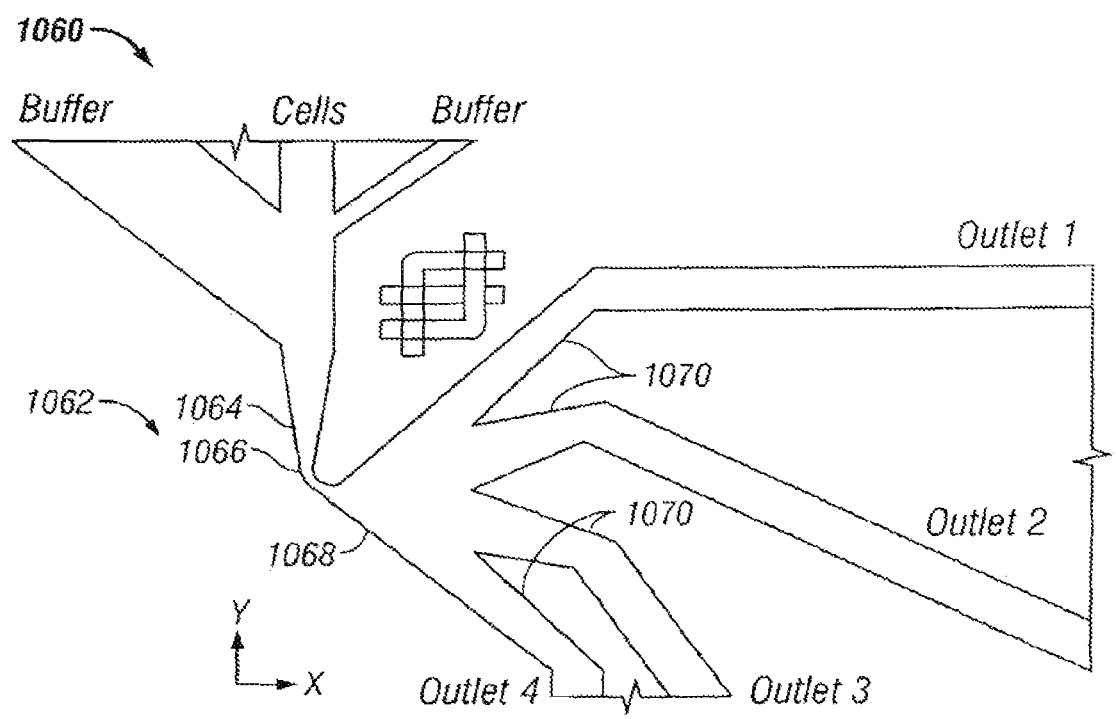
FIG. 33 is a fragmentary, top plan view of another microfluidic system having a sorting mechanism based on centrifugal force, in accordance with aspects of the invention.

FIG. 33 shows a microfluidic system 1060 having a sorting mechanism 1062 with modified sorting parameters, in accordance with aspects of the invention. Sorting mechanism 1062 has a narrower acceleration region 1064 than acceleration region 1042 of sorting mechanism 1022, potentially imparting greater velocity to the particles, and thus better focusing. In addition, sorting mechanism 1062 has a curved region 1066 with a distinct radius of curvature relative to curved region 1044 of sorting mechanism 1022. Furthermore, sorting mechanism 1062 has a separation region 1068 having a greater angle of separation (subtended angle) than separation region 1046 of sorting mechanism 1022, connected to four, rather than three, sorting channels 1070.

Embodiment 3

Figure 34:
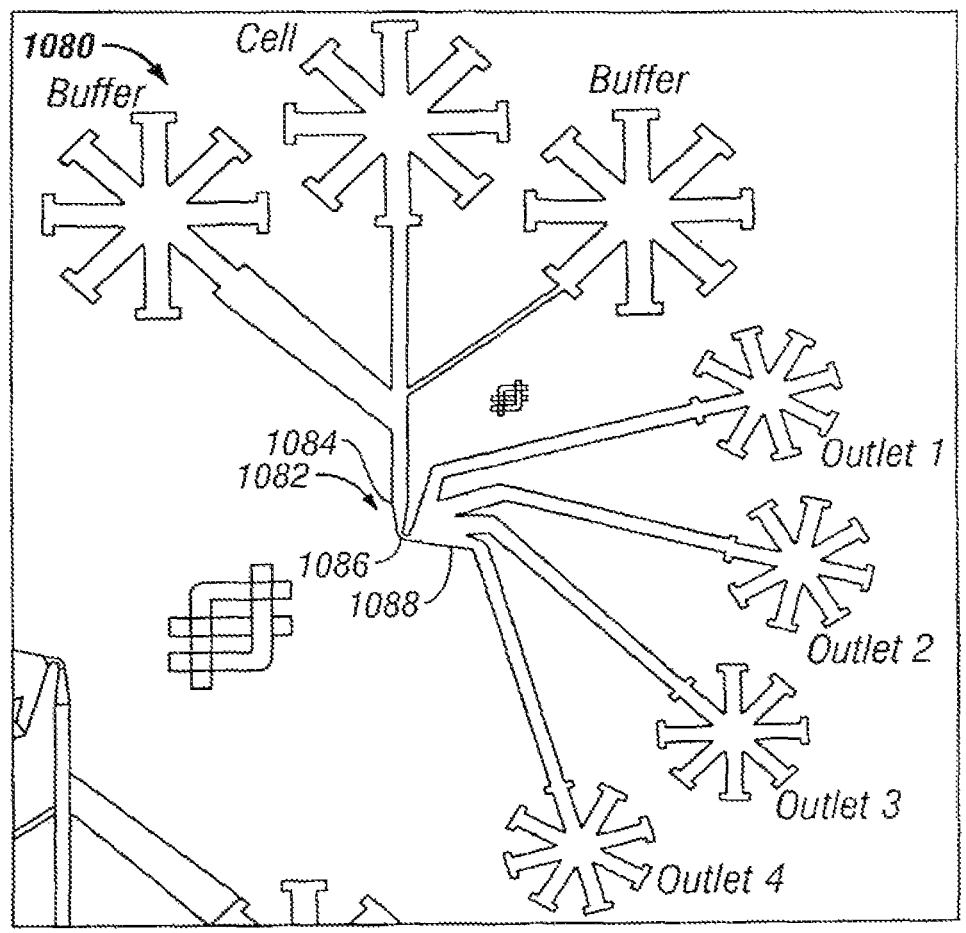
FIG. 34 is a top plan view of a yet another microfluidic system having a sorting mechanism based on centrifugal force, in accordance with aspects of the invention.
Figure 35:
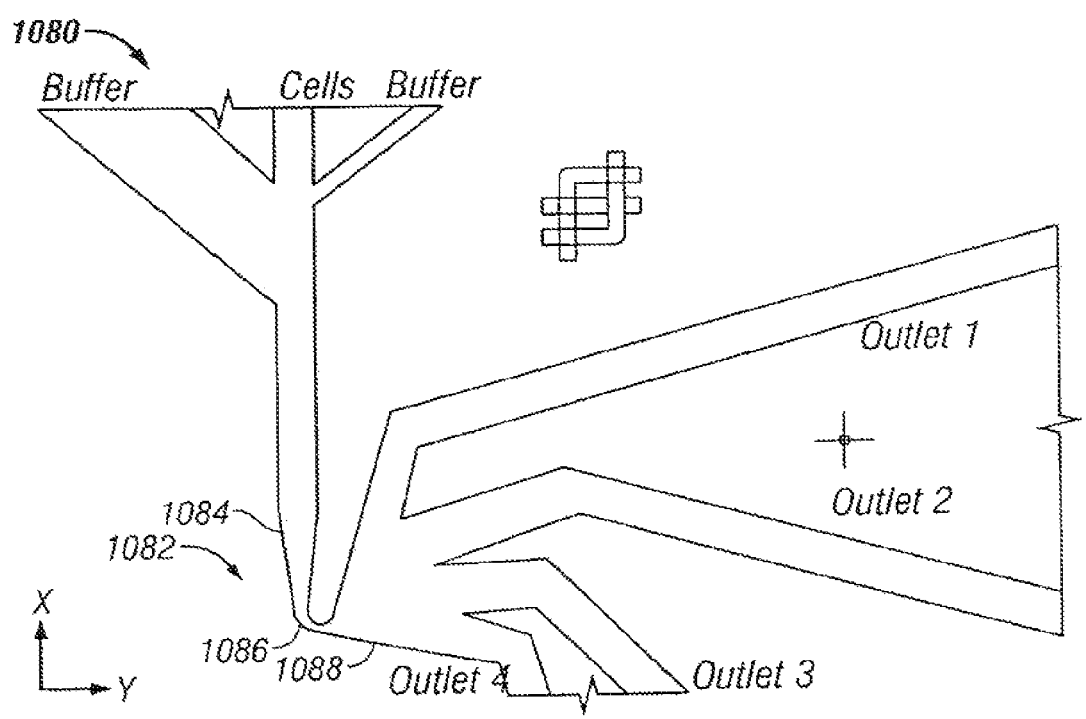
FIG. 35 is a fragmentary view of the system of FIG. 34, showing the sorting mechanism in greater detail.

FIGS. 34 and 35 show another microfluidic system 1080 having a sorting mechanism 1082 with modified sorting parameters, in accordance with aspects of the invention. Sorting mechanism 1082 has a narrower acceleration region 1084 than either region 1042 or region 1064, providing even greater velocity and focusing. In addition, sorting mechanism 1082 has a curved region 1086 with a smaller radius of curvature than curved regions 1044 and 1066 of FIGS. 31-33. Furthermore, sorting mechanism 1082 has a separation region 1088 with an even greater angle of separation, compared to regions 1046 and 1068.

Applications

Figure 36:
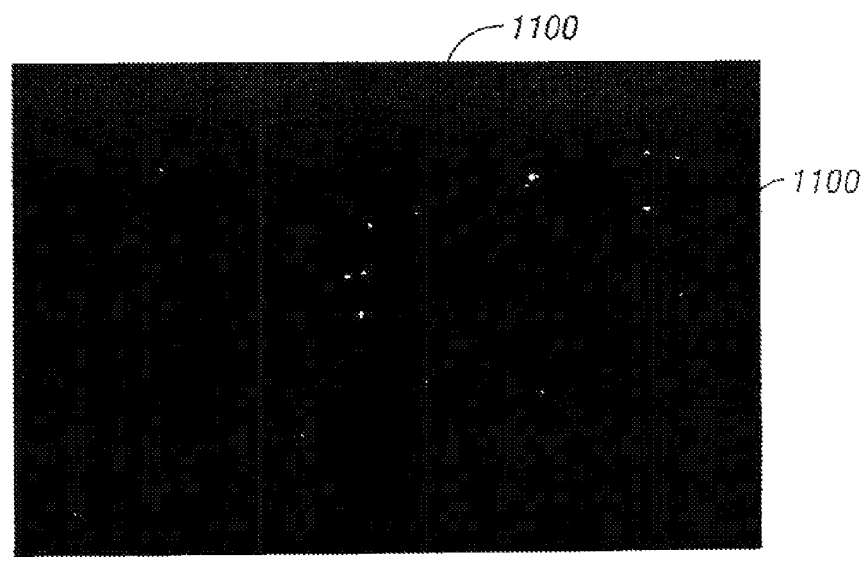
FIG. 36 is a photographic image of fluorescent beads and particles being separated by the sorting mechanism of FIGS. 34 and 35.
Figure 37:
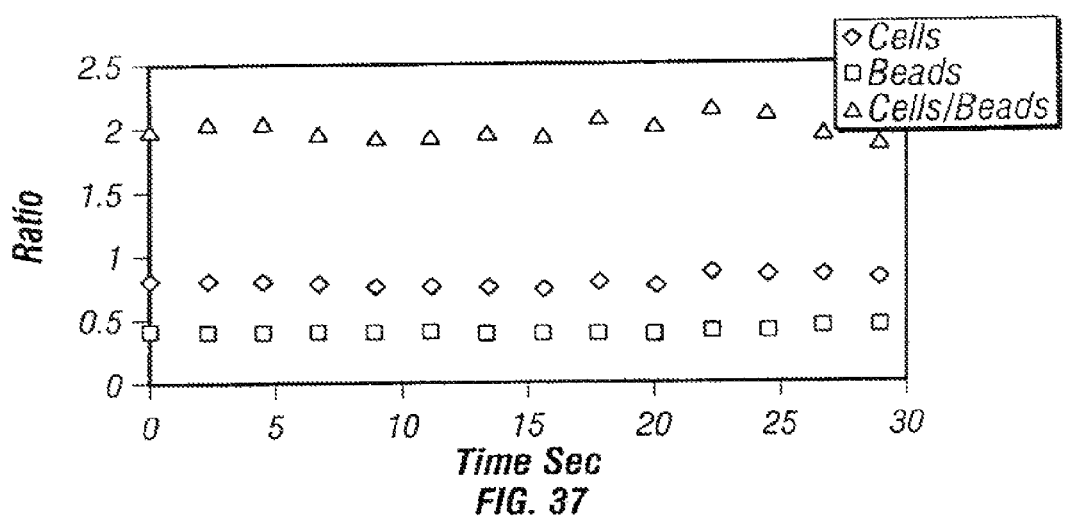
FIG. 37 is a graph plotting the ratio of cells to beads over time during sorting with the system of FIGS. 34 and 35.
Figure 38:
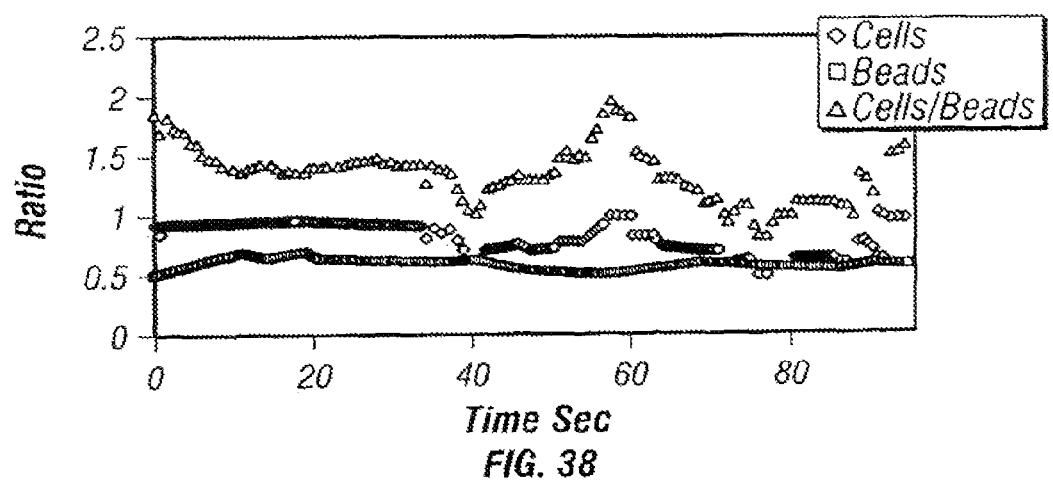
FIG. 38 is a graph plotting the ratio of cells to beads over time during sorting with the system of FIGS. 31 and 32.
Figure 39:
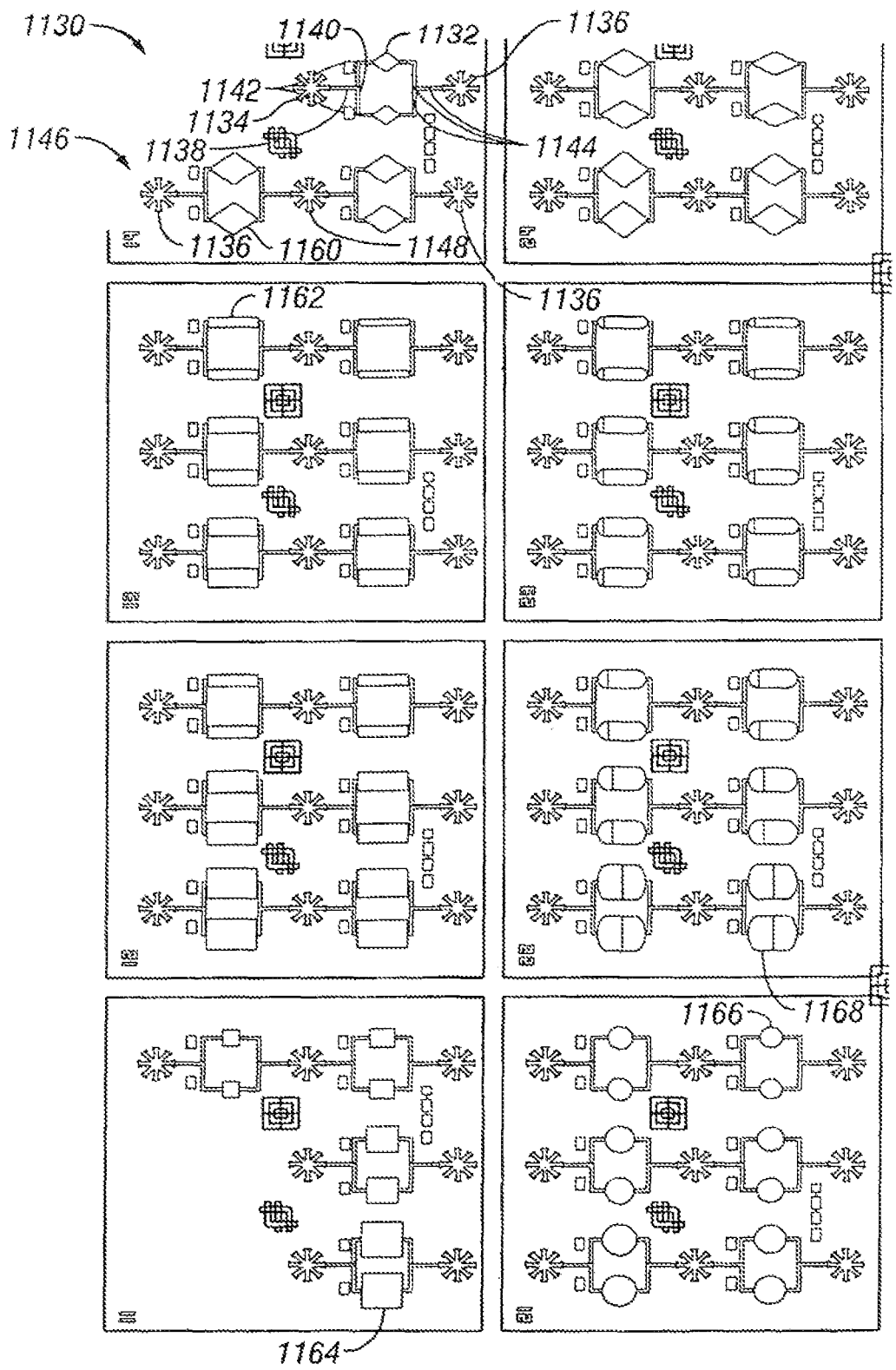
FIGS. 39-43 are top plan composite views of various cell-chamber networks for microfluidic manipulation of cells, in accordance with aspects of the invention.
Figure 40:
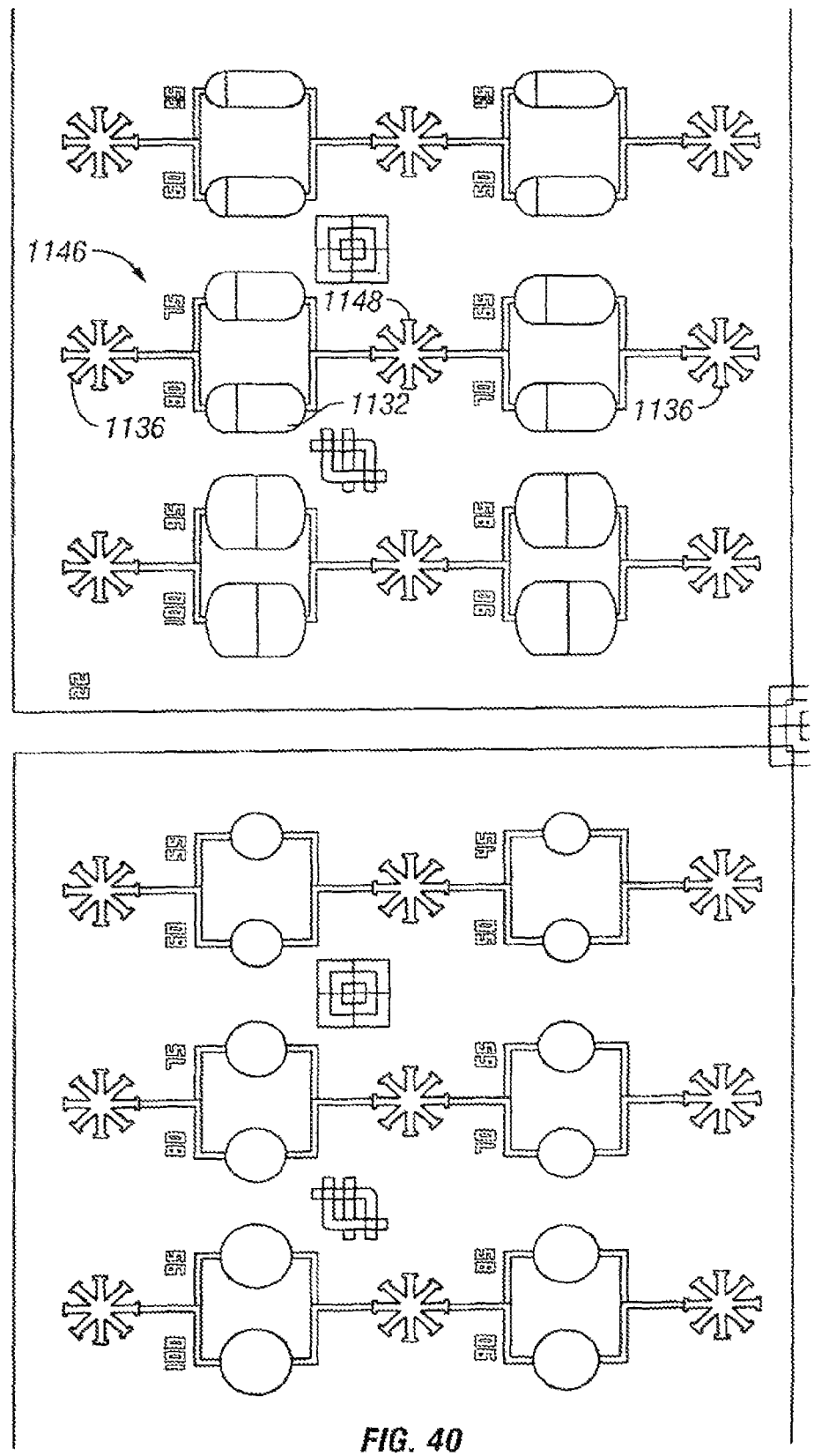
Figure 41:
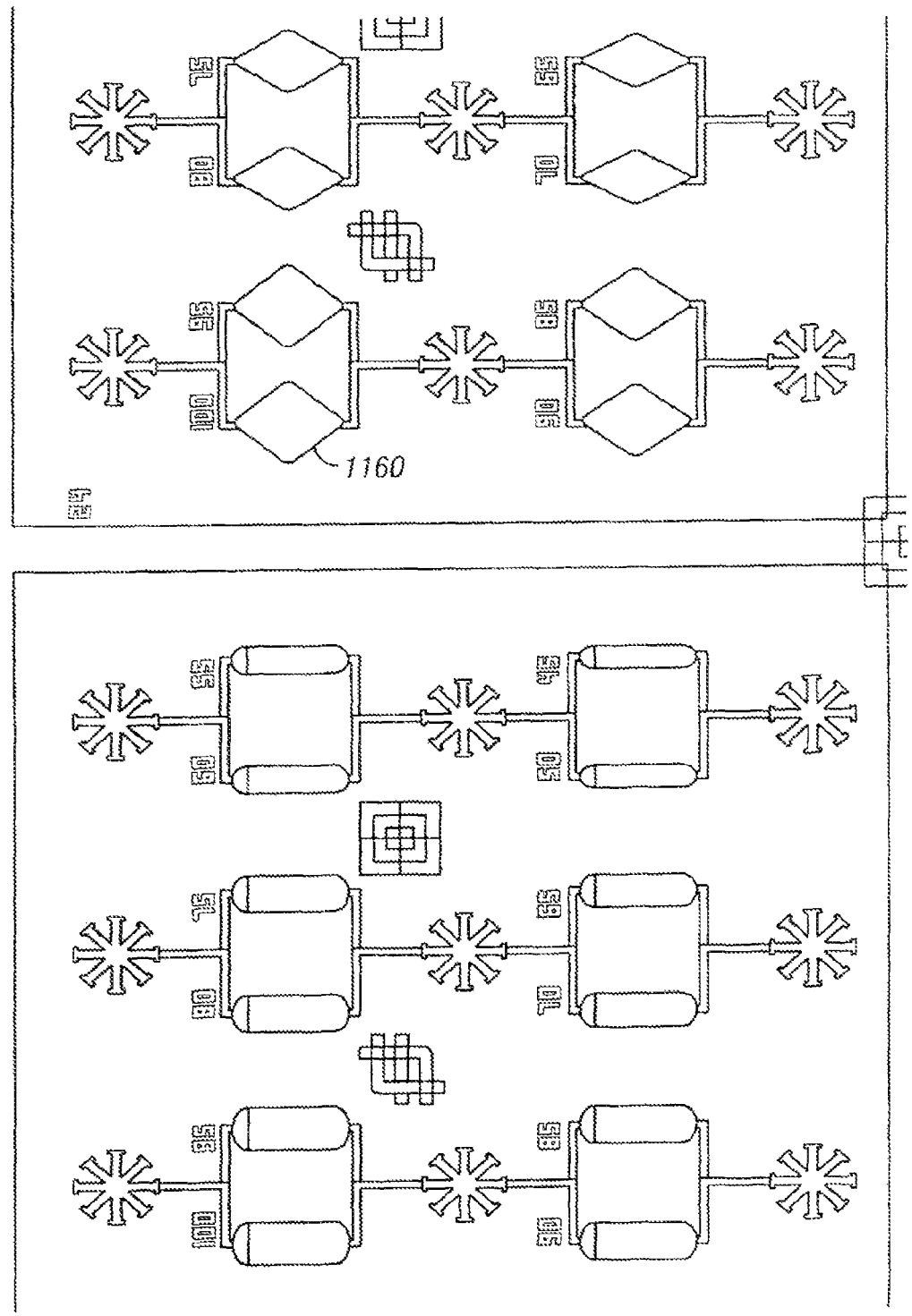
Figure 42:
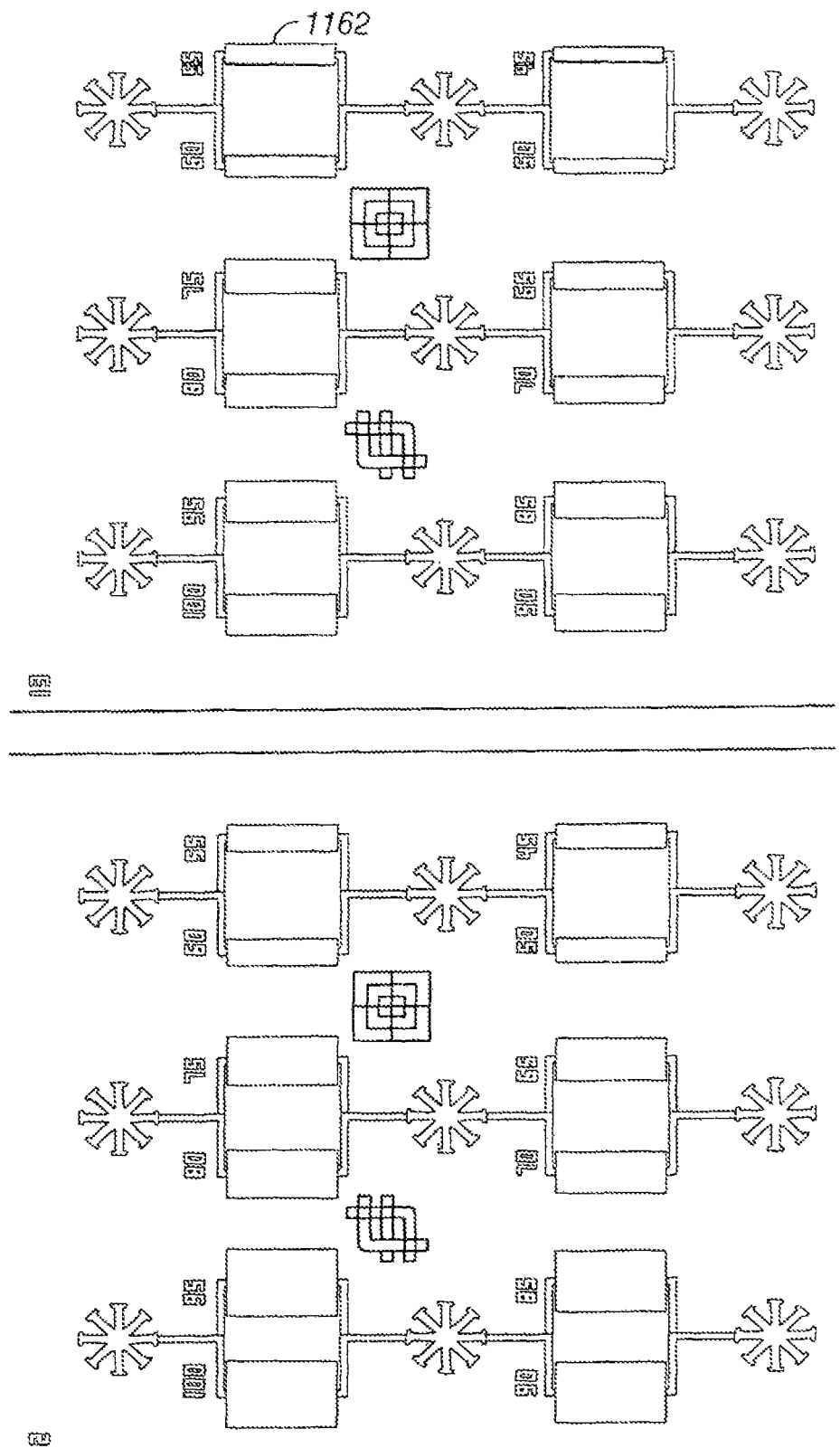
Figure 43:
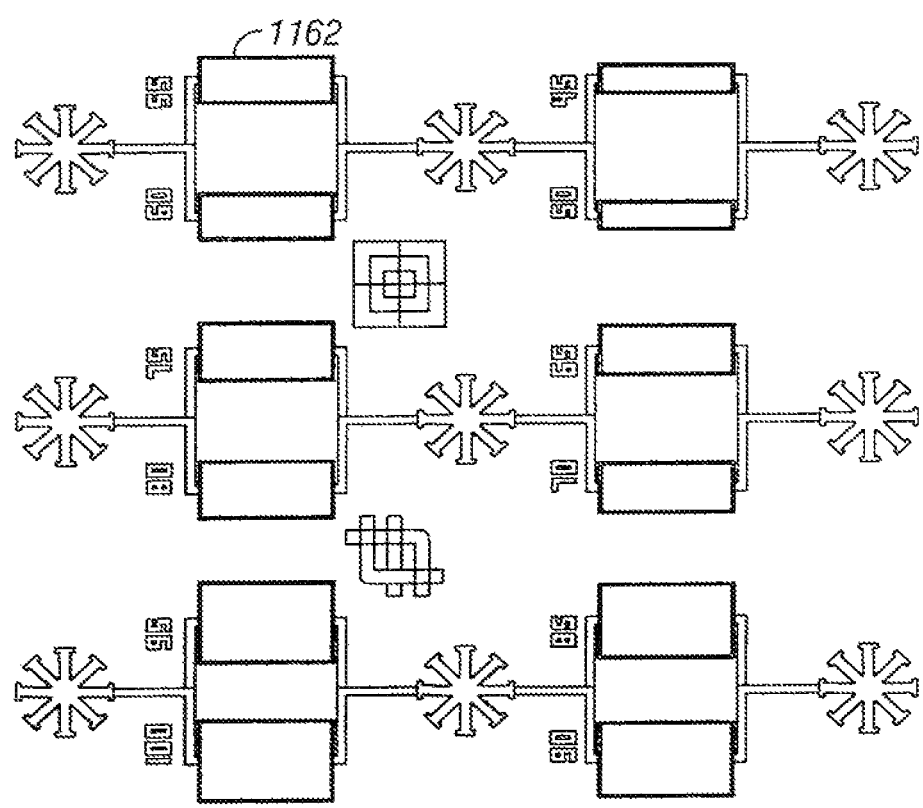

FIGS. 36-38 show experimental results demonstrating the ability of systems 1020 and 1060 to sort a mixed population of particles. In these experiments, the mixed population of particles was formed, prior to loading into an input reservoir, using two sizes (and types) of particles: beads with an average diameter of about 1 µm, and Jurkat cells with an average diameter of about 10 µm. These two sizes of particles are distinguishably labeled with distinct fluorescent dyes: the beads emit green light, and the cells emit red light.

FIG. 36 shows an image of particles being sorted using a sorting mechanism as described in this example. The particles are split into two streams 1100 in the separation region. The lower stream is enriched for cells (red), and the upper stream is enriched for beads (green). Flow of particles through the system is powered by a 1-cm high column of fluid in the inlet reservoir.

FIGS. 37 and 38 show graphs of data obtained with systems 1080 and 1020, respectively, as each sorted the mixed population of beads and cells, described above. These graphs were generated by counting the relative numbers of particles that entered each of two receiving channels. The graphs each plot the fraction of cells (blue diamonds) and beads (pink squares) that distribute to the lower receiving channel, either sorting channel 1102 or 1048, respectively. The ratio of cells to beads in the lower receiving channel is plotted in yellow. In both system 1080 and 1020, a greater fraction of cells than beads are entering the lower receiving channel. In system 1080, about twice as many cells as beads entered the lower receiving channel. In system 1020, this ratio was slightly lower and more variable.

Summary

The systems shown in this example have the ability to passively enrich particles based on sorting mechanisms that distinguish physical properties of particles. The approximately two-fold enrichment obtained using these systems may be sufficient to facilitate or improve some microfluidic analyses. Furthermore, each of these systems may be modified and refined, and/or connected in series to improve enrichment of desired particles.

Example 10

Microfluidic Systems for Manipulating Sets of Particles

This example describes microfluidic systems having relatively large chambers, in which larger sets of particles, such as adherent and/or nonadherent cells, can be retained, stored, cultured, treated, and/or released; see FIGS. 39-50D.

Background

The introduction and/or removal of particles into and out of microfluidic systems, at macroscopic/microscopic interfaces, may inefficient and/or harmful. For introduction, particles must be placed in suspension and often are introduced through an inlet reservoir. During this loading process, a substantial fraction of the particles may be lost, which may be problematic if the particles are expensive and/or in limited supply, such as with cells from a clinical or forensic sample. Furthermore, during introduction and/or removal, particles may be contaminated, for example, by exposure to contaminating microorganisms, and/or damaged, for example, by evaporation of inlet- or outlet-reservoir liquid. Accordingly, it is desirable to avoid repeatedly introducing and removing particles from microfluidic systems during a sequential set of assays. Therefore, there is a need for chambers for storing, treating, maintaining, measuring, and/or in particular, amplifying (i.e., culturing) particles, such as cells, particularly for serial analyses of particle populations. With such chambers, these serial analyses could be conducted without transferring the populations to a macroscopic environment between analyses.

However, such chambers need to address a number of problems or issues related to their use with cells. First, these chambers may need a ceiling height that does not interfere with cell movement within the chambers. In particular, the ceiling of larger chambers, particularly those formed of elastomeric materials, may tend to sag, obstructing cell movement. Second, these chambers may need a substrate that promotes adhesion, survival, and growth of adherent cells, when such cells are being used. Many adherent cells do not behave normally unless they are attached to a substrate. Third these chambers may need to pass media and/or reagents over cells in the chambers, without loss of, or damage to, the cells. Pumps that circulate fluid may crush fragile eukaryotic cells, and some filters that restrict cell movement may be clogged by cells and/or allow cells to pass. Fourth, these chambers may require an ability for gas to diffuse into cell chambers, to maintain a proper pH during cell growth.

Description

This example describes various microfluidic systems that address and solve some or all of the problems and issues cited above. These microfluidic systems may be formed using multilayer soft lithography, as described elsewhere in this Detailed Description and in the Cross-References. Channels or chambers for particle storage, treatment, analysis, and cell growth are formed using molds fabricated as described generally in Example 13, using plural layers of photoresist, when needed. Such molds may be used to construct channels large enough for cell entry and growth, for example, about 200 µm wide by about 20-35 µm high. Furthermore, as described below, such molds may be used to form particle chambers of various dimensions. These channels and/or chambers may be integrated into microfluidic systems that include valves, pumps, rotary mixers, filters; sorters, multiplexers, perfusion mechanisms, and/or additional particle retention sites, among others, to perform any suitable analysis of particles.

Embodiment 1

FIGS. 39-43 illustrate exemplary microfluidic networks 1130 that include relatively large chambers 1132 for retaining particles, in accordance with aspects of the invention. These networks have been fabricated using multilayer soft lithography, with large chambers that did not collapse. These chambers have a height of about 36 microns. The chambers were formed by a modified process using molds in which two layers, each of about 18 microns, were sequentially layered on top of a substrate, and selectively retained at the positions where the cell chambers were formed. The chambers were rounded. This process produces a generally arcuate (arch-like) cross-sectional configuration that may enhance stability. As a result, this process allows formation of chambers with width-to-height ratios less than about 10:1 that do not collapse. In contrast, microfluidic channels having width-to-height ratios greater than 10:1 formed by a standard soft lithography process may collapse more frequently.

Figure 44:
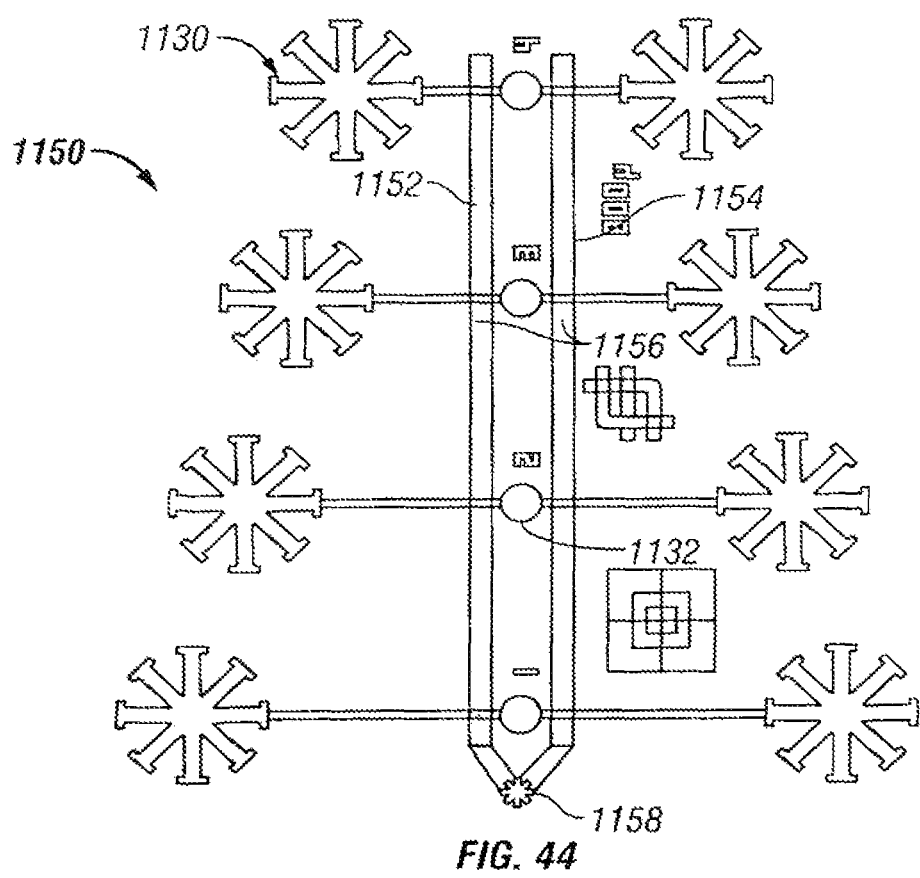
FIG. 44 is a top plan view of a microfluidic system with a parallel array of separate, isolatable cell-chamber networks, in accordance with aspects of the invention.

The large chambers may be connected to an input reservoir 1134 and an output reservoir 1136. The input reservoir may connect to an inlet channel 1138 that bifurcates, as shown at 1140, to direct flow into each of two channels 1142. Outlet channels 1144 extend from each pair of chambers to join and carry fluid to output reservoir 1136. For more efficient use of space and input reservoirs, some systems, such as system 1146, share a common inlet reservoir 1148 for two pairs of chambers. Thus, particles may be loaded into inlet reservoir 1148 to distribute the particles to each of four chambers. In other embodiments, an input reservoir may be fluidically connected to one, two, three, four, or more chambers using any suitable number of channels. The channels may extend directly between a particle reservoir and a cell chamber, or they may branch any desired number of times at any desired number of positions. The movement of fluid through these chambers may be controlled by any suitable mechanism, such as valves and/or pumps, among others. For example, FIG. 44 shows a system 1150, in which an array of networks 1130 are controlled in parallel by control lines 1152, 1154 that regulate valves 1156 flanking each chamber 1132. In this case, each of the eight valves shown is opened or closed in parallel through actuation at control port 1158, either providing an open chamber for particle loading, or a closed chamber for particle isolation, respectively.

Chambers 1132 may have any desired shape and size. Suitable cross-sectional shapes may include diamonds 1160 (FIGS. 39 and 41), rectangles 1162 (FIGS. 39, 42, and 43), squares 1164 (FIG. 39), circles 1166 (FIGS. 39 and 40), ellipses or elongated circles 1168 (FIGS. 39, 40, and 41), and/or the like. Suitable sizes are about 100 microns to about 1 centimeter in diameter, depending on particle type, assay, and so on. Specific chambers shown in FIGS. 39-43 that have been constructed successfully have diameters of from about 0.9 mm to 2.6 mm.

Chambers may be completely isolated from the substrate in their interiors, or they may be supported by columns, posts, or other structures. These columns or posts may project downward from the roof of the channel to contact the substrate, generally being integrally formed in the microfluidic layer during fabrication of this layer. Alternatively, or in addition, these columns or posts may project upward from the substrate, being formed as a portion of the substrate or an addition to the substrate. To be effective, the columns or posts should be spaced adequately to avoid obstructing cell movement through the chambers, although more tightly spaced structures could be used to form a cell pen or other subchamber.

Embodiment 2

Figure 45:
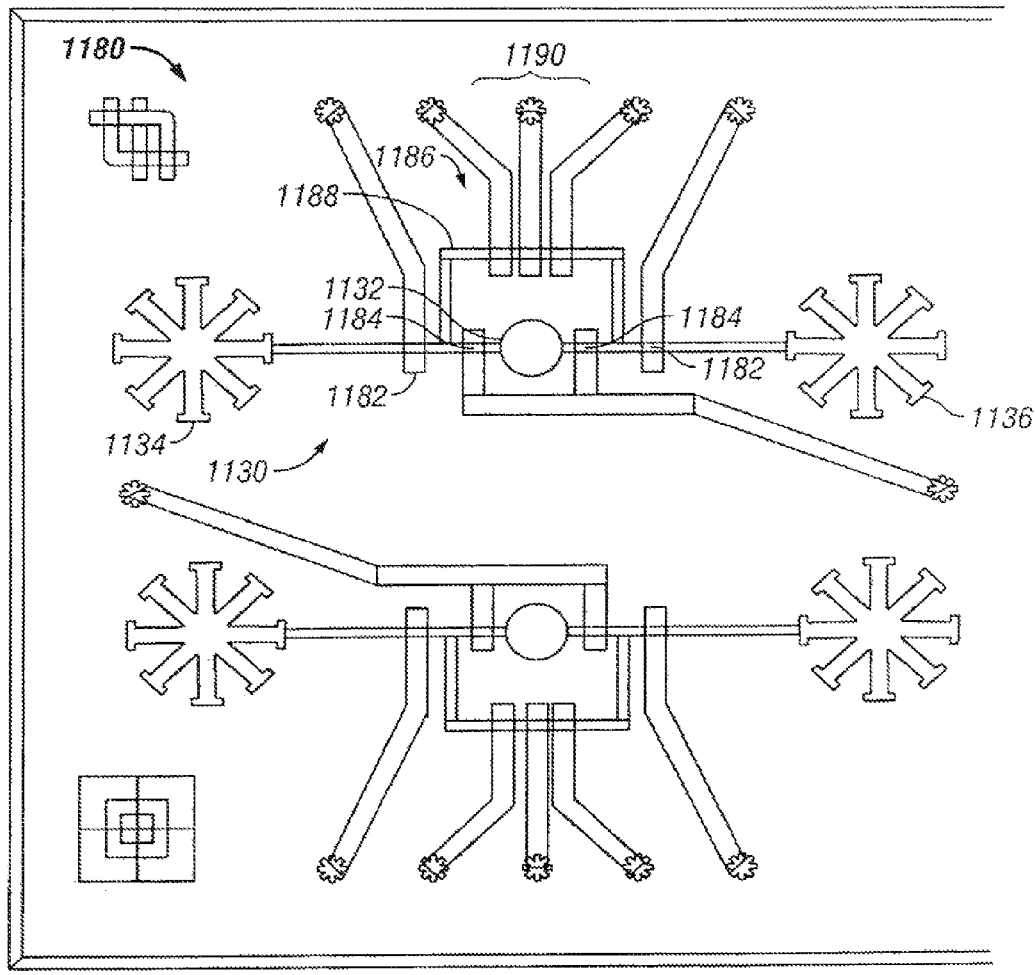
FIG. 45 is a top plan view of a microfluidic system with an isolatable cell chamber that may be fed or bypassed by a parallel fluidic circuit, in accordance with aspects of the invention.

FIG. 45 shows a microfluidic system 1180 having a microfluidic network 1130 through which fluid flow is more flexibly controlled. Specifically, fluid flow through chamber 1132 is controllable by two nested sets of flanking control valves 1182, 1184 that sit to both sides of chamber 1132. A parallel pumping circuit 1186 is disposed as an parallel fluid path 1188, having pump 1190 and extending from upstream and downstream cell chamber 1132, at an intermediate nested-position between nested valve sets 1182, 1184.

System 1180 may be operated as follows. During cell (particle) loading, nested valve sets 1182, 1184 are opened and fluid flows passively from input reservoir 1134 to output reservoir 1136, bringing cells to chamber 1132. When a desired number of cells have entered chamber 1132, one or both of valve sets 1182, 1184 are closed to isolate chamber 1132. If only valve set 1182 is closed, pump 1190 may be activated to circulate fluid through a loop that include chamber 1132 and alternate fluid path 1188, to prevent cell adhesion to the substrate, or to maintain a fluid flow over cells that have adhered. Alternatively, only valve set 1184 may be closed, allowing fluid to flow between input and output reservoirs using alternate, parallel fluid path 1188, to the exclusion of a path through chamber 1132. Thus, fluid channels may be flushed and re-equilibrated with any desired reagent. Once the fluid channels have been re-equilibrated, the desired reagent, valve set 1182 may be closed and the desired valve set 1184 may be opened, to actively pump the desired reagent in a closed loop that includes chamber 1132. For example, the reagent may be a mixture of trypsin and EDTA, or another suitable detaching reagent. Pumping the mixture of trypsin and EDTA through the closed loop detaches adhered cells. Opening valve set 1182 then allows the detached cells to be flushed from the system, either to output reservoir 1136 or to any additional microfluidic mechanism or set of mechanisms, as described throughout this detailed description.

Embodiment 3

Figure 46:
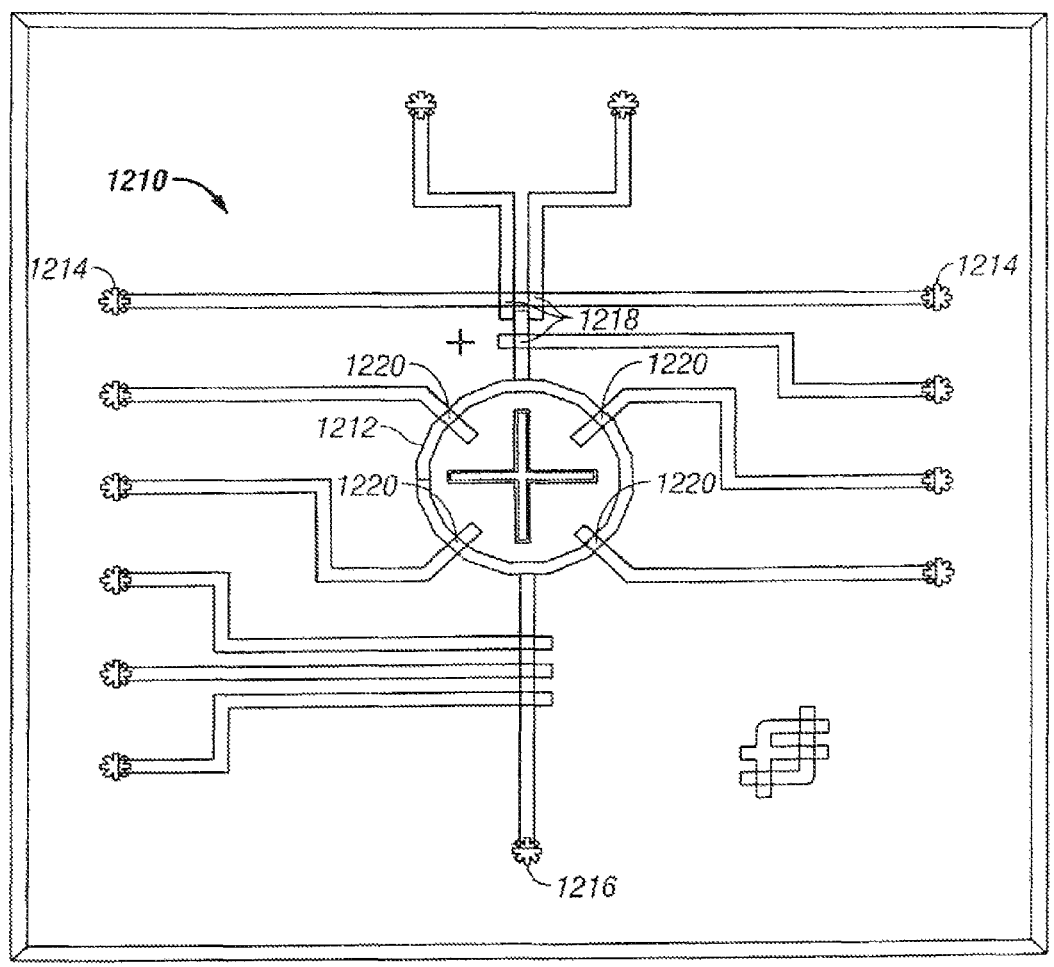
FIG. 46 is a top plan view of a microfluidic system having a cell chamber that forms a loop, in accordance with aspects of the invention

FIG. 46 shows a microfluidic system 1210 with a cell chamber 1212 formed as a looped channel or ring structure, in accordance with aspects of the invention. Cells (or particles) are introduced into chamber 1212 and retained there, either by balancing fluid height between input and output reservoir 1214, 1216, respectively, or by closing one or more valves 1218 that interconnect these reservoirs. Partial closure of valves 1218, particularly valves adjacent or within chamber 1212, may be used to permit fluid flow, while preventing cell flow, past the valves. Once cells are loaded into chamber 1212, four valves 1220 may be actuated in an appropriate order to move fluid around chamber 1212

Embodiment 4

Figure 47:
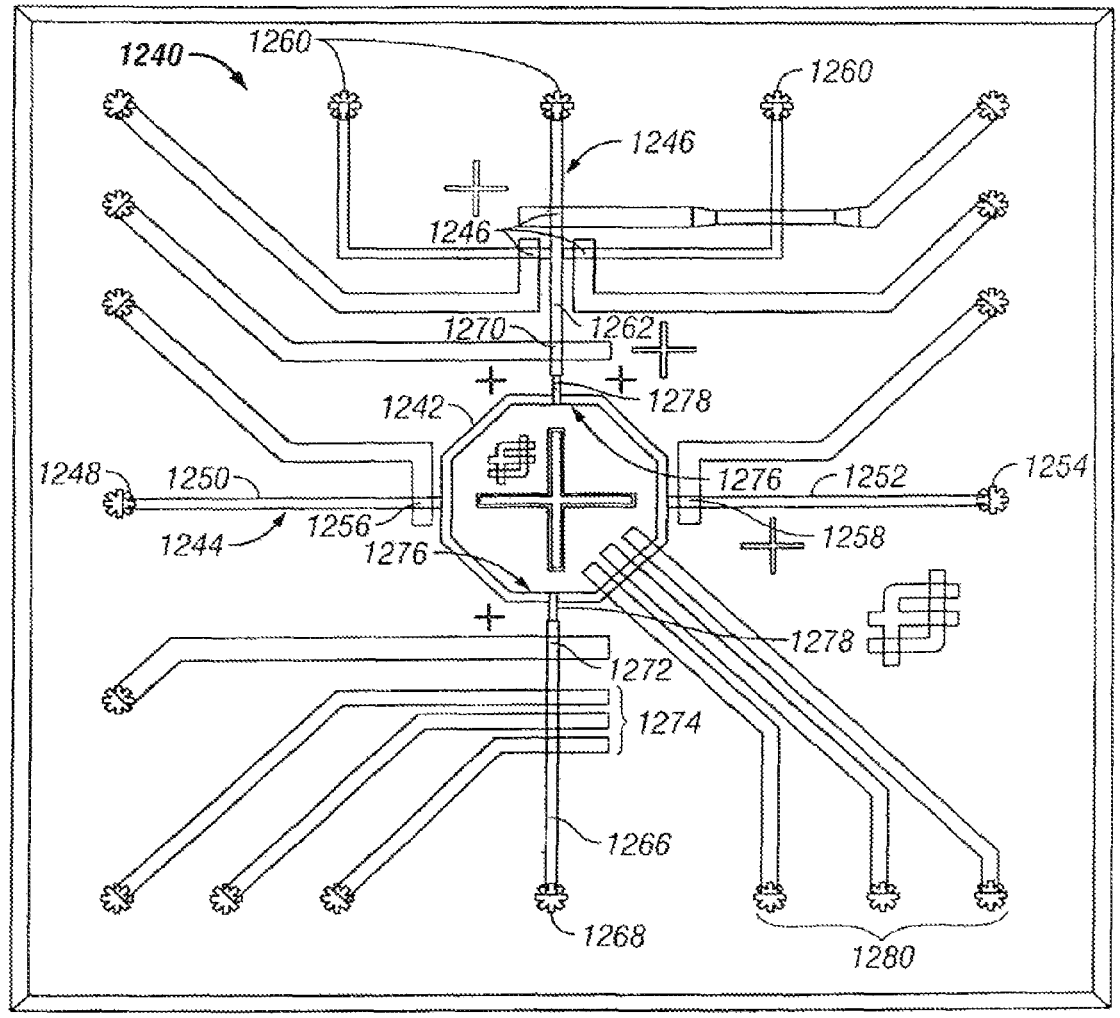
FIG. 47 is a top plan view of a microfluidic system in which particle and reagent networks intersect at a common cell chamber, in accordance with aspects of the invention.
Figure 48:
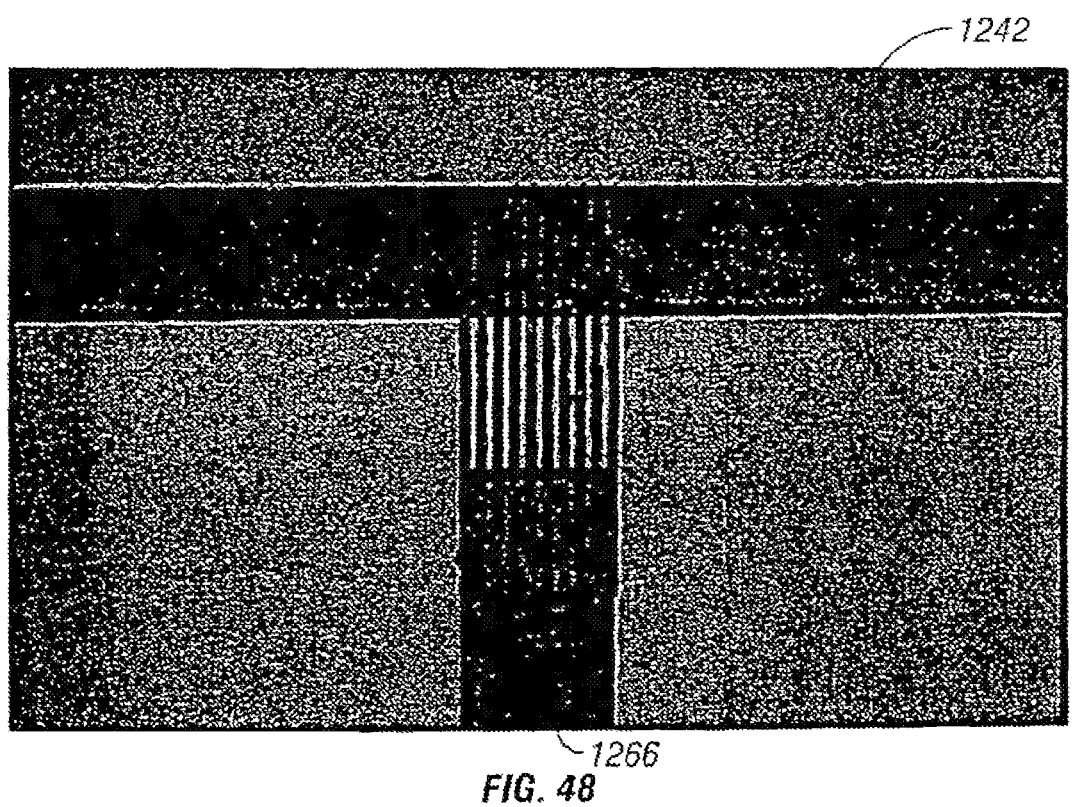
FIGS. 48 and 49 are photographic images of filtering mechanisms with size-selective channels that are included in the reagent networks of chips fabricated according to the system of FIG. 47.
Figure 49:
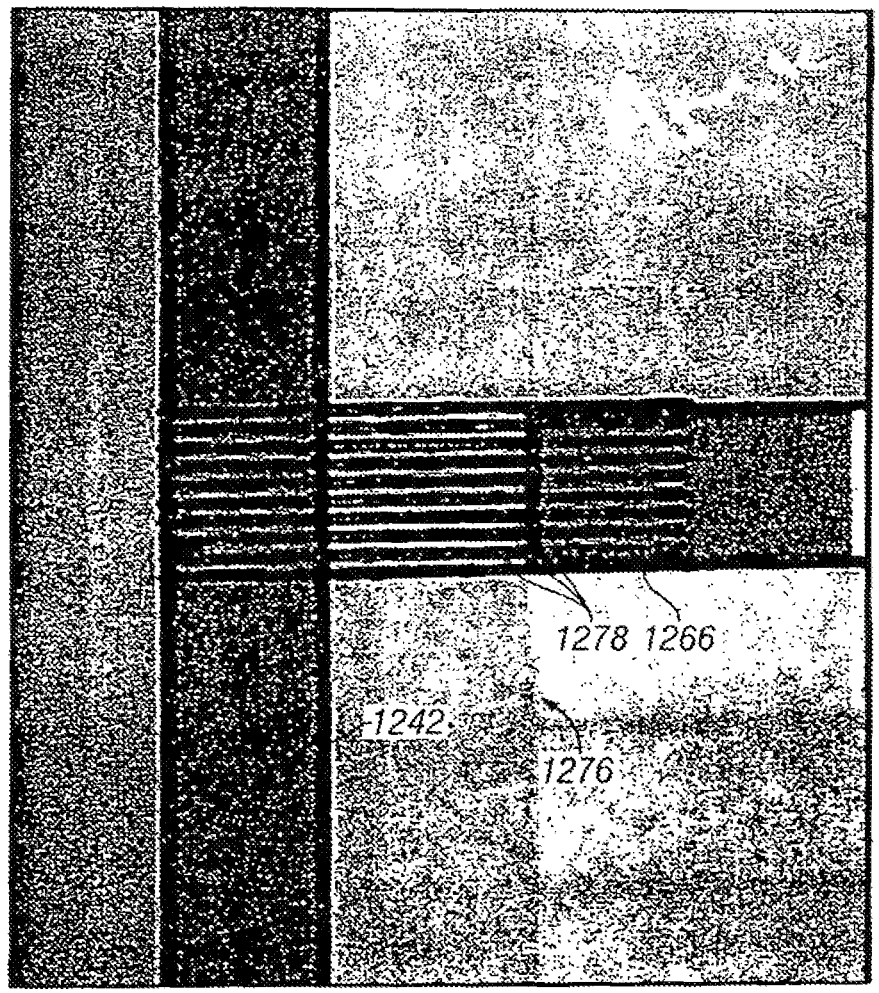

FIGS. 47-49 shows another microfluidic system 1240 with a chamber 1242 formed as a looped channel or ring structure, in accordance with aspects of the invention. System 1240 offers distinct networks for particle inflow/outflow—particle network 1244—and for reagent inflow/outflow—reagent network 1246. These distinct networks overlap at chamber 1242.

Particle network 1244 is used to load particles into chamber 1242 and to receive particles flowing from chamber 1242. Particles are loaded initially into input reservoir 1248, which feeds the particles into input channel 1250. Input channel 1250 flows into chamber 1242 Chamber 1242 bifurcates and rejoins at outlet channel 1252. Outlet channel 1252 carries fluid to output reservoir 1254. Fluid flow between reservoirs 1248 and 1254 can be terminated at any selected time by closing one or both of valves 1256 and 1258. Closing both valves fluidically isolates chamber 1242 from the remainder of particle network 1244.

Reagent network 1246 is used to move fluid, particularly fluid carrying reagents, through chamber 1242, while selectively retaining particles. Reagent network 1246 directs fluid and reagents from one or more reagent reservoirs 1260 through inlet channel 1262 into chamber 1242. Flow from each reagent reservoir 1260 is independently regulated by valves 1264, which control flow of a single reagent or a mixture of reagents. Desired ratios and/or dilutions of reagents may be formed by precisely controlling flow rate through each valve, for example, as described above in Example 8. Reagents entering chamber 1242 from inlet channel 1262 follow a bifurcated path that rejoins at outlet channel 1266. Outlet channel 1266 carries fluid to waste reservoir 1268. Inflow or outflow can be regulated with valves 1270, 1272, respectively, which may be closed to isolate chamber 1242 from reagent network 1246, particularly during particle loading and/or removal. Furthermore, a reagent pump 1274 may be used to pull reagents from reagent reservoirs 1260 to waste reservoir 1268.

Reagent network 1246 blocks exit (and entry) of particles from (and to) chamber 1242, based on particle size. To achieve this, reagent network 1246 interfaces with chamber 1242 using filtering mechanisms 1276. FIGS. 48 and 49 show photographs of size-selective channels 1278 disposed in outlet channel 1266, adjacent chamber 1242.

Chamber 1242 includes a chamber pump 1280 (see FIG. 47). Chamber pump 1280 is used to circulate fluid through chamber 1242, for example, (1) to suspend cells (such as during detachment of adhered cells with trypsin), (2) to move cells away from filtering mechanism 1276, reducing or preventing clogging of the mechanism, (3) to promote mixing within chamber 1242, and/or the like.

An exemplary method for feeding cells in chamber 1242 is a follows. One of reagent reservoirs 1260 is loaded with about 20 μL media, and waste reservoir 1268 is loaded with about 10 μL media (or buffer). These reservoirs have the same diameter, so this asymmetrical loading gives reagent reservoir 1260 a fluid head of about 10 μL. Flow to equalize fluid heights subsequently transfers about 5 μL of media through chamber 1242 to waste reservoir 1268 over the course of about 30 min. Particle network 1244 may be used instead, or in addition, if the cells in chamber 1242 are adherent.

Figure 50:
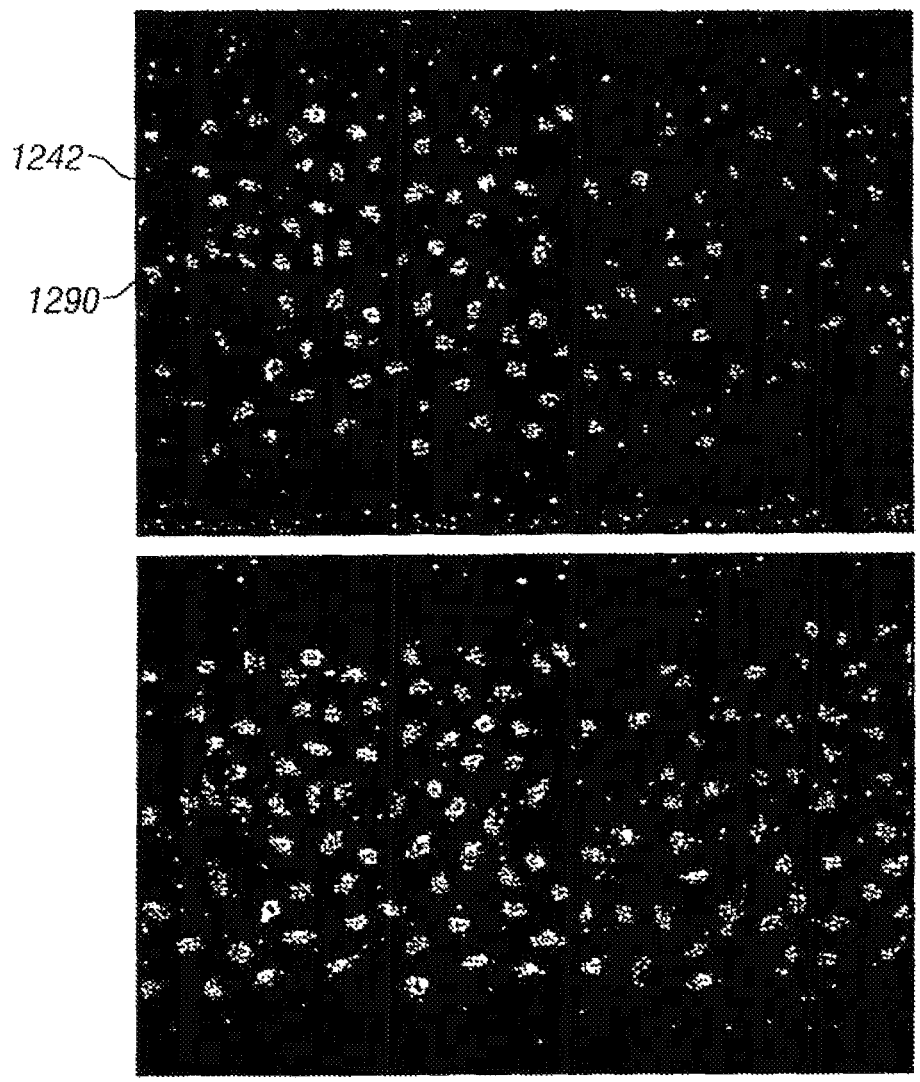
FIG. 50 is a composite of two photographic images showing cells cultured in a cell chamber of a chip fabricated according to the system of FIG. 47.

System 1240 allows extended culture of adherent cells. FIG. 50 shows NIH 3T3 cells 1290 that are alive and adherent in chamber 1242, 3 weeks after they were seeded. The field of cells shown has been tested for viability (top panel) and visualized for general morphology by bright field illumination (bottom panel). A substantial majority of cells was determined to be alive, as evidenced by lack of ethidium homodimer staining (Molecular Probes; Live/Dead Viability Assay Kit), and to have normal morphology. During the 3-week incubation, cells 1290 were subjected to the passive-flow feeding regimen described above, repeated once every 2 days.

Embodiment 5

Figure 50A:
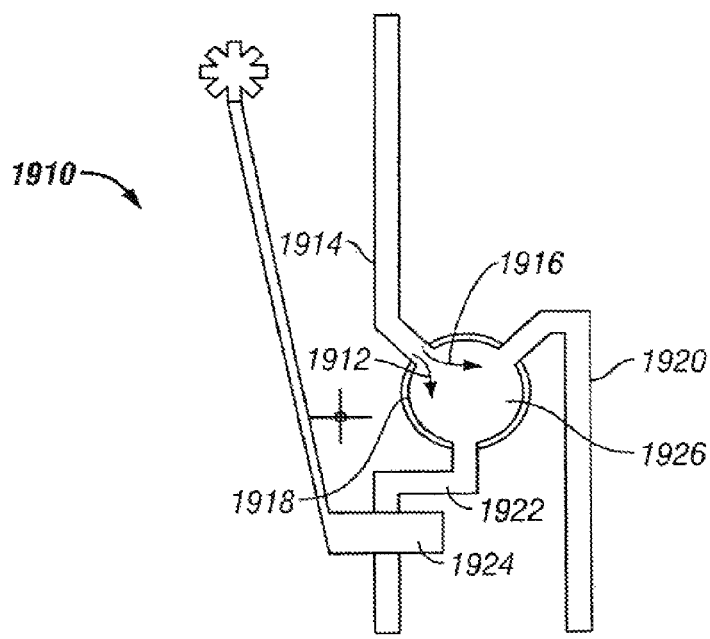
FIG. 50A is a fragmentary, top plan view of a system for depositing cells in a cell chamber, based on a nonlinear, asymmetrical flow path, in accordance with aspects of the invention.

FIG. 50A shows a system 1910 for depositing cells (or other particles) in a microfluidic chamber 1912, based on an asymmetrically disposed flow path. Particles and fluid flow into chamber 1912 from inlet channel 1914. The particles and fluid may follow plural distinct flow paths 1916, 1918 toward outlet channels 1920, 1922, respectively. One or more valves 1924 may be used to select one or both of the flow paths.

Selection of asymmetrically disposed flow path 1916 allows a subset of inputted cells to be deposited in chamber 1912. Main flow path 1916 may be both asymmetrically disposed and nonlinear. Such a flow path defines a highest velocity main stream corresponding to main flow path 1916. However, some of the fluid also follows lower-velocity auxiliary streams (weaker flow streams) disposed more distally in chamber 1912, in quasi-stagnant region 1926. Accordingly, the subset of cells that follows the auxiliary streams within chamber 1912 tend to be deposited in chamber 1912 by settling out and contacting a substrate defined by the chamber. Such contact diminishes the ability of fluid flow to move the settled cells and may promote additional interactions between the settled cells and the substrate, such as formation of a secreted extracellular matrix. In other embodiments, the subset of cells that are deposited may be determined by varying any suitable parameters including degree of nonlinearity of flow path 1916, location of flow path 1916 relative to the chamber, chamber dimensions, fluid flow rate, and/or the like.

Embodiment 6

Figure 50B:
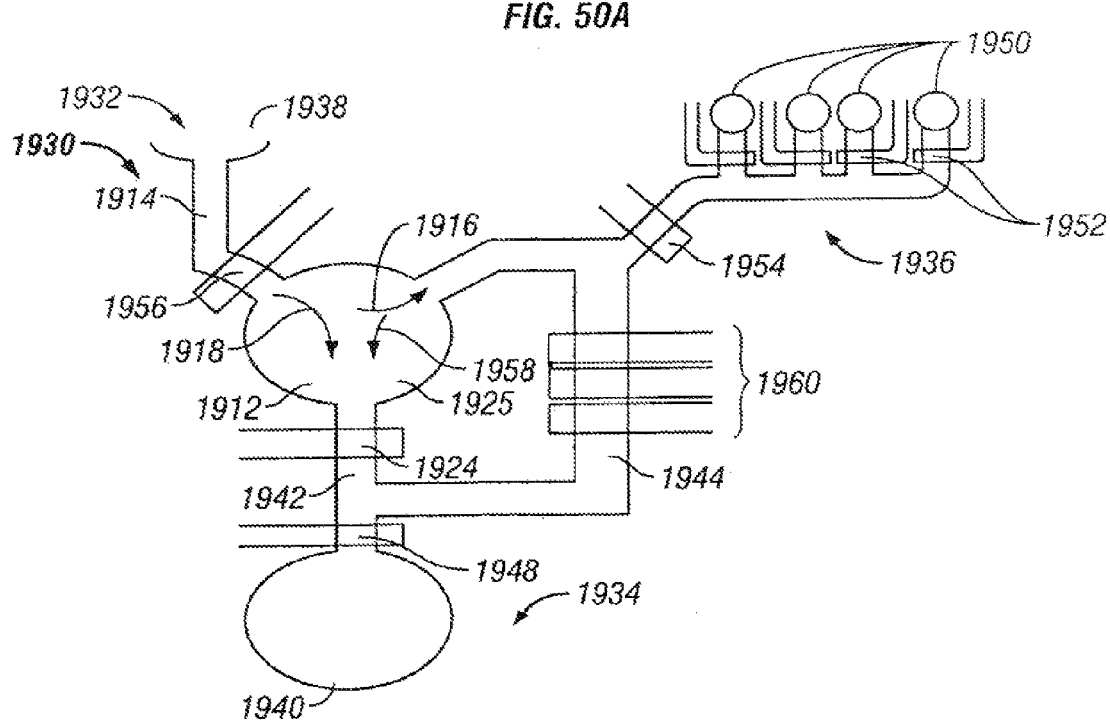
FIG. 50B is a fragmentary, top plan view of a modified version of the system of FIG. 50A, in which reagent(s) may be recirculated through the cell chamber, in accordance with aspects of the invention.

FIG. 50B shows a system 1930 that is based on system 1910 but includes additional mechanisms and features. System 1930 includes an input mechanism 1932, an output mechanism 1934, and a treatment mechanism 1936. Input mechanism 1932 includes an input reservoir 1938 for introducing cells and/or fluid, such as buffer or media. Output mechanism 1934 includes an output reservoir 1940 that may receive fluid from outlet channels 1942 and/or 1944, provided by flow paths 1918 and/or 1916, respectively. Valve 1924 may be operated to block flow along path 1918, whereas valve 1948 may be operated to block flow to output reservoir 1940 from either flow path. Treatment mechanism 1936 may include plural reagent reservoirs 1950, valves 1952 that regulate flow from each reagent reservoir, and a valve 1954 to regulate communication between entire treatment mechanism 1936 and chamber 1912.

System 1930 may be used to deposit cells as follows. Cells are inputted by input mechanism 1932, generally with valve 1948 opened, and valve 1924 closed. Cells travel along flow path 1916, with a subset following auxiliary flow streams to be deposited in quasi-stagnant region 1926, as described above.

Once a sufficient number of cells have been deposited within chamber 1912, the deposited cells may be manipulated further as follows. Valve 1956 may be closed and the contents of input reservoir 1938 replaced with media to achieve a fluid head that is approximately equal to that of output reservoir 1940, to produce no net flow between reservoirs (a "balanced flow" condition), and then valve 1956 may be reopened. The deposited cells may be incubated a suitable time period, such as overnight, during which time they may adhere by interaction with a substrate defined by the chamber. Such adhered cells are retained within chamber 1926. Alternatively, nonadherent cells may be used without attachment to chamber 1912.

Adhered (or nonadhered) cells may be treated with reagents from reagent reservoirs 1950 by operating treatment mechanism 1936. First, reagents may be introduced into chamber 1912 by opening one or more valves 1952, and valve 1954, to direct selected reagents along flow path 1958, along a reverse of flow path 1916, and/or along outlet channel 1944. Next, chamber 1912 may be placed within a closed loop by closing valves 1948, 1954, and 1956. Pump 1960 may be started to circulate reagent around the closed loop, providing a mixing action that continuously perfuses cells in chamber 1912 with reagent.

Embodiment 7

Figures 50C, 50D:
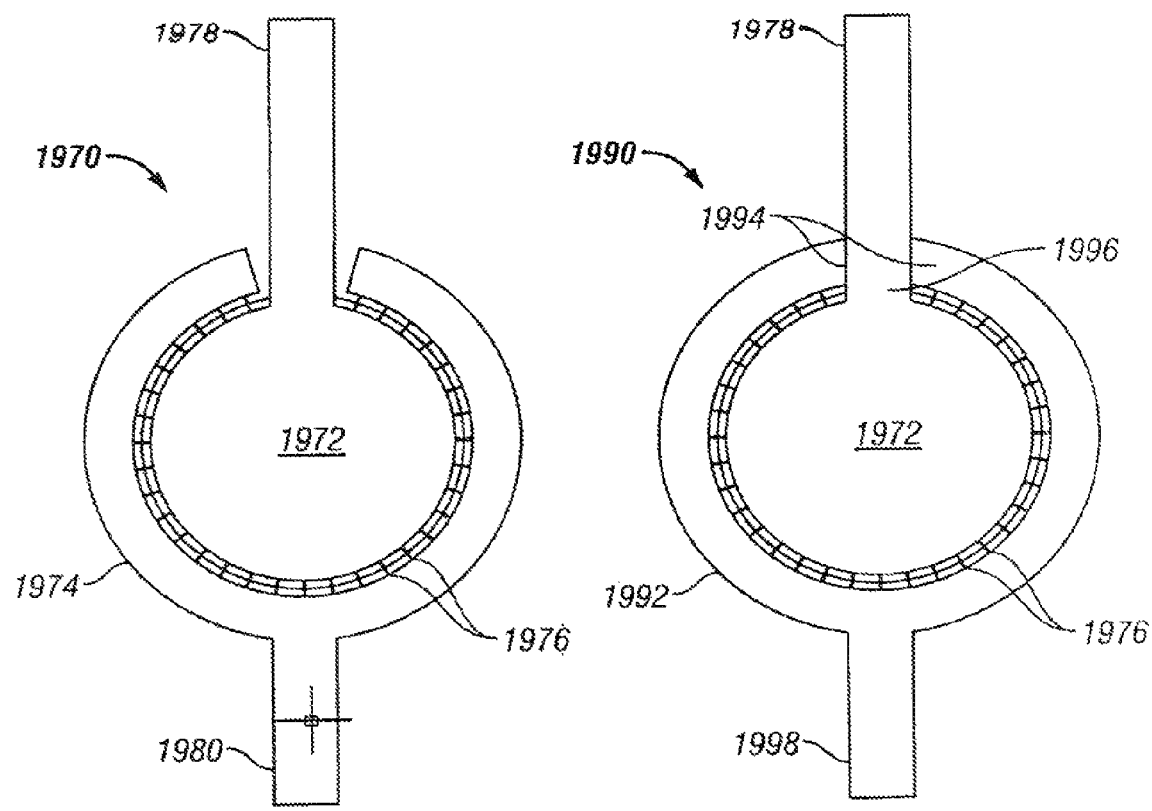
FIG. 50C is a top plan view of a cell chamber having two distinct compartments connected by a set of radially arrayed, size-selective channels, in accordance with aspects of the invention.
FIG. 50D is a top plan view of a version of the cell chamber of FIG. 50C, modified to interconnect the two compartments more fully, in accordance with aspects of the invention.

FIG. 50C shows a cell chamber 1970 that may be used to deposit (and retain) cells in one or two compartments 1972, 1974. Compartments 1972, 1974 may be connected by radially arrayed, size-selective channels 1976 to form a "spoked wheel" structure. Cells (or other particles) may be inputted from first input channel 1978 and deposited in compartment 1972. Fluid may flow through size-selective channels 1976 to second input channel 1980. Alternatively, or in addition, additional cells, such as a distinct cell type, may be inputted from second input channel 1980 to be deposited in outer compartment 1974, with fluid flowing toward first input channel 1978. With each of the two compartments occupied by distinct cell populations, cell-cell communication may be analyzed by passage of released cell components (or extended cell structures) through the size-selective channels between the two compartments. In alternative embodiments, the first and second compartments may have any suitable geometry, such as interdigitated fingers or intermeshed spirals, among others, to increase the area of communication between the two compartments. Furthermore, additional compartments may be added to measure interactions between additional cell types.

Embodiment 8

Cell chamber 1990 is a modified version of chamber 1970 that includes an overflow capability. Here, inner compartment 1972 acts as a chamber that is connected to overflow compartment 1992 by transverse passages 1994, in addition to size-selective channels 1976. Accordingly, input channel 1978 may be used to direct most of inputted cells (or other particles) into inner compartment 1972 using entrance 1996. However, once inner compartment 1972 becomes filled, additional cells may travel along transverse passages, through overflow compartment 1992 and out outlet channel 1998.

Applications

The microfluidic systems described here may be used for the manipulation of adherent and nonadherent cells. For example, after, introduction to a chamber, NIH 3T3 cells adhere to the substrate to retain the cells effectively within the chamber. Once adhered, these cells remain attached to the substrate as fluidic flows are directed over them passively and/or actively. These cells remain viable at a range of flow rates and valve closure pressures. However, cell viability may be compromised when higher valve actuation pressures are used, because higher pressures lead to complete valve closure. A valve that closes upon a cell can crush it. In particular, at high pumping frequencies, all cells within a population inside a ring may be crushed, since they have a high probability of being crushed. In this case, the ring may become filled with cell debris, which may be a starting point for assays on cell components. The nuclear membrane may or may not be compromised by this treatment.

In general, manipulation of adherent cells on the chips is achieved in the following manner. Adherent cells are prepared from seed flasks by releasing the cells from the flasks, for example, by trypsinization, followed by washing, centrifugation, and resuspension in a standard tissue culture medium, such as DMEM or RPMI. Once a desired concentration has been achieved, cells are loaded using a manual pipettor into the input well and cells flow into the microfluidic channel structures under the head flow generated by the column of liquid. Once adhered, adherent cells can be resuspended in the microfluidic channel by addition of trypsin-EDTA or other cell-detaching agents.

The microfluidic layer and substrate may be treated (or left untreated) to promote cell flow, cell viability, cell adhesion or nonadhesion, cell growth, and/or the like. Fluidic channels and/or the substrate may be treated with a nonionic detergent, such as TWEEN; a serum protein, such as a serum albumin (e.g., BSA); whole or fractionated serum from any suitable animal; extracellular matrix extracts, components, or mixtures, such as collagen, polylysine, SIGMACOTE, MATRI-GEL, etc.; and/or the like.

Example 11

Systems for Electrophysiological Analysis of Cells in a Microfluidic Environment This example describes microfluidic systems for positioning, retaining, treating, and/or measuring cells, particularly for electrophysiological analyses; see FIGS. 51-58.

Background

Cell-surface membranes are an essential part of all cells, defining their extent, and separating and maintaining the differences between the cell interior (cytoplasm) and the extracellular milieu. Accordingly, controlling membrane permeability and the selectivity of ion movement across membranes, mediated by ion channels and transporters, is fundamental to cell survival, cell physiology, and signal transduction mechanisms, particularly neurotransduction. Thus, many cell-surface receptors couple to ion channels and transporters, making measurement of membrane currents a very rapid and sensitive indicator of cell physiology and receptor activity. Therefore, many drug assays benefit from or, in some cases, require a measurement of the effects of drugs on ion currents, referred to as electrophysiology.

The preferred method for conducting electrophysiological analyses of cells membranes is the "patch-clamp" analysis of individual cells. Typically, in this approach, a glass electrode with a diameter of about 0.1-1 µm is electrically sealed against the membrane of a single cell, surrounding a membrane "patch" on the cell. The patch then may be left intact, separated from the cell, "perforated" with channel-forming agents, or penetrated, based on the type of information desired. With both intact patches and patches separated from a cell, the size of the patch and the density of channels in the membrane determine the number of channels being analyzed. Thus, different sizes of patches may allow "single-channel recordings" from small regions of membrane, or recordings from many of channels in "macropatch recording." Alternatively, membrane patches can be perforated or penetrated to measure electrical properties of the entire cell membrane, in "whole-cell" patch-clamp studies. Perforated patches introduce a channel-forming agent, such as the antibiotics nystatin or amphotericin B, into the membrane. Perforated patches enable whole cell recording of channel activity with loss of larger cytoplasmic components. Penetrated patches place an electrode inside a cell, so that the electrode and the cell's cytoplasm are continuous. Accordingly, penetrated patches also enable whole-cell patch-clamp recording.

Despite the importance of electrophysiology as an assay tool and the variety of patch-clamp methods available for measuring electrical activity at membranes, these methods require substantial time and skill for their proper execution. In particular, each of these methods generally is carried out manually, by a highly-skilled electrophysiologist. The electrophysiologist must precisely position an electrode against the membrane of each cell, and manipulate the electrode and/or cell additionally to form a gigaseal and/or penetrate the cell. Accordingly, the electrophysiologist must devote considerable time and energy to the execution of patch-clamp methods, making them expensive and ill-suited to screening applications in which many samples must be studied. Thus, there is a need for a more automated system that simplifies cell manipulation and at least partially automates patch formation.

Description

This example describes microfluidic devices that allow measurements of ion channel activity. These devices position a single cell in abutment with an aperture, so that the cell's membrane forms a high resistance, gigaohm seal, termed a gigaseal, around the aperture. The gigaseal allows channel currents across the cell membrane to be measured, by "whole cell" patch-clamp recording. Measurement of currents in the presence and absence of potential modulators of channel activity, such as agonists and antagonists of receptors that couple with channels, provides a rapid and sensitive method for testing these modulators. Since changes in channel currents often are transient, the device also facilitates rapid perfusion of the cell with potential modulators and wash solutions. This allows rapid exposure and removal of the modulators. The device may be configured as a system that simultaneously and/or sequentially analyzes more than one single cell (see, among others, Example 12).

Embodiment 1

Figure 51:
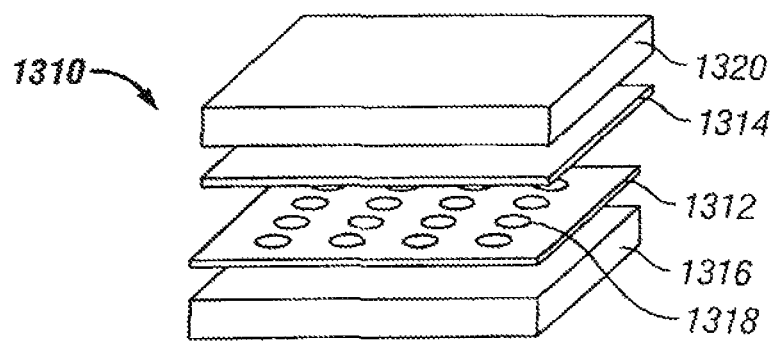
FIG. 51 is an isometric schematic view of a microfluidic system for performing electrophysiological analysis on an array of cells, in accordance with aspects of the invention.

FIG. 51 shows a microfluidic device 1310 for measuring ion currents, in accordance with aspects of the invention. Device 1310 includes a planar patch clamp electrode consisting generally of three layers: a substrate layer 1312, a fluidic layer 1314, and a base layer 1316.

Substrate layer 1312 includes one or more patchable orifices 1318, of about 0.1-5 µm, or about 1-5 µm in diameter. The perimeter of each orifice forms a gigaseal with the membrane of a single cell being analyzed. Accordingly, substrate layer 1312 may be fabricated from any nonconducting material capable of forming a highly resistant seal, and may be relatively hard. Suitable materials for the substrate layer include glass, silicon, and/or plastic, among others.

The substrate layer separates fluidic layer 1314 and base layer 1316. The fluidic and base layers each are filled with one or more buffer solutions that mimic the external and internal ionic environments, respectively, of single cells being analyzed. These buffer solutions may be referred to as external and internal buffers, respectively. The movement of ions through the cell membrane, effectively between the fluidic and base layers, creates currents that can be measured using sensitive amplification equipment. The fluidic layer may be formed by any suitable technique, such as multilayer soft lithography, for example, as described elsewhere in this Detailed Description. The fluidic layer may be controlled by any suitable control mechanism, such as an overlying microfluidic control layer 1320. The base layer may be formed out of any suitable material, such as glass, plastic, and/or an elastomeric material, among others. The base layer may be cut (punched), molded, etched, and/or embossed, among others, to (1) form a tight seal with substrate layer 1312, and (2) form a reservoir holding internal buffer that is in fluidic contact with each orifice and that accepts an electrode and/or electrode plate, typically connected to suitable stimulation and recording equipment. In preferred embodiments, the bore of the patch clamp channel may be large enough to permit dislocation or dislodging of the particle from the patch clamp when fluid flow is reversed through the bore of the patch clamp channel.

Embodiment 2

FIGS. 52-58 shows a microfluidic system 1340 for single-cell patch-clamp recordings, in accordance with aspects of the invention. System 1340 includes a fluid-layer network 1342 and a fluid control layer 1344, both formed by multilayer soft lithography, for example, as described elsewhere in this Detailed Description. Network 1342 and control layer 1344 position a single cell over a patchable orifice or aperture formed by a substrate layer (see below). Positioning the single cell establishes an appropriate buffer gradient between fluid-layer network 1342 and a base-layer fluidic chamber, as described above for FIG. 51. Once a high-resistance seal is formed between the positioned cell and the substrate, around the orifice, system 1340 allows the positioned cell to be perfused with one or more of a set of reagents, such as drugs, ligands (for the case of ligand-gated channels), buffers with distinct ionic compositions, and/or wash solutions. Perfusion of these reagents permits rapid measurement of the effect of these reagents on the electrical activity of the cell.

To carry out these functions, system 1340 includes several mechanisms that cooperate serially and/or in parallel. A cell manipulation mechanism 1346 inputs, positions, and retains single cells. A cell perfusion mechanism 1348 exposes and washes the retained single cells in a precisely controlled manner using a set of reagent-input networks. An electrical monitoring mechanism 1350 electrically contacts both the fluid-layer network 1342 and a base-layer fluidic chamber (not shown) to measure current, voltage, and/or resistance of retained single cells before, during, and/or after exposure to desired reagents and/or electrical manipulations.

Cell manipulation mechanism 1346 itself includes a set of mechanisms, including a cell input mechanism 1352, a cell positioning mechanism 1354, and a cell retention mechanism 1356. These mechanisms act in a coordinated fashion to manipulate single cells for patch-clamp experiments.

Cell input mechanism 1352 generally comprises any mechanism that acts through an input reservoir 1358 to introduce cells into fluid-layer network 1342. Input mechanism 1352 is similar to input mechanism 263 of Example 2. Other suitable input mechanisms are described above, in Section IV.

Figure 53:
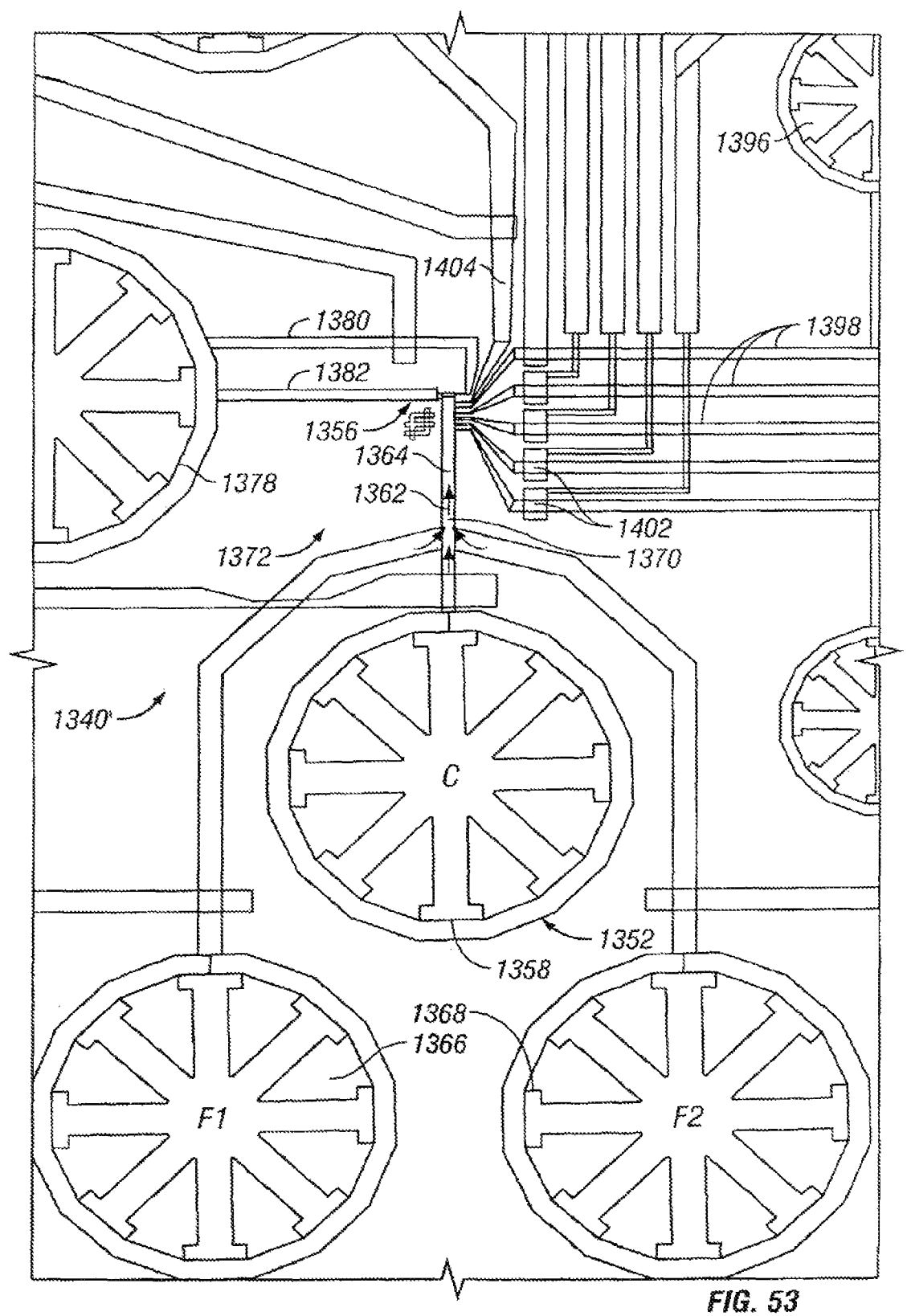
FIG. 53 is a fragmentary top plan view of a microfluidic system related to the system of FIG. 52, showing a modified focusing mechanism, in accordance with aspects of the invention.

Cell positioning mechanism 1354 generally comprises any mechanism that acts to position single cells within microfluidic network 1342. In addition to simple flow channels, the cell-positioning mechanism may include a focusing mechanism 1360. Focusing mechanism 1360 places input cells in an input stream 1362 at a central portion of inlet channel 1364, labeled "E1," flanked by focusing flow streams from focusing reservoirs 1366, 1368, labeled "F1" and "F2." Mechanism 1360 directs fluid from input and focusing reservoirs 1358, 1366, 1368 to junction 1370 from three orthogonal directions. FIG. 53 shows an alternative cell-focusing mechanism 1372, in which cell-input and focusing streams join at acute angles, forming an "arrowhead" configuration. Focusing mechanisms 1360 and 1372 are similar to aspects of positioning mechanism 263 of Example 2.

Figure 54:
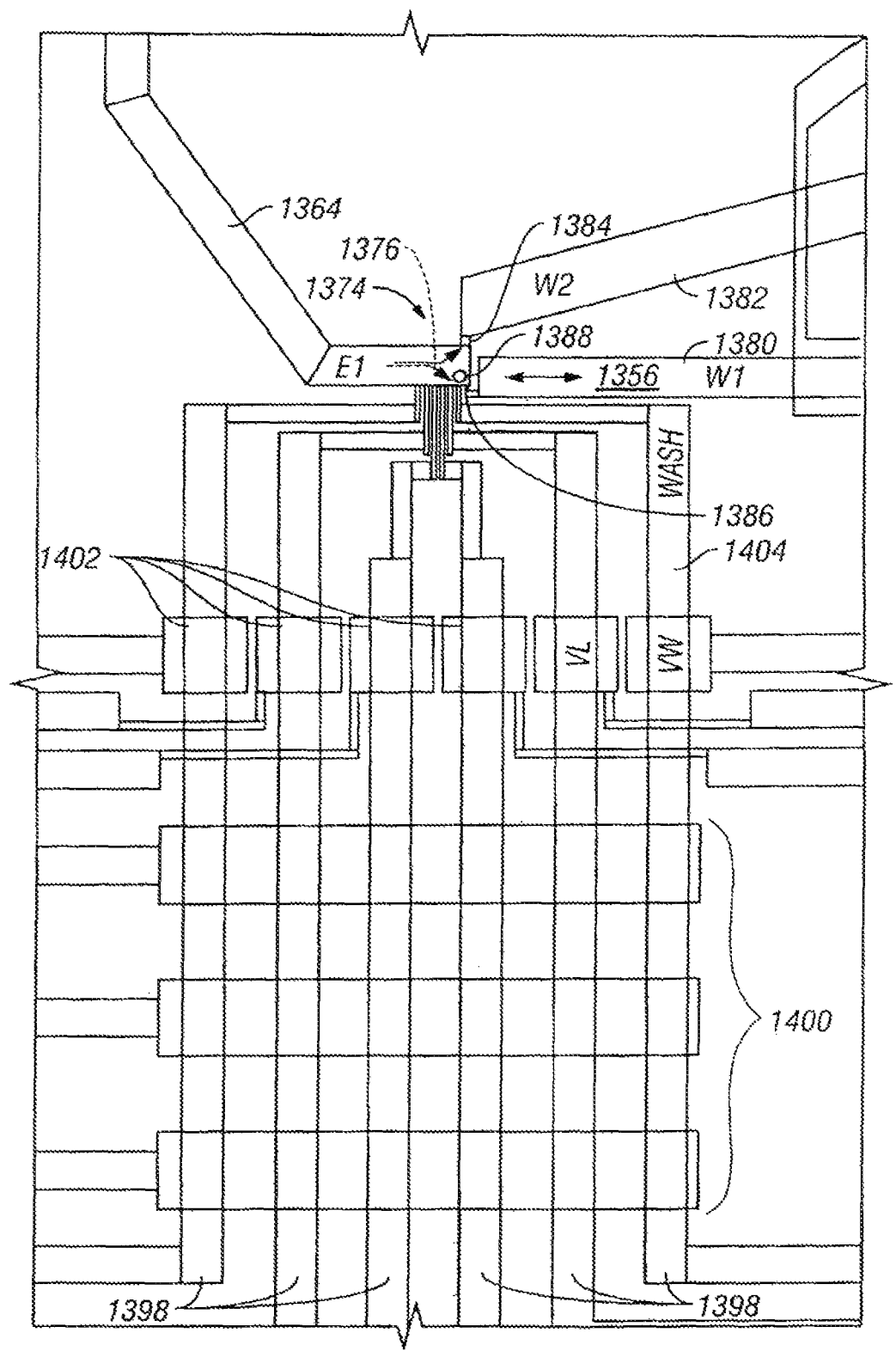
FIG. 54 is a top plan view of selected portions of the system of FIG. 52 with a retained cell, in accordance with aspects of the invention.

Cell positioning mechanism 1354 stochastically segregates single cells using a divided-flow mechanism 1374, downstream from focusing mechanism 1360 or 1372; see FIG. 54. Specifically, focused cells are directed down inlet channel E1 and encounter a divided flow path 1376. Divided flow path 1376 directs fluid to a waste reservoir 1378 (see FIGS. 52 and 53) through outlet channels 1380, 1382 (labeled "W1" and "W2," respectively, in FIG. 54). These outlet channels include a narrowed portion 1384 and a size-restrictive channel 1386 that determine the relative flow rate through each corresponding outlet channel. Narrowed portion 1384 has a substantially larger diameter than size-selective channel 1386, so that most of the flowing fluid (and cells) passes through narrowed portion 1384. However, some fluid passes through size-restrictive channel 1386, eventually bringing a single cell 1388 to the mouth of the channel.

Cell retention mechanism 1356 generally comprises any mechanism for retaining a cell at a desired position, generally adjacent an orifice and/or electrode(s). Here, the cell retention mechanism functions at the channel mouth; see FIGS. 54 and 57. In particular, cell 1388 cannot enter size-restrictive channel 1386 because the cell is too large. However, the pressure drop across size-restrictive channel 1386 pulls cell 1388 against the channel mouth, holding cell 1388 in position. Positioned cell 1388 may restrict or block flow through size-restrictive channel 1386, so that additional cells no longer are urged toward channel 1386. Cell 1388 also is positioned over an orifice 1390 (see FIG. 56) defined by the substrate layer. In alternative embodiments, single cells may be positioned and retained over an orifice by any suitable positioning and/or retention mechanisms, for example, those described elsewhere in this Detailed Description.

With cell 1388 in position over orifice 1390, flow from input reservoir 1358 is terminated, but flow from focusing reservoir F1 and/or F2 continues. Continued flow from F1 and/or F2 may be used to prevent additional cells from stopping near cell 1388, which might interfere with measurements. In addition, continued flow from F1 and/or F2 ensures that buffer in the region surrounding cell 1388 is refreshed. To perform whole-cell recordings, reservoirs F1 and/or F2, and generally input reservoir 1358, are filled with external buffer, so that all of fluidic network 1342 is equilibrated with external buffer. In contrast, base-layer chamber, below orifice 1390, is filled with internal buffer from a lower face (or side) of the base layer, generally prior to cell input. The contents of these reservoirs could be reversed, if the cell is positioned on the opposite side of the aperture, or for reasons of experimental design.

Positioned cell 1388 is pulled against orifice 1390 by applying a vacuum from the base-layer chamber. This establishes a highly resistant seal, the formation of which can be measured as an increase in resistance between fluid-layer network 1342 and the base-layer chamber (below orifice 1390) using electrodes in each chamber. Generally, fluid-layer network 1342 serves as a ground, and a recording electrode is positioned in the base-layer chamber. Once the seal is formed, the resulting patched cell can be measured for its baseline electrical activity or properties.

Figure 52:
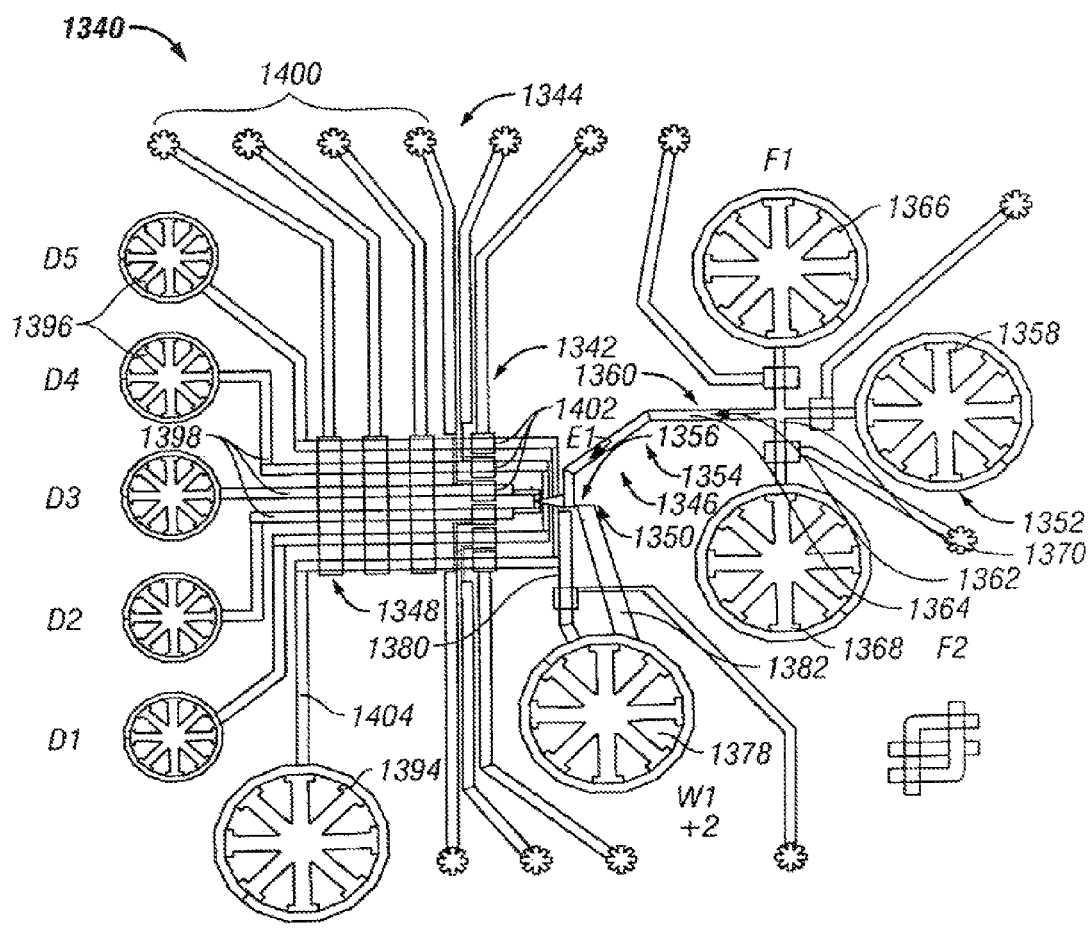
FIG. 52 is a top plan view of a microfluidic system for performing electrophysiological analysis on a single cell, in accordance with aspects of the invention.

After establishing this baseline, and/or using an average or calculated baseline, the effect of reagents, such as drugs, may be tested using perfusion mechanism 1348. FIG. 52 shows the general layout of mechanism 1348, which includes a shield or wash reservoir 1394, and a series of reagent reservoirs 1396, in this case five reservoirs, labeled D1-D5. Flow through inlet channels 1398 extending from reservoirs 1394, 1396 is actively promoted by a pump 1400 in control layer 1344. Pump 1400 acts in concert on all inlet channels 1398 to provide a uniform force for delivering the reagents and wash buffer. In contrast, flow through each individual inlet channel 1398 is regulated by a corresponding control valve 1402 that determines whether fluid flows through the inlet channel 1398. Valves 1402 are shown in more detail in FIGS. 53, 54, 56-58, where these valves are labeled $V_W$, and V1-V5, corresponding to control of wash reservoir ("W") and reagent reservoirs D1-D5, respectively.

Figure 55:
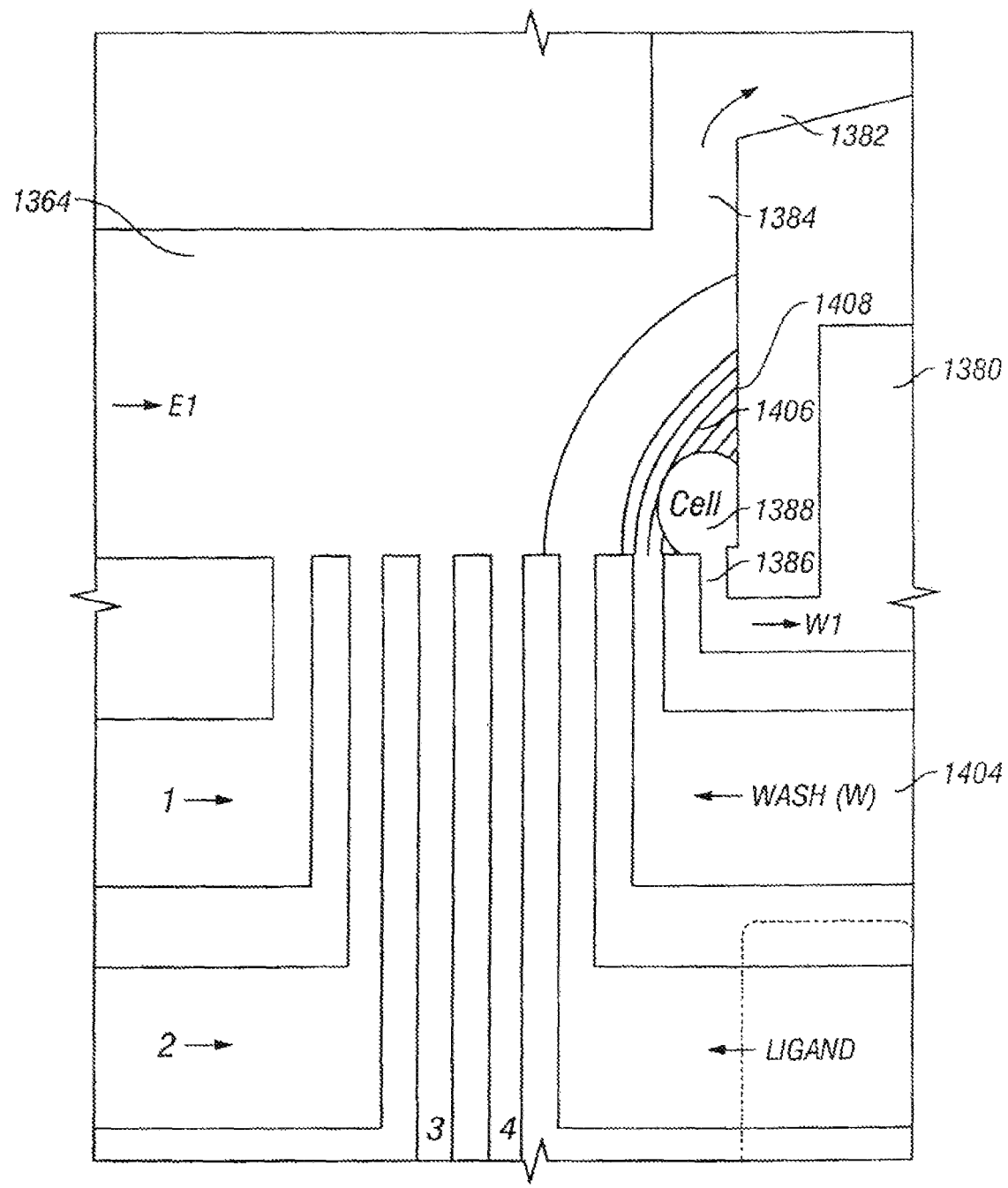
FIG. 55 is a top plan view of selected portions of the system of FIG. 52 during perfusion of a retained cell, in accordance with aspects of the invention.
Figure 56:
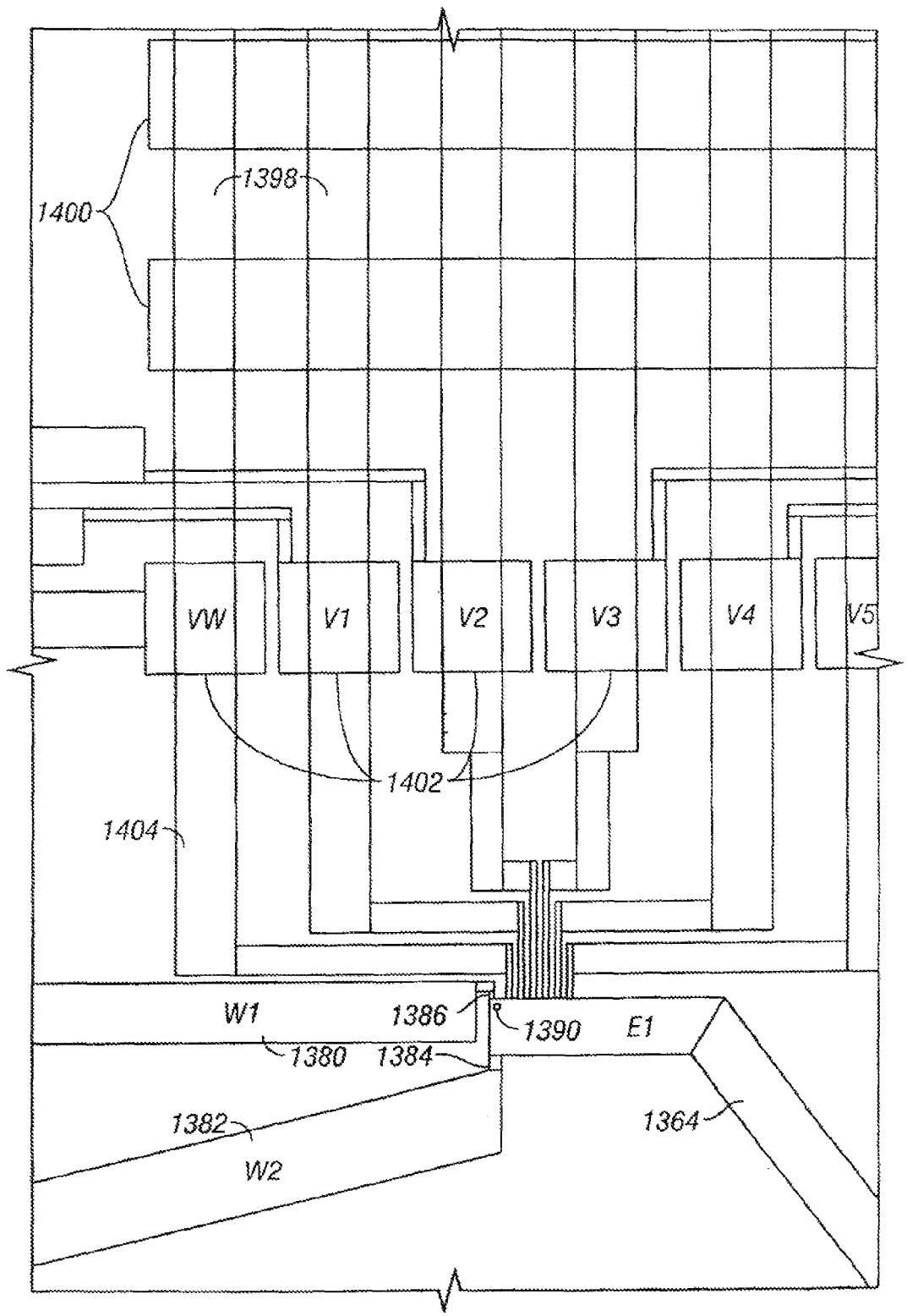
FIG. 56 is another top plan view of selected portions of the system of FIG. 52, in accordance with aspects of the invention.
Figure 57:
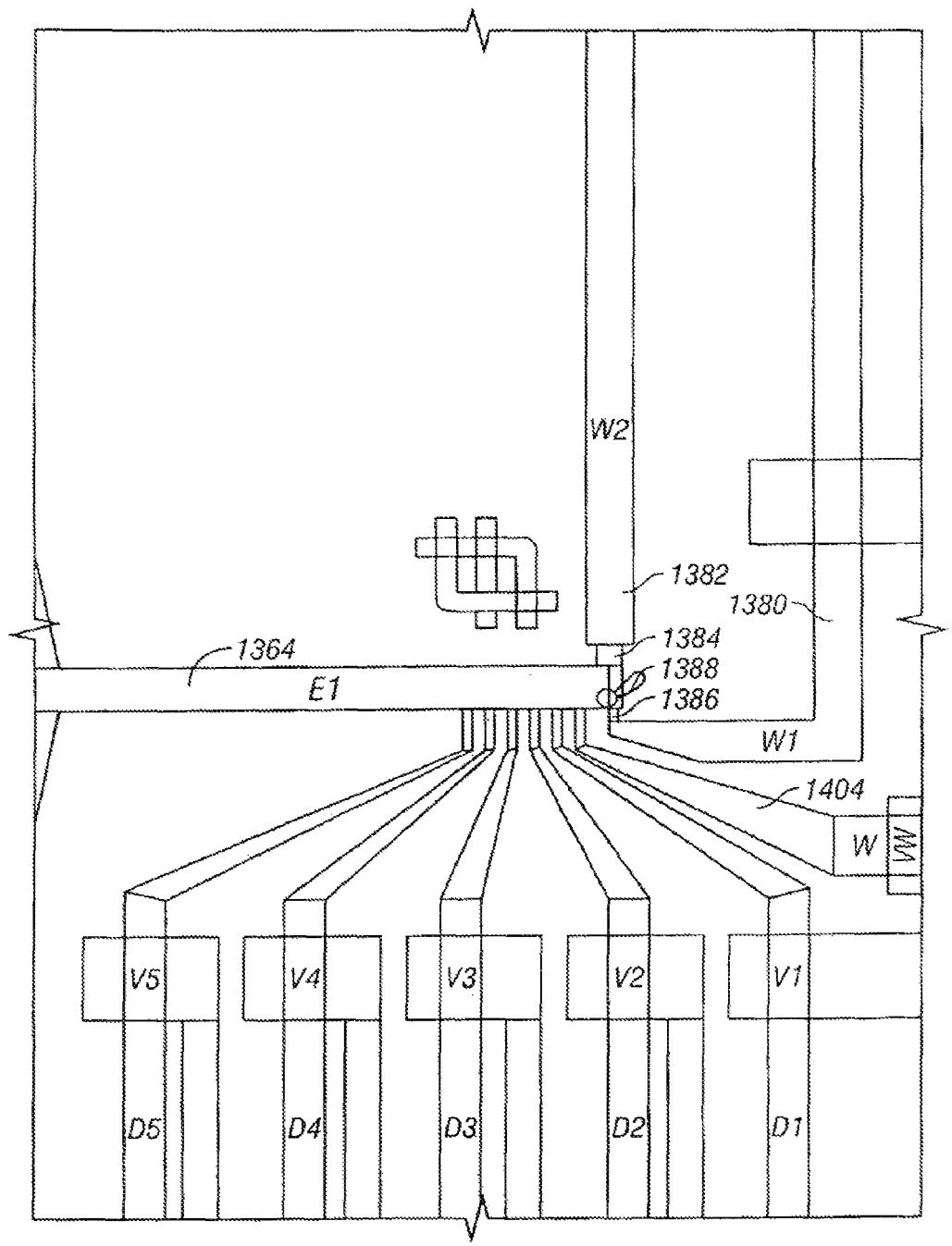
FIG. 57 is yet another top plan view of selected portions of the system of FIG. 52, in accordance with aspects of the invention.
Figure 58:
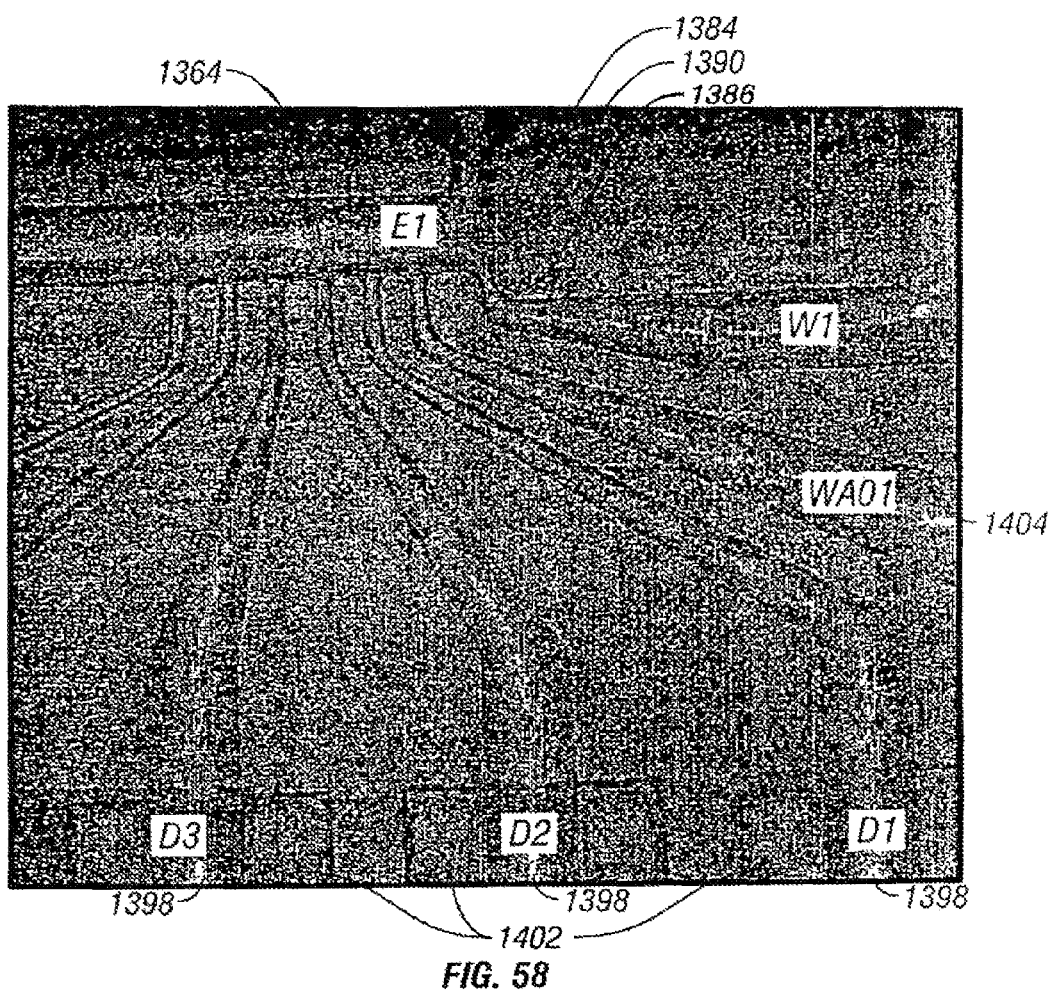
FIG. 58 is a photographic image of a portion of a chip fabricated according to the system of FIG. 52.

FIG. 55 show perfusion mechanism 1348 in more detail. Perfusion mechanism 1348 controls exposure of cell 1388 to each selected reagent using a regulatable fluid sheath or shield, similar to that described for perfusion mechanism 268 of Example 2. Wash reservoir W is filled with external buffer, and the buffer is flowed past cell 1388 from wash inlet-channel 1404 by opening valve $V_W$. Specifically, focusing buffer from F1 and/or F2 entering chamber E1 pushes the wash buffer in a laminar flow pattern or sheath flow 1406 over cell 1388, against wall 1408. Because wash inlet-channel 1404 is closer to cell 1388 than any of the reagent inlet channels 1398, sheath flow 1406 spaces and prevents contact of reagents flowed from any of the reagent inlet channels. Upon closing valve $V_W$, any flowing reagent rapidly contacts the cell, and recordings can be made as desired. Accordingly, cell 1388 may be exposed rapidly to any reagents in reservoirs D1-D5 in a controlled manner by selective opening and closing valves $V_W$ and V1-V5, allowing measurement of electrical responses in a correspondingly rapid time frame. Therefore, ligands introduced through reservoirs D1-D5 may be used to study their antagonist or agonist activity on ligand gated channels, among others.

Microfluidic system 1340 may be configured in many suitable ways. For example, reagent inlet channels may unite, entering chamber E1 through a common port, as shown in system 250 of Example 2 (see FIG. 8). In this way, each reagent is equally spaced by sheath flow 1406 of the wash buffer and thus will reach cell 1388 at the same time when the sheath flow is terminated. Furthermore, such a design would allow reagent mixing and dilution, as described above in Example 8. Alternatively, or in addition, a pump may be included to drive flow from input reservoir 1358 and focusing reservoirs 1366, 1368. Furthermore, system 1340 may be modified to be reusable by including a cell removal mechanism, as described in Example 7. System 1340 may be modified additionally or alternatively to include a parallel or serial array of retention/analysis sites, for example, as described above in Examples 3-5, or below in Example 12.

Example 12

Microfluidic System for Multiplexed Analysis of Cells by Patch Clamp

Figure 59:
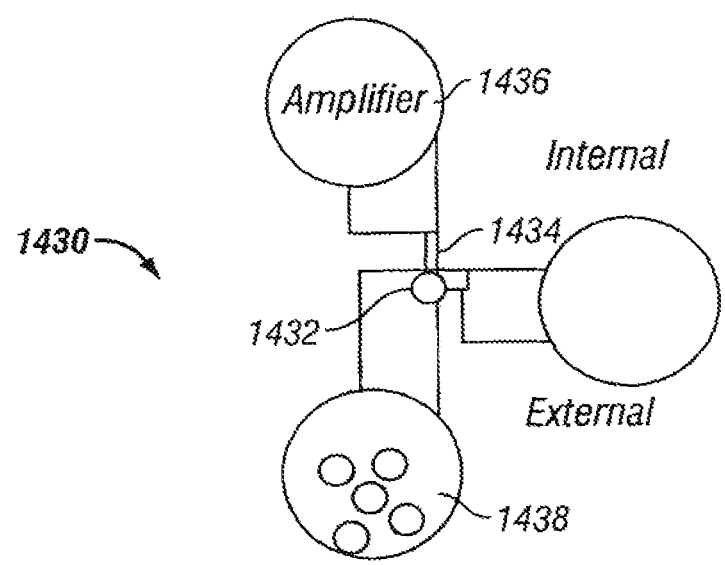
FIG. 59 is an abstracted view of a microfluidic device for performing patch-clamp analysis of cells, in accordance with aspects of the invention.
Figure 60:
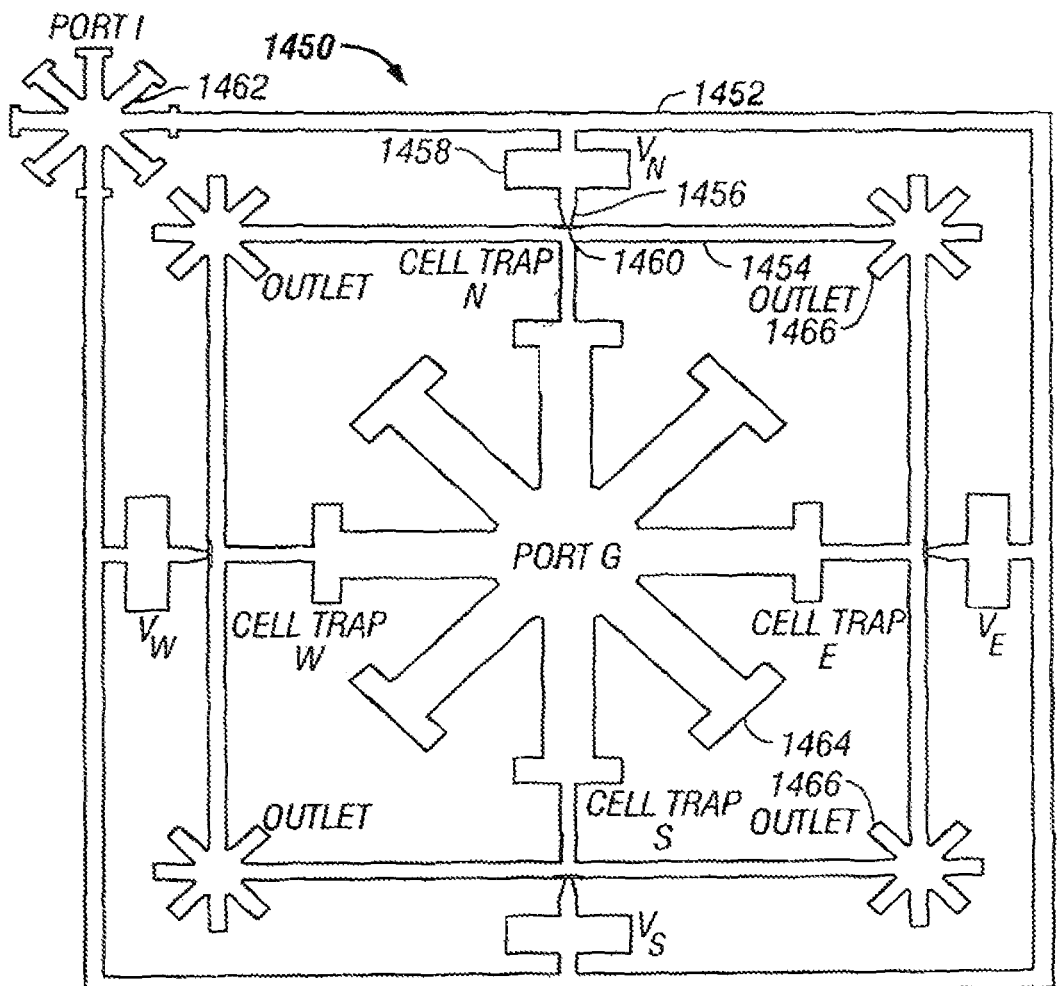
FIG. 60 is a fragmentary top plan view of a microfluidic device for performing patch-clamp analysis of multiple individual cells, in accordance with aspects of the invention.
Figure 61:
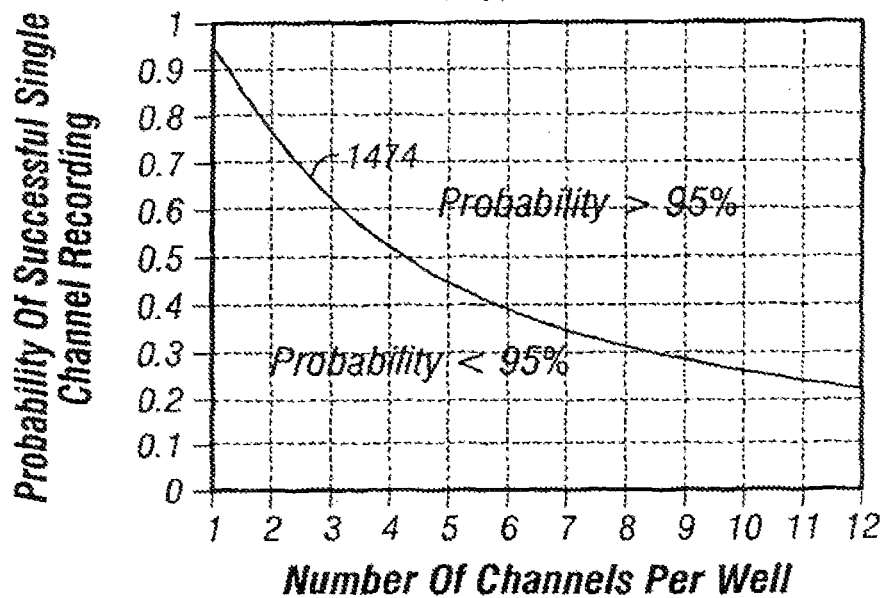
FIG. 61 is a graph showing 95% probability of successfully obtaining an electrophysiological reading as a function of both the number of apertures (channels) analyzed and the fraction of individual apertures that give a successful reading.

This example describes microfluidic systems for performing electrophysiological analysis on one or more cells out of a set of single cells; see FIGS. 59-61.

Background

Patch clamping is an electrophysiological method that relies on the formation of a seal between a biological membrane (for instance, a cell) and an aperture. This seal may facilitate the measurement of small currents created by the passage of ions across the membrane. However, the seal generally should be tight, since current leakage around the seal may interfere with, or prevent, measurement of the small currents across the membrane.

The efficiency of seal formation is an important issue for the development of automated, high-throughput devices for screening drugs based on electrophysiological effects on cells. In manual patch-clamp systems, the efficiency with which cells can be successfully analyzed varies, but very skilled technicians typically achieve properly sealed patches at an efficiency of only about 50%. A similar efficiency achieved by an automated device would require the device to "cherry-pick" wells containing properly sealed patches for use in drug screens, limiting the utility of such a device. Furthermore, even when properly sealed patches are formed, more than one cell may need to be analyzed to identify a typical or average cell response. Thus, there is a need for an automated device that more efficiently forms sealed patches on cells, facilitating averaged analysis of multiple cells and reducing problems associated with cell-to-cell variation in electrophysiological response.

Description

This example provides a multiplexed version of a single-aperture microfluidic device, with a defined number ("n") of individually controllable apertures. Each individually controllable aperture may be used to analyze a single cell by patch-clamp methods. Because only one patched cell is required to form an effective seal for each experiment, the use of multiple apertures increases the probability of forming this seal with the device. In addition, the device allows each aperture, and its associated cell, to be included in, or excluded from, an analysis. Thus, signals may be obtained from each individual cell that is successfully sealed by electrically isolating each corresponding aperture. Alternatively, or in addition, an "averaged" signal may be obtained from two or more of the individually controllable apertures, either by averaging separate measurements or measuring from two or more apertures concurrently. Averaged signals may improve the robustness of any data obtained.

Single-Aperture Embodiment

FIG. 59 shows a one-aperture device 1430 to illustrate how each of the n apertures is structured. Device 1430 directs a single cell 1432 into abutment with an aperture 1434. Aperture 1434 connects chambers 1436, 1438. These internal and external chambers, 1436 and 1438, respectively, carry buffers whose compositions resemble that of the internal (cytoplasm) and external (extracellular) environments, respectively, of cell 1432. A vacuum may be applied to internal chamber 1436 to pull cell 1432 toward aperture 1434, forming a seal between the cell and aperture. Sealing and rupture of the cell membrane (whole cell entry) make the inside of cell 1432 electrically continuous with internal chamber 1436. In other embodiments, the membrane may be left unruptured but perforated, for example, by addition of channel-forming agents to internal chamber 1436, or the membrane may be left unruptured and unperforated.

Electrical measurements then may be obtained. External chamber 1438 may be connected to ground, while internal chamber 1436 may carry a recording electrode, generally connected to an amplifier. Ions passing through the membrane of cell 1432 create a current that may be measured following amplification with the amplifier. Device 1430 may be used to measure changes in ion channel-associated and/or transporter-associated currents in the presence of potential drug candidates or other modulators.

Multi-Aperture Embodiment

FIG. 60 shows a microfluidic device 1450 that is a multiplexed version of device 1430, in accordance with aspects of the invention. Device 1450 may include a shared internal chamber 1452 that extends around the perimeter of device 1450. Internal chamber 1452 may connect to a shared external chamber 1454 using a plurality of apertures 1456, in this case, four. Each aperture may be isolatable, both electrically and fluidically, using control valves 1458 ($V_N$, $V_S$, $V_E$, and $V_W$). In addition, each aperture may be disposed immediately adjacent a cell retention mechanism, such as retention site or trap 1460. Traps 1460 may be arranged so as to facilitate parallel loading from a single suspension of cells (one reservoir) or from plural suspensions of cells (plural reservoirs). Internal chamber 1452 may be connected to a vacuum supply, and a recording electrode and ground may be connected to external and internal chambers, 1452 and 1454, respectively.

Device 1450 may be readied and used as follows. First, internal chamber 1452 may be loaded with internal buffer at internal-chamber port 1462 (Port I), so that internal buffer is loaded up to apertures 1456. Next, open valves $V_N$, $V_S$, $V_E$, and $V_W$ may be closed, and cells may be loaded as a suspension using an input mechanism at a common input port 1464 (Port C). Then, the cell suspension may flow from Port C to output reservoirs 1466 ("outlet"). Single cells may be positioned and retained at each trap 1460 (N, S, E, W) using any suitable positioning and retention mechanisms, such as those described elsewhere in this Detailed Description, for example, Examples 1-3. Once a desired number of cells are retained by retention mechanisms, device 1450 may be used for cell analysis. The vacuum supply may be turned on, and one or more valves at a time may be opened to form an electrical connection between the internal and external chambers, through the corresponding aperture 1456. The resistance of the connection may be used to determine if a sufficient seal has been produced at the aperture, with the membrane of the retained cell. If so, recording may be commenced.

Device 1450 may be modified in any suitable fashion, incorporating any suitable microfluidic mechanisms, such as those described in this Detailed Description. For example, device 1450 may be structured to load cells serially and/or in parallel, as described above in Examples 3-5. Furthermore, device 1450 may be included in an array of such devices to form a microfluidic array. Alternatively, or in addition, device 1450 may include a perfusion mechanism, such as that described in Examples 2 and 8, to allow precise delivery of selected reagents, to individual cells or to a plurality of cells, serially or in parallel. Similarly, device 1450 may measure electrical parameters of cells serially, that is, by using one aperture at a time, or in parallel, by using two or more apertures at a time, to obtain a summed reading of all connected apertures.

FIG. 61 shows data from a simple statistical analysis illustrating a few of the advantage of a multiplexed patch-clamp system, such as system 1450. The fractional probability of successfully obtaining a seal in a well containing n apertures, $P_n$, is related to the fractional probability of failed seal formation, $P_f$, at a single aperture by the equation $P_n = 1 - P_f^n$. The probability of successful seal formation for a single aperture, $P_s$, is related to $P_f$ by the equation $P_f + P_s = 1$. Therefore, if a seal is obtained successfully in 50% of attempts, then with 4 apertures, $P_4 = 1-(0.5)^4 = 1-0.0625 = 0.9375$. This corresponds to a 93.75% chance of obtaining at least one seal among the four apertures. FIG. 61 graphs the relationship between n (x-axis) and $P_s$ (y-axis), with curve 1474 indicating (n, $P_s$) pairs that give a 95% probability of at least one of the n apertures forming a successful seal. (Apertures are called "channels" in FIG. 61.) $P_n$ approaches unity, as $P_s$ and/or n are increased.

Example 13

Multilayer Mold-Fabrication Method of Varying Height and/or Cross-Sectional Geometries of Molded Microfluidic Structures This example describes a method for producing, by soft lithography, microfluidic devices in which the cross-sectional geometry and/or height of structures within and/or between microfluidic networks vary; see FIGS. 62-71.

Background

A microfluidic network may include structures having a variety of functions. For example, regulatable channels may include deflectable valves, acting to partially or completely close the channels and/or to propel fluid through the channels. These channels generally are formed with a semicircular or arcuate cross-sectional geometry to enable efficient valve closure. By contrast, particle-positioning channels may act primarily as conduits for particles carried by fluid. These particle-positioning channels generally have a height sufficient to allow particle movement. Accordingly, particle-positioning channels may benefit from a rectangular cross section to enable particles to move unrestrictedly from side-to-side (transversely) within the channels. Such unrestricted movement may allow particles to occupy a greater proportion of the width of the channels, rather than just the central portion, as with arcuate channels. Other channels may be size-selective or particle-restrictive, preventing entry of particles greater than a given size. These particle-restrictive channels may have a height that is less than the diameter of particles of interest. Furthermore, microfluidic networks may include cell/culture chambers with roof heights that are greater than more narrow channels, as described in Example 10, to improve the functionality of the chambers. Therefore, these and other structures described elsewhere in this Detailed Description may benefit from, or require, roof height to vary in order to function properly.

Single-layer molds often are formed using a desired thickness of photoresist on a substrate. The photoresist is patterned using a corresponding template that allows selective light exposure and photosensitization of patterned regions of the photoresist. Depending on whether the photoresist is positive or negative, the selectively exposed regions are either resistant or sensitive, respectively, to subsequent removal during development with a suitable developing agent. This development nonspecifically removes all sensitive regions, generally down to the substrate. The resistant regions are generally rectangular in cross-section, but may be heated to round their edges into an rounded/arcuate configuration. Accordingly, these remaining regions of the resulting mold may produce microfluidic channels of complementary structure using soft lithography. In other embodiments, multiple layers of photoresist may be built up by sequential coating, masking, and Despite the importance of varying height and/or cross-sectional shape across a microfluidic network, molds formed from a single layer of selectively removable material, such as photoresist, may not allow sufficient flexibility in the structure of a microfluidic network formed from the mold. For example, the depth to which the single layer may be removed cannot be varied readily, producing features of a single height, generally equal to the thickness of the single layer. Similarly, cross-sectional geometry may be difficult to vary within a single layer of the mold. Treatments that alter cross-sectional geometry, such as heating, also may act nonselectively across the single layer. Therefore, a method is needed for forming a mold using plural selectively removable layers.

Description of Method

The method described in this example may be used to form channels with different cross-sectional geometries and/or heights at distinct positions within a microfluidic network. A mold is fabricated using plural layers of photoresist that are each individually patterned, selectively removed according to the pattern, and optionally rounded by heating. Thus, each of the plural layers may contribute only a subset of the resulting mold, so that the mold's relief pattern is the sum of the remaining portions from each of the plural layers. Using the mold to form a microfluidic network allows various types of channels or other passages to be formed. Channels with a rounded/arcuate cross-sectional shape may be formed in sections of the network where valves are needed. These sections may be connected with other portions of the network that are formed to have a rectangular profile, to promote particle movement and to enable precise delivery of one or more particles to a specific area of a microfluidic network. The specific area can be as small as the dimension of a single particle, such as a cell. These structures and other suitable microfluidic structures may be produced using the method described below. This method focuses on formation of a fluid layer, but may be suitable for any portion(s) of a microfluidic system, including a control layer or a base layer (see Example 11).

A fluid-layer mold is fabricated in a first series of steps by micromachining techniques. The fluid-layer mold may be used subsequently in a second series of steps, as described below, to mold a complementary microfluidic layer by soft lithography. FIGS. 62-68 illustrate how fluid-layer mold 1480 may be formed by sequentially disposing, patterning, and selectively removing three layers of photoresist on or above a silicon wafer. Each layer is formed at a desired thickness by applying the photoresist, and then rotating the wafer according to a defined rotational profile to produce the structure of FIGS. 62, 64, and 67. Next, the photoresist is baked, patterned by exposure to UV light, and then developed to selectively remove portions of each layer, shown in FIGS. 63, 65, and 68. To mold closable channels, a photoresist layer may be baked at high temperature to round remaining portions, shown in FIG. 66. Each individual step is detailed further below.

Figure 62:
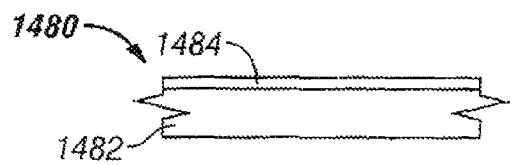
FIG. 62 is a fragmentary side elevation view of a microfluidic mold spin-coated with a first layer of patternable, selectively removable material, in accordance with aspects of the invention.

The first layer may be applied directly to a bare silicon wafer (the substrate). The first layer may have any suitable thickness, in this case 5 µm, and may be formed with any suitable material, such as a negative photoresist, SU8 2005 (Microchem, Newton, Mass.). After application of the negative photoresist, the wafer may be rotated according to a suitable rotational protocol to achieve a desired thickness and consistency. For example, the wafer may be rotated as follows: rotate to 500 rpm over 5 sec, maintain at 500 rpm for 5 sec, ramp to 3000 rpm over 8 sec, and then maintain at this speed for 30 sec. Then the rotation may be halted and the wafer heated according to a suitable heating protocol. For example, the wafer may be heated for 1 min at 65° C., 2 min at 95° C., and finally 30 sec at 65° C. This heating process may drive off the solvent in which the photoresist may be supplied. FIG. 62 shows mold 1480 with substrate 1482 carrying first layer 1484. The relative sizes of components here and in related FIGS. 63-69 are not drawn to scale.

Figure 63:
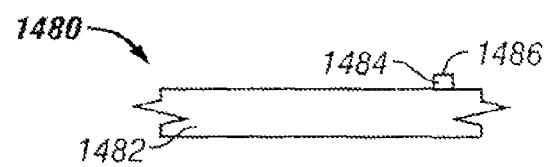
FIG. 63 is a fragmentary side elevation view of the mold of FIG. 62 after patterned removal of the first layer, in accordance with aspects of the invention.

The first layer may be patterned and selectively removed as follows. A desired template may be positioned in contact with the first layer and then exposed to UV light, 160 J/cm$^2$. Next, the substrate/first layer may be subjected to a suitable post-exposure heating protocol, such as: 1 min at 65° C., 2 min 30 sec at 95° C., and 30 sec at 65° C. Unpolymerized (unexposed) first layer may be washed away with any suitable developer, such as that supplied by Microchem, followed by washing with acetone and then isopropanol. Then, the first layer may be subjected to a suitable post-development heating protocol, such as 1 min at 65° C., 5 min at 95° C., and then 30 sec at 65° C. This heating protocol may be followed by a post-development exposure with UV light, 400 J/cm$^2$. FIG. 63 shows mold 1480 with first layer 1484 contributing first-layer relief-structure 1486 (residual first layer), which may have a height of 5 µm.

Figure 64:
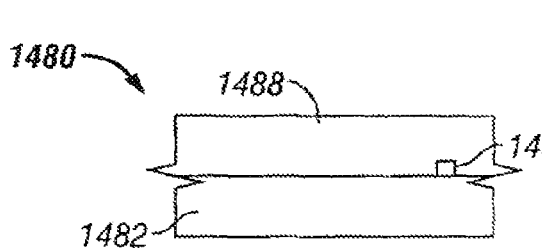
FIG. 64 is a fragmentary side elevation view of the mold of FIG. 63 spin-coated with a second layer of patternable, selectively removable material, in accordance with aspects of the invention.

The second layer may be added next and may have any suitable thickness, in this case a thickness of 20 µm formed by spin coating. First, mold 1480 may be treated with hexamethyldisilazane (HMDS) for 10 min. Next, a suitable patternable material, such as a positive photoresist, PLP 100 (AZ Electronic Materials/Clariant Corporation) may be applied. Application may be by spin coating, using any suitable protocol, such as the following: spin the wafer at 500 rpm, dispense the positive photoresist to the wafer/residual first layer over 14 sec, spin 15 sec, ramp to 2000 rpm over 5 sec, and maintain at this speed for 30 sec. Rotation then may be stopped, and the second layer may be baked for 2 min at 100° C. FIG. 64 shows mold 1480, at this intermediate stage, carrying second layer 1488, which covers first-layer relief-structure 1486.

Figure 65:
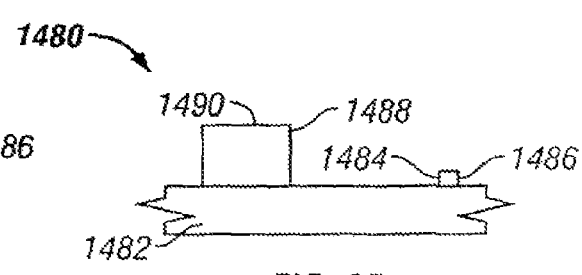
FIG. 65 is a fragmentary side elevation view of the mold of FIG. 64 after patterned removal of the second layer, in accordance with aspects of the invention.

The second layer may be patterned and selectively removed as follows. Any suitable template may be positioned in contact with the second layer and exposed to UV light, 450 J/cm$^2$. Next, the second layer may be developed (selectively removed) by any suitable protocol, such as 3 min. in AZ 400K ⅓ with deionized water. FIG. 65 shows mold 1480 after patterned removal of both first and second layers 1484, 1488. First-layer relief-structure 1486 and a second-layer relief-structure 1490 may have distinct heights based on the thickness of photoresist from which they are formed.

Figure 66:
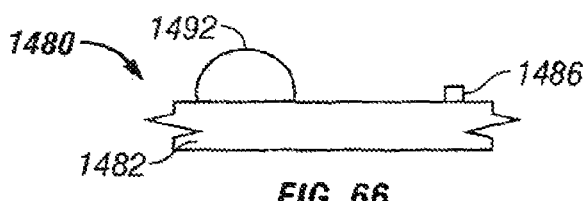
FIG. 66 is a fragmentary side elevation view of the mold of FIG. 65 after heating at elevated temperatures to round remaining portions of the second layer, in accordance with aspects of the invention.

Second-layer relief-structure 1490 may be rounded by any suitable heating protocol. For example structure 1490 may be rounded by the following heating protocol: ramp from 70° C. to 100° C. (1° C./min), maintain 60 min at 100° C., ramp to 200° C. (1° C./min), maintain 60 min at 200° C., and ramp down to 40° C. (1° C./min). FIG. 66 shows how this heating protocol may convert rectangular second-layer relief-structure 1490 (FIG. 65) to rounded second-layer relief-structure 1492.

Figure 67:
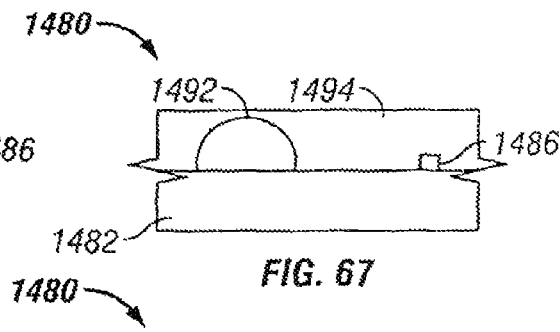
FIG. 67 is a fragmentary side elevation view of the mold of FIG. 66 spin-coated with a third layer of patternable, selectively removable material, in accordance with aspects of the invention.

A third layer may be added next and may have any suitable thickness, for example, a thickness of 20 µm. A suitable selectively removable material, such as negative photoresist SU8 2050 (Microchem), may be applied to the wafer carrying the residual first and second layers. Spin coating may be achieved by the following protocol: the wafer is ramped to 500 rpm over 5 sec, maintained at this speed for 5 sec, ramped to 5000 rpm over 17 sec, and maintained at this higher speed for 30 sec. The rotation is stopped. Next, the third layer may be heated by any suitable, such as: 2 min. at 65° C., 3 min. at 95° C., and 30 sec at 65° C. FIG. 67 shows third layer 1494, which covers first-layer and second-layer relief-structures 1486, 1492 at this stage.

Figure 68:
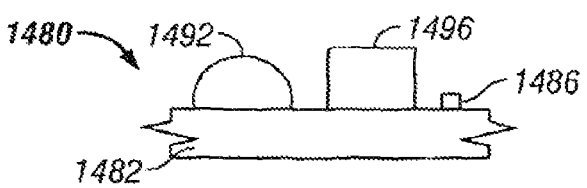
FIG. 68 is a fragmentary side elevation view of the mold of FIG. 67 following patterned removal of the third layer, in accordance with aspects of the invention.

The third layer may be patterned and selectively removed as follows. A desired template may be positioned in contact with the third layer and exposed to UV light, 310 J/cm$^2$. The exposed layer may be heated by any suitable protocol, such as 1 min. at 65° C., 4 min. at 95° C., and 30 sec at 65° C. Next, the third layer may be selectively removed with a suitable developer, such as that of Microchem, and then may be washed with acetone followed by isopropanol. Subsequently, the third layer may be subjected to a suitable post-development heating protocol, such as 1 min. at 65° C., 5 min. at 95° C., and 30 sec at 65° C. Finally, the third layer may be exposed to UV light in a post-development exposure of 500 J/cm$^2$. FIG. 68 shows mold 1480 having a third-layer relief-structure 1496.

Any suitable aspects of the method described above may be modified, and any patternable, selectively removable material may be used. In addition, any suitable number of layers may be used. Furthermore, each layer may have any desired thickness, according to the height of a desired relief structure. When optically patternable layers are used, each layer may be negative or positive photoresist, and may be used to form a rectangular or rounded cross-sectional profile. Relief structures formed by distinct layers may be nonoverlapping, partially overlapping, and/or completely overlapping in specific regions or all regions of the mold. Accordingly, relief structures may represent the sum of plural selectively removed layers.

An exemplary method for forming a control-layer mold is as follows. The mold may be fabricated from a single layer of positive photoresist. A 20-µm layer of suitable photoresist, such as positive photoresist PLP 100, may be applied, patterned, selectively removed, and rounded as described above for the second layer of the fluid-layer mold.

The fluid-layer and control-layer molds fabricated above may be used to mold a microfluidic chip using any suitable material, particularly an elastomeric material, such as polydimethylsiloxane (PDMS). Exemplary PDMS elastomers are General Electric Silicones RTV 615, produced from a two-component mixture of a prepolymer/catalyst and a crosslinker. In this two-component mixture, the prepolymer/catalyst (component A) is a polydimethylsiloxane bearing vinyl groups and a platinum catalyst, and the crosslinker (component B) bears silicon hydride (Si—H) groups. Using these specific components, components A and B may function optimally at a ratio of about 10:1 (A:B). However, "off-ratios" above and below this ratio may be used for the fluid-layer membrane and the control layer to promote subsequent bonding. For example, the control layer may be formed at a ratio of about 4:1, to provide rigidity and thus mechanical stability, and the fluid-layer membrane at a ratio of about 30:1. The excess of either component A or B in these two layers remain reactive near the membrane surface. Accordingly, these two layers may be abutted and bonded by post-curing with baking to fuse these layers into a monolithic structure (see below).

Figure 69:
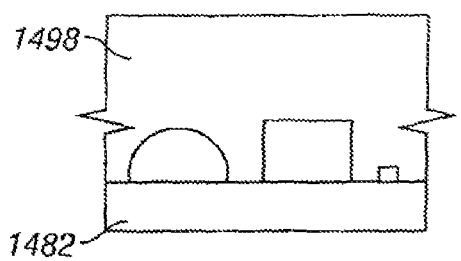
FIG. 69 is a fragmentary side elevation view of the mold of FIG. 68 acting to mold complementary surface features of a fluid-layer membrane, in accordance with aspects of the invention.

The fluid-layer and control-layer molds may be fabricated and joined as follows. After treatment with trichloromethylsilane (TCMS), a relatively thin PDMS membrane, for example, about 50-150 µm, may be spun on completed fluid-layer mold 1480. FIG. 69 shows a membrane 1498 being formed on fluid-layer mold 1480. In addition, a thicker PDMS layer, for example, approximately 5-10 mm, may be formed on the control-layer mold. After suitable first-step curing, such as 90 min at 80° C., the control layer may be detached from the mold, cut, and punched to interface properly with control lines of the control layer. Then, this control layer may be aligned with the fluid layer, while the fluid-layer membrane 1498 is still attached to the fluid-layer mold. Once assembled, the fluid and control layers may be cured a second time to chemically bond them, using a post-curing step of heating for about 3 hours at 80° C. After post-curing, the resulting chip may be detached from the fluid-layer mold, cut, and punched to create fluid reservoirs that interface at desired positions with channels. Finally, the chip may be bonded to a suitable substrate, such as a glass cover slip, to complete the fluid channels.

The post-curing step may be modified to enhance compatibility with cells. Lower ratios of PDMS components A and B, such as 4:1 (A:B), tend to be toxic to cells, particularly during cell culture. This toxicity may be due to a diffusible, toxic material(s) in the control layer. Thus, when a much thicker control layer, formed at a ratio of 4:1, is fused to a thin fluid-layer membrane, formed at a ratio of 30:1, the resulting monolithic structure may have the toxic characteristics of a 4:1 layer, even within the fluid-layer portion. However, suitable treatment of the control layer, either alone in contact with the fluid layer membrane, reduces or eliminates this toxic characteristic. Suitable treatments that remove or modify the toxic material may include exposure to heat, a chemical (such as a gas, a liquid, a plasma, etc.), radiation, light, and/or the like. (Such treatments also may reduce the movement of fluids within the channel, or components thereof, into the chip.) In some embodiments, longer post-curing at elevated temperature may remove or modify the toxic material(s), enhancing the effectiveness of the resulting chips for cell experiments. Such a longer post-curing step may be conducted for about 6 hours, 12 hours, or more preferably about 24 hours or more at about 80° C.

Images of Molds and Chips

Figure 70:
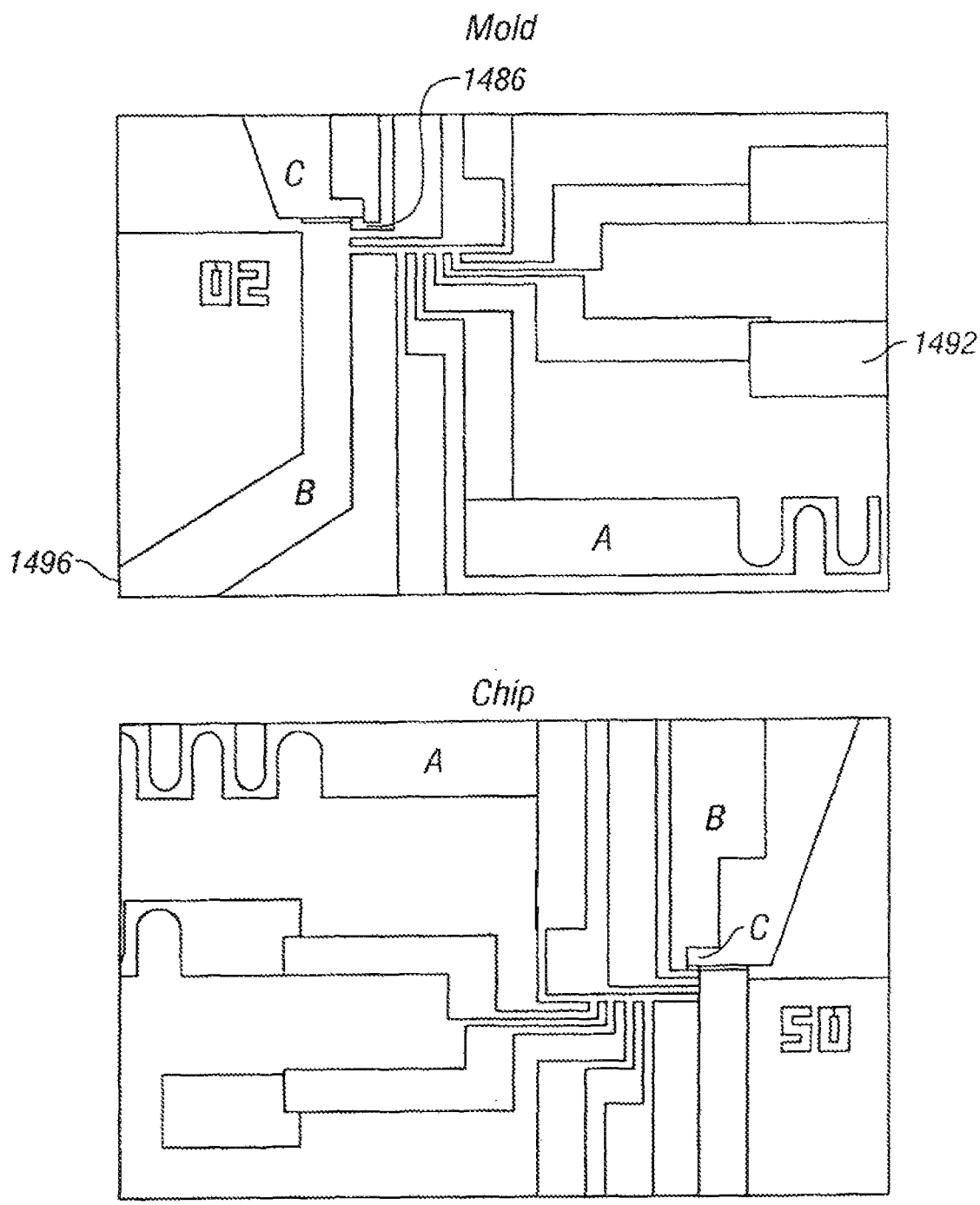
FIG. 70 is a composite of photographic images of 1) a fluid-layer mold formed using the method depicted in FIGS. 62-68 and 2) a corresponding molded chip formed from the fluid-layer mold, in accordance with aspects of the invention.
Figure 71:
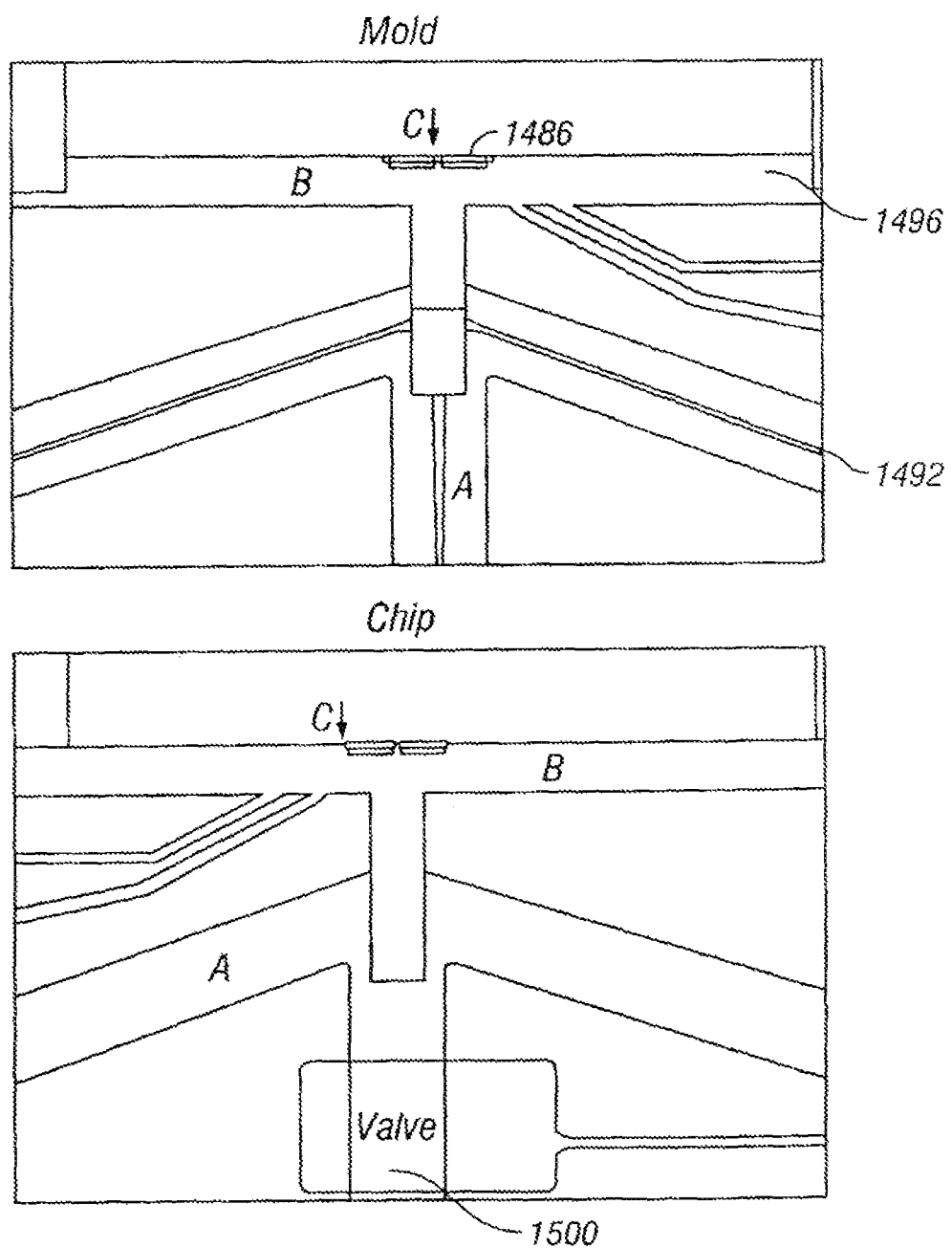
FIG. 71 is a composite of photographic images of 1) a fluid-layer mold formed using the method depicted in FIGS. 62-68 and 2) a corresponding molded chip formed partially from the fluid-layer mold, in accordance with aspects of the invention.

FIGS. 70 and 71 show photographic images of fluid-layer molds and the corresponding microfluidic chips formed with these molds. The microfluidic networks represented here, have been shown and described in system 1340 of Example 11 (FIG. 70) and in a modified form in system 850 of Example 7 (FIG. 71). Distinct regions of each mold and fluid layer are indicated by letters A, B, and C. Area A corresponds to rounded second-layer relief-structures 1492 described above. These areas are color-coded in blue on many of the figures presented above. Channels of area A are about 200 µm wide and approximately 20 µm high. Area A may be used to form valves and pumps by overlapping control lines from a control layer with this area, such as valve 1500 in FIG. 71. Area B corresponds to third-layer relief-structure 1496. These areas are color-coded in red on many of the figures presented above. Channels of area B have a rectangular profile, approximately 100 µm wide and 20 µm high. These channels enable precise particle control, because they allow particles to distribute across the width of the channel, following the walls and/or the center of a fluid stream(s). Such channels may be used to drive particles to precise areas of each chip. Area C corresponds to first-layer relief structure 1486. These areas are color-coded in turquoise on several of the figures presented above. These channels have a rectangular profile, 10 µm wide and 5 µm high. Small channels of this type are used in combination with channels of area A or B to trap cells or beads. Fluid may flow in these channels entry of cells or beads may be restricted.

Example 14

Detection System for Kinetic Analyses in Microfluidic Systems

This example describes a detection system, including a modulation-demodulation method and the use of tracer materials, for analysis of kinetic reactions involving particles in microfluidic systems; see FIGS. 71A-F.

Background

Microfluidic systems may be used to measure the kinetics of many aspects of cellular metabolism. However, metabolic processes of physiological significance can occur at substantially different rates, with characteristic times that may range from microseconds ($10^{-6}$ sec) or less to days ($10^5$ sec) or more. Therefore, detection methods are needed to measure cellular events that occur at these vastly differing rates.

Time-resolved fluorescence spectroscopy has been one of the most popular approaches to cellular kinetics studies. Typically, dye molecules are introduced into cells, and emission from the molecules is produced by excitation with an intense light source (such as an arc lamp or laser). The intensity of this emission is monitored over the course of the analysis to infer the kinetics of a process under study. However, the emission intensity of the dye molecules may be reduced or extinguished over time by photobleaching. As a result, some cellular processes that occur over relatively longer time periods may be more difficult to monitor in a microfluidic system due to this photobleaching.

Figure 71A:
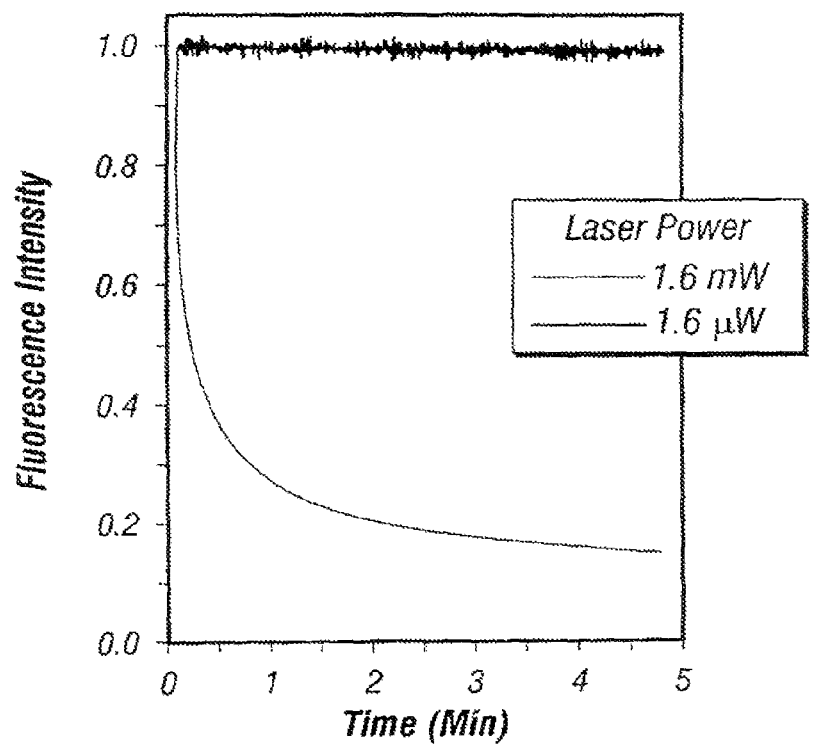
FIG. 71A is a graph of fluorescence emission versus time for a fluorophore being excited at different light intensities, in accordance with aspects of the invention.

Because the rate of photobleaching is related to the intensity of exciting light, a weaker light source may be used to reduce this rate. For example, FIG. 71A shows a comparison of photobleaching rates versus time using a relatively stronger laser (1.6 mW) and a relatively weaker laser (1.6 µW). However, the exciting light source produces a reduced emission signal and signal-to-noise ratio, since the emission signal is proportional to the illumination intensity. Therefore, microfluidic analyses would benefit from a detection system that reduces photobleaching, increases the ratio of signal-to-noise, and/or allows kinetic analysis of both fast and slow processes.

Description of Detection System

This example describes an exemplary detection system for use with microfluidic assays, in accordance with aspects of the invention. The detection system may include a modulation-demodulation mechanism; see FIGS. 71B-71E. This mechanism may improve signal-to-noise ratios, allowing use of weaker light sources, and/or reduce photobleaching, allowing use of stronger light sources. The detection system also may include a method using tracer dyes to measure initiation of rapid kinetic reactions with particles; see FIG. 71F.

Light Detection Device

Figure 71B:
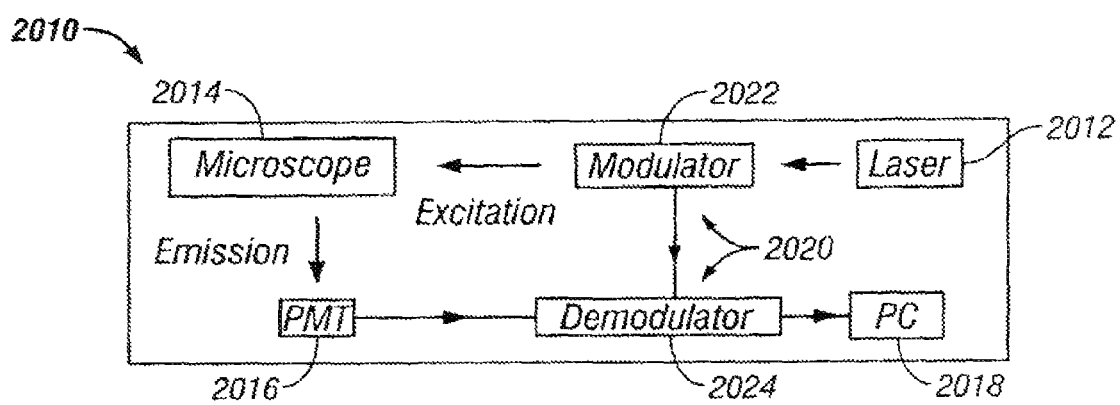
FIG. 71B is a schematic diagram of an embodiment of a method for increasing the signal-to-noise ratio of a detected signal by modulation of an exciting light source and demodulation of the detected signal, based on the modulation, in accordance with aspects of the invention.

FIG. 71B shows an exemplary system 2010 for detecting an optical signal from a sample. System 2010 may include a light source 2012, optics 2014, a detector 2016, a digital storage device 2018, and a modulation-demodulation mechanism 2020.

Light source 2012 may be used to illuminate one or more particles with light to visualize the particle and/or to perform an assay. The light source may generally may include any mechanism for producing light having the desired characteristics, including time-dependent and/or continuous light sources. Suitable examples may include a laser, a light-emitting diode (LED), or a lamp, among others.

Optics 2014 may be used to receive light from light source 2012 and direct the light at the particles and/or to receive light from the particles and direct it to detector 2016. Optics may mediate any suitable alteration of light to facilitate analysis, including refraction, reflection, diffraction, polarization, attenuation, spectral alteration, and/or scattering, among others. Suitable optics may include lenses, mirrors, fiber optics, filters, gratings, etalons, and/or the like. Exemplary optics may include a conventional microscope or other suitable optical device that is separate from, or partially or wholly integrated with, a microfluidic system.

Modulation-demodulation mechanism 2020 may include a modulator 2022 and/or a demodulator 2024. Modulator 2022 generally comprises any mechanism to provide time-dependent variation in the intensity of exposure of sample to source 2012. This variation may be intrinsic and/or extrinsic to the light source. Intrinsic modulation occurs when the light source itself changes in intensity, as with a pulsed or strobe laser (such as a diode laser). Such a pulsed laser may be pulsed very rapidly, up to millions of pulses per second, allowing for high-frequency illumination of particles. Extrinsic modulation occurs when the light source is continuous (or quasi-continuous), but a downstream mechanism alters the intensity of light before it is incident on the sample. Suitable extrinsic modulators include optical chopper wheels, Pockels cells, Kerr cells, acousto-optic modulators, and/or electroacoustic and other modulation devices. By contrast, demodulators generally comprise any mechanism for interpreting signals from detector 2016 based on the activity of the modulator. The control and interplay between the modulator and demodulator may be performed using any suitable mechanism, such as lock-in amplification using custom-designed and/or commercial devices.

Detector 2016 may be used to detect light, rapidly and/or repeatedly, and convert the detected light into representative electrical signals. Such a detector may include a photomultiplier tube, avalanche photodiode, and/or other photodetector that provides the ability to rapidly detect light signals produced by a source 2012 illuminating the particles. Collecting light emitted through optical filters into photomultiplier tubes or other photodetectors may enable conversion of photons to electrons for collection of quantitative information.

Digital storage device 2018 may digitize and/or store electrical signals received from detector 2016. These stored signals may be retrieved, corrected, and/or otherwise converted or manipulated, and printed or displayed, as desired.

Figure 71C:
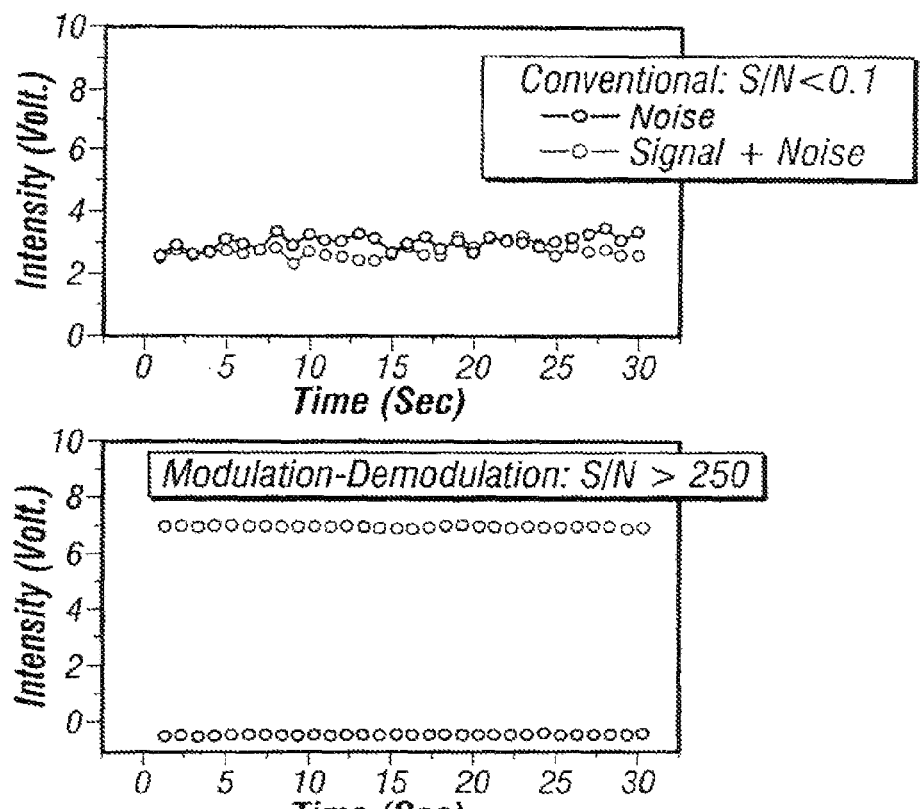
FIG. 71C is a pair of graphs of time-dependent measured noise and measured signal plus noise without (top) and with (bottom) implementation of the modulation-demodulation method of FIG. 71B in a microfluidic system, in accordance with aspects of the invention.

Exemplary Results Using a Modulation-Demodulation Mechanism for Microfluidic Analysis FIG. 71C shows a comparison of signal-to-noise ratios over time without (top) and with (bottom) source and signal modulation-demodulation. In this example, an embodiment of modulation-demodulation mechanism 2020 boosts the signal-to-noise ratio by a factor of over 2000-fold. Accordingly, weaker light sources may be used and an emitted fluorescence signal may be measured over a longer time course.

Figure 71D:
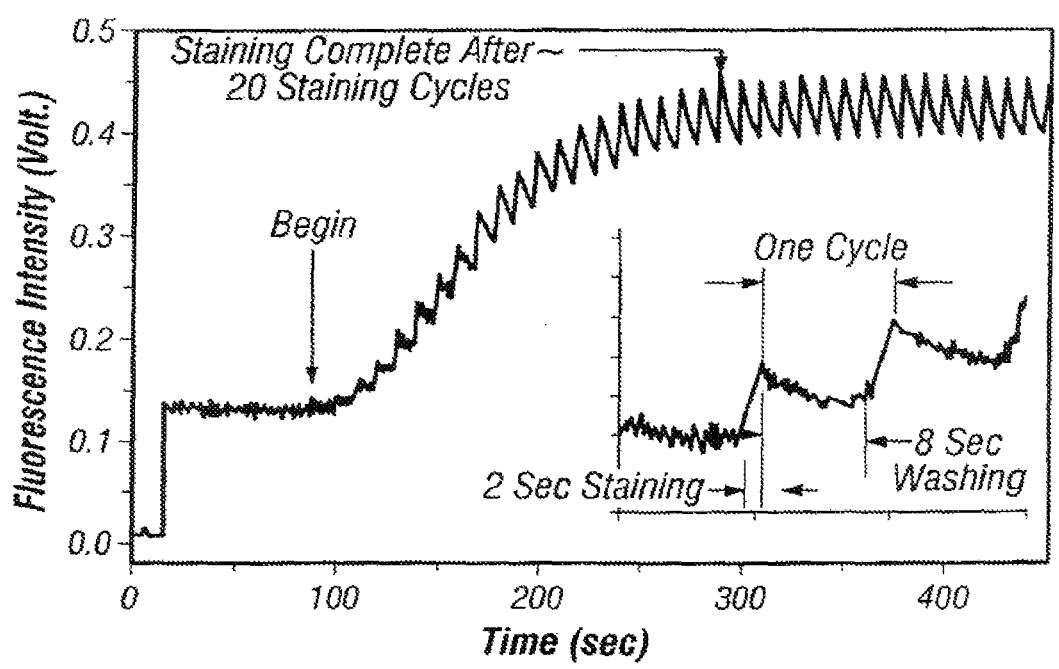
FIG. 71D is a graph of measured fluorescence intensity versus time prior to and during cycles of exposure of a biotinylated bead to a streptavidin-dye conjugate in a microfluidic system, in accordance with aspects of the invention.

FIG. 71D shows use of an embodiment of mechanism 2020 to determine the rate at which a reagent-particle interaction occurs in a single experiment. Here, a biotinylated bead has been loaded into a trap on a microfluidic chip, such as a chip designed according to system 250 of Example 2. Dye-labeled streptavidin (reagent) is exposed to the bead in a pulsatile fashion, using cycles of staining and washing controlled by automated operation of control valves. In this case, each ten-second cycle includes a two-second exposure to reagent, followed by an eight-second exposure to wash buffer. Each cycle produces a spike in fluorescence intensity. However, the average fluorescence intensity achieves a near-maximal level in about twenty cycles. Accordingly, maximal staining occurred in about forty seconds (twenty cycles times two seconds per cycle). Therefore, flow-based exposure and washing may be optimized to avoid time- and labor-intensive labeling and washing steps, and to minimize use of reagent. The pulsatile exposure illustrated here may be used with any suitable particle and dye combination to measure the rate at which interaction occurs.

Figure 71E:
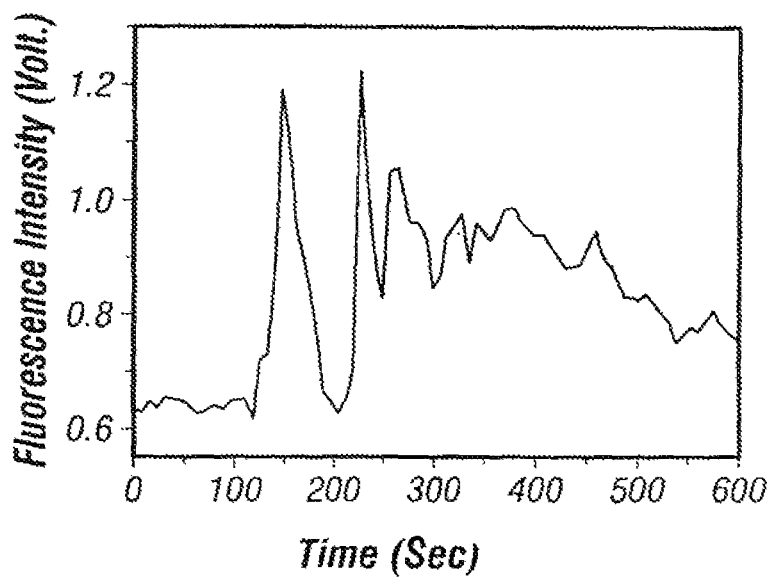
FIG. 71E is a graph of measured fluorescence intensity versus time prior to and during exposure of ionomcyin to a retained cell that was preloaded with a calcium-sensor dye, using the method of FIG. 71B in a microfluidic system, in accordance with aspects of the invention.

FIG. 71E shows the ability of an embodiment of the microfluidic detection system to measure a kinetic response of signal transduction in a cell. A calcium sensor dye, Fluo-3, was loaded into a cell, and the cell was trapped in a microfluidic chip, such as a chip designed according to system 250 of Example 2. The trapped cell was stimulated with ionomycin, at about time=120 sec, to promote release of intracellular calcium. The graph shows intensity of fluorescence, corresponding to intracellular calcium concentrations, versus time. Such an analysis measures the response of an individual cell, so compensatory oscillations in calcium levels are visible.

Method Using Tracer Dyes

Most rapid reactions or events are difficult or impossible to measure unless their starting points can be precisely defined. Accordingly, a tracer material, such as a tracer dye, may be included in a reagent of interest to indicate the time at which fluid containing the tracer dye and reagent contacts a particle(s). Thus, first detection of the tracer dye in contact with the particle defines a zero time point at which a reaction or event was initiated.

The tracer dye may have any optically detectable property and may be inert or reactive. Suitable optically detectable properties are described above in Section VIII. Inert dyes generally do not contribute directly to a detected assay result. Therefore, inert dyes generally do not affect cellular metabolism, and may not interfere optically or chemically with reagent dyes used to measure information about particles. Inert dyes may be nonbinding or binding. Nonbinding dyes do not bind to particles and may simply mark fluid volumes. Binding dyes may bind to particles, but do not contribute directly to a detected result from particles. By contrast, reactive dyes react with particles and contribute to a detected result. Suitable reactive dyes may be detectable when first combined with particles, but may show a change in an optical property during an assay. Inert or reactive dyes may be excluded from cells, may partition into particles, or may be transported into the interior of cells. Inert and reactive dyes that may be suitable are sold by Molecular Probes, Eugene, Oreg.

Rapid perfusion mechanisms, such as perfusion mechanism 268 of Example 2 above, coupled with a tracer dye and detection system described in this example, may allow very rapid analyses to be performed on particles. Such rapid analyses may measure events that occur in less than about 2 sec, 1 sec, or 500 msec. Furthermore, these rapid analyses may be performed on living cells to measure cell responses that are not detectable readily by other methods.

Figure 71F:
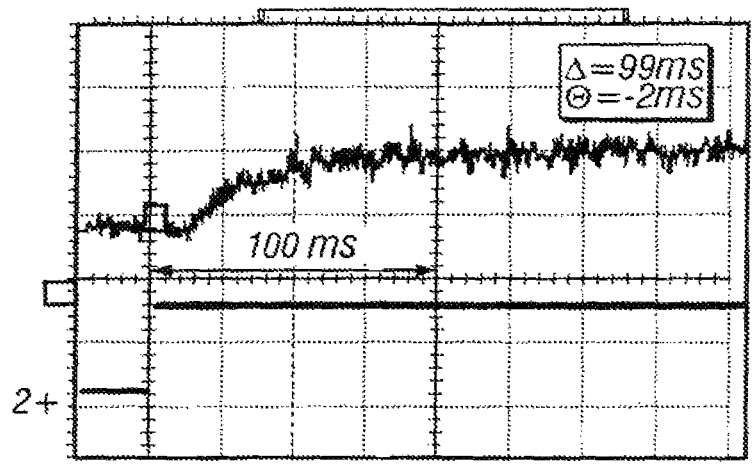
FIG. 71F is a graph of measured fluorescence intensity versus time at a position in a microfluidic system prior to and during exposure to a dye, in accordance with aspects of the invention.

FIG. 71F shows use of an embodiment of modulation-demodulation mechanism 2020 and a tracer dye in a microfluidic system to measure the rate at which reagent is exposed to particles. A perfusion mechanism, such as mechanism 268, was used to expose a retention site to a fluorescent dye. The resulting increase in fluorescence was measured over time. At time "T," an electrical signal was sent to a valve controller. After a short mechanical delay of about 5 msec, fluorescence measured at the retention site begins to increase, reaching a maximum value in less than 100 milliseconds. Accordingly, rapid kinetic analyses on a millisecond time scale may be performed using microfluidic systems described herein.

Example 15

Microfluidic Analysis of a Heterogeneous Particle Population—Part I

This example describes microfluidic systems for sorting and analyzing heterogeneous populations of particles, particularly cells, based on differences in particle size; see FIG. 72.

Background

Heterogeneous cell populations, such as blood, present a challenge for rapid analysis. Cells of interest in blood generally need to be separated from other cells that are of less interest to avoid interference from these other cells. Accordingly, blood may need to be treated/manipulated to selectively lyse, coagulate, pellet, bind, and/or modify, among others, specific cells within the blood. Such manipulations add to the time and expense required for analysis of blood, because they involve trained personnel, expensive equipment, lengthy incubations, repeated transfer of relatively large volumes of reagent or sample, and/or the like. In addition, such manipulations expose personnel to increased risk of exposure to infectious agents in the blood. As a result, many diagnostic procedures using whole blood are expensive and slow. Therefore, integrated systems are needed that automatically sort and analyze heterogeneous cell populations on a microfluidic scale.

Description

This example describes microfluidic systems that sorts blood cells and other heterogeneous particle populations according to diameters of individual particles. With these systems very small volumes of blood may be sufficient for statistically significant diagnoses or prognoses. Such systems may facilitate analysis of patient samples with improved speed, accuracy, safety, and/or cost, among others.

FIG. 72 shows a microfluidic system 1520 sorting cells. System 1520 is based on system 250 of Example 2 and includes positioning and retention mechanisms 264, 266 described in that example. A blood sample was introduced into system 1520 and directed toward retention chamber 270. Cells 1522 of this sample include red blood cells and platelets, but do not include detectable white blood cells, which would be retained by the retention mechanism due to their larger diameters. Cells 1522 enter chamber 270 but exit through size-selective side-wall channels 300. FIGS. 72A-D show time-lapse video images that include cells in chamber 270 and in channels 300. White blood cells such as lymphocytes, monocytes, and granulocytes (neutrophils, eosinophils, and basophils), when present, would be retained in chamber 270. These white blood cells are too large to pass through channels 300. Therefore, system 1520 may be used to separate red blood cells and platelets from white blood cells, for selective analysis of the white blood cells (or red blood cells) in the system.

System 1520 may be modified to select plural populations of particles of different size. For example, the system may be modified to include a serial set of retention mechanisms. Outflow through size-selective channels 300 for each retention mechanism 270 may be directed partially or completely toward an input site of a successive retention mechanism. Each successive mechanism may have a reduced diameter of channel 300, so that a reduced diameter of particle is retained in each successive mechanism. With this arrangement, larger particles are retained earlier in the series of mechanisms, whereas smaller particles are retained later in the series. Any suitable retention mechanism may be used at each position in the series.

Particles retained in the retention mechanism of system 1520 or related systems may be treated and analyzed. Particles may be treated by exposing them to desired reagents, for example, using perfusion mechanism 268 of Example 2, or by introducing reagents from any other reservoirs included in system 1520. Thus, particles retained in distinct retention mechanisms may be isolated and exposed to distinct reagents, as described in Example 4. Systems such as system 1520 may enable on-chip staining and washing, eliminating any need for multiple pipeting and/or centrifugation steps during manipulation and detection.

Suitable characteristics of retained particles may be detected by flow or scanning cytometry, among others. In flow cytometry, particles are detected while flowing past a detection mechanism, such as a light source coupled to a photodetector. Accordingly, particles may be released from each retention mechanism, for example, using a release mechanism, such as described above in Example 7, to flow past a detector. Alternatively, or in addition, characteristics of particles may be detected or otherwise detected while the particles are relatively stationary, such as when localized in chamber 270. Photons may be converted to electrons using photomultiplier tubes, avalanche photodiodes, CCDs, or similar technologies. Light emitted from dyes may be bright enough to detect using a single CCD, and scattered light may yield enough structural information from particles, when combined with functional information, to identify specifically the type and state of particles.

Additional aspects of sorting a heterogeneous particle population are described below in Example 26.

Example 16

Microfluidic Interaction of Specific Binding Pairs on Beads

Figure 73:
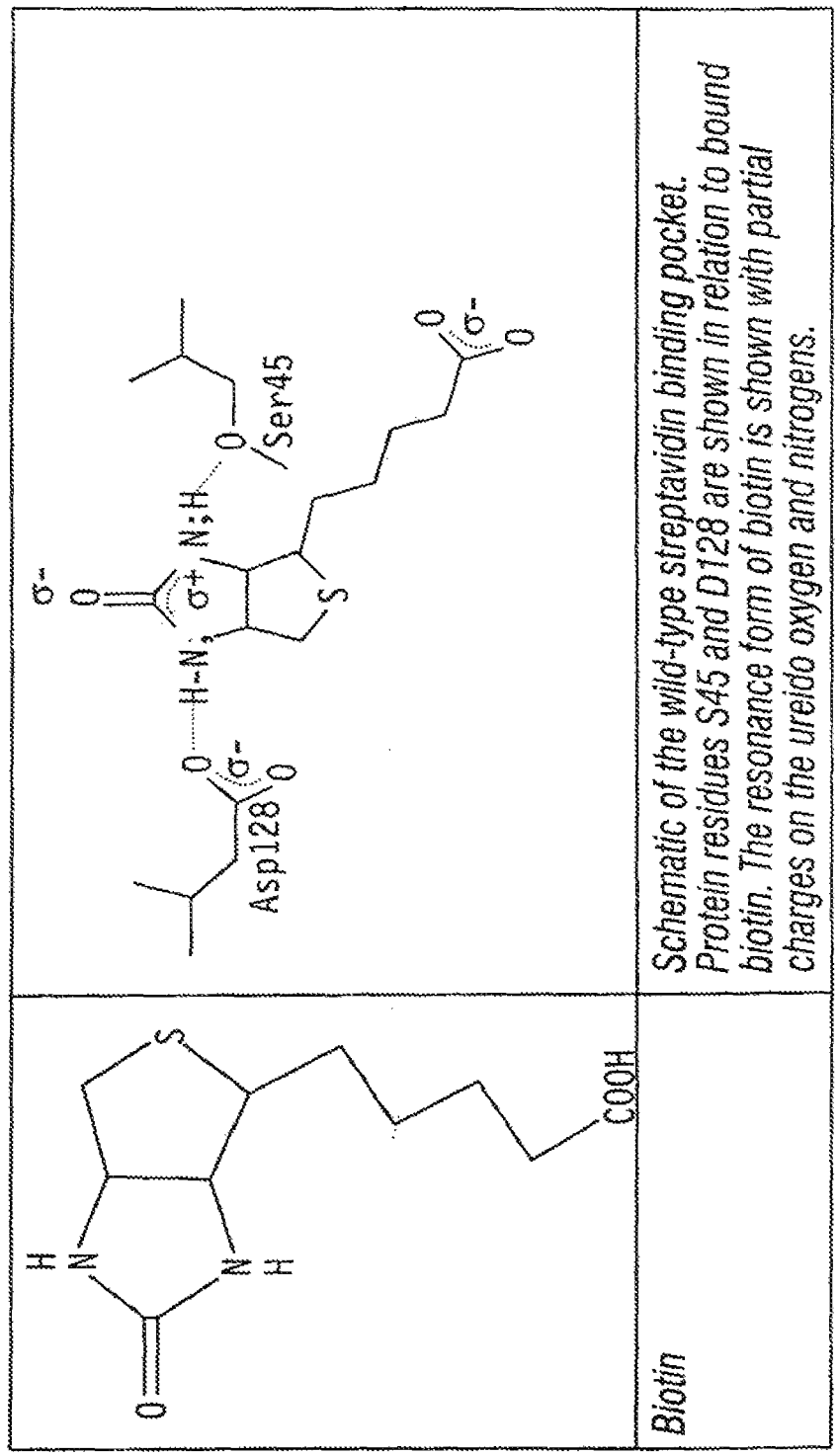
FIG. 73 is diagram showing the structure of biotin and its mode of binding to streptavidin.

This example describes detection of interaction between a specific binding pair, biotin and avidin, on beads in a microfluidic system; see FIGS. 73-74.

Background

Beads are used frequently by pharmaceutical and biotechnology companies as carriers for drug targets, drug candidates, chemical syntheses, immunoassays, chromatography, and/or so on. However, small numbers of beads are difficult to manipulate, particularly to detect reactions that occur rapidly. As a result, using currently available technology, assays with beads generally are conducted on a relatively large scale, wasting valuable reagents and/or may measuring a reaction endpoint that misses valuable earlier reaction information. Therefore, systems are needed to study interaction, including rapid interactions, using small numbers of beads.

A specific binding pair, biotin/streptavidin, was selected for interaction on beads; see FIG. 73. Biotin is a vitamin with a molecular weight of 244 daltons. Its partner, avidin, binds biotin with fierce tenacity, being the strongest non-covalent attachment known, with an association constant of $10^{15}$ $M^{-1}$. This binding reaction has been studied intensively for many decades, and there is a rich literature. The great strength of this binding suggests that it might be a good model system for the study of biological binding reactions in general. It has also formed the basis for many detection and signal amplification strategies for both research and clinical labs.

Avidin and streptavidin are vertebrate and bacterial biotin partners, respectively. Avidin is a protein with a molecular weight of about 68 kilodaltons, including four identical subunit chains, each 128 amino acids long. Avidin is found predominantly in the egg white of birds, amphibia, and reptiles. The protein streptavidin, produced by the bacterium *Streptomyces avidinii*, has a structure very similar to avidin, also binding biotin tightly. However, streptavidin often exhibits lower nonspecific binding, and thus is frequently used in place of avidin.

Method

Materials for measuring biotin/avidin interaction were as follows. A microfluidic chip was fabricated based on system 250 of Example 2. Beads, 6.7-micron biotinylated polystyrene microspheres, were obtained from Spherotech Corporation. Other buffers and reagents included phosphate-buffered saline (PBS) containing 0.5% BSA (sterile filtered), and the streptavidin conjugated fluorophores streptavidin-Alexa 350, streptavidin-Alexa 488, and streptavidin-PE (phycoerythryn), each obtained from Molecular Probes. Binding reactions were monitored with an inverted fluorescent microscope connected to a video camera.

The analysis was conducted according to the following numbered steps.

The fluid network of the chip was washed with water, then with PBS/BSA/Tween-20.

Beads were captured on the chip using its retention chamber.

Streptavidin-conjugates were loaded into reagent-wells on the chip (2 µL of each conjugate in 1 mL PBS).

The captured beads were exposed to each of the conjugates.

A 63× oil-immersion lens on the inverted microscope was used to maximize fluorescent signal. Blue and green/red filter sets were used.

In some cases the rate of photobleaching by the detection mechanism exceeded the rate at which fluorescent conjugates were captured by the beads. In these cases, the procedure was repeated without constant exposure to UV, opening the UV shutter only long enough to document binding.

Results

FIG. 74 shows the results of portions of the analysis as selected video frames during exposure of streptavidin-Alexa 488 conjugate to retained beads. In FIG. 74A, the beads have been loaded in chamber 270, but have not bound detectable amounts of the conjugate and are not detectable. In FIG. 74B, beads 1550 are detectable above background. In FIG. 74C, they have become readily detectable, after unbound conjugate is washed out of the chamber. FIG. 74D shows beads 1550 under bright field illumination to localize the beads and demonstrate that all beads in the chamber are stained with conjugate.

Similar exposures to the other conjugates gave less intense staining. Detectable staining with streptavidin-Alexa 350 was visible, but streptavidin-PE did not yield a detectable signal. However, more sensitive detection mechanisms, such as a laser scanning cytometer may allow detection of streptavidin-PE binding.

Example 17

Measuring Ion Flux in Cells Using a Microfluidic System

This example describes analysis of intracellular ion concentrations, such as calcium ion concentrations, using a microfluidic system; see FIG. 75.

Background

Calcium is a very important intracellular ion. It plays a vital role in the transduction of signals from the cell membrane to the cell cytoplasm and nucleus. A change in intracellular calcium levels is an indication that the cell is responding to a stimulus. Many stimuli cause mobilization of calcium, either as an influx from the extracellular medium or by release from intracellular pools. Fluorescent calcium indicators allow this mobilization to be observed.

Method

Materials used for measuring intracellular calcium levels were as follows. A microfluidic chip was constructed based on a modified version of system 850 of Example 7. Fluo 3/AM, a fluorescent $Ca^{+2}$ indicator dye was obtained from Calbiochem, and used as a 5 mM stock. Ionomycin, free acid form, was also obtained from Calbiochem. Cells were Jurkat T-cells and were grown in RPMI media.

The analysis was conducted according to the following numbered steps.

Cells were cultured in RPMI media.

Cells/media (5 mL) were pelleted at 1000 rpm for 5 min.

The cells were resuspended in RPMI containing 5 µM Fluo-3 (10 mL RPMI plus 8 µL FLUO-3 AM).

The cell/Fluo-3 mixture was incubated at 37° C. for 30 min to load the cells with indicator dye.

The cells were pelleted and washed twice with Hanks' balanced salt solution (HBBS) containing 20 mM HEPES (200 µL 1M Hepes in 10 mL HBBS).

The cells were placed in the input reservoir of the chip.

The microscope and video camera were set up.

HBBS/Hepes buffer was pumped across cells, acting as a shield buffer to regulate exposure to reagent.

HBBS/Hepes containing ionomycin was pumped past the cells, but in a layer spaced from the cells by the shield buffer.

The flow of shield buffer flow was terminated, exposing the cells to ionomycin.

Calcium flux was recorded with the video camera as ionomycin contacted the cells.

Results

FIG. 75 shows the results of the analysis, as selected video frames, before and after exposure of Jurkat cells, loaded with indicator dye, to ionomycin. FIG. 75A shows two cells 1570 captured in retention site 1572 and visualized under bright field illumination. In FIG. 75B, these cells lack fluorescence before ionomycin exposure. In contrast, FIG. 75C reveals fluorescence (green signal) of cells 1570 very soon after ionomycin exposure. A negative control demonstrated that ionomycin was required for this fluorescence (not shown).

Example 18

Microfluidic Analysis of Cell-Surface Markers

This example describes a method for detection of cell-surface markers, such as CD4 and CD8, on cultured T-cells using labeled antibodies.

Background

The CD4 molecule recognizes an antigen that interacts with class II molecules of the major histocompatibility complex (MHC) and is the primary receptor for the human immunodeficiency virus (HIV) (Dalgleish et al., 1984; Maddon et al., 1986). The cytoplasmic portion of the antigen is associated with the protein tyrosine kinase $p56^{lck}$ (Rudd et al., 1989). The CD4 antigen may regulate the function of the CD3 antigen/T-cell antigen receptor (TCR) complex (Kurrle et al., 1989). The CD4 antibody reacts with monocytes/macrophages that have an antigen density lower than that on helper/inducer T lymphocytes (Wood et al., 1983).

The CD8 antigen is present on the human suppressor/cytotoxic T-lymphocyte subset (Evans, et al., 1981; Ledbetter et al., 1981) as well as on a subset of natural killer (NK) lymphocytes (Lanier et al., 1983). The CD8 antigenic determinant interacts with class I MHC molecules, resulting in increased adhesion between the CD8$^+$ T lymphocytes and the target cells (Anderson et al., 1987; Eichmann et al., 1987; Gallagher et al., 1988). Binding of the CD8 antigen to class I MHC molecules enhances the activation of resting T lymphocytes. CD8 recognizes an antigen expressed on the 32-kDa a-subunit of a disulfide-linked bimolecular complex (Moebius, 1989). The cytoplasmic domain of the α-subunit of the CD8 antigen is associated with the protein tyrosine kinase $p56^{lck}$ (Rudd et al., 1989; Gallagher et al., 1989).

Determining the percentages of CD4+ and CD8+ lymphocytes may be useful in monitoring the immune status of patients with immune deficiency diseases, autoimmune diseases, or immune reactions. The relative percentage of the CD4+ subset is depressed and the relative percentage of the CD8$^+$ subset is elevated in many patients with congenital or acquired immune deficiencies such as severe combined immunodeficiency (SCID) and acquired immunodeficiency syndrome (AIDS) (Schmidt, 1989; Giorgi, 1990).

The percentage of suppressor/cytotoxic lymphocytes can be outside the normal reference range in some autoimmune diseases (Antel et al., 1986) and in certain immune reactions such as acute graft-versus-host disease (GVHD) and transplant rejection (Gratama et al., 1984; Bishop et al., 1986). The relative percentage of the CD8$^+$ lymphocyte population may often be decreased in active systemic lupus erythematosus (SLE) but can also be increased in SLE patients undergoing steroid therapy (Wolde-Mariam et al., 1984).

The CD4$^+$/CD8$^+$ (helper/suppressor) lymphocyte ratio, quantified as the ratio of CD4 fluorescein isothiocyanate (FITC)-positive lymphocytes to CD8 phycoerythrin (PE)-positive lymphocytes, has been used to evaluate the immune status of patients with, or suspected of developing, autoimmune disorders or immune deficiencies (Antel et al., 1986; Wolde-Mariam et al., 1984; Smolen et al., 1982). In many cases, the relative percentages of helper lymphocytes decline and suppressor lymphocytes increase in immune deficiency states. These states may also be marked by T-cell lymphopenia (Ohno et al., 1988). In addition, the ratio has been used to monitor bone marrow transplant patients for onset of acute GVHD (Gratama et al., 1984).

The Jurkat cell, a human mature leukemic cell line, phenotypically resembles resting human T lymphocytes and has been widely used to study T cell physiology. These cells are round, growing singly or in clumps in suspension. They were established from a human T cell leukemia in the peripheral blood of a 14-year-old boy with acute lymphoblastic leukemia (ALL) at first relapse in 1976. This cell line is also called "JM" (JURKAT and JM are derived from the same patient and are sister clones). Occasionally JM may be a subclone with somewhat divergent features confirmed as human with IEF of AST, LDH, and NP. Jurkat cells have the following general restriction properties: CD2+, CD3+, CD4+, CD5+, CD6+, CD7+, CD8−, CD13−, CD19−, CD34+, TCRalpha/beta+, and TCRgamma/delta−.

Method

Materials used for analysis of CD4 and CD8 were as follows. Microfluidic chips was constructed based on a modified version of system 850 of Example 7. Jurkat T-cells were cultured in RPMI. Fluorophore-conjugated antibodies, CD4-fluorescein isothiocyanate (FITC) and CD8-phycoerythryn (PE), were used. Buffer for dilution, focusing, washing, etc. was PBS containing 0.5% BSA. Data were collected with an inverted fluorescent microscope equipped with a video camera.

The analysis was conducted according to the following numbered steps.

Jurkat cells were grown in RPMI and then pelleted (10 mL of media/cells).

The cells were resuspended in 1 mL PBS containing 0.5% BSA.

Anti-CD4-FITC and anti-CD8-PE-antibody-conjugates were diluted 1:100 in PBS containing 0.5% BSA.

The chip was prepared by running deionized water through the microfluidic network and then was mounted on an inverted fluorescent microscope. The 100× or 63× oil-immersion lens was used to maximize fluorescent signal.

Cells were loaded onto the chip, positioned, and retained.

The diluted antibody-conjugates were loaded into separate reagent input-wells of the chip.

Exposure to light from the UV lamp was minimized to avoid photobleaching.

Anti-CD4-FITC was exposed to cells for 2 min.

The valve regulating CD4 antibody-conjugate flow was closed.

The shield-buffer flow line was opened to remove unbound antibodies.

The UV excitation shutter was opened and cell fluorescence was recorded.

When fluorescence was dim or invisible, the UV shutter was closed and steps 8 through 11 were repeated.

Step 12 was repeated until fluorescence was observed and documented.

As a negative control, steps 8 through 12 were repeated using anti-CD8-PE.

Results

Anti-CD8 antibody-conjugate did not bind to Jurkat cells, and therefore little or no red fluorescence was visible in the time frame needed to visualize the green fluorescence of the anti-CD4 antibody-conjugate. The procedure may be repeated with continuous UV exposure to observe antibody binding in real-time.

References

Maddon P, Dalgleish A, McDougal J, Clapham P, Weiss R, Axel R. The T4 gene encodes the AIDS virus receptor and is expressed in the immune system and the brain. *Cell.* 1986; 47:333-348.

Dalgleish A, Beverly P, Clapham P, Crawford D, Greaves M, Weiss R. The CD4 (T4) antigen is an essential component of the receptor for the AIDS virus. *Nature.* 1984; 312 (December):763-767.

Rudd C, Burgess K, Barber E, Schlossman S. Monoclonal antibodies to the CD4 and CD8 antigens precipitate variable amounts of CD4/CD8-associated p56-lck activity. In: Knapp W, Dörken B, Gilks W R, et al, eds. *Leucocyte Typing IV: White Cell Differentiation Antigens.* Oxford: Oxford University Press; 1989:326-327.

Kurrle R. Cluster report: CD3. In: Knapp W, Dörken B, Gilks W R, et al, eds. *Leucocyte Typing IV: White Cell Differentiation Antigens.* Oxford: Oxford University Press; 1989: 290-293.

Wood G, Warner N, Warnke R. Anti-Leu-3/T4 antibodies react with cells of monocyte/macrophage and Langerhans lineage. *J Immunol.* 1983; 131(1):212-216.

Evans R, Wall D, Platsoucas C, et al. Thymus-dependent membrane antigens in man: Inhibition of cell-mediated lympholysis by monoclonal antibodies to the $TH_2$ antigen. *Proc Natl Acad Sci USA.* 1981; 78(1):544-548.

Ledbetter J A, Evans R L, Lipinski M, Cunningham-Rundles C, Good R A, Herzenberg L A. Evolutionary conservation of surface molecules that distinguish T lymphocyte helper/inducer and T cytotoxic/suppressor subpopulations in mouse and man. *J Exp Med.* 1981; 153 (February):310-323.

Lanier L L, Le A M, Phillips J H, Warner N L, Babcock G F. Subpopulations of human natural killer cells defined by expression of the Leu-7 (HNK-1) and Leu-11 (NK-15) antigens. *J Immunol.* 1983; 131(4):1789-1796.

Anderson P, Blue M-L, Morimoto C, Schlossman S. Cross-linking of T3 (CD3) with T4 (CD4) enhances the proliferation of resting T lymphocytes. *J Immunol.* 1987; 139: 678-682.

Eichmann K, Johnson J, Falk I, Emmrich F. Effective activation of resting mouse T lymphocytes by cross-linking submitogenic concentrations of the T-cell antigen receptor with either Lyt-2 or L3T4. *Eur J Immunol.* 1987; 17:643-650.

Gallagher P, Fazekas de St. Groth B, Miller J. CD4 and CD8 molecules can physically associate with the same T-cell receptor. *Proc Natl Acad Sci USA.* 1989; 86:10044-10048.

Moebius U. Cluster report: CD8. In: Knapp W, Dörken B, Gilks W R, et al, eds. *Leucocyte Typing IV: White Cell Differentiation Antigens.* Oxford: Oxford University Press; 1989:342-343.

Bernard A, Boumsell L, Hill C. Joint report of the First International Workshop on Human Leucocyte Differentiation Antigens by the investigators of the participating laboratories: T2 protocol. In: Bernard A, Boumsell L, Dausett J, Milstein C, Schlossman S, eds. *Leucocyte Typing.* Berlin: Springer-Verlag; 1984:25-60.

Schmidt R. Monoclonal antibodies for diagnosis of immunodeficiencies. *Blut.* 1989; 59:200-206.

Centers for Disease Control. Guidelines for the performance of $CD4^+$ T-cell determinations in persons with human immunodeficiency virus infection. *MMWR.* 1992; 41 (No. RR-8):1-17.

Giorgi J, Hultin L. Lymphocyte subset alterations and immunophenotyping by flow cytometry in HIV disease. *Clin Immunol Newslett.* 1990; 10(4):55-61.

Antel J, Bania M, Noronha A, Neely S. Defective suppressor cell function mediated by $T8^+$ cell lines from patients with progressive multiple sclerosis. *J Immunol.* 1986; 137: 3436-3439.

Gratama J, Naipal A, Oljans P, et al. T lymphocyte repopulation and differentiation after bone marrow transplantation: Early shifts in the ratio between $T4^+$ and $T8^+$ T lymphocytes correlate with the occurrence of acute graft-versus-host disease. *Blood.* 1984; 63(6):1416-1423.

Bishop G, Hall B, Duggin G, Horvath J, Sheil A, Tiller D. Immunopathology of renal allograft rejection analyzed with monoclonal antibodies to mononuclear cell markers. *Kidney Internat.* 1986; 29:708-717.

Wolde-Mariam W, Peter J. Recent diagnostic advances in cellular immunology. *Diagnost Med.* 1984; 7:25-32.

Smolen J, Chused T, Leiserson W, Reeves J, Ailing D, Steinberg A. Heterogeneity of immunoregulatory T-cell subsets in systemic lupus erythematosus: Correlation with clinical features. *Am J Med.* 1982; 72:783-790.

Ohno T, Kanoh T, Suzuki T, et al. Comparative analysis of lymphocyte phenotypes between carriers of human immunodeficiency virus (HIV) and adult patients with primary immunodeficiency using two-color immunofluorescence flow cytometry. *J Exp Med.* 1988; 154:157.

Example 19

Measuring Cell Lysis in a Microfluidic System

This example describes capture, lysis, and staining of cells.

Background

Acridine orange (AO) was used for staining. AO binds to single stranded nucleic acids as a dimer, which fluoresces red in color, and to double stranded nucleic acids as a monomer, which fluoresces green. This difference in fluorescent wavelength is caused by differential accessibility of AO molecules to the nucleic acid binding sites. AO fluorescence is also pH sensitive, staining acidic organelles, such as lysosomes, orange.

Method

Materials used for measuring lysis were as follows. Microfluidic chips was constructed based on system 250 of Example 2. Jurkat T-cells were cultured in RPMI. Acridine Orange was dissolved at 5 µg/ml in PBS. Solutions or liquids to lyse cells included PBS containing 0.05% hydrogen peroxide, deionized water, PBS containing 2% TWEEN 20 (0.2 µm filtered), and WINDEX. Data were collected on an inverted fluorescent microscope equipped with a video camera.

The analysis was conducted according to the following numbered steps.

Jurkat cells were grown in RPMI and pelleted (10 mL of culture media/cells).

The cells were resuspended in 5 mL PBS containing 5 µg/ml Acridine Orange, or left unstained for use on a control chip. For the control chip, proceed to step 5.

The cells were incubated 10 min at room temperature.

The cells were pelleted and washed twice in PBS.

The cells were resuspended in 1 mL PBS.

The chip was preparing by washing the microfluidic network with deionized water, and then was mounted on an inverted fluorescent microscope. The microscope's 63× oil-immersion lens was used to maximize fluorescent signal.

The cells were loaded onto the chip, positioned, and retained.

PBS containing peroxide was loaded into a reagent-well of the chip.

Exposure of the chip to light from the UV lamp was minimized, to minimize photobleaching.

The UV shutter was opened to expose stained cells to fluorescent light.

PBS containing peroxide was pumped over the cells for 2 min or until lysis or photobleaching occurred.

Cells were then exposed sequentially to PBS/2% TWEEN-20, WINDEX, and finally water.

Results

The conditions of peroxide, TWEEN, and WINDEX did not lyse the cells on the first attempt of this experiment. Subsequently, water was used successfully to demonstrate cell lysis. Lysis probably occurred under the other conditions, but was not as obvious. Jurkat cells are fairly robust and may not be a good model cell line for this experiment.

Example 20

Inducing and Detecting Cell Apoptosis in a Microfluidic Environment

This example describes induction and detection of cell apoptosis in a microfluidic system; see FIG. 76.

Background

Apoptosis, also termed programmed cell death, is a carefully regulated process of cell death that Occurs as a normal part of development. Inappropriately regulated apoptosis is implicated in disease states, such as Alzheimer's disease and cancer. Apoptosis is distinguished from necrosis, or accidental cell death, by characteristic morphological and biochemical changes, including compaction and fragmentation of the nuclear chromatin, shrinkage of the cytoplasm, and loss of membrane asymmetry.[1-5]

Phosphatidylserine (PS) distribution also can act as a marker for apoptosis. In normal viable cells, phosphatidylserine is located on the cytoplasmic side of the cell membrane. However, in apoptotic cells, PS is translocated from the inner to the outer leaflet of the plasma membrane, thus exposing PS to the cell exterior.[6] In leukocyte apoptosis, PS on the outer surface of the cell marks the cell for recognition and phagocytosis by macrophages.[7,8] The human anticoagulant, annexin V, is a 35-36 kD $Ca^{+2}$-dependent phospholipid-binding protein that has a high affinity for PS.[9] Annexin V can identify apoptotic cells by binding to PS exposed on the outer leaflet.[10] Bound annexin V may be detected through a dye, a specific binding member conjugated to annexin V, an anti-annexin-V antibody, and/or the like.

Hydrogen peroxide has been shown to induce markers of apoptosis, such as PS translocation, in cultured cells. The cellular toxicity of hydrogen peroxide ($H_2O_2$) is initiated by oxidative stress, resulting in rapid modification of cytoplasmic constituents, depletion of intracellular glutathione (GSH) and ATP, a decrease in $NAD^+$ level, an increase in free cytosolic $Ca^{2+}$, and lipid peroxidation.[11] $H_2O_2$ also activates the mitochondria permeability transition pore and the release of cytochrome c.[12] In the cytoplasm, cytochrome c, in combination with Apaf-1, activates caspase-9, leading to the activation of caspase-3 and subsequent apoptosis[13-15].

Method

This example demonstrates induction and detection of cell apoptosis in a microfluidic system. Jurkat cells are positioned and retained in a microfluidic system, and then programmed cell death is initiated by exposure of these cells to hydrogen peroxide. Translocation of PS to the outer membrane leaflet is monitored with annexin V, to measure apoptosis. At the same time, cells are exposed to propidium iodide, which stains cells with disrupted membranes, an indicator of necrosis rather than apoptosis.

Materials used were as follows. Microfluidic chips were constructed based on system 250 of Example 2. Jurkat T-cells were cultured in RPMI. The VYBRANT Apoptosis Assay Kit #2 was obtained from Molecular Probes, Eugene, Oreg. This kit includes fluorophore-conjugated annexin V (green) and propidium iodide (red). Data were collected on an inverted fluorescent microscope equipped with a video camera.

The analysis was conducted according to the following numbered steps.

The video camera was turned on.

Cells were trapped in the retention chamber of the chip.

Annexin-V-conjugate was loaded into reagent well #1 of the chip.

Propidium iodide was loaded into reagent well #2 of the chip.

Binding Buffer (BB) was loaded into the shield buffer well of the chip.

The cells were perfused with BB for 5 min.

The cells were perfused with annexin-V-conjugate for 5 min.

Cells were checked for staining. (Note: This is a negative control. No staining occurred at this stage because the cells had not apoptosed.)

The valves regulating flow of the shield buffer and reagent wells were each closed.

The BB was replaced with 800 μM $H_2O_2$ in PBS.

The cells were exposed to the $H_2O_2$/PBS by opening the valve regulating flow from of the shield buffer.

Cells were observed under light microscopy during induction of apoptosis.

After 15 min, the valve regulating flow of the shield buffer was closed. The well was washed with BB, and then replaced with BB.

The cells were then perfused with BB for 5 min.

The valve for the annexin-V-conjugate was opened, and the shielding buffer valve was closed.

The cells were exposed to the annexin-V-conjugate for 5 min.

The valve controlling the annexin-V-conjugate was closed, and the BB valve was opened to wash the cells.

The cells were exposed to excitation light by opening the microscope shutter. Green fluorescence indicated a positive reaction for phosphatidylserine.

The valve that regulates flow of propidium iodide ("the PI valve") was opened, while the valve that regulates BB ("the BB valve") was closed.

After 2 min, the BB valve was reopened, and the PI valve was closed.

After washing for 5 min, the fluorescent shutter was opened while using the red filter set on the microscope.

Finally, the BB was replaced with water, and the cells were lysed and then re-exposed to the PI.

Results

FIG. 76 shows selected video frames from this analysis. In panel A, cells 1590 have been trapped in chamber 270 and are visible under bright field illumination. Panels B and C compare labeling of cells with the annexin-V-conjugate before (B) and after (C) exposure to hydrogen peroxide. Cells 1590 do not label with the annexin-conjugate before exposure to hydrogen peroxide (panel B), but a weak annexin-conjugate signal is detectable after hydrogen peroxide exposure (panel C), demonstrating that at least some of the cells have initiated apoptosis. Panels D-F compare propidium iodide staining of cells 1590 at different times during the analysis. Panels D and E show no propidium iodide staining, either before or after induction of apoptosis by exposure to hydrogen peroxide. In contrast, panel F reveals detectable propidium-iodide staining after exposure of cells to water, which renders the cells necrotic.

References

Immunol. Cell Biol. 76, 1 (1998).

Cytometry 27, 1 (1997).

J. Pharmacol Toxicol. Methods 37, 215 (1997).

FASEB J. 9, 1277 (1995).

Am J. Pathol. 146, 3 (1995).

Cytometry 31, 1 (1998).

J. Immunol. 148, 2207 (1992).

J. Immunol. 151, 4274 (1993).

J. Biol. Chem. 265, 4923 (1990).

Blood 84, 1415 (1994).

Am. J. Physiol. 273, G7 (1997).

Free Radic. Biol. Med. 24, 624 (1998).

FEBS Lett. 447, 274 (1999).

Cell 91, 479 (1997).

Annu. Rev. Cell Dev. Biol. 15, 269 (1999).

Example 21

Analysis of Aquatic Microorganisms in a Microfluidic System

This example describes the capture and visualization of aquatic microorganisms, such as plankton, using a microfluidic system.

Background

Plankton are a very diverse group of marine and fresh water organisms that spend some or all of their lives drifting in water. Plankton represent both the animal and plant kingdoms and include a range of sizes from submicron to over a centimeter. These seemingly listless organisms play critical roles, both positive and negative, in the health of not only other aquatic organisms but also in the composition of the earth's atmosphere. For example, these organisms are thought to produce a large fraction of the earth's oxygen. In addition, they play a critical role in global carbon dioxide exchange, removing much of the excess carbon dioxide produced by burning fossil fuels and sending this carbon dioxide to the ocean floor. In contrast, some plankton are infamous for their negative impact on the economy. For example, explosive population growth of dinoflagellate plankton produce a toxic "red tide" that poisons fish and shellfish. However, occurrences of red tides are difficult to predict and/or prevent, resulting in extensive fish-kills and beach closures, which have a large economic impact. Therefore, systems are needed to manipulate, treat, and analyze plankton, including laboratory or natural populations that benefit or harm the environment.

Method and Results

This example provides a microfluidic system capable of manipulating and detecting small plankton, particularly picoplankton (0-2 μm), ultraplankton (2-5 μm), and/or nannoplankton (5-60 μm). Plankton may be retained, treated, and/or detected in an integrated microfluidic environment.

Plankton were manipulated and detected in a microfluidic system as follows. A sample of seawater was collected from San Francisco Bay and centrifuged to concentrate organisms in the sample. A 20 μL aliquot of the concentrated sample was loaded into the input reservoir of microfluidic system 250, described in Example 2 above. Naturally-fluorescent plankton were retained in chamber 270 and detected successfully by fluorescent microscopy (not shown).

This method of this example may be modified by changing any suitable parameters. For example, plankton may be collected from freshwater sources or cultured, an aqueous plankton sample may be loaded directly into a microfluidic environment without concentration, and/or retained plankton may be exposed to any suitable reagents. Alternatively, or in addition, microfluidic systems may be used that sort a heterogeneous population of plankton according to a physical property (such as size or density, among others) or a measured property/characteristic (such as labeling with a dye and/or specific binding member).

Example 22

Analysis of Membrane Trafficking in a Microfluidic System Using Membrane Dyes

This example describes microfluidic analysis of membrane trafficking pathways in cells treated with membrane-labeling dyes.

Background

Studies of vesicle trafficking often rely on optically detectable dyes that label membranes. Brief exposure of cells to such a dye results in labeling of the surface-membrane of these cells. Subsequent dye movement to interior membranes, such as endosomes, Golgi apparatuses, lysosomes, and/or endoplasmic reticulum, tracks corresponding transit of surface membranes, receptors, and/or ligands, among others, through intracellular vesicle trafficking pathways. Using this approach, cell endocytic, recycling, degradative, and/or secretory pathways may be monitored and analyzed.

Some "FM" dyes available from Molecular Probes bind to cell membranes. Thus these FM membrane dyes may be used as general-purpose probes for endocytosis, because they are generally nontoxic. FM membrane dyes are virtually nonfluorescent in aqueous solution, but become intensely fluorescent upon association with a membrane.

Goals and Method

The goals of this analysis included the following. I) Define the staining conditions for two FM membrane dyes, FM 1-43 and FM 4-64, using Jurkat cells. FIGS. 77 and 78 show the structure and excitation/emission spectra of these dyes. These two FM dyes have substantially nonoverlapping emission spectra. II) Test the affinity of FM dyes for microfluidic chips formed with PDMS, to define a background level of staining. III) Trap a Jurkat cell in a microfluidic chip and perform two-color staining of the cell using the two FM membrane dyes.

Materials used for this analysis included the following. FM 1-43 and FM 4-64 were obtained from Molecular Probes. Microfluidic chips were produced based on system 250 of Example 2. Results were collected and recording using an inverted fluorescent microscope equipped with a video camera.

Conditions for labeling Jurkat cells with FM membrane dyes were determined with the following labeling protocol.

Cultured Jurkat cells (5 mL of cells/media) were pelleted by centrifugation at 1000 rpm for 5 min.

The cell pellet was washed twice with PBS.

The cell pellet was resuspended in 2 mL PBS.

Aliquots (500 µL) of the resulting cell suspension were dispensed into four microcentrifuge tubes.

Dye was added to each of the four tubes as follows: no dye was added to tube #1, FM 1-43 was added to tube #2, FM 4-64 was added to tube #3, and both FM 1-43 and FM 4-64 were added to tube #4. The final dye concentration for each dye was 2 µM.

The cells were observed with the fluorescent microscope.

Each staining condition was documented by saving digital image files.

Labeling of the microfluidic chip with the FM membrane dyes to determine background signal was carried out as follows.

Each dye was diluted to a final concentration of 2 µM in PBS. FM 1-43 (5 µL) was introduced into a first chip. FM 4-64 (5 µL) was introduced into a second available chip.

A mixture of the FM 1-43 and 4-64 dyes (1:1) was introduced into a third chip.

Each dye-loaded chip was observed using a fluorescent microscope.

The level of background staining was determined relative to fluorescence intensity of the cells stained with FM dyes in part A above.

Cells were labeled with FM dyes in a microfluidic system as follows.

Unlabeled Jurkat cells were loaded and captured in a microfluidic chip using PBS as a carrier buffer.

Each FM membrane dye (5 µL) was placed in one of the two reagent wells on the chip.

Chip features and cells were visualized using minimal incandescent light.

The video camera was turned on, and the 100× oil-immersion objective on the fluorescent scope was used.

The first FM membrane dye (1-43) was delivered to the cells.

The fluorescent signal was observed.

The second FM membrane dye (4-64) was delivered to the cells.

The fluorescent signal was observed.

Steps 5-8 were repeated as necessary until the signal intensity was maximized.

Results

The results of the three protocols are as follows.

Figure 79:
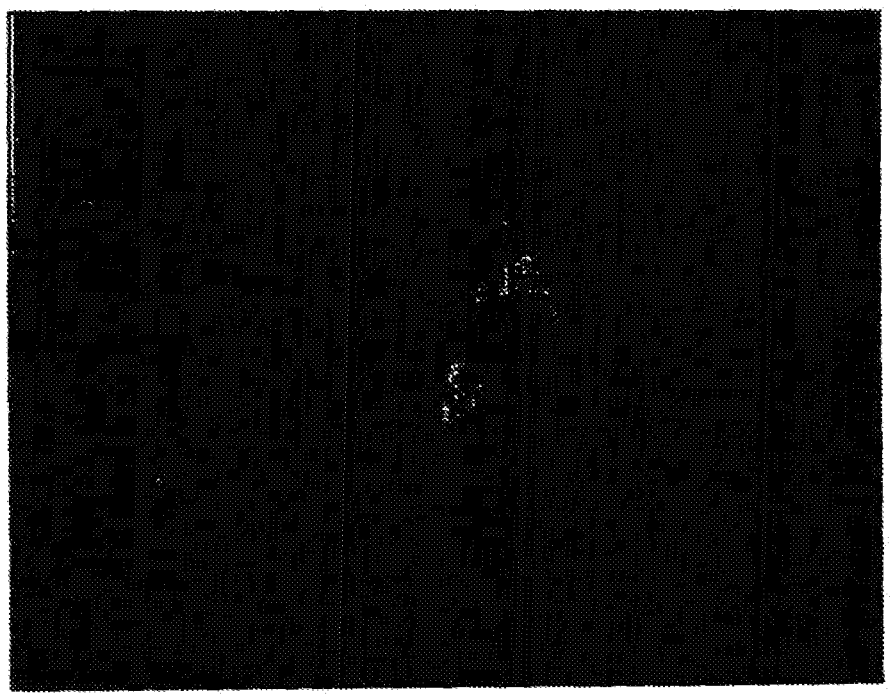
FIG. 79 is a photographic image recording successful staining of a cell's membrane in a non-microfluidic environment.

Protocol A produced significant labeling of Jurkat cells with the dyes after a 5-minute incubation at room temperature. Each dye stained the cells with sufficient intensity to visualize using the fluorescent microscope. For example, FIG. 79 shows Jurkat cells stained with FM 1-43. However, the emission profile of each dye was not distinguishable as a discrete color using the green/red filter set on a Leica microscope. Properly selected filter sets may allow a two-color assay using these dyes.

Protocol B produced significant background labeling of microfluidic chips formed with PDMS, using either dye. The PDMS may be surface-modified to minimize binding of these dyes to the chip.

Protocol C was foiled by the high background produced by dye binding to PDMS. After trapping a single cell in the chip, FM 1-43 bound to the chip more efficiently than to the membrane of the trapped cell.

Example 23

Capturing Cells in Single-Cell or Multi-Cell Microfluidic Chambers

Figure 80:
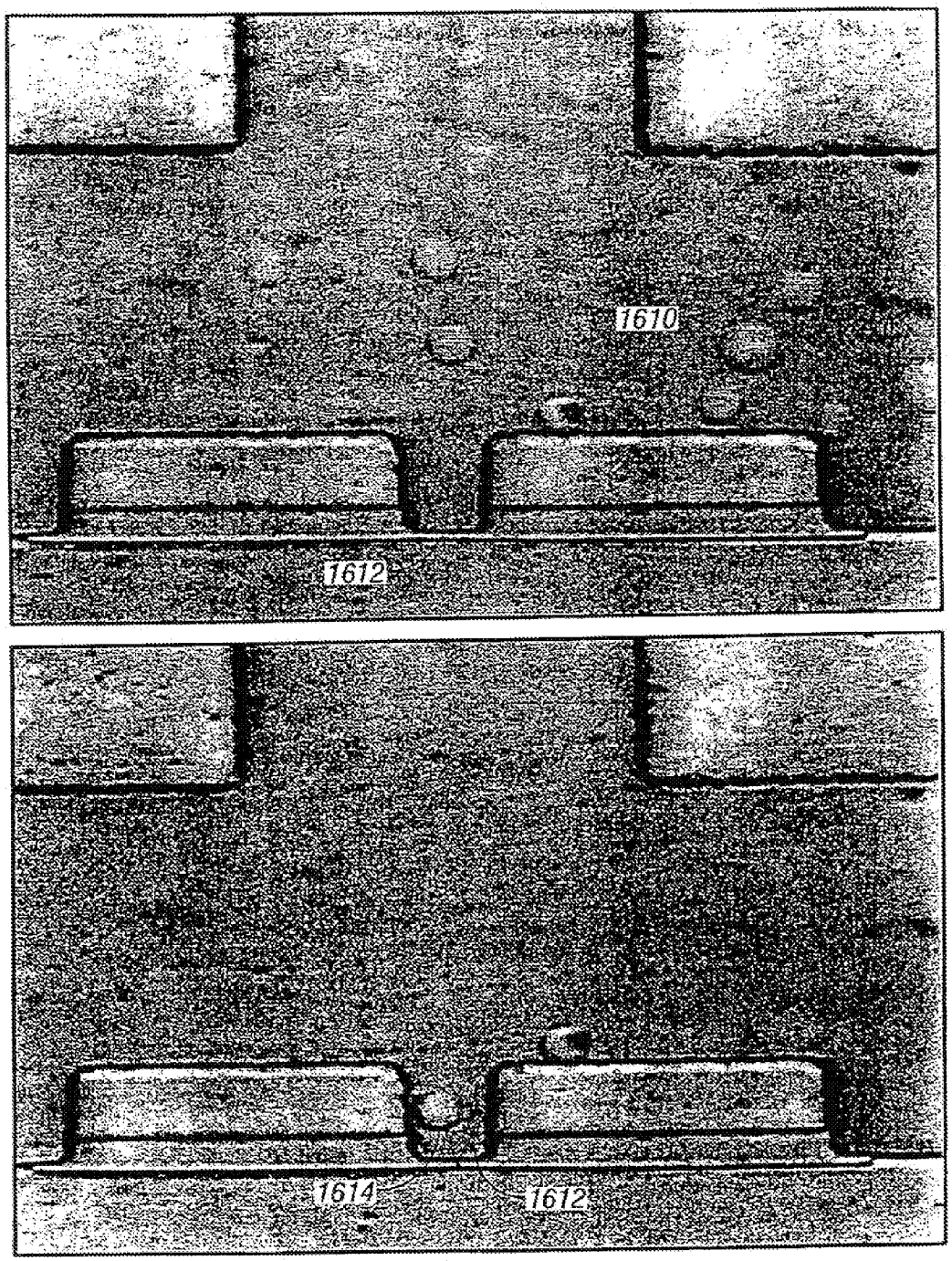
FIG. 80 is a time-lapse set of photographic images recording retention of a single cell at a preselected site in a microfluidic system, in accordance with aspects of the invention.
Figure 81:
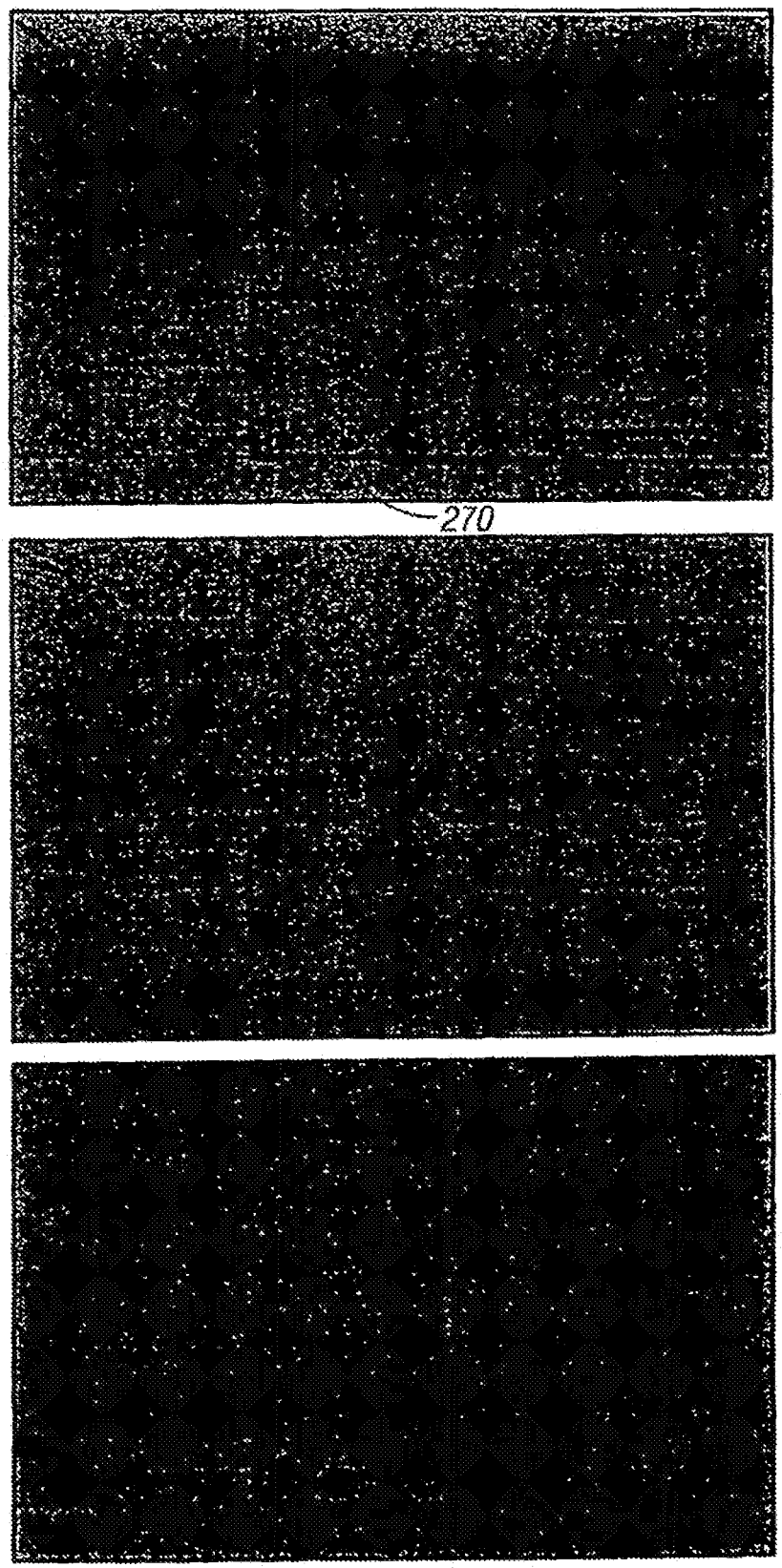
FIG. 81 is a time-lapse set of photographic images recording retention of a group of cells at a preselected site in a microfluidic system, in accordance with aspects of the invention.
Figure 82:
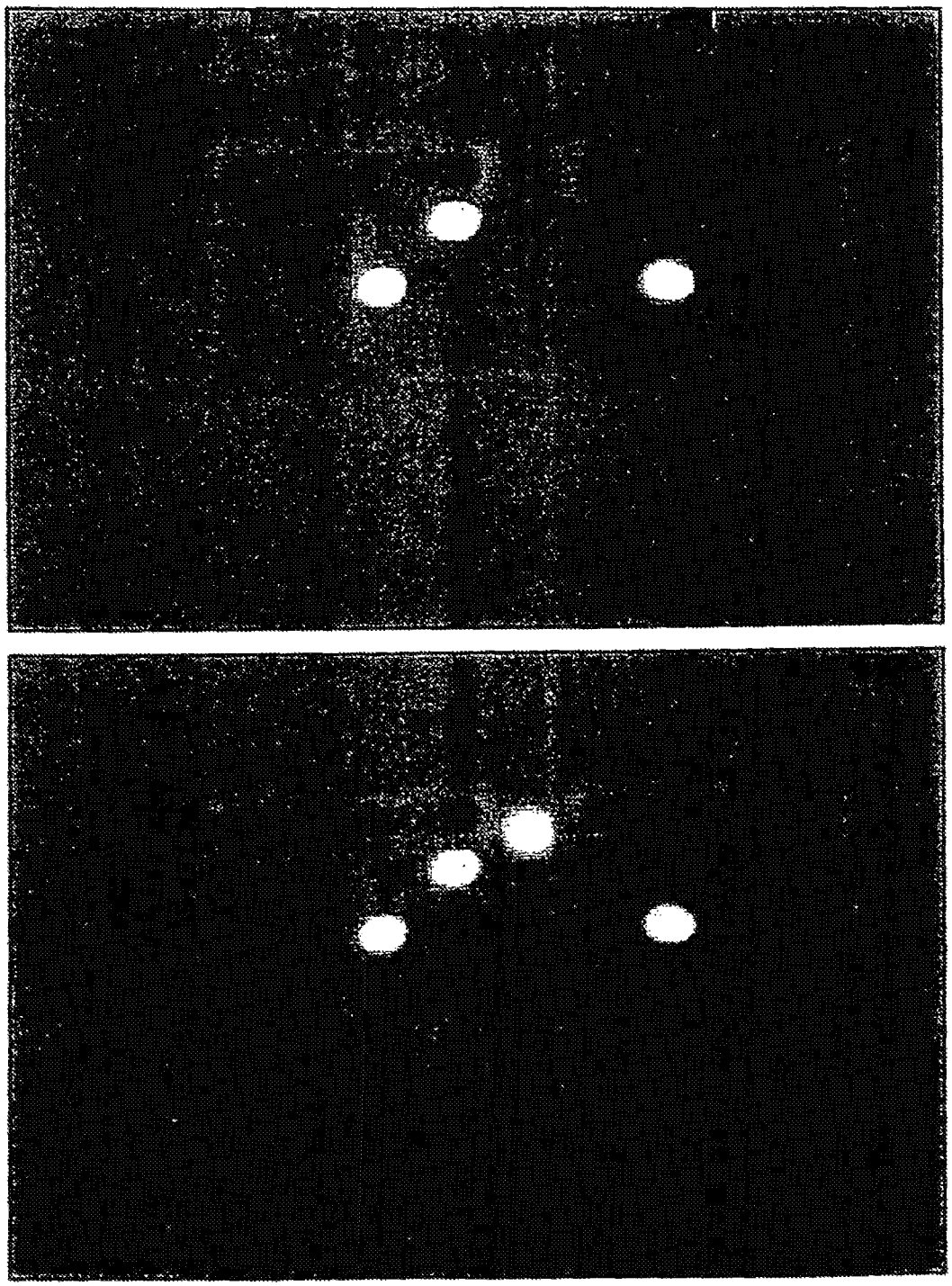
FIG. 82 is a time-lapse set of photographic images recording entry of a fluorescent cell into a retention chamber already holding several cells, in accordance with aspects of the invention.

This example describes capture of a single cell or a cell population in a microfluidic system; see FIGS. 80-82.

FIG. 80 shows a single cell captured at a retention site using a chip fabricated generally according to system 850 of Example 7. In FIG. 80A, cells 1610 follow a divided flow path extending in opposite directions above retention site 1612. In FIG. 80B, a trapped cell 1614 is positioned at the retention site.

Multiple cells were captured in a larger retention chamber formed by a chip fabricated generally according to system 250 of Example 2. FIGS. 81A, 81B, and 81C show empty chamber 270, the chamber with two cells, and with six cells, respectively. FIG. 82 shows a similar capture of cells, but here the cells are prelabeled with a fluorescent dye so that the cells are easily visible as bright green using fluorescent microscopy. FIGS. 82A and 82B show a chamber with only three cells and during the entry of a fourth cell, respectively.

Example 24

Fixing and Staining Cells in a Microfluidic System

Figure 83:
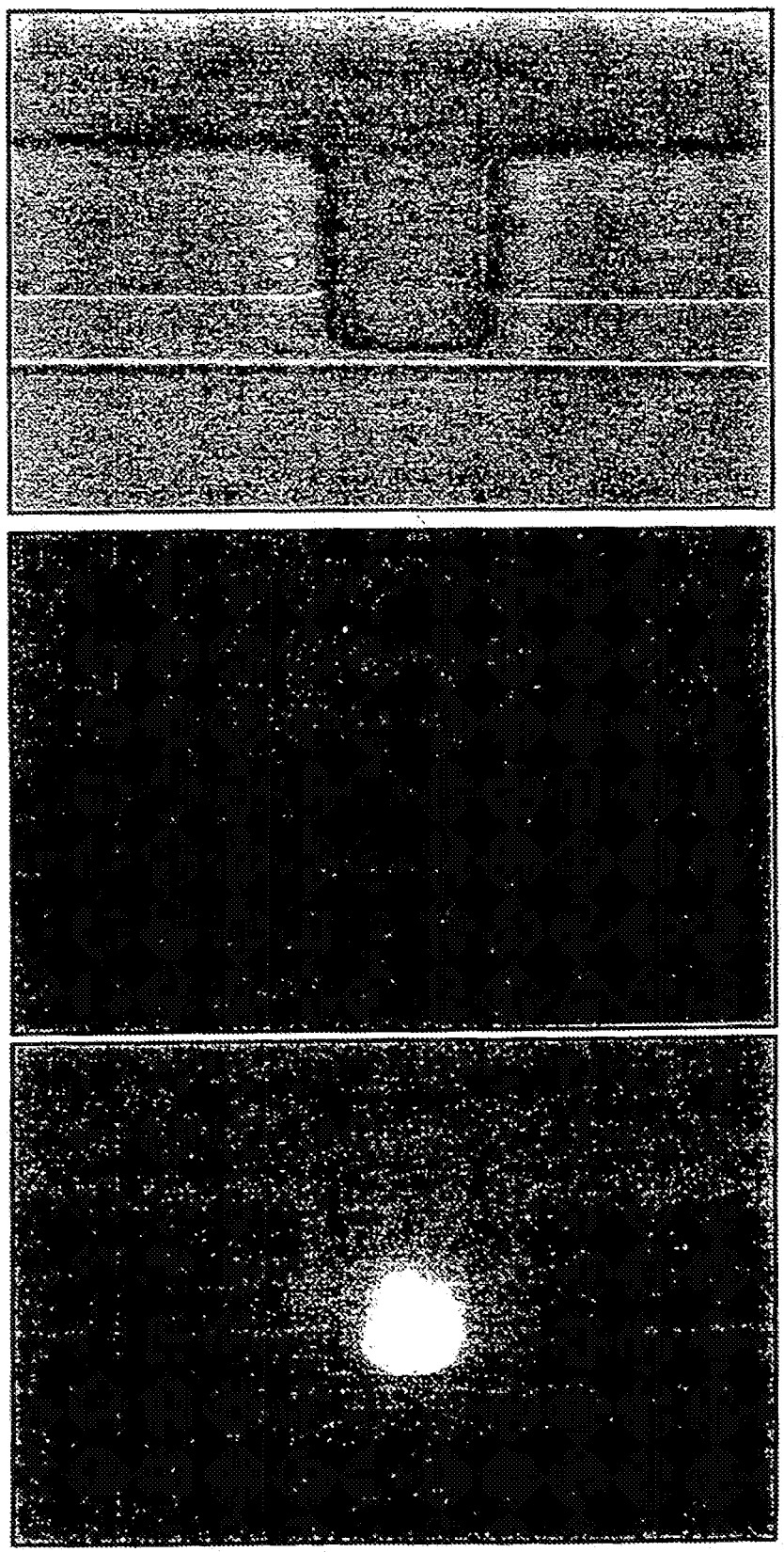
FIG. 83 is a time-lapse set of photographic images recording fixation and staining of a retained cell in a microfluidic system, in accordance with aspects of the invention.

This example describes the use of a microfluidic system to fix a cell with an organic solvent, methanol, and label the cell with acridine orange; see FIG. 83.

All cell manipulations and treatments were as described in Example 2. FIG. 83A shows a single cell 1630 retained at the bottom of retention site 1632. The cell is barely visible due to the low level of light used. The cell was perfused with methanol to fix the cell, and visible cell-shrinkage was evident (not shown). FIG. 83B shows that the cell exhibits no fluorescence. However, after the cell was perfused with a solution of acridine orange, the cell fluoresces brightly (see FIG. 83C).

Example 25

Microfluidic Mechanism for Measuring Cell Secretion

This example describes the structure and use of a soft lithography-based, microfluidic system for measuring secretion of molecules, complexes, and/or small particles from cells.

Many cell analyses measure release, and/or secretion of materials from cells. In some cases, the cells secrete material naturally. For example, neurons are analyzed for their ability to secrete neurotransmitters at neural synapses; endocrine cells for secretion of endocrine hormones, such as insulin, growth hormone, prolactin, steroid hormones, etc.; and a broad range of cell types for secretion of cytokines. In other cases, cells are lysed to define an aspect of their internal contents. However, in any of these cases, a secreted or released material of interest may no longer be held in a fixed position by the cells, and thus may be free to diffuse into the ambient solution. Accordingly, such secreted or released materials may be difficult to analyze without concentrating them and/or without using immobilized, high-affinity binding partners, for example, in ELISA.

Microfluidic systems may ameliorate some of the difficulties associated with measuring material released from cells, but may introduce additional considerations. In microfluidic systems, cells may be grown in isolated chambers having small volumes, as described above in Example 10. The chambers may maintain released materials in the small volumes, promoting subsequent analysis. However, to maintain the released materials in a concentrated form, the chambers may be isolated from other portions of the microfluidic network. Such isolated chambers do not promote ready analysis of the released materials, since the materials may be isolated from analytical reagents and may be difficult to collect without substantially diluting the released materials. Therefore, a microfluidic mechanism is needed that allows material released from cells to be collected and/or analyzed in a distinct fluidic compartment that is not part of a primary fluidic layer of a microfluidic system.

This example provides a microfluidic system having a cell chamber and a separate material collection compartment that communicate fluidically through a semi-permeable membrane. The semi-permeable membrane permits movement of material that is secreted/released from cells, but prevents movement of cells themselves. The membrane may be form a portion of a fluid layer, or interface with a fluid layer above and/or below the fluid layer. When disposed below, the membrane may form some or all of the substrate for the fluid layer. Accordingly, secreted/released material may pass through the membrane for collection and/or analysis in another compartment of the fluid layer, a compartment above the fluid layer, and/or below the substrate. For example, the microfluidic system may include a layer similar to the base layer of Example 11.

Example 26

Microfluidic Analysis of a Heterogeneous Particle Population—Part II

This example describes microfluidic systems for sorting and analyzing heterogeneous populations of particles, such as blood samples, based on differences in particle size; see FIGS. 84-88. Example 26 expands upon aspects of Example 15 above.

Description

Figure 84:
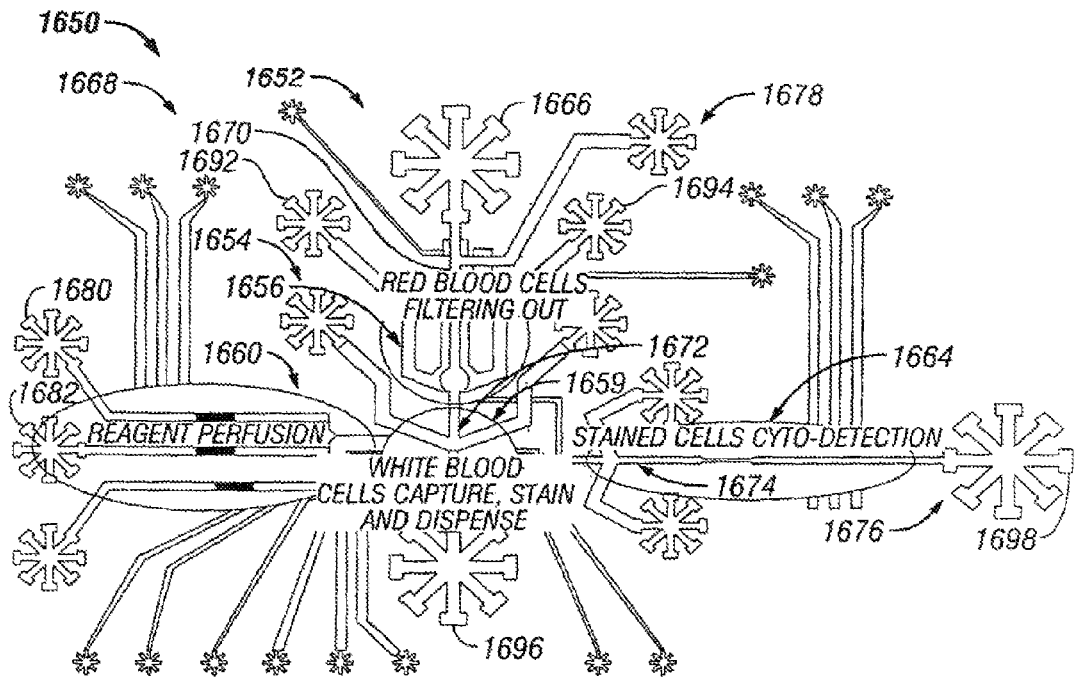
FIG. 84 is a top plan view of a microfluidic system for analyzing a size-selected set of cells, in which the system includes serially disposed filtration and retention mechanisms, a perfusion mechanism, and a flow-based detection mechanism, in accordance with aspects of the invention.
Figure 85:
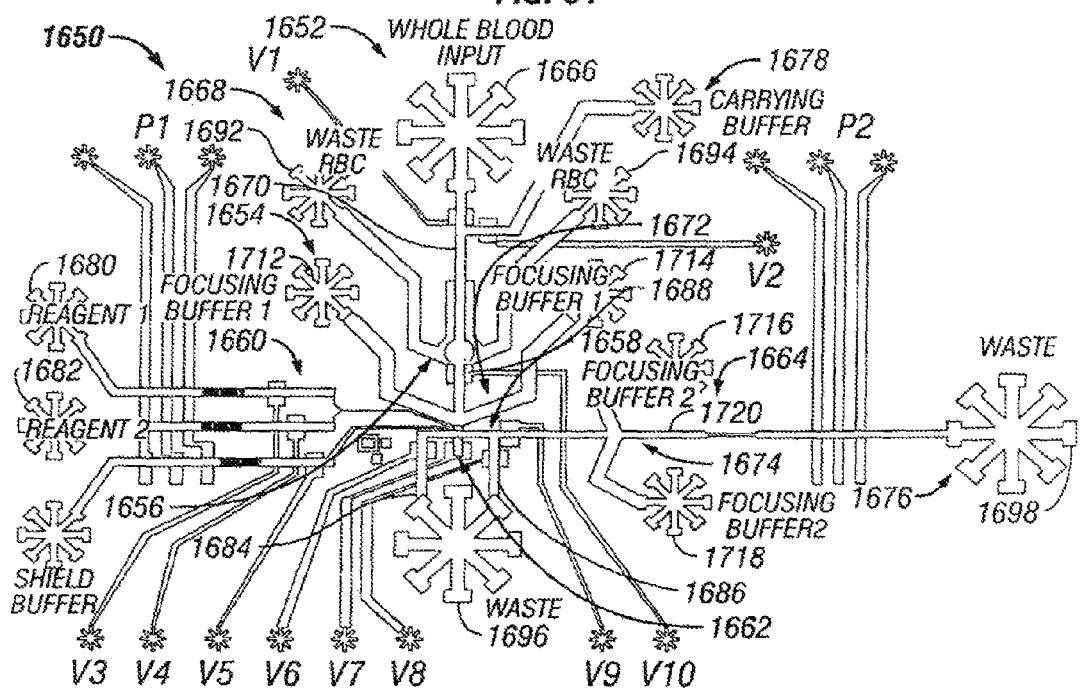
FIG. 85 is another top plan view of the microfluidic system of FIG. 84, showing identifying labels for reservoirs and valves, in accordance with aspects of the invention.

This example provides a microfluidic system 1650 that selectively retains and analyzes larger particles from a mixture of larger and smaller particles; see FIGS. 84 and 85. System 1650 includes an input mechanism 1652, a positioning mechanism 1654, a filtration mechanism 1656, a retention mechanism 1658, a perfusion mechanism 1660, a release mechanism 1662, and a flow-based detection mechanism 1664, among others. These mechanisms may be grouped into a first set for inputting sample and size-selecting the sample, and a second set for retaining, treating, measuring, and outputting the size-selected sample.

The first set of mechanisms may functionally interconnect as follows. Input mechanism 1652 introduces particles from a particle sample placed in particle input-reservoir 1666, into microfluidic network 1668 of system 1650. Particles are moved by positioning mechanism 1654 to filtration mechanism 1656 by flow along inlet channel 1670. Filtration mechanism 1656 may act as a size-dependent and regulatable retention mechanism, or prefilter, that removes smaller particles from the inputted particles, while retaining larger particles. After suitable filtration, the larger particles may be released from filtration mechanism 1656 and moved by positioning mechanism 1654 toward retention mechanism 1658.

The second set of mechanisms may functionally interconnect as follows. Positioning mechanism 1654 may use a first focusing mechanism 1672 to focus and direct particles toward retention mechanism 1658. Particles retained by retention mechanism 1658 may be perfused with desired reagents from perfusion mechanism 1660, then released by release mechanism 1662. Released cells may be moved by positioning mechanism 1654 toward flow-based detection mechanism 1664. During positioning, cells may be focused into a single stream of particles by a second focusing mechanism 1674. Finally, detected cells may be passed to output mechanism 1676.

System 1650 may include a plurality of regulators, or valves, that may regulate various aspects of the mechanisms described above; see FIG. 85. Valve V1 may regulate input mechanism 1652. Valve V2 may regulate alternative input mechanism 1678. Alternative input mechanism 1678 may provide an alternative source of input fluid, and may be used to supply particle-free fluid for washing filtration mechanism 1658, for carrying particles from filtration mechanism to first focusing mechanism 1672 and on to retention mechanism 1658, and/or the like. Valve V3 may regulate input from first reagent reservoir 1680. Valve V4 may regulate input from second reagent reservoir 1682. Valve V5 may regulate flow of a shield buffer to space reagents from retained particles until the desired moment for beginning treatment. V6 may regulate flow through a first waste channel 1684. V7 may regulate release mechanism 1662. V8 may regulate flow through a second waste channel 1686. V9 may regulate flow toward detection mechanism 1664. Finally, V10 may regulate a filter-release mechanism 1688 that regulates release of particles from regulatable retention mechanism 1656.

Further aspects of input mechanism 1652, positioning mechanism 1654, retention mechanism 1658, perfusion mechanism 1660, release mechanism 1662, and output mechanism 1676 elsewhere in Section XIII.

Applications

The description that follows exemplifies use of system 1650 for separation and analysis of white blood cells from a sample of whole blood. However, system 1650 may be suitable for use with any heterogeneous (or homogeneous) population of particles.

System 1650 first separates white blood cells from smaller red blood cells and platelets. These separated white blood cells are directed to a retention site, retained, and then processed by the perfusion mechanism to stain the retained white blood cells. These stained cells are then released from the retention site and then positioned to a separate flow-based detection site. The detection site then detects a characteristic of the stained cells, based on the staining method/reagents used.

A chip fabricated according to system 1650 may be readied for use as follows. First, the chip may be loaded with water. Next, when all the channels are filled, the water may be replaced with a buffer solution. At this point, the following valves generally are closed: V1, V2, V3, V4, V5, V9, and V10. By contrast, the following valves generally are open: V6, V7, and V8. All input reservoirs may be loaded with their respective buffers/reagents. However, particle input-reservoir 1666 typically is not loaded yet. Each waste reservoir 1692, 1694, 1696, and 1698 may be emptied (or is already empty).

Figure 86:
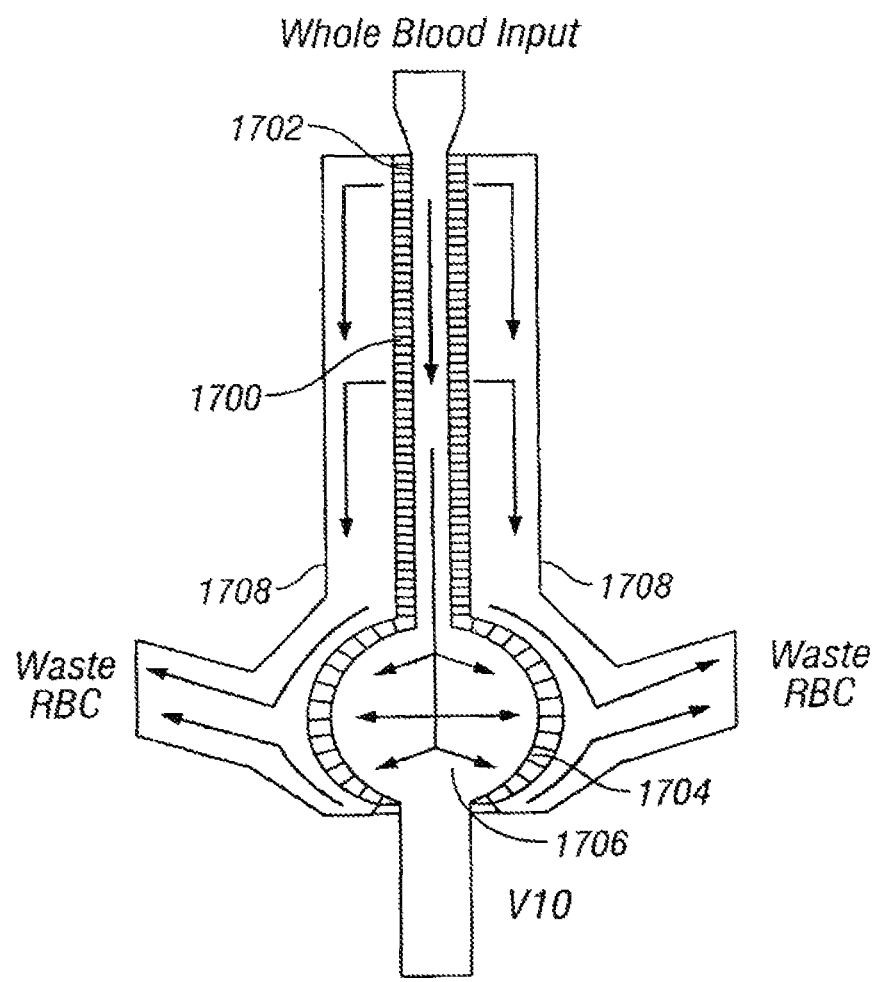
FIG. 86 is a top plan view of selected portions of the system of FIG. 84, illustrating selected aspects including a filtration mechanism, in accordance with aspects of the invention.

A sample of whole blood may be loaded and filtered as follows. An aliquot of blood is loaded into particle input-reservoir 1666. Valve V1 may be opened and the blood allowed to flow into filtration mechanism 1656. FIG. 86 shows the operation of filtration mechanism 1656 in greater detail. A first set of particle-selective channels 1700, for example, channels that are about 7 μm wide and 5 μm high, may be disposed along the walls of inlet channel 1702. A second set of particle-selective channels or chamber channels 1704 also may be disposed around the perimeter of capture chamber 1706. Accordingly, red blood cells may travel to flow-through chambers 1708 and then waste reservoirs 1692, 1694, along a substantial area formed by inlet channel 1702 and chamber 1706. In particular, travel of red blood cells through particle-selective channels 1700 from inlet channel 1702 may avoid clogging chamber channels 1704. However, the white blood cells may be retained in chamber 1704, because they cannot pass through channels 1700 and may not travel past chamber 1704 because filter-release mechanism 1688 (valve V10) is closed.

White blood cells retained in capture chamber 1706 may be washed as follows. After a suitable number of white blood cells have entered chamber 1706, valve V1 may be closed so that no more whole blood enters inlet channel 1702 and chamber 1706. Then, valve V2 may be opened to allow the carrying buffer provided by alternative input mechanism 1678 to wash residual red blood cells out of chamber 1706. At this point, waste reservoirs 1692, 1694 may be emptied to avoid reverse flow of the red blood cells back into chamber 1706.

Figure 87:
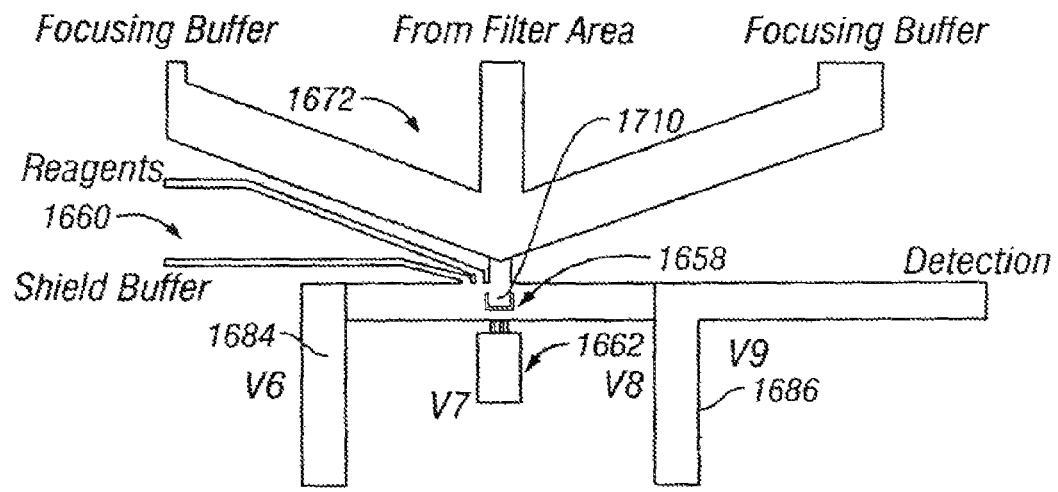
FIG. 87 is another top plan view of selected portions of the system of FIG. 84, in accordance with aspects of the invention.
Figure 88:
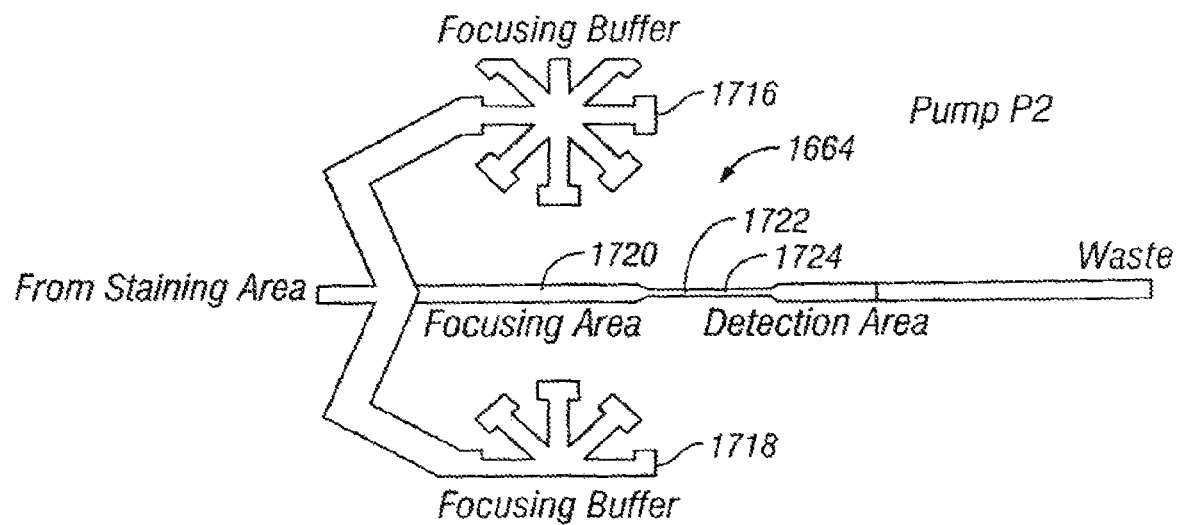
FIG. 88 is yet another top plan view of selected portions of the system of FIG. 84, in accordance with aspects of the invention.

Filtered white blood cells may be retained by retention mechanism 1658 as follows; see FIGS. 85-87. Valve V10 may be opened to allow the filtered white blood cells from chamber 1706 to be released. The released cells may be focused by first focusing mechanism 1672 and carried toward retention site 1710 (see FIG. 87). Flow of carrying buffer from alternative input mechanism 1678 may act during this process to reposition the white blood cells from chamber 1706 to retention site 1710.

Retained white blood cells may be stained with reagents as follows. Valve V10 may be closed to prevent additional white blood cells from leaving chamber 1706 and entering retention site 1710. Next, valve V6 may be closed to facilitate directing reagents along a flow path toward the retained white blood cells by perfusion mechanism 1660. Next, white blood cells may be stained or otherwise treated/processed using perfusion mechanism 1660, as described elsewhere in Section XIII, particularly Example 2. Pump P1 may be used by perfusion mechanism 1660 to actively move reagents, buffer, and/or fluid during particle treatment (see FIG. 85). At this point, the valves may be in the following configuration. Valves V1, V3, V4, V5, V6, V9, are V10 closed. Valves V2, V7, and V8 are open. After cell treatment has been completed, pump P1 may be turned off, and valves V3, V4, and V5 may be closed to terminate action of perfusion mechanism 1660.

Treated/processed cells may be released and detected as follows; see FIGS. 84, 85, 87, and 88. Pump P2 may be turned on. This pump may be used to pull fluid, particles, and/or reaction products toward detection mechanism 1664 and waste (output) reservoir 1698. Next, valve V8 may be closed and valve V9 opened (see FIG. 87). With this valve configuration, fluid and particle may be directed toward waste reservoir 1698 instead of waste reservoir 1696 (see FIG. 85). At this point, each focusing reservoir 1712, 1714, 1716, 1718 may be refilled with buffer and waste reservoir 1698 may be emptied. Then, partial or complete closure of valve V7 may be used to release white blood cells from retention mechanism 1658. During release, buffer flowing from reservoirs 1712, 1714, or alternative input mechanism 1678, may be used to carry the released white blood cells toward detection mechanism 1664. Buffer flowing from reservoirs 1716, 1718 may act in second focusing mechanism 1674, to position (focus) the released cells to a desired cross-sectional portion of outlet channel 1720, generally a central portion (see FIG. 88). After cell focusing, outlet channel 1720 may constrict to a narrowed channel 1722, which may facilitate positioning the cells in single file, that is, one-by-one at detection site 1724, rather than in groups.

System 1650 may be used to measure any suitable aspect of a blood sample or other inputted particle population, including samples from patients, research subjects, volunteers, forensic studies, cadavers, etc. Suitable aspects may include analysis of leukemias, anemias, blood abnormalities, blood health, genetic diseases, infections, ratios of specific blood cell types, presence of nonblood cells, and/or the like. Exemplary leukemias may include acute lymphoblastic leukemias, chronic myelogenous leukemias, acute myelogenous leukemias, acute lymphoid leukemias, chronic lymphocystic leukemias, and/or juvenile myelolymphocystic leukemias, among others. Exemplary anemias and/or genetic diseases may include aplastic anemias, Faconi anemias, sickle-cell anemias, and/or the like. Other aspects or characteristics of blood cells (or other heterogeneous particle populations) that may be suitable for analysis are described above in Sections VIII and XII.

Figure 89:
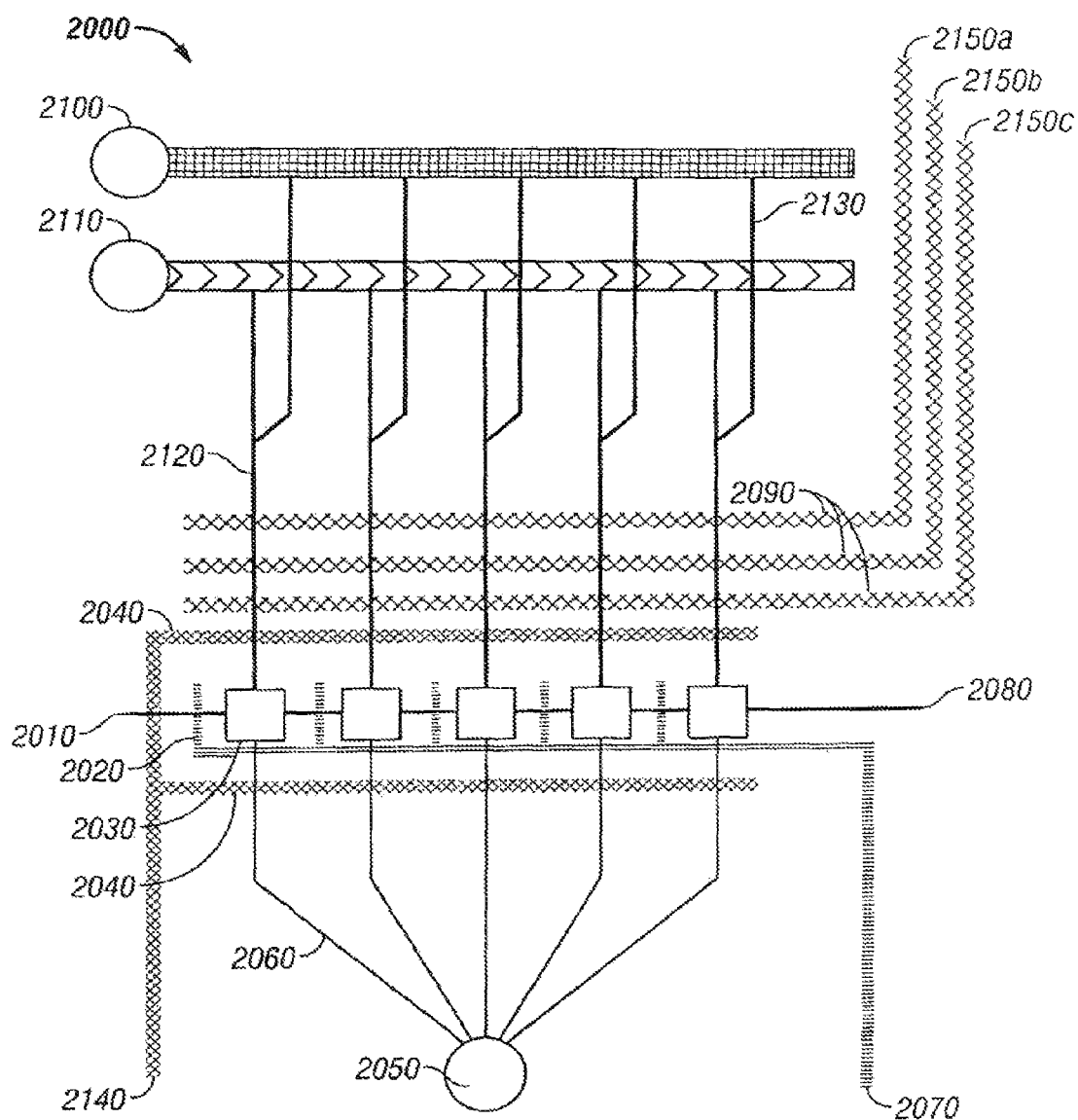
FIG. 89 is a top plan view of a perfusion device for exposing particles to an array of different reagents or different reagent concentrations.
Figure 90:
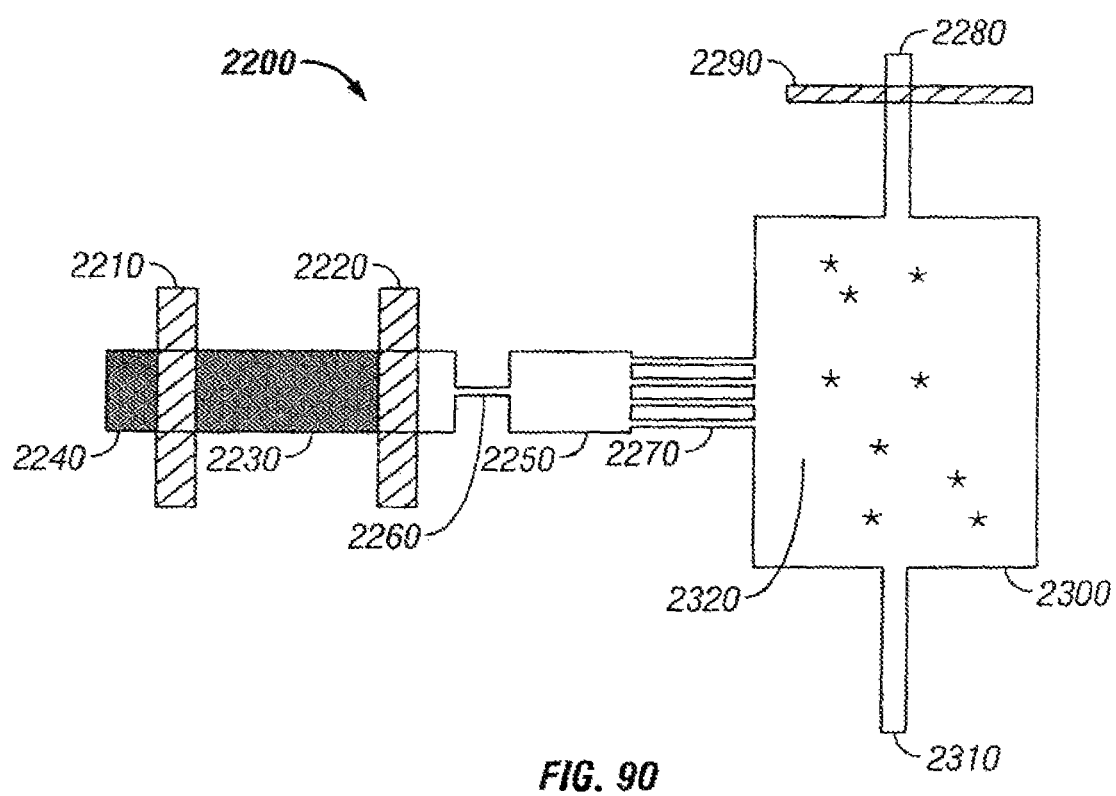
FIGS. 90 through 94 depict a top plan view of a device being used to measure chemotactic response of cells to a chemoattractant.

FIG. 89 is a top plan view of a perfusion device for exposing particles to an array of different reagents or different reagent concentrations. Here, microfluidic passage device 2000 provides a plurality of growth/perfusion chambers 2030 for loading particles, such as cells, through loading passage 2010 which is controlled by valving line 2020 which is in operable communication with control input 2070, and which, when actuated, isolates each chamber 2030 from one another. Particles may then be flushed out the chambers 2030 by opening valving line 2020 and pushing fluid from loading passage 2010 through each chamber 2030 towards exit passage 2080. Once each chamber 2030 is loaded with particles, such as cells, and isolated, valve line 2040, which is in operable communication with control input 2140, then opens to permit flow of reagent and diluent, such as media or a fluid that dilutes the reagent, through flow lines 2120, which originate from a diluent reservoir 2110, and optionally, reagent reservoir 2100, which may hold a reagent for exposure to the particles. The ratio of diluent to reagent may be controlled by valving, or, preferably, by controlling the bore of the lines connecting the diluent reservoir 2110 to flow line 2120 and reagent reservoir 2100 to flow line 2120. Diluent and reagent are then fed into chambers 2030 by pumping action caused by, for example, a peristaltic pump 2090, which is actuated by pump input lines 2150a-c, thus particles are perfused with reagent/diluent. Diluent, in the case of cells, may be cell culture media. Effluent from chambers 2030 may be collected into waste reservoir 2050.

Figure 91:
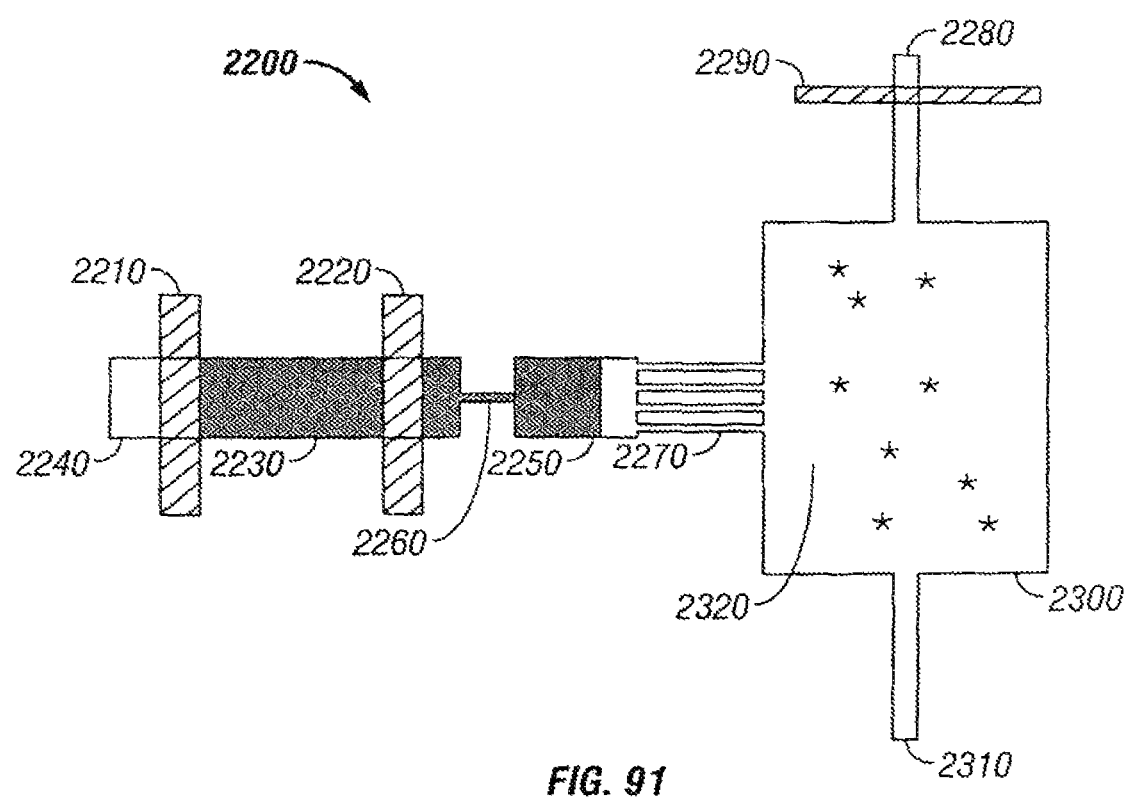
Figure 92:
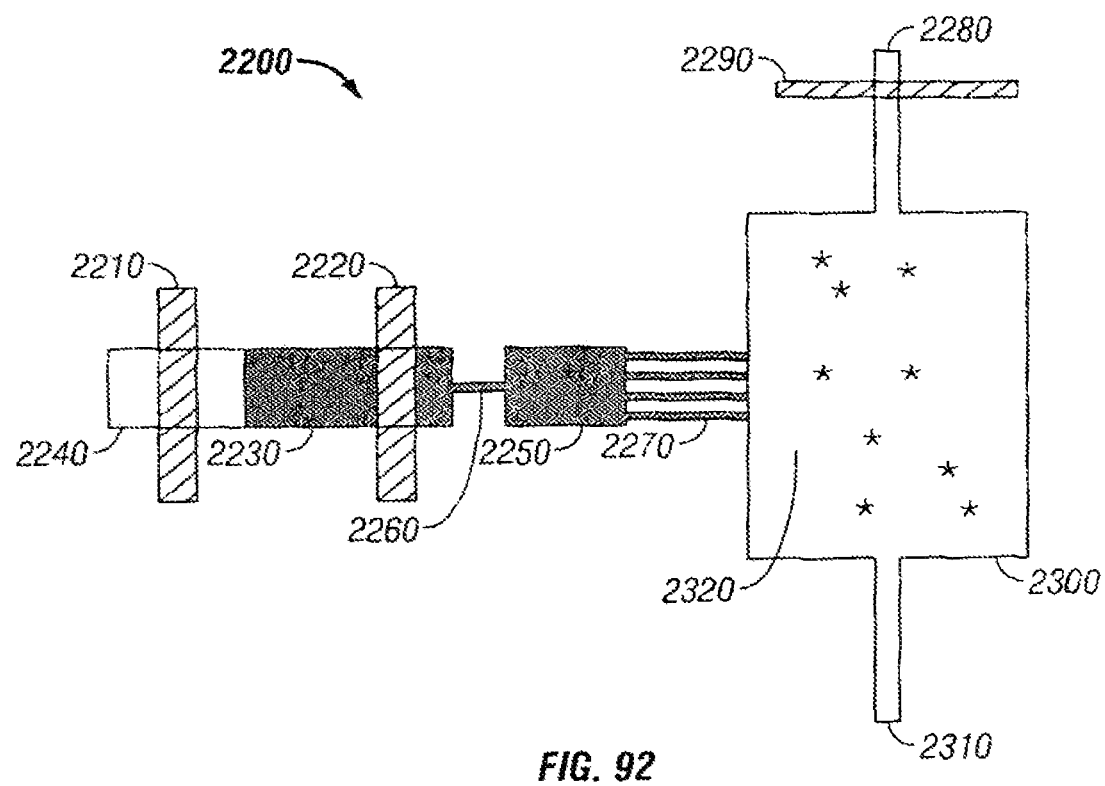
Figure 93:
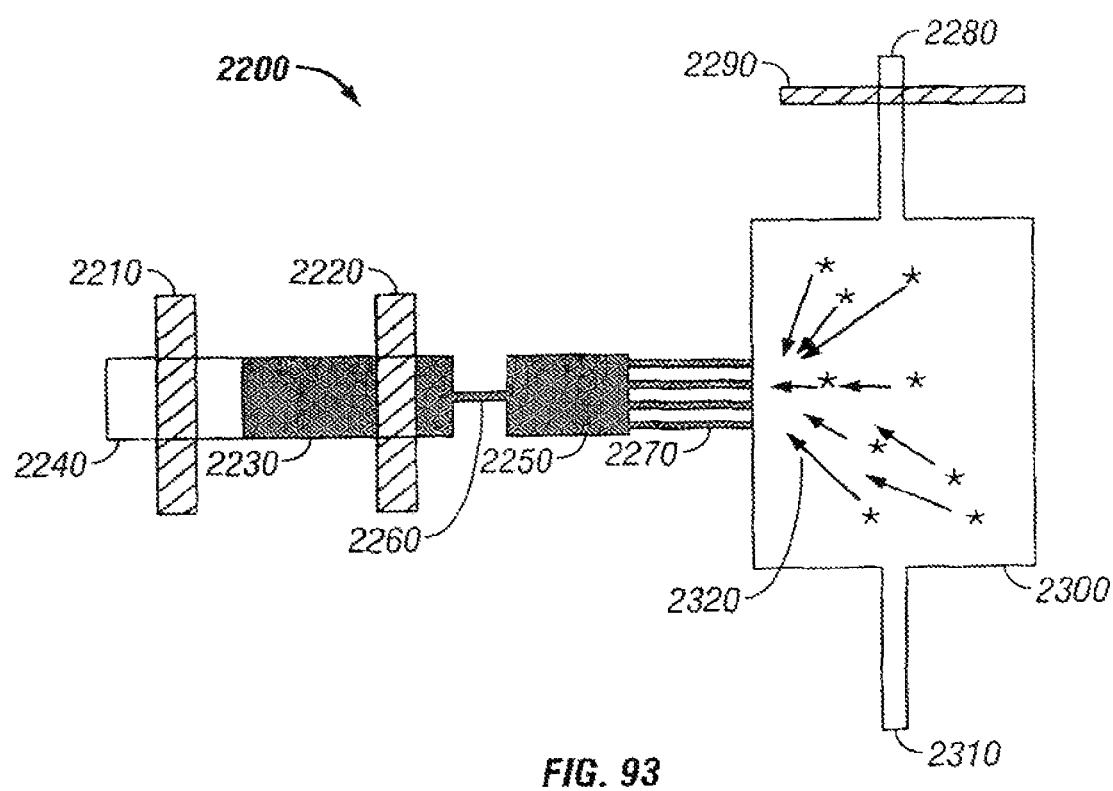
Figure 94:
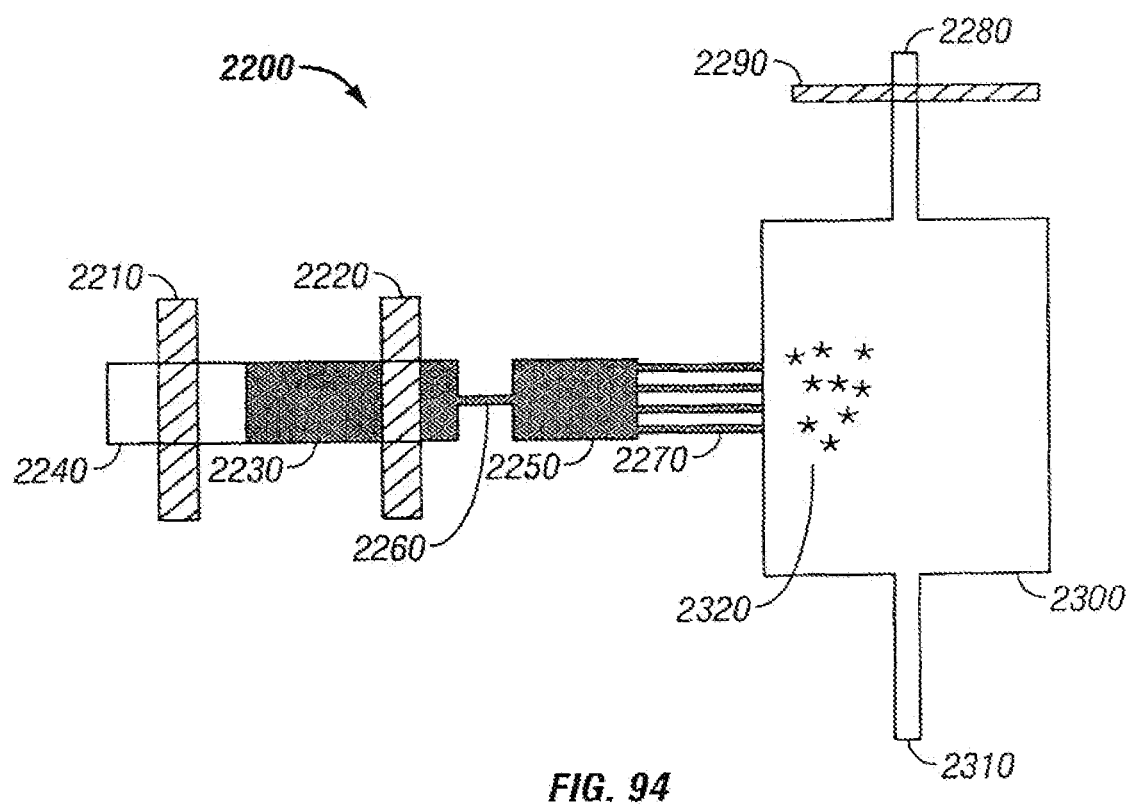

FIGS. 90 through 94 depict a top plan view of a device being used to measure the response of cells to a chemoattractant. Microfluidic passage device 2200 provides reagent loading chamber 2230, wherein reagent is metered into reagent chamber 2300 by the opening of valve 2210 and blind filling reagent into reagent chamber 2300. Once reagent chamber 2230 is filled, particles 2320, such as cells, which were previously introduced into particle chamber 2300 are then exposed to a gradient of reagent upon the opening of valve 2220, valve 2210, preferably, remains, closed during the formation of the gradient. FIG. 91 shows reagent entering into gradient forming mechanism 2250, which has channels 2270 for limiting reagent flow into particle chamber 2320. FIG. 92 depicts the advancement of reagent towards particle chamber 2300. FIGS. 93 and 94 depict the movement of particles 2320 toward channels 2270 where the chemo-attractant reagent is emanating from.

Figure 95:
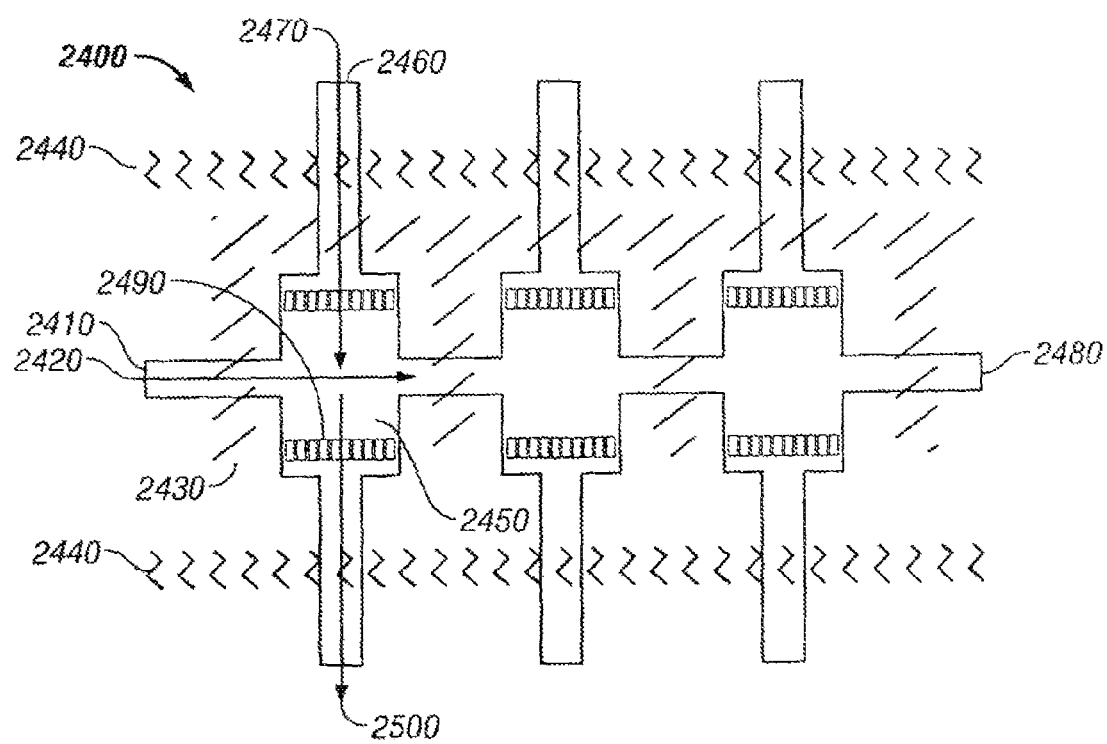
FIG. 95 is a close-up top plan view of a perfusion chamber with associated valving system.

FIG. 95 is a close-up top plan view of a perfusion chamber with associated valving system. Particles, such as cells, can be loaded into a series of particle chambers 2450 by opening isolation valve line 2430 which, when closed, isolates each chamber 2450 from each other. Particles do not enter flow line 2460 since they are retained in chamber 2450 by screen or comb 2490, which each obstruction is spaced-apart from the other at a distance less than that of the particle, so as to retain the particle on one side of the screen or comb 2490. In use, particles are introduced into chamber 2450 by the opening of isolation valve line 2430 which allows the particles to flow through and fill each chamber 2450. Once filled with the desired amount of particles, isolation valves 2430 are closed to isolate each chamber 2450 from each other, and then flow valves 2440 are opened to allow for flow of reagent through chamber 2450 to perfuse the particles with reagent. Once an experiment is complete, flow valves 2440 may then be closed, isolation valves 2430 may than be opened to flush out particles. If the particles are adherent cells, such cells can be liberated if attached by exposing such adhered cells to a cell dislodging reagent such as trypsin. Once liberated, the cells can be flushed out of the system, and the system reused.

Figure 96A:
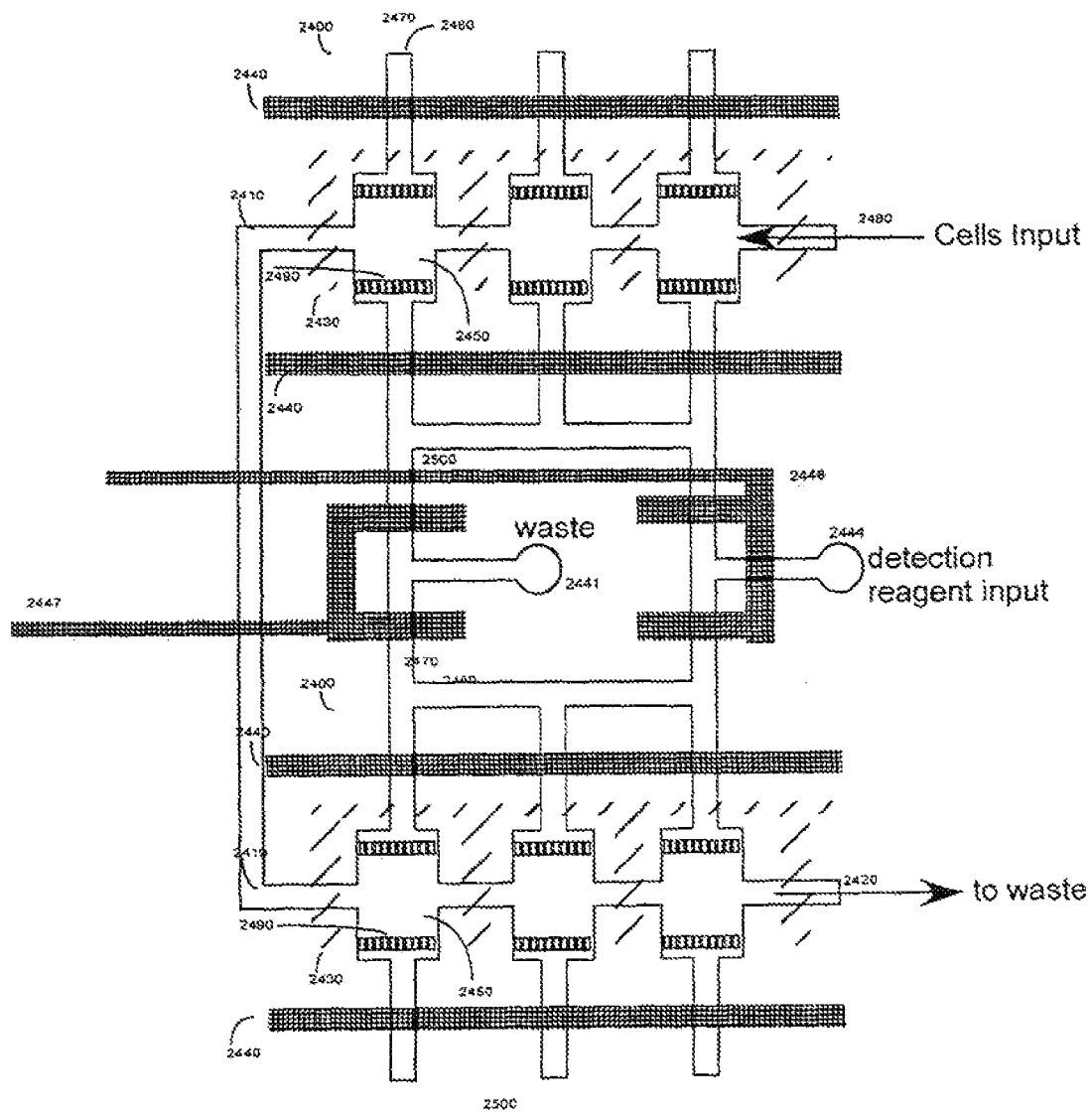
FIGS. 96*a* through 96*c* are top plan views of a perfusion chamber device.
Figure 96B:
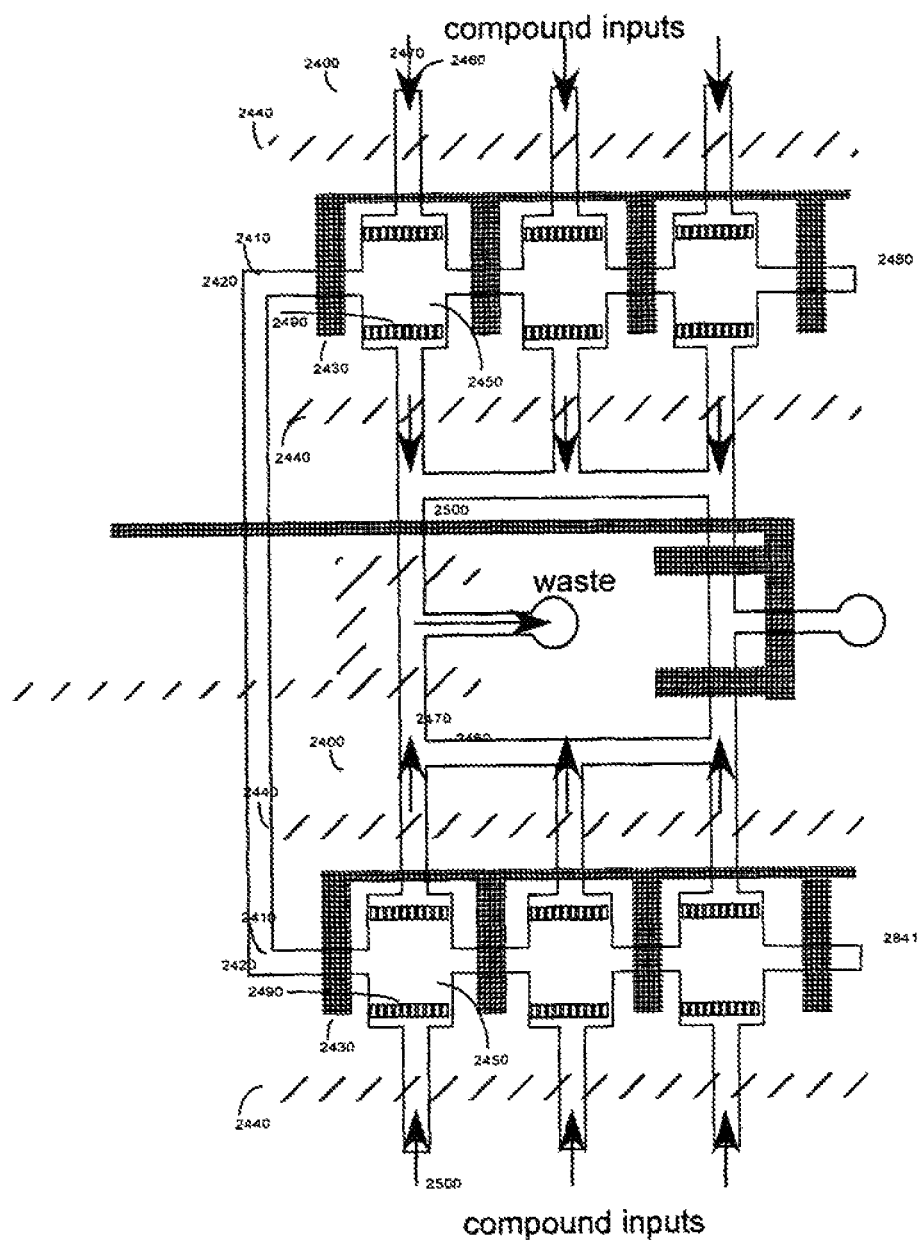
Figure 96C:
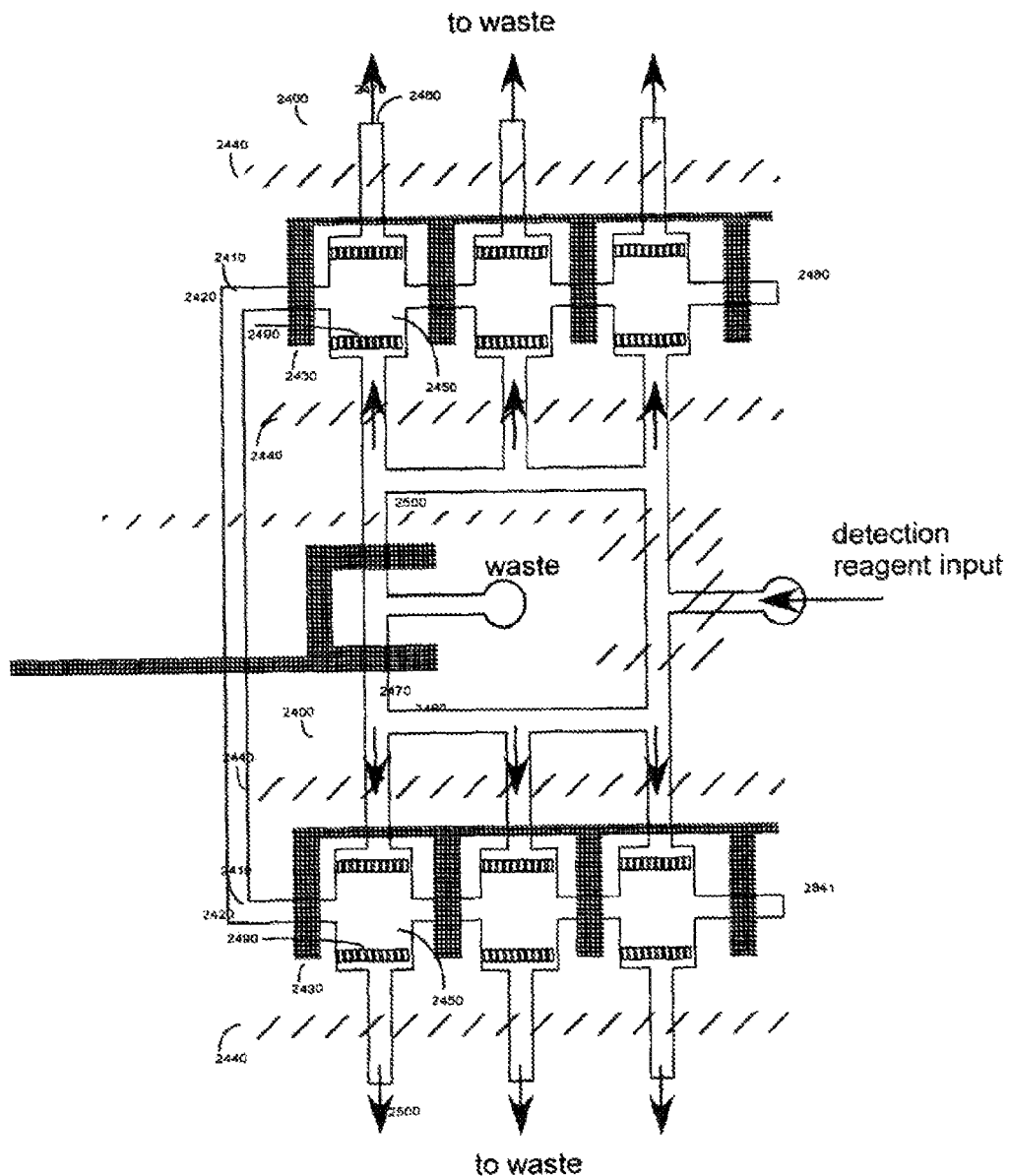

FIGS. 96a through 96c depict a preferred embodiment of a perfusion chamber device wherein a plurality of different compounds from a plurality of different compound sources can be perfused through a plurality of cell chambers such that each different compound is perfused through a different chamber, and then a common detection reagent can be perfused through each different cell chamber from a common detection reagent source. In some embodiments, the different compounds are perfused in one direction through each cell chamber and the common detection agent is perfused in an different direction through the detection chamber. In some embodiments, the common detection reagent source is in fluid communication, preferably selectively, with a waste receptacle. In some embodiments, the different compound sources may also serve as a second waste receptacle after the different compounds have been delivered to the different cell chambers.

For example, FIG. 96a shows a device 2400 wherein cells are introduced through cell inlet 2480 and flowed through until line 2410 is filled with cell containing solution. During cell loading, chamber valves 2440 are closed, and, preferably, detection reagent valve 2448 and waste valve 2447 remain closed. Once chambers 2450 have been loaded with cells, chamber isolation valves 2430 close to isolate each chamber from the other, as shown in FIG. 96b. As shown in FIG. 96c, with isolation valves 2430 remaining closed, cells contained within chambers 2450 are then exposed different compounds supplied by opening valves 2440, which permits flow of the different compounds through channels 2460 and 2500 into chambers 2450, perfusing across through chamber 2450, and out through to waste 2441. After a selected period of perfusion, waste valve 2447 may be closed and detection reagent valve 2448 may be opened wherein a reagents, for example, media, wash solution, detection agent(s), and/or developing reagents may be flowed back through chambers 2450 out through channels 2460 and 2500. Alternatively, a single common compound may be first flowed to each of chambers 2450 from detection reagent input 2448, and then different detection reagents may be flowed through each chamber from channels 2460 and 2500.

Perfusion type devices, such as those described above, may be useful for conducting toxicological assays. The invention provides in one aspect for devices and methods for conducting cell toxicity assays wherein cells are exposed, preferably transiently for a selected period of time, to a compound which may be toxic to the cells, or becomes toxic to the cells through further processing. For example, liver cells, previously loaded into chambers, may be introduced into the chambers, and then a drug candidate, or a plurality of drug candidates may be presented to the cells within the chambers for a selected period of time and/or at selected concentrations. The drug candidates may then be flushed out by a wash step, which is then followed, after a selected period of time, by a detection treatment, where the drug exposed cells are treated with a reagent to detect a change in state caused by the drug candidate. In some embodiments, no detection reagent is used. Instead, a change in some physical property of the cells is observed or measured, such as impedance, resistivity, conductivity, cell morphology, proliferation, and lysis. Changes in state may include, for example, apoptosis, proliferation, senescence, changes in membrane chemistry, and changes in nuclear or organelle structure. Detection reagents may include, annexin V type assays, apoptosis detection reagents, vital dye reagents, Quinn2 dyes, LDH Assays: (lactase dehydrogenase enzyme leakage from plasma membrane), ATP measurements (cell proliferation/cytotocicity assessment), and MTT salt assay, WST-1 type assays.

Cell assays may include: trypan blue; eosin Y nigrosine; propidium iodide; ethidium bromide, wherein dead and viable cells are discriminated by differential staining and counted using a light or fluorescence microscope. These methods do not allow the processing of large sample numbers and do not account for dead cells which may have lysed. Thus, the rate of cell death in long term cultures can be underestimated. In other embodiments, fluorescent dyes: [51Cr]; [3H]-thymidine; [3H]-proline; [75Se]-methionine; [125J]-5-iodo-2-deoxyuridine; bis-carboxyethyl-carboxyfluorescein (BCECF); calcein-AM from prelabeled target cells.

Yet another embodiment includes assays based on the measurement of cytoplasmic enzyme activity released by damaged cells. The amount of enzyme activity detected in the culture supernatant correlates to the proportion of lysed cells. Enzyme release assays have been described for alkaline and acid phosphatase; glutamate-oxalacetate transaminase; glutamate pyruvate transaminase; arginosuccinate lyase.

The disclosure set forth above may encompass one or more distinct inventions, with independent utility. Each of these inventions has been disclosed in its preferred form(s). These preferred forms, including the specific embodiments thereof as disclosed and illustrated herein, are not intended to be considered in a limiting sense, because numerous variations are possible. The subject matter of the inventions includes all novel and nonobvious combinations and subcombinations of the various elements, features, functions, and/or properties disclosed herein.

What is claimed is:

1. A microfluidic device for exposing cells to a plurality of compounds comprising:
    (a) a cell inlet;
    (b) a plurality of cell chambers in fluidic communication with said cell inlet and at least one of the other cell chambers;
    (c) a plurality of chamber isolation valves, said isolation valves, when actuated, fluidically isolating said chambers from each other;
    (d) a plurality of compound inlets and compound outlets, wherein each chamber is in fluidic communication with a compound inlet and a compound outlet, wherein each chamber includes a channel sized for retaining a single cell within said chamber;
    (e) a shared waste receptacle, said shared waste receptacle being configured to receive waste from said compound outlets;
    (f) a shared reagent reservoir, said shared reagent reservoir being configured to provide reagent to said chambers;
    (g) a plurality of compound outlet valves, said compound outlet valves configured to fluidically isolate said chambers from said shared waste receptacle and said shared reagent reservoir when closed;
    (h) a plurality of analysis sites, wherein each cell chamber has a corresponding analysis site, wherein each chamber is in fluidic communication with a respective analysis site via its channel;
    wherein the plurality of cell chambers includes a first cell chamber and a second cell chamber downstream from the first cell chamber,
    wherein the first cell chamber is configured to hold a first cell using a retaining force fluidically applied via its channel and thereby allow a second cell following the first cell to be diverted downstream along a shared cell input channel to the second cell chamber.

2. The device of claim 1 wherein at least one of said plurality of compounds is a cell toxic compound.

3. The device of claim 1 wherein said common reagent reservoir contains a detection agent responsive to a toxic response of said cells to one of said compounds.

4. The device of claim 1, wherein the plurality of cell chambers is arranged such that an entrance of each cell chamber following the first cell chamber is sequentially arranged downstream to the entrance of another cell chamber.

5. The device of claim 1, wherein the first cell chamber is physically sized to hold only a single cell according a size range encompassing each of the first and second cells, and thereby configured to only hold the first cell, which blocks the second cell from coupling to the first cell chamber.

6. The device of claim 1, wherein the fluidic retaining force fluidically applied to the channel prevents backflow of the first cell into the shared cell input channel while the second cell is flowed within the input channel.

7. The device of claim 1, wherein each chamber is in permanent fluidic communication with its respective analysis site via its channel.

8. The device of claim 1, wherein each channel comprises a switchable filter.

9. A method for determining whether one of a plurality of compounds causes a toxic response in one of a plurality of cells comprising the steps of:
    providing the device of claim 1;
    introducing said cells into said device of claim 1,
    isolating said cells within said chambers of said device of claim 1,
    exposing said cells to said plurality of said compounds while said cells are retained in said chambers,
    determining whether any of said cells had a toxic response resulting from exposure to one of said plurality of compounds.

* * * * *